United States Patent
Mohan et al.

(10) Patent No.: US 10,421,759 B2
(45) Date of Patent: Sep. 24, 2019

(54) FUSED BICYCLIC COMPOUNDS FOR THE TREATMENT OF DISEASE

(71) Applicant: AKARNA THERAPEUTICS, LTD., London (GB)

(72) Inventors: Raju Mohan, Encinitas, CA (US); Benjamin Anthony Pratt, Encinitas, CA (US)

(73) Assignee: AKARNA THERAPEUTICS, LTD., London (GB)

( * ) Notice: Subject to any disclaimer, the term of this patent is extended or adjusted under 35 U.S.C. 154(b) by 0 days.

(21) Appl. No.: 15/714,013

(22) Filed: Sep. 25, 2017

(65) Prior Publication Data
US 2018/0118752 A1   May 3, 2018

Related U.S. Application Data

(63) Continuation of application No. PCT/IB2016/000606, filed on Mar. 25, 2016.

(60) Provisional application No. 62/138,725, filed on Mar. 26, 2015.

(51) Int. Cl.
| | |
|---|---|
| *C07D 487/04* | (2006.01) |
| *C07D 471/04* | (2006.01) |
| *A61P 9/10* | (2006.01) |
| *A61P 1/16* | (2006.01) |
| *A61P 3/00* | (2006.01) |
| *A61P 3/04* | (2006.01) |
| *A61P 3/06* | (2006.01) |
| *A61P 3/10* | (2006.01) |
| *C07D 471/14* | (2006.01) |

(52) U.S. Cl.
CPC .............. *C07D 487/04* (2013.01); *A61P 1/16* (2018.01); *A61P 3/00* (2018.01); *A61P 3/04* (2018.01); *A61P 3/06* (2018.01); *A61P 3/10* (2018.01); *A61P 9/10* (2018.01); *C07D 471/04* (2013.01); *C07D 471/14* (2013.01)

(58) Field of Classification Search
CPC ................................. C07D 487/04; A61P 9/10
See application file for complete search history.

(56) References Cited

U.S. PATENT DOCUMENTS

| | | | |
|---|---|---|---|
| 2009/0131409 A1 | 5/2009 | Mehlmann et al. | |
| 2009/0203577 A1 | 8/2009 | Baik et al. | |

FOREIGN PATENT DOCUMENTS

| | | |
|---|---|---|
| WO | 03099821 A1 | 12/2003 |
| WO | 2005009387 A2 | 2/2005 |
| WO | 2010036362 A1 | 4/2010 |

OTHER PUBLICATIONS

Joseph T. Lundquist et al., "Improvement of Physiochemical Properties of the Tetrahydroazepinoindole Series of Farnesoid X Receptro (FXR) Agonists: Beneficial Modulation of Lipids in Primates", Journal of Medicinal Chemistry, US, vol. 53, No. 4, Feb. 25, 2010, pp. 1774-1787.
Mehlmann J F et al., "Pyrrole[2,3-d]azepino compounds as agonists of the farnesoid X receptor (FXR)", Bioorganic & Medicinal Chemistry Letters, Pergamon, Amsterdam, NL, vol. 19, No. 18, Sep. 15, 2009, pp. 5289-5292.
Sep. 29, 2016 Written Opinion and International Search Report of the International Search Authority issued in PCT International Application No. PCT/IB2016/000606.

*Primary Examiner* — Golam M Shameem
(74) *Attorney, Agent, or Firm* — Mintz Levin Cohn Ferris Glovsky and Popeo, P.C.

(57) ABSTRACT

Described herein are fused bicyclic compounds, compositions, and methods for their use for the treatment of disease.

16 Claims, 2 Drawing Sheets
Specification includes a Sequence Listing.

FUSED BICYCLIC COMPOUNDS FOR THE TREATMENT OF DISEASE

CROSS-REFERENCE

This application is a continuation of International Patent Application No. PCT/IB2016/000606, filed Mar. 25, 2016, which claims benefit of U.S. Provisional Application No. 62/138,725, filed on Mar. 26, 2015, the contents of which are incorporated herein by reference in their entirety.

BACKGROUND OF THE INVENTION

Farnesoid X receptor (FXR) is a member of the nuclear hormone receptor superfamily of ligand-activated transcription factors. Bile acids are FXR physiological ligands. On activation by bile acids, FXR regulates a wide variety of target genes that are critically involved in the control of bile acid, lipid and glucose homeostasis. Thus, FXR plays a key role in the pathogenesis of cholestatic diseases, non-alcoholic fatty liver disease and inflammatory bowel disease.

SUMMARY OF THE INVENTION

Described herein are compounds of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), pharmaceutical compositions that include such compounds, and methods of use thereof, for modulating FXR. In one aspect is the administration of at least one FXR modulator described herein to a mammal in the treatment of diseases, disorders or conditions that would benefit from FXR modulation.

In one aspect, provided herein is a compound of Formula (I), or a pharmaceutically acceptable salt or solvate thereof:

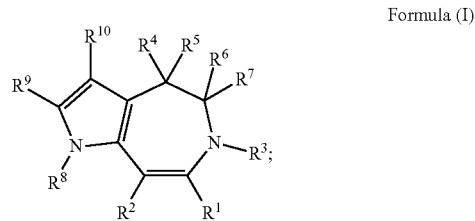

Formula (I)

wherein:
- $R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);
- $R^2$ is selected from the group consisting of —CN, —C(=O)OR$^{25}$, —C(=O)N(R$^{25}$)R$^{26}$,

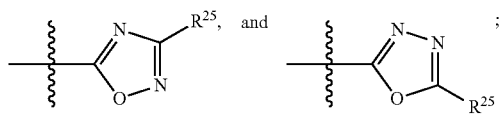

or $R^1$ and $R^2$ together with the carbon atoms to which they are attached, form an optionally substituted $C_2$-$C_9$heterocycloalkyl ring or an optionally substituted heteroaryl ring;
- $R^3$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_{10}$cycloalkyl, optionally substituted aryl, optionally substituted —($C_1$-$C_2$alkylene)-(aryl), optionally substituted heteroaryl, optionally substituted $C_2$-$C_9$heterocycloalkyl, optionally substituted —($C_1$-$C_2$alkylene)-(heteroaryl), —C(=O)R$^{20}$, —C(=O)OR$^{20}$, —S(=O)$_2$R$^{20}$, —C(=O)N(R$^{21}$)R$^{22}$, —C(=O)N(R$^{21}$)S(=O)$_2$R$^{24}$, —C(=O)N(R$^{23}$)N(R$^{21}$)R$^{22}$, —C(=O)N(R$^{23}$)N(R$^{21}$)S(=O)$_2$R$^{24}$, —N(R$^{23}$)C(=O)R$^{20}$, —N(R$^{23}$)C(=O)N(R$^{21}$)R$^{22}$, —N(R$^{23}$)C(=O)N(R$^{21}$)S(=O)$_2$R$^{24}$, —N(R$^{20}$)C(=O)N(R$^{23}$)N(R$^{21}$)R$^{22}$, —N(R$^{20}$)C(=O)N(R$^{23}$)N(R$^{21}$)S(=O)$_2$R$^{24}$, —N(R$^{23}$)C(=O)OR$^{20}$, —P(=O)OR$^{20}$, and —P(=O)(OR$^{19}$)OR$^{20}$;
- $R^4$ and $R^5$ are each independently selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl; or $R^4$ and $R^5$ together with the carbon atom to which they are attached, form an optionally substituted $C_3$-$C_6$cycloalkyl ring or an optionally substituted $C_2$-$C_7$heterocycloalkyl ring;
- $R^6$ is selected from the group consisting of hydrogen, halogen, optionally substituted $C_1$-$C_6$alkyl, optionally substituted $C_2$-$C_6$alkenyl, optionally substituted $C_2$-$C_6$alkynyl, and —C(=O)N(R$^{27}$)R$^{28}$;
- $R^7$ is selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl;
- $R^8$ is selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl);
- $R^9$ and $R^{10}$ together with the carbon atoms to which they are attached, form a phenyl ring substituted with (R$^{11}$)$_n$ and R$^{15}$; or $R^9$ and $R^{10}$ together with the carbon atoms to which they are attached, form a nitrogen containing 6-membered heteroaryl ring substituted with (R$^{11}$)$_n$ and R$^{15}$; or $R^9$ and $R^{10}$ together with the carbon atoms to which they are attached, form a 5-membered heteroaryl ring substituted with (R$^{11}$)$_p$, (R$^{12}$)$_q$, and R$^{15}$;
- each R$^{11}$ is independently selected from the group consisting of halogen, —CN, amino, alkylamino, $C_1$-$C_6$alkyl, $C_1$-$C_6$haloalkyl, $C_1$-$C_6$alkoxy, $C_1$-$C_6$haloalkoxy, $C_3$-$C_8$cycloalkyl, $C_2$-$C_9$heterocycloalkyl, aryl, heteroaryl, —C(=O)OR$^{12}$, —C(=O)N(R$^{13}$)R$^{14}$;
- each R$^{12}$ is independently selected from the group consisting of hydrogen and $C_1$-$C_6$alkyl;
- each R$^{13}$ and R$^{14}$ are each independently selected from the group consisting of hydrogen and $C_1$-$C_6$alkyl; or R$^{13}$ and R$^{14}$ together with the nitrogen atom to which they are attached, form an optionally substituted $C_2$-$C_9$heterocycloalkyl ring;
- R$^{15}$ is —OC(=J)OR$^{16a}$, —N(R$^{12}$)C(=J)OR$^{16a}$, —OC(=J)N(H)R$^{16a}$, —N(R$^{12}$)C(=J)N(H)R$^{16a}$, —OC(=J)N(H)(C$_2$-$C_6$alkyl)R$^{30}$, —N(R$^{12}$)C(=J)O(C$_2$-$C_6$alkyl)R$^{30}$, —N(R$^{12}$)C(=J)N(H)(C$_2$-C$_6$alkyl)R$^{30}$, —OC(=J)O(C$_2$-C$_6$alkyl)R$^{30}$, —C(=J)R$^{31}$, —OC(=J)R$^{31}$, —N(R$^{12}$)C(=J)R$^{31}$, —O(C$_2$-C$_6$alkyl)R$^{30}$, —N(R$^{12}$)(C$_2$-C$_6$alkyl)R$^{30}$, —OS(=O)$_v$R$^{31}$, —N(R$^{12}$)S(=O)$_v$R$^{31}$, —OS(=O)$_v$(C$_2$-C$_6$alkyl)R$^{30}$, or —N(R$^{12}$)S(=O)$_v$(C$_2$-C$_6$alkyl)R$^{30}$;

R$^{30}$ is R$^{16a}$, R$^{16b}$, or R$^{16c}$;
R$^{31}$ is R$^{16a}$ or R$^{16c}$;
J is O, S, or N(R$^{12}$);
R$^{16a}$ is

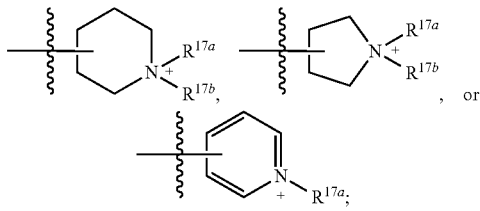

R$^{16b}$ is

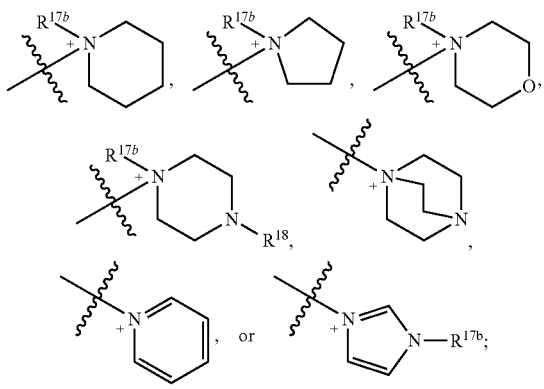

R$^{16c}$ is

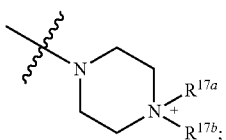

R$^{17a}$ is C$_1$-C$_6$alkyl;
R$^{17b}$ is C$_1$-C$_6$alkyl optionally substituted with phenyl, —C(=O)OH or —S(=O)$_2$OH;
R$^{18}$ is hydrogen, —OH, —(C$_0$-C$_6$alkyl)-C(=O)OH, or C$_1$-C$_6$alkyl;
n is 0, 1, or 2;
p is 0 or 1;
q is 0 or 1;
v is 1 or 2;
R$^{19}$, R$^{20}$, and R$^{23}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

R$^{21}$ and R$^{22}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl); or R$^{21}$ and R$^{22}$ together with the nitrogen atom to which they are attached, form an optionally substituted C$_2$-C$_9$heterocycloalkyl ring;

R$^{24}$ is selected from the group consisting of optionally substituted C$_1$-C$_6$alkyl, optionally substituted C$_2$-C$_6$alkenyl, optionally substituted C$_2$-C$_6$alkynyl, optionally substituted C$_3$-C$_5$ cycloalkyl, optionally substituted aryl optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl); and R$^{25}$ and R$^{26}$ are each independently selected from the group consisting of hydrogen, optionally substituted C$_1$-C$_6$alkyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

R$^{27}$ and R$^{28}$ are each independently selected from the group consisting of hydrogen, optionally substituted C$_1$-C$_6$alkyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl); or R$^{27}$ and R$^{28}$ together with the nitrogen atom to which they are attached, form an optionally substituted C$_2$-C$_9$heterocycloalkyl ring.

In some embodiments provided herein, the compound of Formula (I) has the structure of Formula (Ia), or a pharmaceutically acceptable salt or solvate thereof:

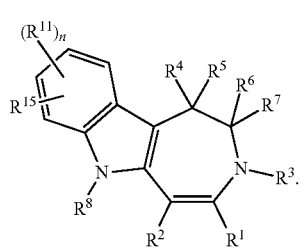

Formula (Ia)

In some embodiments provided herein, the compound of Formula (I) has the structure of Formula (Ib), or a pharmaceutically acceptable salt or solvate thereof:

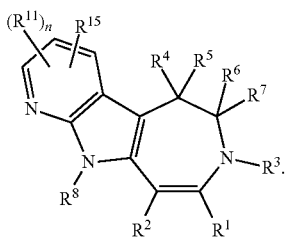

Formula (Ib)

In some embodiments provided herein, the compound of Formula (I) has the structure of Formula (Ic), or a pharmaceutically acceptable salt or solvate thereof:

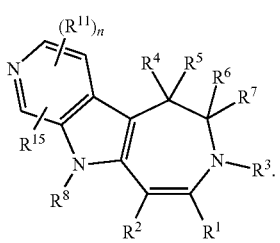

Formula (Ic)

In some embodiments provided herein, the compound of Formula (I) has the structure of Formula (Id), or a pharmaceutically acceptable salt or solvate thereof:

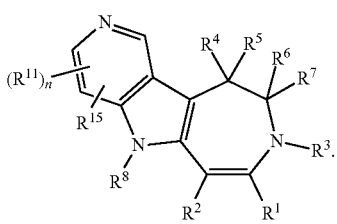

Formula (Id)

In some embodiments provided herein, the compound of Formula (I) has the structure of Formula (Ie), or a pharmaceutically acceptable salt or solvate thereof:

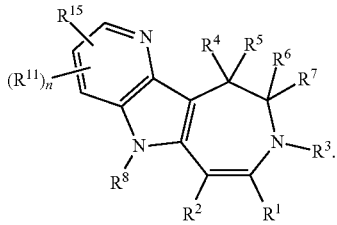

Formula (Ie)

In some embodiments provided herein, the compound of Formula (I) has the structure of Formula (If), or a pharmaceutically acceptable salt or solvate thereof:

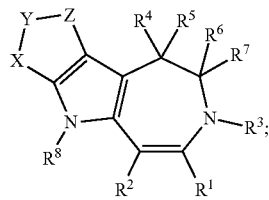

Formula (If)

wherein:
—X—Y—Z— is selected from

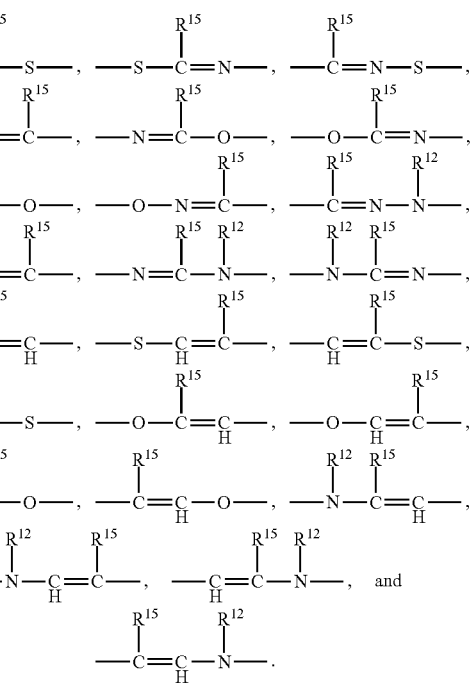

In another aspect provided herein is a compound of Formula (II), or a pharmaceutically acceptable salt or solvate thereof:

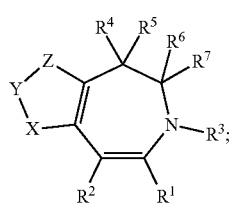

Formula (II)

wherein:
—X—Y—Z— is selected from

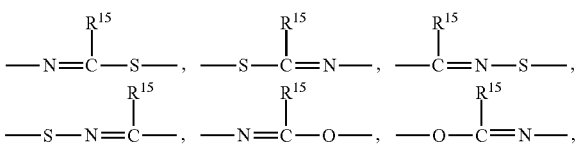

-continued

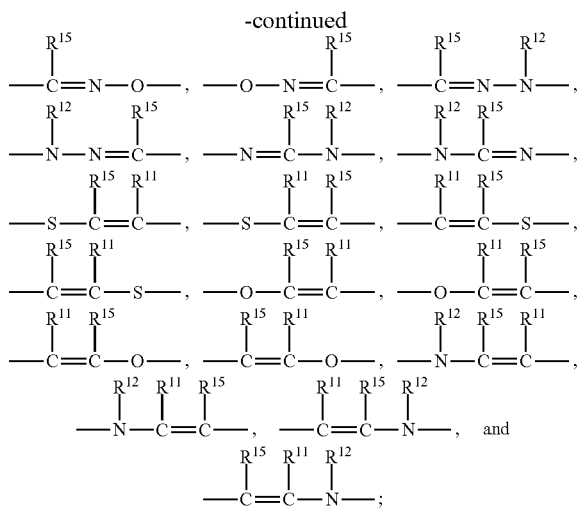

R$^1$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

R$^2$ is selected from the group consisting of —CN, —C(=O)OR$^{25}$, —C(=O)N(R$^{25}$)R$^{26}$,

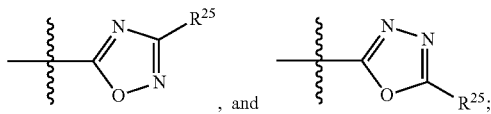

or R$^1$ and R$^2$ together with the carbon atoms to which they are attached, form an optionally substituted C$_2$-C$_9$heterocycloalkyl ring or an optionally substituted heteroaryl ring;

R$^3$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_{10}$cycloalkyl, optionally substituted aryl, optionally substituted —(C$_1$-C$_2$alkylene)-(aryl), optionally substituted heteroaryl, optionally substituted C$_2$-C$_9$heterocycloalkyl, optionally substituted —(C$_1$-C$_2$alkylene)-(heteroaryl), —C(=O)R$^{20}$, —C(=O)OR$^{20}$, —S(=O)$_2$R$^{20}$, —C(=O)N(R$^{21}$)R$^{22}$, —C(=O)N(R$^{21}$)S(=O)$_2$R$^{24}$, —C(=O)N(R$^{23}$)N(R$^{21}$)R$^{22}$, —C(=O)N(R$^{23}$)N(R$^{21}$)S(=O)$_2$R$^{24}$, —N(R$^{23}$)C(=O)R$^{20}$, —N(R$^{23}$)C(=O)N(R$^{21}$)R$^{22}$, —N(R$^{23}$)C(=O)N(R$^{21}$)S(=O)$_2$R$^{24}$, —N(R$^{20}$)C(=O)N(R$^{23}$)N(R$^{21}$)R$^{22}$, —N(R$^{20}$)C(=O)N(R$^{23}$)N(R$^{21}$)S(=O)$_2$R$^{24}$, —N(R$^{23}$)C(=O)OR$^{20}$, —P(=O)OR$^{20}$, and —P(=O)(OR$^{19}$)OR$^{20}$;

R$^4$ and R$^5$ are each independently selected from the group consisting of hydrogen, halogen, optionally substituted C$_1$-C$_6$alkyl, optionally substituted C$_1$-C$_6$alkoxy, optionally substituted C$_2$-C$_6$alkenyl, and optionally substituted C$_2$-C$_6$alkynyl; or R$^4$ and R$^5$ together with the carbon atom to which they are attached, form an optionally substituted C$_3$-C$_6$cycloalkyl ring or an optionally substituted C$_2$-C$_7$heterocycloalkyl ring;

R$^6$ is selected from the group consisting of hydrogen, halogen, optionally substituted C$_1$-C$_6$alkyl, optionally substituted C$_2$-C$_6$alkenyl, optionally substituted C$_2$-C$_6$alkynyl, and —C(=O)N(R$^{27}$)R$^{28}$;

R$^7$ is selected from the group consisting of hydrogen, halogen, optionally substituted C$_1$-C$_6$alkyl, optionally substituted C$_1$-C$_6$alkoxy, optionally substituted C$_2$-C$_6$alkenyl, and optionally substituted C$_2$-C$_6$alkynyl;

R$^{11}$ is selected from the group consisting of hydrogen, halogen, —CN, amino, alkylamino, C$_1$-C$_6$alkyl, C$_1$-C$_6$haloalkyl, C$_1$-C$_6$alkoxy, C$_1$-C$_6$haloalkoxy, C$_3$-C$_8$cycloalkyl, C$_2$-C$_9$heterocycloalkyl, aryl, heteroaryl, —C(=O)OR$^{12}$, —C(=O)N(R$^{13}$)R$^{14}$;

each R$^{12}$ is independently selected from the group consisting of hydrogen and C$_1$-C$_6$alkyl;

R$^{13}$ and R$^{14}$ are independently selected from the group consisting of hydrogen and C$_1$-C$_6$alkyl; or R$^{13}$ and R$^{14}$ together with the nitrogen atom to which they are attached, form an optionally substituted C$_2$-C$_9$heterocycloalkyl ring;

R$^{15}$ is —OC(=J)OR$^{16a}$, —N(R$^{12}$)C(=J)OR$^{16a}$, —OC(=J)N(H)R$^{16a}$, —N(R$^{12}$)C(=J)N(H)R$^{16a}$, —OC(=J)N(H)(C$_2$-C$_6$alkyl)R$^{30}$, —N(R$^{12}$)C(=J)O(C$_2$-C$_6$alkyl)R$^{30}$, —N(R$^{12}$)C(=J)N(H)(C$_2$-C$_6$alkyl)R$^{30}$, —OC(=J)O(C$_2$-C$_6$alkyl)R$^{30}$, —C(=J)R$^{31}$, —OC(=J)R$^{31}$, —N(R$^{12}$)C(=J)R$^{31}$, —O(C$_2$-C$_6$alkyl)R$^{30}$, —N(R$^{12}$)(C$_2$-C$_6$alkyl)R$^{30}$, —OS(=O)$_x$R$^{31}$, —N(R$^{12}$)S(=O)$_x$R$^{31}$, —OS(=O)$_x$(C$_2$-C$_6$alkyl)R$^{30}$, or —N(R$^{12}$)S(=O)$_x$(C$_2$-C$_6$alkyl)R$^{30}$;

R$^{30}$ is R$^{16a}$, R$^{16b}$, or R$^{16c}$;

R$^{31}$ is R$^{16a}$ or R$^{16c}$;

J is O, S, or N(R$^{12}$);

R$^{16a}$ is

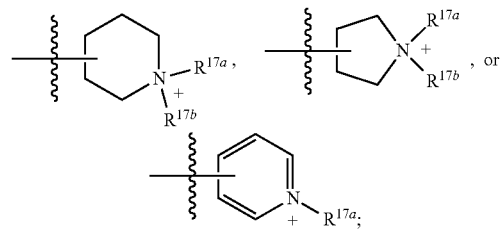

R$^{16b}$ is

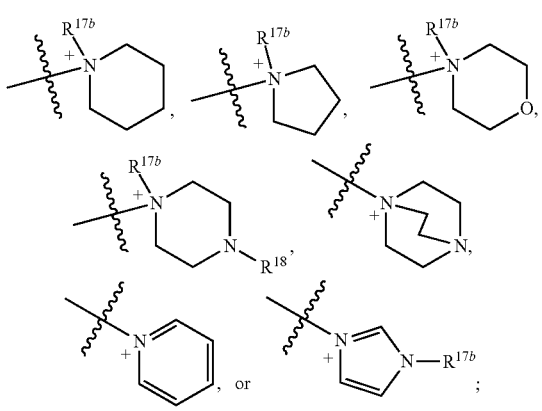

R$^{16c}$ is

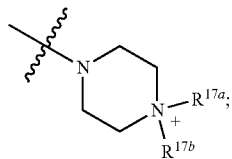

R$^{17a}$ is C$_1$-C$_6$alkyl;
R$^{17b}$ is C$_1$-C$_6$alkyl optionally substituted with phenyl, —C(=O)OH or —S(=O)$_2$OH;
R$^{18}$ is hydrogen, —OH, —(C$_0$-C$_6$alkyl)-C(=O)OH, or C$_1$-C$_6$alkyl;
v is 1 or 2;
R$^{19}$, R$^{20}$, and R$^{23}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);
R$^{21}$ and R$^{22}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl); or R$^{21}$ and R$^{22}$ together with the nitrogen atom to which they are attached, form an optionally substituted C$_2$-C$_9$heterocycloalkyl ring;
R$^{24}$ is selected from the group consisting of optionally substituted C$_1$-C$_6$alkyl, optionally substituted C$_2$-C$_6$alkenyl, optionally substituted C$_2$-C$_6$alkynyl, optionally substituted C$_3$-C$_5$ cycloalkyl, optionally substituted aryl optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl); and
R$^{25}$ and R$^{26}$ are each independently selected from the group consisting of hydrogen, optionally substituted C$_1$-C$_6$alkyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);
R$^{27}$ and R$^{28}$ are each independently selected from the group consisting of hydrogen, optionally substituted C$_1$-C$_6$alkyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl); or R$^{27}$ and R$^{28}$ together with the nitrogen atom to which they are attached, form an optionally substituted C$_2$-C$_9$heterocycloalkyl ring.

In some embodiments provided herein, the compound of Formula (II) has the structure of Formula (IIa), or a pharmaceutically acceptable salt or solvate thereof:

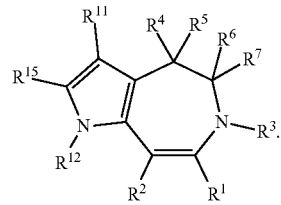

Formula (IIa)

In some embodiments provided herein, the compound of Formula (II) has the structure of Formula (IIb), or a pharmaceutically acceptable salt or solvate thereof:

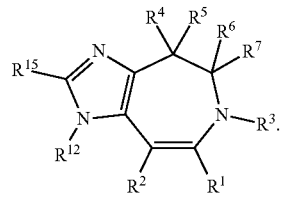

Formula (IIb)

In some embodiments provided herein, the compound of Formula (II) has the structure of Formula (IIc), or a pharmaceutically acceptable salt or solvate thereof:

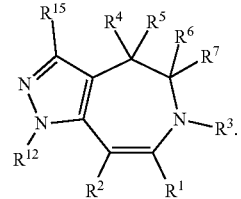

Formula (IIc)

In some embodiments is a compound of Formula (I), (Ia), (Ib), (Ic), (Id), (Ie), (If), (II), (IIa), (IIb), or (IIc), wherein R$^{15}$ is —OC(=J)N(H)(C$_2$-C$_6$alkyl)R$^{30}$, —N(R$^{12}$)C(=J)O(C$_2$-C$_6$alkyl)R$^{30}$, —N(R$^{12}$)C(=J)N(H)(C$_2$-C$_6$alkyl)R$^{30}$, —OC(=J)O(C$_2$-C$_6$alkyl)R$^{30}$, —O(C$_2$-C$_6$alkyl)R$^{30}$, or —N(R$^{12}$)(C$_2$-C$_6$alkyl)R$^{30}$. In some embodiments is a compound of Formula (I), (Ia), (Ib), (Ic), (Id), (Ie), (If), (II), (IIa), (IIb), or (IIc), wherein J is O. In some embodiments is a compound of Formula (I), (Ia), (Ib), (Ic), (Id), (Ie), (If), (II), (IIa), (IIb), or (IIc), wherein R$^3$ is —C(O)N(R$^{21}$)R$^{22}$. In a further embodiment is a compound of Formula (I), (Ia), (Ib), (Ic), (Id), (Ie), (If), (II), (IIa), (IIb), or (IIc), wherein R$^3$ is —C(O)N(R$^{21}$)R$^{22}$, and R$^{21}$ is hydrogen and R$^{22}$ is optionally substituted aryl. In some embodiments is a compound of Formula (I), (Ia), (Ib), (Ic), (Id), (Ie), (If), (II), (IIa), (IIb), or (IIc), wherein R$^3$ is —C(O)R$^{20}$. In a further embodiment is a compound of Formula (I), (Ia), (Ib), (Ic), (Id), (Ie), (If), (II), (IIa), (IIb), or (IIc), wherein R$^3$ is —C(O)R$^{20}$, and R$^{20}$ is optionally substituted aryl. In some embodiments is a compound of Formula (I), (Ia), (Ib), (Ic), (Id), (Ie), (If), (II), (IIa), (IIb), or (IIc), wherein R$^3$ is —S(O)$_2$R$^{20}$. In a further embodiment is a compound of Formula (I), (Ia), (Ib), (Ic), (Id), (Ie), (If), (II), (IIa), (IIb), or (IIc), wherein R$^3$ is —S(O)$_2$R$^{20}$, and R$^{20}$ is optionally substituted aryl.

In another aspect provided herein is a compound of Formula (III), or a pharmaceutically acceptable salt or solvate thereof:

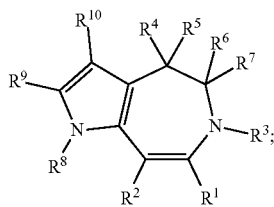

Formula (III)

wherein:
R¹ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

R² is selected from the group consisting of —CN, —C(=O)OR²⁵, —C(=O)N(R²⁵)R²⁶,

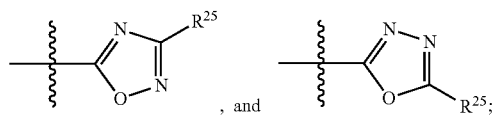

, and or R¹ and R² together with the carbon atoms to which they are attached, form an optionally substituted $C_2$-$C_9$heterocycloalkyl ring or an optionally substituted heteroaryl ring;

R³ is —C(=O)R²⁰ or —S(=O)₂R²⁰;

R⁴ and R⁵ are each independently selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl; or R⁴ and R⁵ together with the carbon atom to which they are attached, form an optionally substituted $C_3$-$C_6$cycloalkyl ring or an optionally substituted $C_2$-$C_7$heterocycloalkyl ring;

R⁶ is selected from the group consisting of hydrogen, halogen, optionally substituted $C_1$-$C_6$alkyl, optionally substituted $C_2$-$C_6$alkenyl, optionally substituted $C_2$-$C_6$alkynyl, and —C(=O)N(R²⁷)R²⁸;

R⁷ is selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl;

R⁸ is selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl);

R⁹ and R¹⁰ together with the carbon atoms to which they are attached, form a phenyl ring substituted with ($R^{11}$)ₙ; or R⁹ and R¹⁰ together with the carbon atoms to which they are attached, form a nitrogen containing 6-membered heteroaryl ring substituted with ($R^{11}$)ₙ; or R⁹ and R¹⁰ together with the carbon atoms to which they are attached, form a 5-membered heteroaryl ring substituted with ($R^{39}$)ₚ and ($R^{12}$)_q;

each R¹¹ is independently selected from the group consisting of halogen, —CN, amino, alkylamino, $C_1$-$C_6$alkyl, $C_1$-$C_6$haloalkyl, $C_1$-$C_6$alkoxy, $C_1$-$C_6$haloalkoxy, $C_3$-$C_8$cycloalkyl, $C_2$-$C_9$heterocycloalkyl, aryl, heteroaryl, —C(=O)OR¹², —C(=O)N(R¹³)R¹⁴;

each R¹² is independently selected from the group consisting of hydrogen and $C_1$-$C_6$alkyl;

each R¹³ and R¹⁴ are each independently selected from the group consisting of hydrogen and $C_1$-$C_6$alkyl; or R¹³ and R¹⁴ together with the nitrogen atom to which they are attached, form an optionally substituted $C_2$-$C_9$heterocycloalkyl ring;

each R³⁹ is independently selected from the group consisting of hydrogen, halogen, —CN, amino, alkylamino, $C_1$-$C_6$alkyl, $C_1$-$C_6$haloalkyl, $C_1$-$C_6$alkoxy, $C_1$-$C_6$haloalkoxy, $C_3$-$C_8$cycloalkyl, $C_2$-$C_9$heterocycloalkyl, aryl, heteroaryl, —C(=O)OR¹², —C(=O)N(R¹³)R¹⁴;

n is 0, 1, 2, or 3;
p is 0, 1 or 2;
q is 0 or 1;
R²⁰ is selected from the group consisting of —R³⁴R³⁵ or —R³¹;

R³⁴ is selected from the group consisting of optionally substituted $C_1$-$C_6$alkyl, optionally substituted $C_3$-$C_{10}$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl);

R³⁵ is —($C_1$-$C_6$alkyl)-R³⁰, —O($C_2$-$C_6$alkyl)-R³⁰, or —N(R¹²)($C_2$-$C_6$alkyl)-R³⁰;

R³⁰ is $R^{36a}$, $R^{36b}$, or $R^{36c}$;
R³¹ is $R^{36a}$ or $R^{36c}$;
$R^{36a}$ is

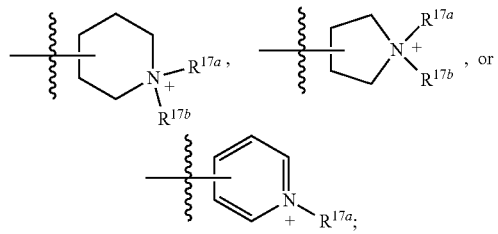

$R^{36b}$ is

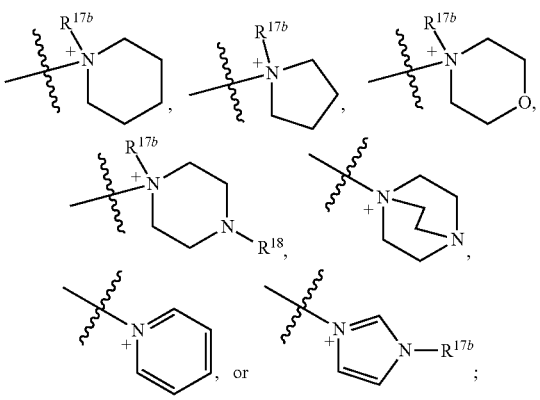

$R^{36c}$ is

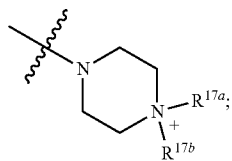

$R^{17a}$ is $C_1$-$C_6$alkyl;
$R^{17b}$ is $C_1$-$C_6$alkyl optionally substituted with phenyl, —C(=O)OH or —S(=O)$_2$OH;
$R^{18}$ is hydrogen, —OH, —($C_0$-$C_6$alkyl)-C(=O)OH, or $C_1$-$C_6$alkyl;
$R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); and
$R^{27}$ and $R^{28}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{27}$ and $R^{28}$ together with the nitrogen atom to which they are attached, form an optionally substituted $C_2$-$C_9$heterocycloalkyl ring.

In some embodiments provided herein, the compound of Formula (III) has the structure of Formula (IIIa), or a pharmaceutically acceptable salt or solvate thereof:

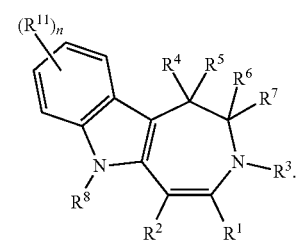

Formula (IIIa)

In some embodiments provided herein, the compound of Formula (III) has the structure of Formula (IIIb), or a pharmaceutically acceptable salt or solvate thereof:

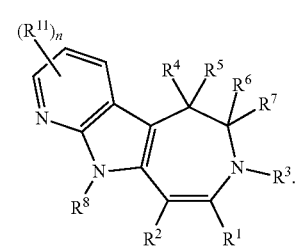

Formula (IIIb)

In some embodiments provided herein, the compound of Formula (III) has the structure of Formula (IIIc), or a pharmaceutically acceptable salt or solvate thereof:

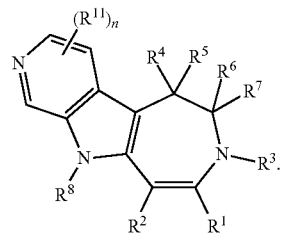

Formula (IIIc)

In some embodiments provided herein, the compound of Formula (II) has the structure of Formula (IId), or a pharmaceutically acceptable salt or solvate thereof:

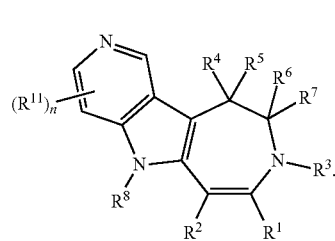

Formula (IIId)

In some embodiments provided herein, the compound of Formula (III) has the structure of Formula (IIIe), or a pharmaceutically acceptable salt or solvate thereof:

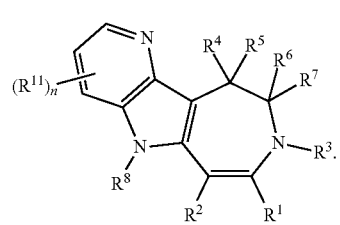

Formula (IIIe)

In some embodiments is a compound of Formula (III), (IIIa), (IIIb), (IIIc), (IIId), or (IIIe), wherein n is 0. In some embodiments is a compound of Formula (III), (IIIa), (IIIb), (IIIc), (IIId), or (IIIe), wherein n is 1. In some embodiments is a compound of Formula (III), (IIIa), (IIIb), (IIIc), (IIId), or (IIIe), wherein n is 1 and $R^{11}$ is $C_1$-$C_6$alkyl. In some embodiments is a compound of Formula (III), (IIIa), (IIIb), (IIIc), (IIId), or (IIIe), wherein n is 1 and $R^{11}$ is $C_1$-$C_6$haloalkyl.

In some embodiments provided herein, the compound of Formula (III) has the structure of Formula (IIIf), or a pharmaceutically acceptable salt or solvate thereof:

Formula (IIIf)

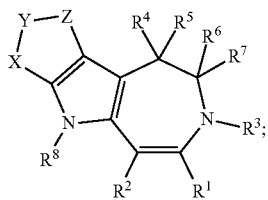

wherein:
—X—Y—Z— is selected from

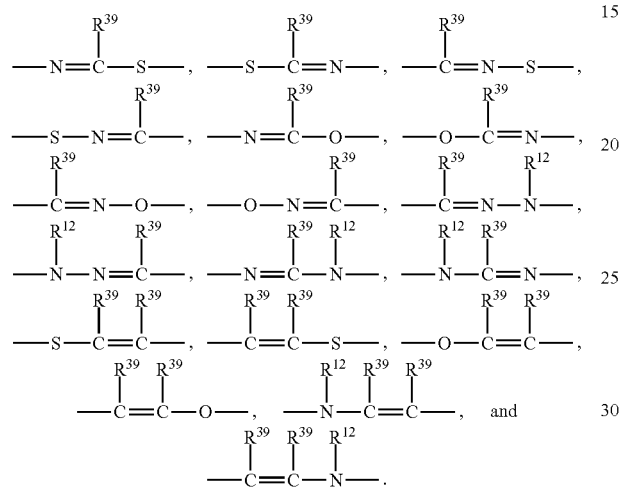

In some embodiments is a compound of Formula (III), (IIIa), (IIIb), (IIIc), (IIId), (IIIe), or (IIIf), wherein $R^8$ is hydrogen.

In another aspect provided herein is a compound of Formula (IV), or a pharmaceutically acceptable salt or solvate thereof:

Formula (IV)

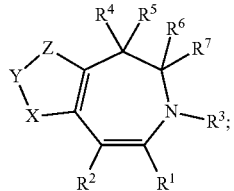

wherein:
—X—Y—Z— is selected from

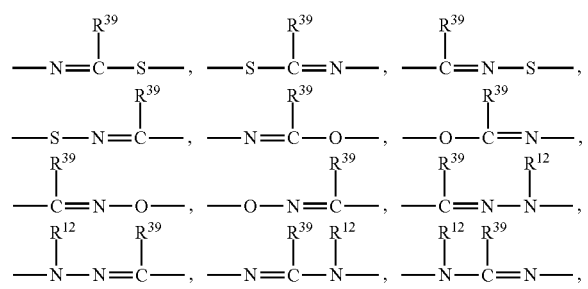

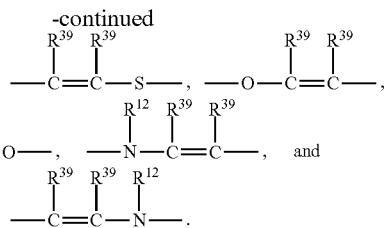

$R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R^2$ is selected from the group consisting of —CN, —C(=O)O$R^2$, —C(=O)N($R^{25}$)$R^{26}$,

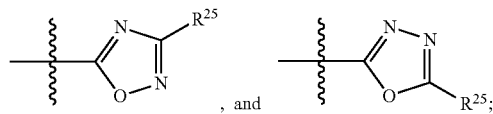, and or $R^1$ and $R^2$ together with the carbon atoms to which they are attached, form an optionally substituted $C_2$-$C_9$heterocycloalkyl ring or an optionally substituted heteroaryl ring;

$R^3$ is —C(=O)$R^{20}$ or —S(=O)$_2$$R^{20}$;

$R^4$ and $R^5$ are each independently selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl; or $R^4$ and $R^5$ together with the carbon atom to which they are attached, form an optionally substituted $C_3$-$C_6$cycloalkyl ring or an optionally substituted $C_2$-$C_7$heterocycloalkyl ring;

$R^6$ is selected from the group consisting of hydrogen, halogen, optionally substituted $C_1$-$C_6$alkyl, optionally substituted $C_2$-$C_6$alkenyl, optionally substituted $C_2$-$C_6$alkynyl, and —C(=O)N($R^{27}$)$R^{28}$;

$R^7$ is selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl;

each $R^{12}$ is independently selected from the group consisting of hydrogen and $C_1$-$C_6$alkyl;

each $R^{13}$ and $R^{14}$ are each independently selected from the group consisting of hydrogen and $C_1$-$C_6$alkyl; or $R^{13}$ and $R^{14}$ together with the nitrogen atom to which they are attached, form an optionally substituted $C_2$-$C_9$heterocycloalkyl ring;

each $R^{39}$ is independently selected from the group consisting of hydrogen, halogen, —CN, amino, alkylamino, $C_1$-$C_6$alkyl, $C_1$-$C_6$haloalkyl, $C_1$-$C_6$alkoxy, $C_1$-$C_6$haloalkoxy, $C_3$-$C_8$cycloalkyl, $C_2$-$C_9$heterocycloalkyl, aryl, heteroaryl, —C(=O)O$R^{12}$, and —C(=O)N($R^{13}$)$R^{14}$;

$R^{20}$ is selected from the group consisting of —$R^{34}R^{35}$ or —$R^{31}$;

$R^{34}$ is selected from the group consisting of optionally substituted $C_1$-$C_6$alkyl, optionally substituted $C_3$-$C_{10}$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl);

$R^{35}$ is —($C_1$-$C_6$alkyl)-$R^{30}$, —O($C_2$-$C_6$alkyl)-$R^{30}$, or —N($R^{12}$)($C_2$-$C_6$alkyl)-$R^{30}$;

$R^{30}$ is $R^{36a}$, $R^{36b}$, or $R^{36c}$;

$R^{31}$ is $R^{36a}$ or $R^{36c}$;

$R^{36a}$ is

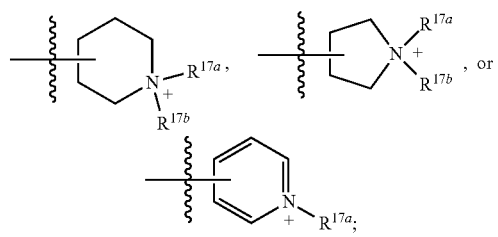

$R^{36b}$ is

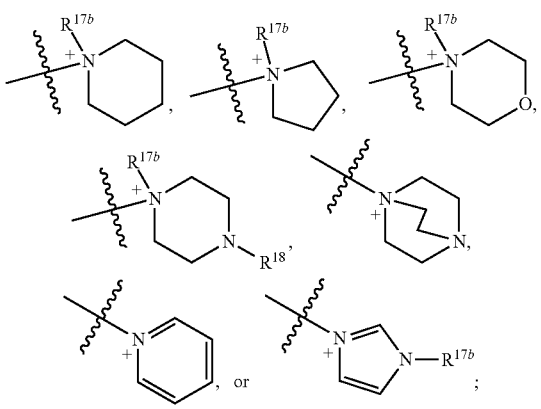

$R^{36c}$ is

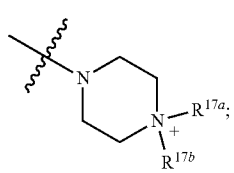

$R^{17a}$ is $C_1$-$C_6$alkyl;

$R^{17b}$ is $C_1$-$C_6$alkyl optionally substituted with phenyl, —C(=O)OH or —S(=O)$_2$OH;

$R^{18}$ is hydrogen, —OH, —($C_0$-$C_6$alkyl)-C(=O)OH, or $C_1$-$C_6$alkyl;

$R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); and $R^{27}$ and $R^{28}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{27}$ and $R^{28}$ together with the nitrogen atom to which they are attached, form an optionally substituted $C_2$-$C_9$heterocycloalkyl ring.

In some embodiments provided herein, the compound of Formula (IV) has the structure of Formula (IVa), or a pharmaceutically acceptable salt or solvate thereof:

Formula (IVa)

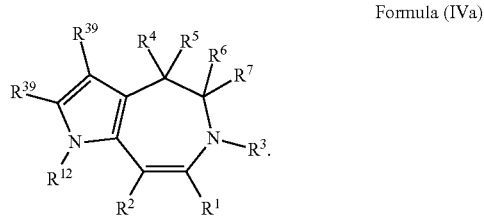

In some embodiments provided herein, the compound of Formula (IV) has the structure of Formula (IVb), or a pharmaceutically acceptable salt or solvate thereof:

Formula (IVb)

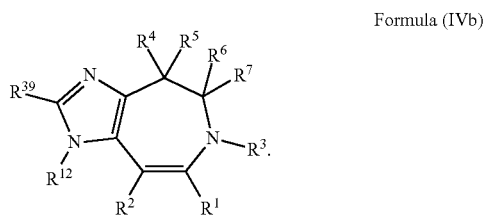

In some embodiments provided herein, the compound of Formula (IV) has the structure of Formula (IVc), or a pharmaceutically acceptable salt or solvate thereof:

Formula (IVc)

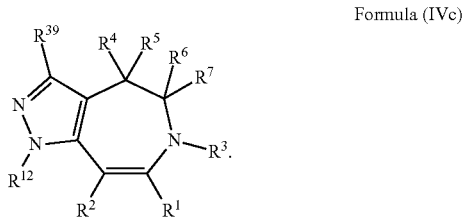

In some embodiments is a compound of Formula (III), (IIIa), (IIIb), (IIIc), (IIId), (IIIe), (IIIf), (IV), (IVa), (IVb), or (IVc), wherein $R^3$ is —C(=O)$R^{20}$. In some embodiments is a compound of Formula (III), (IIIa), (IIIb), (IIIc), (IIId), (IIIe), (IIIf), (IV), (IVa), (IVb), or (IVc), wherein $R^3$ is —C(=O)$R^{20}$ and $R^{20}$ is —$R^{34}R^{35}$. In some embodiments is a compound of Formula (III), (IIIa), (IIIb), (IIIc), (IIId), (IIIe), (IIIf), (IV), (IVa), (IVb), or (IVc), wherein $R^3$ is —C(=O)$R^{20}$, $R^{20}$ is —$R^{34}R^{35}$, and $R^{34}$ is selected from the group consisting of optionally substituted $C_1$-$C_6$alkyl, optionally substituted $C_3$-$C_{10}$cycloalkyl, and optionally substituted aryl. In some embodiments is a compound of Formula (III), (IIIa), (IIIb), (IIIc), (IIId), (IIIe), (IIIf), (IV), (IVa), (IVb), or (IVc), wherein $R^3$ is —C(=O)$R^{20}$, $R^{20}$ is —$R^{34}R^{35}$, $R^{34}$ is optionally substituted aryl, and $R^{35}$ is —O($C_2$-$C_6$alkyl)-$R^{30}$. In some embodiments is a compound of Formula (III), (IIIa), (IIIb), (IIIc), (IIId), (IIIe), (IIIf), (IV), (IVa), (IVb), or (IVc), wherein $R^3$ is —C(=O)$R^{20}$, $R^{20}$ is —$R^{34}R^{35}$, $R^{34}$ is optionally substituted aryl, $R^{35}$ is —O($C_2$-$C_6$alkyl)-$R^{30}$, and $R^{30}$ is $R^{36b}$ or $R^{36c}$. In some embodiments is a compound of Formula (III), (IIIa), (IIIb), (IIIc), (IIId), (IIIe), (IIIf), (IV), (IVa), (IVb), or (IVc), wherein $R^3$ is —C(=O)$R^{20}$ and $R^{20}$ is —$R^{31}$. In some embodiments is a compound of Formula (III), (IIIa), (IIIb), (IIIc), (IIId), (IIIe), (IIIf), (IV), (IVa), (IVb), or (IVc), wherein $R^3$ is —C(=O)$R^{20}$, $R^{20}$ is —$R^{31}$, and $R^{31}$ is $R^{36a}$. In some embodiments is a compound of Formula (III), (IIIa), (IIIb), (IIIc), (IIId), (IIIe), (IIIf), (IV), (IVa), (IVb), or (IVc), wherein $R^3$ is —C(=O)$R^{20}$, $R^{20}$ is —$R^{31}$, and $R^{31}$ is $R^{36c}$. In some embodiments is a compound of Formula (III), (IIIa), (IIIb), (IIIc), (IIId), (IIIe), (IIIf), (IV), (IVa), (IVb), or (IVc), wherein $R^{39}$ is selected from the group consisting of hydrogen, $C_1$-$C_6$alkyl, and $C_1$-$C_6$haloalkyl.

In some embodiments is a compound of Formula (I), (Ia), (Ib), (Ic), (Id), (Ie), (If), (II), (IIa), (IIb), (IIc), (IV), (IVa), (IVb), or (IVc), wherein $R^{12}$ is hydrogen.

In some embodiments is a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), wherein $R^6$ and $R^7$ are hydrogen. In some embodiments is a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), wherein $R^4$ and $R^5$ are each independently optionally substituted $C_1$-$C_6$alkyl. In some embodiments is a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), wherein $R^4$ and $R^5$ are methyl. In another embodiment is a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), wherein $R^2$ is —C(O)O$R^{25}$. In another embodiment is a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), wherein $R^2$ is —C(O)O$R^{25}$ and $R^{25}$ is methyl. In another embodiment is a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), wherein $R^2$ is —C(O)O$R^{25}$ and $R^{25}$ is ethyl. In another embodiment is a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), wherein $R^2$ is —C(O)O$R^{25}$ and $R^{25}$ is isopropyl. In another embodiment is a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), wherein $R^2$ is —C(O)N($R^{25}$)$R^{26}$. In a further embodiment is a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), wherein $R^1$ is hydrogen. In another embodiment is a compound of Formula (I), (Ia), (Ib), (Ic), (Id), (Ie), (If), (II), (IIA), (IIb), (IIc), (III), (IIIa), (IIIb), (IIIc), (IIId), (IIIe), (IIIf), (IV), (IVa), (IVb), or (IVc), wherein $R^1$ is optionally substituted $C_1$-$C_6$alkyl. In another embodiment is a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), wherein $R^1$ is methyl.

Any combination of the groups described above or below for the various variables is contemplated herein. Throughout the specification, groups and substituents thereof are chosen by one skilled in the field to provide stable moieties and compounds.

In another aspect, provided herein is a pharmaceutical composition comprising a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof, and a pharmaceutically acceptable diluent, excipient or binder. In one embodiment, the pharmaceutical composition comprising the compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof, is formulated for a route of administration selected from oral administration, parenteral administration, buccal administration, nasal administration, topical administration, or rectal administration.

In another aspect is a method of treating a disease, disorder or condition in a mammal that would benefit from FXR modulation comprising administering to the mammal a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof.

In a further embodiment is a method of treating a disease, disorder or condition in a mammal that would benefit from FXR modulation comprising administering to the mammal a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof; wherein the disease, disorder or condition in a mammal is nonalcoholic steatohepatitis (NASH), hyperlipidemia, hypercholesterolemia, hypertriglyceridemia, dyslipidemia, lipodystrophy, atherosclerosis, atherosclerotic disease, atherosclerotic disease events, atherosclerotic cardiovascular disease, Syndrome X, diabetes mellitus, type II diabetes, insulin insensitivity, hyperglycemia, cholestasis or obesity. In another embodiment is the use of a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) in the manufacture of a medicament for the treatment of a disease, disorder, or condition that would benefit from FXR modulation. In another embodiment is the use of a FXR modulator in the manufacture of a medicament for use in the treatment of a disease, disorder or condition in a mammal, wherein the disease, disorder or condition in a mammal is nonalcoholic steatohepatitis (NASH), hyperlipidemia, hypercholesterolemia, hypertriglyceridemia, dyslipidemia, lipodystrophy, atherosclerosis, atherosclerotic disease, atherosclerotic disease events, atherosclerotic cardiovascular disease, Syndrome X, diabetes mellitus, type II diabetes, insulin insensitivity, hyperglycemia, cholestasis or obesity.

In another aspect is a method of modulating FXR activity comprising contacting FXR, or portion thereof, with a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
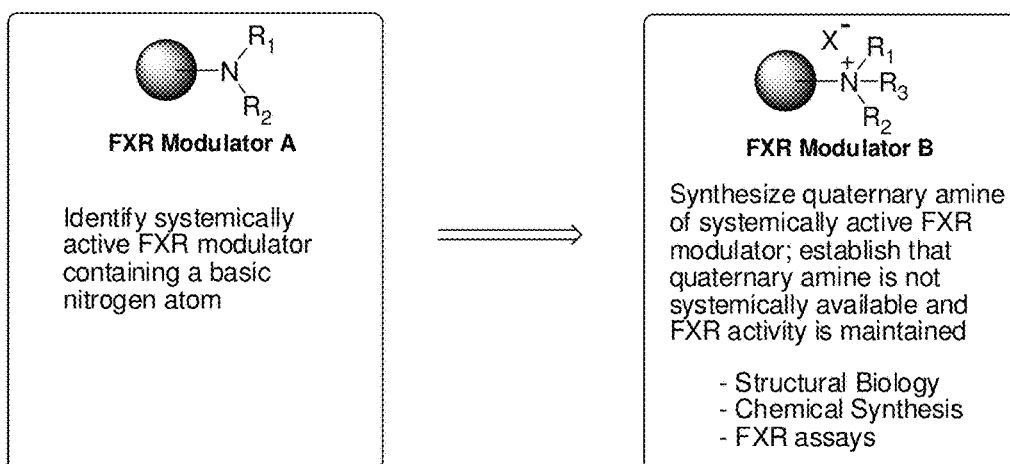
FIG. 1 illustrates Scheme A which depicts a general procedure for the identification of quaternary amine FXR modulators.

The Farnesoid X receptor (FXR; also referred to as NR1H4; nuclear receptor nomenclature committee 1999) is a member of the steroid and thyroid hormone nuclear receptor superfamily of ligand regulated transcription factors. FXR is highly expressed in the liver, kidney, intestines and the adrenals and at lower levels in the vasculature (Forman et al., Cell 1995, 81(5):687-93). Bile acids, the end-products of cholesterol catabolism, bind directly to the ligand binding pocket of FXR and act as agonists to increase the receptor's ability to activate transcription (Makishima et al., Science 1999, 284(5418):1362-5 1999; Mi et al., Mol Cell 2003, 11(4):1093-100; Parks et al., Science 1999, 284(5418):1365-8; Wang et al., Mol Cell 1999, 3(5):543-53). In response to bile acid binding FXR regulates a network of genes that control the synthesis, transport, and catabolism of bile acids, but also triglycerides and cholesterol (Chawla et al., Cell 2000, 103(1):1-4; Repa and Mangelsdorf, Annu Rev Cell Dev Biol 2000, 16:459-81). Thus FXR functions as a regulator of lipid metabolism by modifying gene expression in response to quantitative changes in the metabolism and breakdown of cholesterol. In support of this conclusion, studies in humans and in animals have demonstrated that modifying bile acid levels can have profound effects on plasma triglyceride and cholesterol levels (Angelin et al., J Lipid Res 1978, 19(8): 1017-24; Bateson et al., Br J Clin Pharmacol 1978, 5(3):249-54; Iser and Sali, Drugs 1981, 21(2):90-119; Kuroki et al., Lipids 1999, 34(8):817-23).

Metabolic disease including obesity, diabetes, hypertension, and cardiovascular disease, are diseases driven by both mulitfactorial genetics (thrifty genotypes) as well as lifestyle habits, and are now reaching epidemic proportions in developed nations. It is believed that increasingly high caloric diets combined with sedentary life styles are major contributors to the growing incidence of these diseases. Importantly hyperlipidemia is associated with many types of metabolic disease, and statistics from the American Heart Association indicate that approximately half of the adult population in the United States has plasma cholesterol levels that put individuals at risk for the development of cardiovascular disease (American Heart Association, Heart disease and stroke statistics—2005 update; 2005:1-59). Furthermore, the Third Report of the National Cholesterol Education Program Expert Panel on Detection, Evaluation, and Treatment of High Blood Cholesterol in Adults (Adult Treatment Panel III; ATPIII, National Cholesterol Education Program 2001) has identified elevated triglyceride levels as an independent risk factor for the development of cardiovascular disease. Approximately one third of the adult population in the United States that have elevated cholesterol levels also have increased triglycerides. The elevation in plasma triglycerides has now been recognized as an early and dominant dyslipidemic symptom in patients with obesity, metabolic syndrome and diabetes and has been suggested to play a causative role in the development of insulin resistance and type II diabetes (Hegarty et al., Acta Physiol Scand 2003; 178(4):373-83; Shulman, J Clin Invest 2000; 106(2):171-6).

Current standard of care for hyperlipidemia focuses on lowering low density lipoprotein cholesterol (LDL) using the statin class of hydroxymethy-glutaryl-CoA reductase inhibitors (National Cholesterol Education Program 2001). However, even after statin therapy a significant number of patients still exhibit elevated levels of plasma triglycerides and triglyceride-rich lipoproteins including very low density lipoproteins (VLDL) and intermediate density lipoproteins (IDL) (Friday, Exp Biol Med (Maywood) 2003, 228(7):769-78; Quilliam et al., J Manag Care Pharm 2004, 10(3):244-50). To treat this population of patients with concurrent high plasma triglyceride levels the ATPIII has identified lowering of triglyceride-rich cholesterol fractions (VLDL+IDL) as a secondary target of drug therapy (National Cholesterol Education Program 2001). Unfortunately treatment of such patients with fibrates, an approved class of triglyceride lowering drugs, has potential adverse side effects, including the possibility of increased LDL cholesterol as well as carrying the risk of fatal rhabdomyolysis, so that combination therapy must proceed cautiously (National Cholesterol Education Program 2001). Similarly nicotinic acid, a second approved triglyceride lowering agent, is contraindicated in patients with insulin resistance and type II diabetes (Capuzzi et al., Curr Atheroscler Rep 2000, 2(1):64-71). Taken together these observations highlight the need for an effective therapeutic agent for the lowering of triglycerides and non-HDL cholesterol in patients with cardiovascular disease, diabetes, and metabolic syndrome.

The maintenance of lipid homeostasis requires coordinate control of cholesterol and triglyceride synthesis, transport, up-take, and excretion. Interestingly, studies in human and in animal models have uncovered a link between bile acids, the metabolic end-product of cholesterol metabolism, and lipid homeostasis. Clinical studies in the late 1970s exploring the effect of bile acids on cholesterol gallstones demonstrated that treatment with chenodeoxycholic acid (CDCA) reduces plasma triglyceride levels (Bateson et al., Br J Clin Pharmacol 1978, 5(3):249-54; Iser and Sali, Drugs 1981, 21(2): 90-119). In contrast, treatment with bile acid sequestrants, which deplete intestinal bile acids, increase triglycerides (Angelin et al., J Lipid Res 1978; 19(8):1017-24). Importantly the bile acid-dependent decrease in triglycerides is mediated, at least in part, through a reduction in the production of VLDL (Hirokane et al., J Biol Chem 2004, 279(44):45685-92; Post et al., Arterioscler Thromb Vasc Biol 2004, 24(4):768-74; Sirvent et al., FEBS Lett 2004, 566(1-3): 173-7; Kang and Davis, Biochim Biophys Acta 2000, 1529(1-3):223-30). While bile acids are known to mediate the absorption of cholesterol and fat in the intestine the mechanistic basis for the connection between bile acids and lipid levels remained unclear until the recent characterization of FXR.

The FXR was originally cloned and classified as an orphan member of the nuclear hormone receptor superfamily based upon DNA sequence homology. Initial studies identified farnesol as a ligand for FXR (Forman et al., Cell 1995, 81(5):687-93), however, subsequent analysis demonstrated that bile acids bind directly to the ligand binding domain of FXR and function as activators of the receptor's transcriptional activity. The binding affinities of bile acids for FXR is near the concentration that these compounds reach in animals (µM) lending support to the idea that bile acids function as endogenous ligands in vivo (Makishima et al., Science 1999, 284(5418):1362-5 1999; Mi et al., Mol Cell 2003, 11(4):1093-100; Parks et al., Science 1999, 284(5418):1365-8; Wang et al., Mol Cell 1999, 3(5):543-53). Activation of FXR upon bile acid binding leads to transcriptional down-regulation of cholesterol 7α-hydroxylase (CYP7A1), the rate limiting enzyme in the conversion of cholesterol to bile acids. Inhibition of CYP7A1 by bile acids occurs via FXR-dependent induction of the small heterodimeric partner (SHP; also referred to as NR0B2, Nuclear Receptor Nomenclature Committee 1999), a transcriptional repressor. Binding sites for FXR have been identified in the SHP promoter indicating that this gene is a direct target of FXR (Lu et al., Mol Cell 2000, 6(3):507-15; Goodwin et al., Mol Cell 2000, 6(3):517-26). Thus bile acid-dependent repression of CYP7A1 is indirect and results from a transcriptional cascade initiated by FXR. A similar SHP-dependent mechanism has been described for the bile acid repression of another gene involved in bile acid synthesis, CYP8B1 (sterol 12α hydroxylase; Yang et al., Biochim Biophys Acta 2002, 1583(1):63-73), and for the sodium/taurocholate cotransporter peptide (NTCP) which is one of two major transporters responsible for bile acid up-take by the liver (Denson et al., Gastroenterology 2001; 121(1):140-7). In contrast the genes encoding the bile salt export pump (BSEP) and the multidrug resistance protein 2 (MDR2) are directly induced by FXR, once again via binding sites in their respective promoter regions (Ananthanarayanan et al., J Biol Chem 2001, 276(31):28857-65; Huang et al., J Biol Chem 2003, 278(51):51085-90; Liu et al., J Clin Invest 2003, 112(11):1678-87). These two transporters are required for the transfer of bile acids (BSEP) and phospholipids (MDR2) out of the hepatocytes into the biliary system. This pattern of FXR-dependent gene expression defines a classic feedback loop where high levels of bile acids inhibit new bile acid synthesis and bile acid uptake while simultaneously promoting their own clearance.

The regulation of bile acid synthesis and transport by FXR has important implications for cholesterol metabolism. Repression of CYP7A1 and CYP8B1 impacts the bile acid synthetic pathway at two important points. First, inhibition of CYP7A1, the rate limiting enzyme, can decrease synthesis and reduce the size of the bile acid pool. Second, inhibition of CYP8B1 alters bile acid composition by favoring the production of more hydrophilic bile acids such as CDCA (muricholic acid/MCA in mice) (Russell, Annu Rev Biochem 2003, 72:137-74). Importantly, studies in mice have demonstrated that the more hydrophilic bile acids are less efficient at promoting intestinal cholesterol absorption (Wang et al., Am J Physiol Gastrointest Liver Physiol 2003, 285(3):G494-502).

Although regulating bile acid synthesis may contribute to the FXR-dependent effects on lipid metabolism, gene expression analysis indicates that FXR also directly influences triglyceride synthesis and VLDL production. FXR agonists induce the genes encoding fibroblast growth factor 19 (Holt et al., Genes Dev 2003, 17(13):1581-91), acylation stimulating protein (a proteolytic product of complement C3; Li et al., J Biol Chem 2005, 280(9):7427-34), apolipoprotein CII (Kast et al., Mol Endocrinol 2001, 15(10): 1720-8), and apolipoprotein AV (Prieur et al., J Biol Chem 2003, 278(28):25468-80) all of which are known to promote the clearance and oxidation of fat carried by triglyceride rich lipoproteins. Additionally FXR inhibits expression of the genes encoding apolipoprotein CIII (Claudel et al., Gastroenterology 2003, 125(2):544-55), an inhibitor of lipoprotein lipase, and the sterol response element binding protein 1c (SREBP1c; Watanabe et al., J Clin Invest 2004, 113(10): 1408-18). SREBP1c, a member of basic helix-loop-helix family of transcription factors, functions as a master transcriptional regulator of the enzymes required for fatty acid synthesis (Osborne, J Biol Chem 2000, 275(42):32379-82). Taken together the genetic network controlled by FXR defines a signal transduction system poised to respond to changes in fat and carbohydrate dietary intake-driven lipid homeostasis. High levels of cholesterol in the liver will lead to increased production of bile acids and subsequent activation of FXR. In response to this activating signal FXR decreases the absorption of cholesterol in the intestine, favoring excretion, increases the clearance and oxidation of triglycerides and decreases the synthesis of fatty acids leading to a reduction in VLDL production.

The ability of FXR to regulate bile-acid synthesis, clearance and homeostasis as supported by the ability of FXR ligands to promote the transport of bile acid and phospholipids out of the liver suggests a utility for such compounds in diseases of disturbed bile acid and cholesterol flow such as Primary Biliary cirrhosis and NASH. In this regard FXR agonists have been shown to be effective in animal models of cholestasis, gallstones, and liver fibrosis (Liu et al., J Clin Invest 2003, 112(11):1678-87; Fiorocci et al., Gastroenterology 2004, 127(5):1497-512; Fiorocci et al., J Pharmacol Exp Ther 2005, 313(2):604-12; Fiorocci et al., J Pharmacol Exp Ther 2005, 314(2):584-95).

In some embodiments, compounds disclosed herein are used in the treatment of a disease, disorder or condition in a mammal that would benefit from FXR modulation.

In some embodiments, is a method of treating a disease, disorder or condition in a mammal that would benefit from FXR modulation comprising administering a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof. In some embodiments, is a method of treating a disease, disorder or condition in a mammal that would benefit from FXR modulation comprising administering a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof, wherein the disease, disorder or condition in a mammal is selected from nonalcoholic steatohepatitis (NASH), hyperlipidemia, hypercholesterolemia, hypertriglyceridemia, dyslipidemia, lipodystrophy, atherosclerosis, atherosclerotic disease, atherosclerotic disease events, atherosclerotic cardiovascular disease, Syndrome X, diabetes mellitus, type II diabetes, insulin insensitivity, hyperglycemia, cholestasis and obesity. In some embodiments, is a method of treating a disease, disorder or condition in a mammal that would benefit from FXR modulation comprising administering a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof, wherein the disease, disorder or condition in a mammal is nonalcoholic steatohepatitis (NASH). In some embodiments, is a method of treating a disease, disorder or condition in a mammal that would benefit from FXR modulation comprising administering a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof, wherein the disease, disorder or condition in a mammal is hyperlipidemia. In some embodiments, is a method of treating a disease, disorder or condition in a mammal that would benefit from FXR modulation comprising administering a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof, wherein the disease, disorder or condition in a mammal is hypercholesterolemia. In some embodiments, is a method of treating a disease, disorder or condition in a mammal that would benefit from FXR modulation comprising administering a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof, wherein the disease, disorder or condition in a mammal is hypertriglyceridemia. In some embodiments, is a method of treating a disease, disorder or condition in a mammal that would benefit from FXR modulation comprising administering a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof, wherein the disease, disorder or condition in a mammal is dyslipidemia. In some embodiments, is a method of treating a disease, disorder or condition in a mammal that would benefit from FXR modulation comprising administering a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof, wherein the disease, disorder or condition in a mammal is lipodystrophy. In some embodiments, is a method of treating a disease, disorder or condition in a mammal that would benefit from FXR modulation comprising administering a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof, wherein the disease, disorder or condition in a mammal is atherosclerosis. In some embodiments, is a method of treating a disease, disorder or condition in a mammal that would benefit from FXR modulation comprising administering a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof, wherein the disease, disorder or condition in a mammal is atherosclerotic disease. In some embodiments, is a method of treating a disease, disorder or condition in a mammal that would benefit from FXR modulation comprising administering a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof, wherein the disease, disorder or condition in a mammal is atherosclerotic cardiovascular disease. In some embodiments, is a method of treating a disease, disorder or condition in a mammal that would benefit from FXR modulation comprising administering a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof, wherein the disease, disorder or condition in a mammal is Syndrome X. In some embodiments, is a method of treating a disease, disorder or condition in a mammal that would benefit from FXR modulation comprising administering a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof, wherein the disease, disorder or condition in a mammal is diabetes mellitus. In some embodiments, is a method of treating a disease, disorder or condition in a mammal that would benefit from FXR modulation comprising administering a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof, wherein the disease, disorder or condition in a mammal is type II diabetes. In some embodiments, is a method of treating a disease, disorder or condition in a mammal that would benefit from FXR modulation comprising administering a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof, wherein the disease, disorder or condition in a mammal is insulin insensitivity. In some embodiments, is a method of treating a disease, disorder or condition in a mammal that would benefit from FXR modulation comprising administering a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof, wherein the disease, disorder or condition in a mammal is hyperglycemia. In some embodiments, is a method of treating a disease, disorder or condition in a mammal that would benefit from FXR modulation comprising administering a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof, wherein the disease, disorder or condition in a mammal is cholestasis. In some embodiments, is a method of treating a disease, disorder or condition in a mammal that would benefit from FXR modulation comprising administering a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof, wherein the disease, disorder or condition in a mammal is obesity.

In some embodiments, is a method of modulating FXR activity comprising contacting FXR, or portion thereof, with a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof. In some embodiments, the compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof, is an FXR agonist. In some embodiments, the compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), or a pharmaceutically acceptable salt or solvate thereof, is an FXR partial agonist.

In some embodiments, the disease, disorder or condition in a mammal that would benefit from FXR modulation is selected from nonalcoholic steatohepatitis (NASH), hyperlipidemia, hypercholesterolemia, hypertriglyceridemia, dyslipidemia, lipodystrophy, atherosclerosis, atherosclerotic disease, atherosclerotic disease events, atherosclerotic cardiovascular disease, Syndrome X, diabetes mellitus, type II diabetes, insulin insensitivity, hyperglycemia, cholestasis and obesity.

Compounds

In one aspect, provided herein is a compound of Formula (I), or a pharmaceutically acceptable salt or solvate thereof:

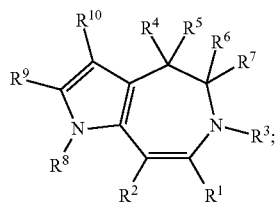

Formula (I)

wherein:
R$^1$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

R$^2$ is selected from the group consisting of —CN, —C(=O)OR$^{25}$, —C(=O)N(R$^{25}$)R$^{26}$,

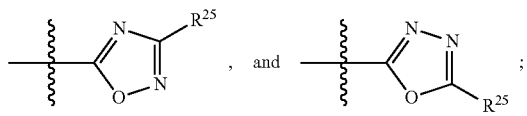

or R$^1$ and R$^2$ together with the carbon atoms to which they are attached, form an optionally substituted C$_2$-C$_9$heterocycloalkyl ring or an optionally substituted heteroaryl ring;

R$^3$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_{10}$cycloalkyl, optionally substituted aryl, optionally substituted —(C$_1$-C$_2$alkylene)-(aryl), optionally substituted heteroaryl, optionally substituted C$_2$-C$_9$heterocycloalkyl, optionally substituted —(C$_1$-C$_2$alkylene)-(heteroaryl), —C(=O)R$^{20}$, —C(=O)OR$^{20}$, —S(=O)$_2$R$^{20}$, —C(=O)N(R$^{21}$)R$^{22}$, —C(=O)N(R$^{21}$)S(=O)$_2$R$^{24}$, —C(=O)N(R$^{23}$)N(R$^{21}$)R$^{22}$, —C(=O)N(R$^{23}$)N(R$^{21}$)S(=O)$_2$R$^{24}$, —N(R$^{23}$)C(=O)R$^{20}$, —N(R$^{23}$)C(=O)N(R$^{21}$)R$^{22}$, —N(R$^{23}$)C(=O)N(R$^{21}$)S(=O)$_2$R$^{24}$, —N(R$^{20}$)C(=O)N(R$^{23}$)N(R$^{21}$)R$^{22}$, —N(R$^{20}$)C(=O)N(R$^{23}$)N(R$^{21}$)S(=O)$_2$R$^{24}$, —N(R$^{23}$)C(=O)OR$^{20}$, —P(=O)OR$^{20}$, and —P(=O)(OR$^{19}$)OR$^{20}$;

R$^4$ and R$^5$ are each independently selected from the group consisting of hydrogen, halogen, optionally substituted C$_1$-C$_6$alkyl, optionally substituted C$_1$-C$_6$alkoxy, optionally substituted C$_2$-C$_6$alkenyl, and optionally substituted C$_2$-C$_6$alkynyl; or R$^4$ and R$^5$ together with the carbon atom to which they are attached, form an optionally substituted C$_3$-C$_6$cycloalkyl ring or an optionally substituted C$_2$-C$_7$heterocycloalkyl ring;

R$^6$ is selected from the group consisting of hydrogen, halogen, optionally substituted C$_1$-C$_6$alkyl, optionally substituted C$_2$-C$_6$alkenyl, optionally substituted C$_2$-C$_6$alkynyl, and —C(=O)N(R$^{27}$)R$^{28}$;

R$^7$ is selected from the group consisting of hydrogen, halogen, optionally substituted C$_1$-C$_6$alkyl, optionally substituted C$_1$-C$_6$alkoxy, optionally substituted C$_2$-C$_6$alkenyl, and optionally substituted C$_2$-C$_6$alkynyl;

R$^8$ is selected from the group consisting of hydrogen, optionally substituted C$_1$-C$_6$alkyl, optionally substituted C$_3$-C$_8$cycloalkyl, optionally substituted aryl, optionally substituted —(C$_1$-C$_2$alkylene)-(aryl), optionally substituted heteroaryl, optionally substituted C$_2$-C$_9$heterocycloalkyl, and optionally substituted —(C$_1$-C$_2$alkylene)-(heteroaryl);

R$^9$ and R$^{10}$ together with the carbon atoms to which they are attached, form a phenyl ring substituted with (R$^{11}$)$_n$ and R$^{15}$; or R$^9$ and R$^{10}$ together with the carbon atoms to which they are attached, form a nitrogen containing 6-membered heteroaryl ring substituted with (R$^{11}$)$_n$ and R$^{15}$; or R$^9$ and R$^{10}$ together with the carbon atoms to which they are attached, form a 5-membered heteroaryl ring substituted with (R$^{11}$)$_p$, (R$^{12}$)$_q$, and R$^{15}$;

each R$^{11}$ is independently selected from the group consisting of halogen, —CN, amino, alkylamino, C$_1$-C$_6$alkyl, C$_1$-C$_6$haloalkyl, C$_1$-C$_6$alkoxy, C$_1$-C$_6$haloalkoxy, C$_3$-C$_8$cycloalkyl, C$_2$-C$_9$heterocycloalkyl, aryl, heteroaryl, —C(=O)OR$^{12}$, —C(=O)N(R$^{13}$)R$^{14}$;

each R$^{12}$ is independently selected from the group consisting of hydrogen and C$_1$-C$_6$alkyl;

each R$^{13}$ and R$^{14}$ are each independently selected from the group consisting of hydrogen and C$_1$-C$_6$alkyl; or R$^{13}$ and R$^{14}$ together with the nitrogen atom to which they are attached, form an optionally substituted C$_2$-C$_9$heterocycloalkyl ring;

R$^{15}$ is —OC(=J)OR$^{16a}$, —N(R$^{12}$)C(=J)OR$^{16a}$, —OC(=J)N(H)R$^{16a}$, —N(R$^{12}$)C(=J)N(H)R$^{16a}$, —OC(=J)N(H)(C$_2$-C$_6$alkyl)R$^{30}$, —N(R$^{12}$)C(=J)O(C$_2$-C$_6$alkyl)R$^{30}$, —N(R$^{12}$)C(=J)N(H)(C$_2$-C$_6$alkyl)R$^{30}$, —OC(=J)O(C$_2$-C$_6$alkyl)R$^{30}$, —C(=J)R$^{31}$, —OC(=J)R$^{31}$, —N(R$^{12}$)C(=J)R$^{31}$, —O(C$_2$-C$_6$alkyl)R$^{30}$, —N(R$^{12}$)(C$_2$-C$_6$alkyl)R$^{30}$, —OS(=O)$_v$R$^{31}$, —N(R$^{12}$)S(=O)$_v$R$^{31}$, —OS(=O)$_v$(C$_2$-C$_6$alkyl)R$^{30}$, or —N(R$^{12}$)S(=O)$_v$(C$_2$-C$_6$alkyl)R$^{30}$;

R$^{30}$ is R$^{16a}$, R$^{16b}$, or R$^{16c}$;
R$^{31}$ is R$^{16a}$ or R$^{16c}$;
J is O, S, or N(R$^{12}$);
R$^{16a}$ is

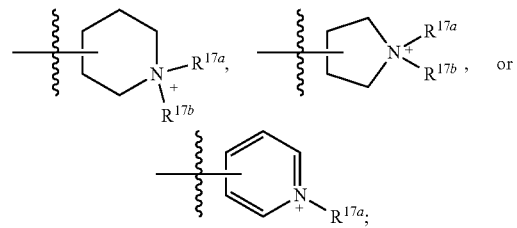

R$^{16b}$ is

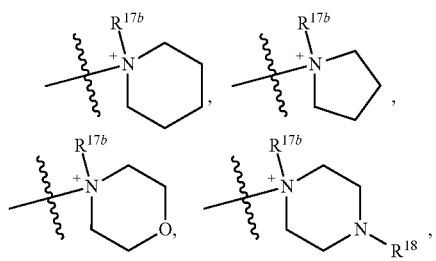

-continued

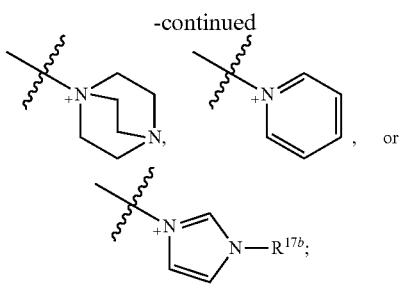

, or $R^{16c}$ is

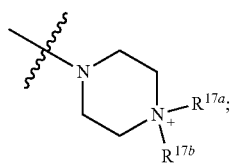

$R^{17a}$ is $C_1$-$C_6$alkyl;
$R^{17b}$ is $C_1$-$C_6$alkyl optionally substituted with phenyl, —C(=O)OH or —S(=O)$_2$OH;
$R^{18}$ is hydrogen, —OH, —($C_0$-$C_6$alkyl)-C(=O)OH, or $C_1$-$C_6$alkyl;
n is 0, 1, or 2;
p is 0 or 1;
q is 0 or 1;
v is 1 or 2;
$R^{19}$, $R^{20}$, and $R^{23}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);
$R^{21}$ and $R^{22}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{21}$ and $R^{22}$ together with the nitrogen atom to which they are attached, form an optionally substituted $C_2$-$C_9$heterocycloalkyl ring;
$R^{24}$ is selected from the group consisting of optionally substituted $C_1$-$C_6$alkyl, optionally substituted $C_2$-$C_6$alkenyl, optionally substituted $C_2$-$C_6$alkynyl, optionally substituted $C_3$-$C_5$ cycloalkyl, optionally substituted aryl optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); and
$R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);
$R^{27}$ and $R^{28}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{27}$ and $R^{28}$ together with the nitrogen atom to which they are attached, form an optionally substituted $C_2$-$C_9$heterocycloalkyl ring.

In one embodiment is a compound of Formula (I) wherein $R^4$ and $R^5$ are each independently selected from the group consisting of hydrogen, halogen, and optionally substituted $C_1$-$C_6$alkyl. In another embodiment is a compound of Formula (I) wherein $R^4$ and $R^5$ are each independently selected from the group consisting of hydrogen and optionally substituted $C_1$-$C_6$alkyl. In another embodiment is a compound of Formula (I) wherein $R^4$ and $R^5$ are each hydrogen. In another embodiment is a compound of Formula (I) wherein $R^4$ and $R^5$ are each independently optionally substituted $C_1$-$C_6$alkyl. In another embodiment is a compound of Formula (I) wherein $R^4$ and $R^5$ are each methyl. In another embodiment is a compound of Formula (I) wherein $R^4$ and $R^5$ form an optionally substituted $C_3$-$C_6$cycloalkyl ring or an optionally substituted $C_2$-$C_7$heterocycloalkyl ring. In some embodiments is a compound of Formula (I) wherein $R^4$ and $R^5$ form an optionally substituted $C_3$-$C_6$cycloalkyl ring. In some embodiments is a compound of Formula (I) wherein $R^4$ and $R^5$ form an optionally substituted $C_2$-$C_7$heterocycloalkyl ring.

In another embodiment is a compound of Formula (I) wherein $R^6$ and $R^7$ are each independently selected from the group consisting of hydrogen, halogen, and optionally substituted $C_1$-$C_6$alkyl. In another embodiment is a compound of Formula (I) wherein $R^6$ and $R^7$ are each independently selected from the group consisting of hydrogen and optionally substituted $C_1$-$C_6$alkyl. In another embodiment is a compound of Formula (I) wherein $R^6$ and $R^7$ are each independently optionally substituted $C_1$-$C_6$alkyl. In another embodiment is a compound of Formula (I) wherein $R^6$ and $R^7$ are each methyl. In another embodiment is a compound of Formula (I) wherein $R^6$ and $R^7$ are each hydrogen.

In another embodiment is a compound of Formula (I) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted aryl. In another embodiment is a compound of Formula (I) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted heteroaryl. In another embodiment is a compound of Formula (I) wherein $R^6$ and $R^7$ are hydrogen, $R^4$ and $R^5$ are methyl, $R^3$ is —C(O)$R^{20}$, and $R^{20}$ is optionally substituted aryl. In another embodiment is a compound of Formula (I) wherein $R^6$ and $R^7$ are hydrogen, $R^4$ and $R^5$ are methyl, $R^3$ is —C(O)$R^{20}$, and $R^{20}$ is optionally substituted heteroaryl.

In another embodiment is a compound of Formula (I) wherein $R^6$ and $R^7$ are hydrogen, $R^4$ and $R^5$ are independently optionally substituted $C_1$-$C_6$alkyl, $R^3$ is —S(O)$_2$$R^{20}$, and $R^{20}$ is optionally substituted aryl. In another embodiment is a compound of Formula (I) wherein $R^6$ and $R^7$ are hydrogen, $R^4$ and $R^5$ are independently optionally substituted $C_1$-$C_6$alkyl, $R^3$ is —S(O)$_2$$R^{20}$, and $R^{20}$ is optionally substituted heteroaryl. In another embodiment is a compound of Formula (I) wherein $R^6$ and $R^7$ are hydrogen, $R^4$ and $R^5$ are methyl, $R^3$ is —S(O)$_2$R$^{20}$, and $R^{20}$ is optionally substituted aryl. In another embodiment is a compound of Formula (I) wherein $R^6$ and $R^7$ are hydrogen, $R^4$ and $R^5$ are methyl, $R^3$ is —S(O)$_2$R$^{20}$, and $R^{20}$ is optionally substituted heteroaryl.

In another embodiment is a compound of Formula (I) wherein $R^6$ and $R^7$ are hydrogen, $R^4$ and $R^5$ are independently optionally substituted $C_1$-$C_6$alkyl, $R^3$ is —C(O)N(R$^{21}$)R$^{22}$, $R^{21}$ is hydrogen and $R^{22}$ is optionally substituted aryl. In another embodiment is a compound of Formula (I) wherein $R^6$ and $R^7$ are hydrogen, $R^4$ and $R^5$ are independently optionally substituted $C_1$-$C_6$alkyl, $R^3$ is —C(O)N(R$^{21}$)R$^{22}$, $R^{21}$ is hydrogen and $R^{22}$ is optionally substituted heteroaryl. In another embodiment is a compound of Formula (I) wherein $R^6$ and $R^7$ are hydrogen, $R^4$ and $R^5$ are methyl, $R^3$ is —C(O)N(R$^{21}$)R$^{22}$, $R^{21}$ is hydrogen and $R^{22}$ is optionally substituted aryl. In another embodiment is a compound of Formula (I) wherein $R^6$ and $R^7$ are hydrogen, $R^4$ and $R^5$ are methyl, $R^3$ is —C(O)N(R$^{21}$)R$^{22}$, $R^{21}$ is hydrogen and $R^{22}$ is optionally substituted heteroaryl.

In a further embodiment of the aforementioned embodiments is a compound of Formula (I) wherein $R^2$ is selected from the group consisting of —CN, —C(O)OR$^{25}$, —C(O)N(R$^{25}$)R$^{26}$,

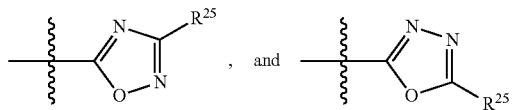

In a further embodiment of the aforementioned embodiments is a compound of Formula (I) wherein $R^2$ is —CN.

In a further embodiment of the aforementioned embodiments is a compound of Formula (I) wherein $R^2$ is —C(O)OR$^{25}$. In a further embodiment of the aforementioned embodiments is a compound of Formula (I) wherein $R^2$ is —C(O)OR$^{25}$, and $R^{25}$ is independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (I) wherein $R^2$ is —C(O)OR$^{25}$, and $R^{25}$ is independently selected from the group consisting of hydrogen, and optionally substituted $C_1$-$C_6$alkyl. In a further embodiment of the aforementioned embodiments is a compound of Formula (I) wherein $R^2$ is —C(O)OR$^{25}$, and $R^{25}$ is hydrogen. In a further embodiment of the aforementioned embodiments is a compound of Formula (I) wherein $R^2$ is —C(O)OR$^{25}$, and $R^{25}$ is optionally substituted $C_1$-$C_6$alkyl. In a further embodiment of the aforementioned embodiments is a compound of Formula (I) wherein $R^2$ is —C(O)OR$^{25}$, and $R^{25}$ is unsubstituted $C_1$-$C_6$alkyl. In a further embodiment of the aforementioned embodiments is a compound of Formula (I) wherein $R^2$ is —C(O)OR$^{25}$, and $R^{25}$ is methyl. In a further embodiment of the aforementioned embodiments is a compound of Formula (I) wherein $R^2$ is —C(O)OR$^{25}$, and $R^{25}$ is ethyl.

In a further embodiment of the aforementioned embodiments is a compound of Formula (I) wherein $R^2$ is —C(O)N(R$^{25}$)R$^{26}$. In a further embodiment of the aforementioned embodiments is a compound of Formula (I) wherein $R^2$ is —C(O)N(R$^{25}$)R$^{26}$, and $R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (I) wherein $R^2$ is —C(O)N(R$^{25}$)R$^{26}$, and $R^{25}$ and $R^{26}$ are each independently selected from the group consisting of hydrogen, and optionally substituted $C_1$-$C_6$alkyl. In a further embodiment of the aforementioned embodiments is a compound of Formula (I) wherein $R^2$ is —C(O)N(R$^{25}$)R$^{26}$, and $R^{25}$ and $R^{26}$ are hydrogen. In a further embodiment of the aforementioned embodiments is a compound of Formula (I) wherein $R^2$ is —C(O)N(R$^{25}$)R$^{26}$, and $R^{25}$ and $R^{26}$ are each independently optionally substituted $C_1$-$C_6$alkyl. In a further embodiment of the aforementioned embodiments is a compound of Formula (I) wherein $R^2$ is —C(O)N(R$^{25}$)R$^{26}$, $R^{25}$ is hydrogen, and $R^{26}$ is optionally substituted $C_1$-$C_6$alkyl. In a further embodiment of the aforementioned embodiments is a compound of Formula (I) wherein $R^2$ is —C(O)N(R$^{25}$)R$^{26}$, and $R^{25}$ and $R^{26}$ are each independently unsubstituted $C_1$-$C_6$alkyl. In a further embodiment of the aforementioned embodiments is a compound of Formula (I) wherein $R^2$ is —C(O)N(R$^{25}$)R$^{26}$, $R^{25}$ is hydrogen, and $R^{26}$ are methyl. In a further embodiment of the aforementioned embodiments is a compound of Formula (I) wherein $R^2$ is —C(O)N(R$^{25}$)R$^{26}$, and $R^{25}$ and $R^{26}$ are methyl. In a further embodiment of the aforementioned embodiments is a compound of Formula (I) wherein $R^2$ is —C(O)N(R$^{25}$)R$^{26}$, and $R^{25}$ and $R^{26}$ are ethyl.

In a further embodiment of the aforementioned embodiments is a compound of Formula (I) wherein $R^2$ is

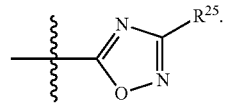

In a further embodiment of the aforementioned embodiments is a compound of Formula (I) wherein $R^2$ is

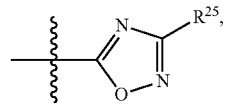

and $R^{25}$ is optionally substituted i-$C_6$alkyl. In a further embodiment of the aforementioned embodiments is a compound of Formula (I) wherein $R^2$ is

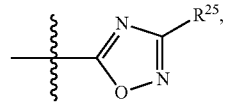

and $R^{25}$ is methyl. In a further embodiment of the aforementioned embodiments is a compound of Formula (I) wherein $R^2$ is

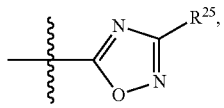

and $R^{25}$ is optionally substituted $C_1$-$C_6$alkyl. In a further embodiment of the aforementioned embodiments is a compound of Formula (I) wherein $R^2$ is

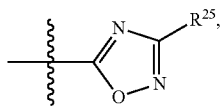

and $R^{25}$ is ethyl.

In a further embodiment of the aforementioned embodiments is a compound of Formula (I) wherein $R^2$ is

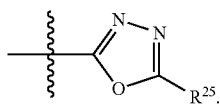

In a further embodiment of the aforementioned embodiments is a compound of Formula (I) where $R^2$ is

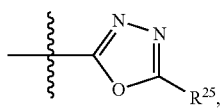

and $R^{25}$ is optionally substituted $C_1$-$C_6$alkyl. In a further embodiment of the aforementioned embodiments is a compound of Formula (I) wherein $R^2$ is

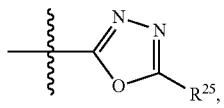

and $R^{25}$ is methyl. In a further embodiment of the aforementioned embodiments is a compound of Formula (I) wherein $R^2$

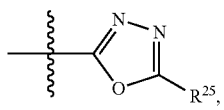

and $R^{25}$ is optionally substituted $C_1$-$C_6$alkyl. In a further embodiment of the aforementioned embodiments is a compound of Formula (I) where $R^2$ is

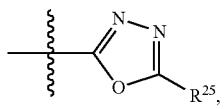

and $R^{25}$ is ethyl.

In a further embodiment of the aforementioned embodiments is a compound of Formula (I) wherein $R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (I) wherein $R^1$ is hydrogen. In a further embodiment of the aforementioned embodiments is a compound of Formula (I) wherein $R^1$ is optionally substituted $C_1$-$C_6$alkyl. In a further embodiment of the aforementioned embodiments is a compound of Formula (I) wherein $R^1$ is methyl. In a further embodiment of the aforementioned embodiments is a compound of Formula (I) wherein $R^1$ is optionally substituted $C_2$-$C_6$alkenyl. In a further embodiment of the aforementioned embodiments is a compound of Formula (I) wherein $R^1$ is optionally substituted $C_2$-$C_6$alkynyl.

In a further embodiment of the aforementioned embodiments is a compound of Formula (I) wherein $R^1$ and $R^2$ together with the carbon atoms to which they are attached, form an optionally substituted $C_2$-$C_9$heterocycloalkyl ring or an optionally substituted heteroaryl ring. In a further embodiment of the aforementioned embodiments is a compound of Formula (I) wherein $R^1$ and $R^2$ together with the carbon atoms to which they are attached, form an optionally substituted $C_2$-$C_9$heterocycloalkyl ring. In a further embodiment of the aforementioned embodiments is a compound of Formula (I) wherein $R^1$ and $R^2$ together with the carbon atoms to which they are attached, form an optionally substituted heteroaryl ring.

In a further embodiment of the aforementioned embodiments is a compound of Formula (I) wherein $R^8$ is selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl). In a further embodiment of the aforementioned embodiments is a compound of Formula (I) wherein $R^8$ is selected from the group consisting of hydrogen, and optionally substituted $C_1$-$C_6$alkyl. In a further embodiment of the aforementioned embodiments is a compound of Formula (I) wherein $R^8$ is optionally substituted $C_1$-$C_6$alkyl. In a further embodiment of the aforementioned embodiments is a compound of Formula (I) wherein $R^8$ is methyl. In a further embodiment of the aforementioned embodiments is a compound of Formula (I) wherein $R^8$ is optionally substituted $C_1$-$C_6$alkyl. In a further embodiment of the aforementioned embodiments is a compound of Formula (I) wherein $R^8$ is ethyl. In a further embodiment of the aforementioned embodiments is a compound of Formula (I) wherein $R^8$ is optionally substituted $C_1$-$C_6$alkyl. In a further embodiment of the aforementioned embodiments is a compound of Formula (I) wherein $R^8$ is hydrogen.

In another embodiment of the aforementioned embodiments is a compound of Formula (I) wherein $R^{15}$ is —OC(=J)OR$^{16a}$. In another embodiment of the aforementioned embodiments is a compound of Formula (I) wherein $R^{15}$ is —N(R$^{12}$)C(=J)OR$^{16a}$. In another embodiment of the aforementioned embodiments is a compound of Formula (I) wherein $R^{15}$ is —OC(=J)N(H)R$^{16a}$. In another embodiment of the aforementioned embodiments is a compound of Formula (I) wherein $R^{15}$ is —N($R^{12}$)C(=J)N(H)$R^{16a}$. In another embodiment of the aforementioned embodiments is a compound of Formula (I) wherein $R^{15}$ is —OC(=J)N(H)($C_2$-$C_6$alkyl)$R^{30}$. In another embodiment of the aforementioned embodiments is a compound of Formula (I) wherein $R^{15}$ is —N($R^{12}$)C(=J)O($C_2$-$C_6$alkyl)$R^{30}$. In another embodiment of the aforementioned embodiments is a compound of Formula (I) wherein $R^{15}$ is —N($R^{12}$)C(=J)N(H)($C_2$-$C_6$alkyl)$R^{30}$. In another embodiment of the aforementioned embodiments is a compound of Formula (I) wherein $R^{15}$ is —OC(=J)O($C_2$-$C_6$alkyl)$R^{30}$. In another embodiment of the aforementioned embodiments is a compound of Formula (I) wherein $R^{15}$ is —C(=J)$R^{31}$. In another embodiment of the aforementioned embodiments is a compound of Formula (I) wherein $R^{15}$ is —OC(=J)$R^{31}$. In another embodiment of the aforementioned embodiments is a compound of Formula (I) wherein $R^{15}$ is —N($R^{12}$)C(=J)$R^{31}$. In another embodiment of the aforementioned embodiments is a compound of Formula (I) wherein $R^{15}$ is —O($C_2$-$C_6$alkyl)$R^{30}$. In another embodiment of the aforementioned embodiments is a compound of Formula (I) wherein $R^{15}$ is —N($R^{12}$)($C_2$-$C_6$alkyl)$R^{30}$. In another embodiment of the aforementioned embodiments is a compound of Formula (I) wherein $R^{15}$ is —OS(=O)$_v$$R^{31}$. In another embodiment of the aforementioned embodiments is a compound of Formula (I) wherein $R^{15}$ is —N($R^{12}$)S(=O)$_v$$R^{31}$. In another embodiment of the aforementioned embodiments is a compound of Formula (I) wherein $R^{15}$ is —OS(=O)$_v$($C_2$-$C_6$alkyl)$R^{30}$. In another embodiment of the aforementioned embodiments is a compound of Formula (I) wherein $R^{15}$ is —N($R^{12}$)S(=O)$_v$($C_2$-$C_6$alkyl)$R^{30}$. In a further embodiment of the aforementioned embodiments is a compound of Formula (I) wherein $R^{30}$ is $R^{16a}$. In a further embodiment of the aforementioned embodiments is a compound of Formula (I) wherein $R^{30}$ is $R^{16b}$. In a further embodiment of the aforementioned embodiments is a compound of Formula (I) wherein $R^{30}$ is $R^{16c}$. In a further embodiment of the aforementioned embodiments is a compound of Formula (I) wherein $R^{31}$ is $R^{16a}$. In a further embodiment of the aforementioned embodiments is a compound of Formula (I) wherein $R^{31}$ is $R^{16b}$. In a further embodiment of the aforementioned embodiments is a compound of Formula (I) wherein J is O. In a further embodiment of the aforementioned embodiments is a compound of Formula (I) wherein J is S. In a further embodiment of the aforementioned embodiments is a compound of Formula (I) wherein J is N($R^{12}$).

In another embodiment of the aforementioned embodiments is a compound of Formula (I) wherein $R^{16a}$ is In another embodiment of the aforementioned embodiments is a compound of Formula (I) wherein $R^{16a}$ is In another embodiment of the aforementioned embodiments is a compound of Formula (I) wherein $R^{16}$ is In another embodiment of the aforementioned embodiments is a compound of Formula (I) wherein $R^{16b}$ is In another embodiment of the aforementioned embodiments is a compound of Formula (I) wherein $R^{16b}$ is In another embodiment of the aforementioned embodiments is a compound of Formula (I) wherein $R^{16b}$ is In another embodiment of the aforementioned embodiments is a compound of Formula (I) wherein $R^{16b}$ is In another embodiment of the aforementioned embodiments is a compound of Formula (I) wherein $R^{16b}$ is In another embodiment of the aforementioned embodiments is a compound of Formula (I) wherein $R^{16b}$ is

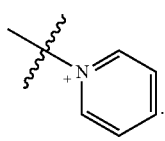

In another embodiment of the aforementioned embodiments is a compound of Formula (I) wherein $R^{16b}$ is

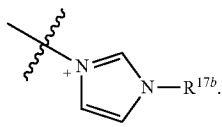

In another embodiment of the aforementioned embodiments is a compound of Formula (I) wherein $R^{16c}$ is

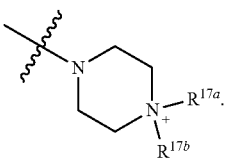

In another embodiment is a compound of Formula (I) wherein $R^{16c}$ is

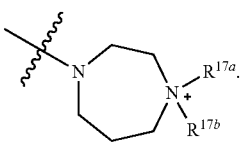

In a further embodiment of the aforementioned embodiments is a compound of Formula (I) wherein $R^{17a}$ is methyl. In a further embodiment of the aforementioned embodiments is a compound of Formula (I) wherein $R^{17a}$ is ethyl. In a further embodiment of the aforementioned embodiments is a compound of Formula (I) wherein $R^{17b}$ is methyl optionally substituted with phenyl, —C(=O)OH or —S(=O)$_2$OH. In a further embodiment of the aforementioned embodiments is a compound of Formula (I) wherein $R^{17a}$ is ethyl optionally substituted with phenyl, —C(=O)OH or —S(=O)$_2$OH.

In another embodiment of the aforementioned embodiments is a compound of Formula (I) wherein n is 0. In another embodiment of the aforementioned embodiments is a compound of Formula (I) wherein n is 1. In another embodiment of the aforementioned embodiments is a compound of Formula (I) wherein n is 1 and $R^{11}$ is $C_1$-$C_6$alkyl. In another embodiment of the aforementioned embodiments is a compound of Formula (I) wherein n is 1 and $R^{11}$ is $C_1$-$C_6$haloalkyl.

In another embodiment is a compound of Formula (I) wherein $R^{15}$ is —OC(=J)OR$^{16a}$, —N(R$^{12}$)C(=J)OR$^{16a}$, —OC(=J)N(H)R$^{16a}$, —N(R$^{12}$)C(=J)N(H)R$^{16a}$, —OC(=J)N(H)(C$_1$-C$_6$alkyl)R$^{31}$, —N(R$^{12}$)C(=J)O(C$_1$-C$_6$alkyl)R$^{31}$, —N(R$^{12}$)C(=J)N(H)(C$_1$-C$_6$alkyl)R$^{31}$, —OC(=J)O(C$_1$-C$_6$alkyl)R$^{31}$, —C(=J)R$^{31}$, —OC(=J)R$^{31}$, —N(R$^{12}$)C(=J)R$^{31}$, —O(C$_1$-C$_6$alkyl)R$^{31}$, —N(R$^{12}$)(C$_1$-C$_6$alkyl)R$^{31}$, —OS(=O)$_v$R$^{31}$, —N(R$^{12}$)S(=O)$_v$R$^{31}$, —OS(=O)$_v$(C$_1$-C$_6$alkyl)R$^{31}$, or —N(R$^{12}$)S(=O)$_v$(C$_1$-C$_6$alkyl)R$^{31}$.

In some embodiments provided herein, the compound of Formula (I) has the structure of Formula (Ia), or a pharmaceutically acceptable salt or solvate thereof:

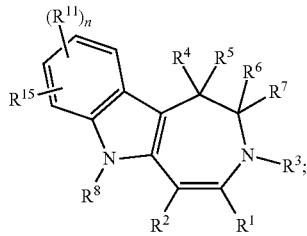

Formula (Ia)

wherein:
$R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —(C$_1$-C$_2$alkylene)-(aryl), optionally substituted $C_2$-$C_9$heterocycloalkyl, optionally substituted heteroaryl, and optionally substituted —(C$_1$-C$_2$alkylene)-(heteroaryl);

$R^2$ is selected from the group consisting of —CN, —C(=O)OR$^{25}$, —C(=O)N(R$^{25}$)R$^{26}$,

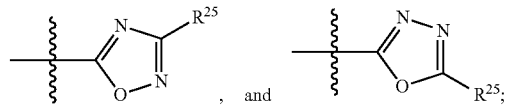

, and or $R^1$ and $R^2$ together with the carbon atoms to which they are attached, form an optionally substituted $C_2$-$C_9$heterocycloalkyl ring or an optionally substituted heteroaryl ring;

$R^3$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_{10}$cycloalkyl, optionally substituted aryl, optionally substituted —(C$_1$-C$_2$alkylene)-(aryl), optionally substituted heteroaryl, optionally substituted $C_2$-$C_9$heterocycloalkyl, optionally substituted —(C$_1$-C$_2$alkylene)-(heteroaryl), —C(=O)R$^{20}$, —C(=O)OR$^{20}$, —S(=O)$_2$R$^{20}$, —C(=O)N(R$^{21}$)R$^{22}$, —C(=O)N(R$^{21}$)S(=O)$_2$R$^{24}$, —C(=O)N(R$^{23}$)N(R$^{21}$)R$^{22}$, —C(=O)N(R$^{23}$)N(R$^{21}$)S(=O)$_2$R$^{24}$, —N(R$^{23}$)C(=O)R$^{20}$, —N(R$^{23}$)C(=O)N(R$^{21}$)R$^{22}$, —N(R$^{23}$)C(=O)N(R$^{21}$)S(=O)$_2$R$^{24}$, —N(R$^{20}$)C(=O)N(R$^{23}$)N(R$^{21}$)R$^{22}$, —N(R$^{20}$)C(=O)N(R$^{23}$)N(R$^{21}$)S(=O)$_2$R$^{24}$, —N(R$^{23}$)C(=O)OR$^{20}$, —P(=O)OR$^{20}$, and —P(=O)(OR$^{19}$)OR$^{20}$;

$R^4$ and $R^5$ are each independently selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl; or $R^4$ and $R^5$ together with the carbon atom to which they are attached, form an optionally substituted $C_3$-$C_6$cycloalkyl ring or an optionally substituted $C_2$-$C_7$heterocycloalkyl ring;

R⁶ is selected from the group consisting of hydrogen, halogen, optionally substituted C₁-C₆alkyl, optionally substituted C₂-C₆alkenyl, optionally substituted C₂-C₆alkynyl, and —C(=O)N(R²⁷)R²⁸;

R⁷ is selected from the group consisting of hydrogen, halogen, optionally substituted C₁-C₆alkyl, optionally substituted C₁-C₆alkoxy, optionally substituted C₂-C₆alkenyl, and optionally substituted C₂-C₆alkynyl;

R⁸ is selected from the group consisting of hydrogen, optionally substituted C₁-C₆alkyl, optionally substituted C₃-C₈cycloalkyl, optionally substituted aryl, optionally substituted —(C₁-C₂alkylene)-(aryl), optionally substituted heteroaryl, optionally substituted C₂-C₉heterocycloalkyl, and optionally substituted —(C₁-C₂alkylene)-(heteroaryl);

each R¹¹ is independently selected from the group consisting of halogen, —CN, amino, alkylamino, C₁-C₆alkyl, C₁-C₆haloalkyl, C₁-C₆alkoxy, C₁-C₆haloalkoxy, C₃-C₈cycloalkyl, C₂-C₉heterocycloalkyl, aryl, heteroaryl, —C(=O)OR¹², —C(=O)N(R¹³)R¹⁴;

each R¹² is independently selected from the group consisting of hydrogen and C₁-C₆alkyl;

each R¹³ and R¹⁴ are each independently selected from the group consisting of hydrogen and C₁-C₆alkyl; or R¹³ and R¹⁴ together with the nitrogen atom to which they are attached, form an optionally substituted C₂-C₉heterocycloalkyl ring;

R¹⁵ is —OC(=J)OR¹⁶ᵃ, —N(R¹²)C(=J)OR¹⁶ᵃ, —OC(=J)N(H)R¹⁶ᵃ, —N(R¹²)C(=J)N(H)R¹⁶ᵃ, —OC(=J)N(H)(C₂-C₆alkyl)R³⁰, —N(R¹²)C(=J)O(C₂-C₆alkyl)R³⁰, —N(R¹²)C(=J)N(H)(C₂-C₆alkyl)R³⁰, —OC(=J)O(C₂-C₆alkyl)R³⁰, —C(=J)R³¹, —OC(=J)R³¹, —N(R¹²)C(=J)R³¹, —O(C₂-C₆alkyl)R³⁰, —N(R¹²)(C₂-C₆alkyl)R³⁰, —OS(=O)ᵥR³¹, —N(R¹²)S(=O)ᵥR³¹, —OS(=O)ᵥ(C₂-C₆alkyl)R³⁰, or —N(R¹²)S(=O)ᵥ(C₂-C₆alkyl)R³⁰;

R³⁰ is R¹⁶ᵃ, R¹⁶ᵇ, or R¹⁶ᶜ;
R³¹ is R¹⁶ᵃ or R¹⁶ᶜ;
J is O, S, or N(R¹²);
R¹⁶ᵃ is

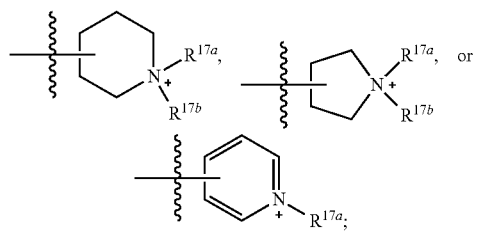

R¹⁶ᵇ is

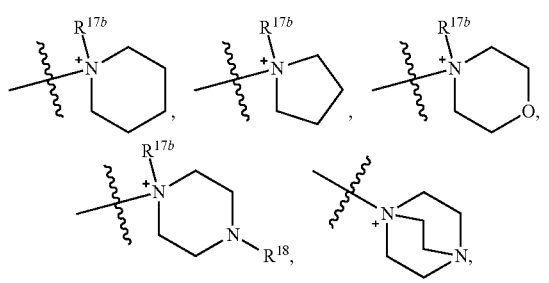

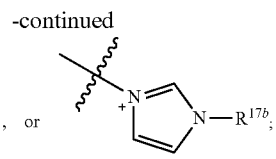

R¹⁶ᶜ is

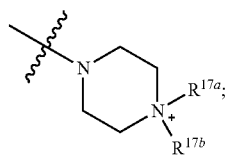

R¹⁷ᵃ is C₁-C₆alkyl;
R¹⁷ᵇ is C₁-C₆alkyl optionally substituted with phenyl, —C(=O)OH or —S(=O)₂OH;
R¹⁸ is hydrogen, —OH, —(C₀-C₆alkyl)-C(=O)OH, or C₁-C₆alkyl;
n is 0, 1, or 2;
v is 1 or 2;
R¹⁹, R²⁰, and R²³ are each independently selected from the group consisting of hydrogen, optionally substituted C₁-C₆alkyl, optionally substituted C₂-C₆alkenyl, optionally substituted C₂-C₆alkynyl, optionally substituted C₃-C₈cycloalkyl, optionally substituted aryl, optionally substituted —(C₁-C₂alkylene)-(aryl), optionally substituted C₂-C₉heterocycloalkyl, optionally substituted heteroaryl, and optionally substituted —(C₁-C₂alkylene)-(heteroaryl);

R²¹ and R²² are each independently selected from the group consisting of hydrogen, optionally substituted C₁-C₆alkyl, optionally substituted C₂-C₆alkenyl, optionally substituted C₂-C₆alkynyl, optionally substituted C₃-C₈cycloalkyl, optionally substituted aryl, optionally substituted —(C₁-C₂alkylene)-(aryl), optionally substituted C₂-C₉heterocycloalkyl, optionally substituted heteroaryl, and optionally substituted —(C₁-C₂alkylene)-(heteroaryl); or R²¹ and R²² together with the nitrogen atom to which they are attached, form an optionally substituted C₂-C₉heterocycloalkyl ring;

R²⁴ is selected from the group consisting of optionally substituted C₁-C₆alkyl, optionally substituted C₂-C₆alkenyl, optionally substituted C₂-C₆alkynyl, optionally substituted C₃-C₅ cycloalkyl, optionally substituted aryl optionally substituted —(C₁-C₂alkylene)-(aryl), optionally substituted C₂-C₉heterocycloalkyl, optionally substituted heteroaryl, and optionally substituted —(C₁-C₂alkylene)-(heteroaryl); and R²⁵ and R²⁶ are each independently selected from the group consisting of hydrogen, optionally substituted C₁-C₆alkyl, optionally substituted C₃-C₈cycloalkyl, optionally substituted aryl, optionally substituted —(C₁-C₂alkylene)-(aryl), optionally substituted C₂-C₉heterocycloalkyl, optionally substituted heteroaryl, and optionally substituted —(C₁-C₂alkylene)-(heteroaryl);

R²⁷ and R²⁸ are each independently selected from the group consisting of hydrogen, optionally substituted C₁-C₆alkyl, optionally substituted C₃-C₈cycloalkyl, optionally substituted aryl, optionally substituted —(C₁-C₂alkylene)-(aryl), optionally substituted $C_2$-$C_9$heterocycloalkyl, optionally substituted heteroaryl, and optionally substituted —($C_1$-$C_2$alkylene)-(heteroaryl); or $R^{27}$ and $R^{28}$ together with the nitrogen atom to which they are attached, form an optionally substituted $C_2$-$C_9$heterocycloalkyl ring.

In one embodiment is a compound of Formula (Ia) wherein $R^4$ and $R^5$ are each independently selected from the group consisting of hydrogen, halogen, and optionally substituted $C_1$-$C_6$alkyl. In another embodiment is a compound of Formula (Ia) wherein $R^4$ and $R^5$ are each independently selected from the group consisting of hydrogen and optionally substituted $C_1$-$C_6$alkyl. In another embodiment is a compound of Formula (Ia) wherein $R^4$ and $R^5$ are each hydrogen. In another embodiment is a compound of Formula (Ia) wherein $R^4$ and $R^5$ are each independently optionally substituted $C_1$-$C_6$alkyl. In another embodiment is a compound of Formula (Ia) wherein $R^4$ and $R^5$ are each methyl. In another embodiment is a compound of Formula (Ia) wherein $R^4$ and $R^5$ form an optionally substituted $C_3$-$C_6$cycloalkyl ring or an optionally substituted $C_2$-$C_7$heterocycloalkyl ring. In some embodiments is a compound of Formula (Ia) wherein $R^4$ and $R^5$ form an optionally substituted $C_3$-$C_6$cycloalkyl ring. In some embodiments is a compound of Formula (Ia) wherein $R^4$ and $R^5$ form an optionally substituted $C_2$-$C_7$heterocycloalkyl ring.

In another embodiment is a compound of Formula (Ia) wherein $R^6$ and $R^7$ are each independently selected from the group consisting of hydrogen, halogen, and optionally substituted $C_1$-$C_6$alkyl. In another embodiment is a compound of Formula (Ia) wherein $R^6$ and $R^7$ are each independently selected from the group consisting of hydrogen and optionally substituted $C_1$-$C_6$alkyl. In another embodiment is a compound of Formula (Ia) wherein $R^6$ and $R^7$ are each independently optionally substituted $C_1$-$C_6$alkyl. In another embodiment is a compound of Formula (Ia) wherein $R^6$ and $R^7$ are each methyl. In another embodiment is a compound of Formula (Ia) wherein $R^6$ and $R^7$ are each hydrogen.

In another embodiment is a compound of Formula (Ia) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted aryl. In another embodiment is a compound of Formula (Ia) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted heteroaryl. In another embodiment is a compound of Formula (Ia) wherein $R^6$ and $R^7$ are hydrogen, $R^4$ and $R^5$ are methyl, $R^3$ is —C(O)$R^{20}$, and $R^{20}$ is optionally substituted aryl. In another embodiment is a compound of Formula (Ia) wherein $R^6$ and $R^7$ are hydrogen, $R^4$ and $R^5$ are methyl, $R^3$ is —C(O)$R^{20}$, and $R^{20}$ is optionally substituted heteroaryl.

In another embodiment is a compound of Formula (Ia) wherein $R^6$ and $R^7$ are hydrogen, $R^4$ and $R^5$ are independently optionally substituted $C_1$-$C_6$alkyl, $R^3$ is —S(O)$_2$$R^{20}$, and $R^{20}$ is optionally substituted aryl. In another embodiment is a compound of Formula (Ia) wherein $R^6$ and $R^7$ are hydrogen, $R^4$ and $R^5$ are independently optionally substituted $C_1$-$C_6$alkyl, $R^3$ is —S(O)$_2$$R^{20}$, and $R^{20}$ is optionally substituted heteroaryl. In another embodiment is a compound of Formula (Ia) wherein $R^6$ and $R^7$ are hydrogen, $R^4$ and $R^5$ are methyl, $R^3$ is —S(O)$_2$$R^2$, and $R^{20}$ is optionally substituted aryl. In another embodiment is a compound of Formula (Ia) wherein $R^6$ and $R^7$ are hydrogen, $R^4$ and $R^5$ are methyl, $R^3$ is —S(O)$_2$$R^{20}$, and $R^{20}$ is optionally substituted heteroaryl.

In another embodiment is a compound of Formula (Ia) wherein $R^6$ and $R^7$ are hydrogen, $R^4$ and $R^5$ are independently optionally substituted $C_1$-$C_6$alkyl, $R^3$ is —C(O)N($R^{21}$)$R^{22}$, $R^{21}$ is hydrogen and $R^{22}$ is optionally substituted aryl. In another embodiment is a compound of Formula (Ia) wherein $R^6$ and $R^7$ are hydrogen, $R^4$ and $R^5$ are independently optionally substituted $C_1$-$C_6$alkyl, $R^3$ is —C(O)N($R^{21}$)$R^{22}$, $R^{21}$ is hydrogen and $R^{22}$ is optionally substituted heteroaryl. In another embodiment is a compound of Formula (Ia) wherein $R^6$ and $R^7$ are hydrogen, $R^4$ and $R^5$ are methyl, $R^3$ is —C(O)N($R^{21}$)$R^{22}$, $R^{21}$ is hydrogen and $R^{22}$ is optionally substituted aryl. In another embodiment is a compound of Formula (Ia) wherein $R^6$ and $R^7$ are hydrogen, $R^4$ and $R^5$ are methyl, $R^3$ is —C(O)N($R^{21}$)$R^{22}$, $R^{21}$ is hydrogen and $R^{22}$ is optionally substituted heteroaryl.

In a further embodiment of the aforementioned embodiments is a compound of Formula (Ia) wherein $R^2$ is selected from the group consisting of —CN, —C(O)O$R^{25}$, —C(O)N($R^{25}$)$R^{26}$,

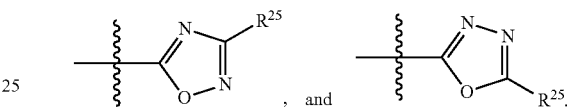

In a further embodiment of the aforementioned embodiments is a compound of Formula (Ia) wherein $R^2$ is —CN.

In a further embodiment of the aforementioned embodiments is a compound of Formula (Ia) wherein $R^2$ is —C(O)O$R^{25}$. In a further embodiment of the aforementioned embodiments is a compound of Formula (Ia) wherein $R^2$ is —C(O)O$R^{25}$, and $R^{25}$ is independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (Ia) wherein $R^2$ is —C(O)O$R^{25}$, and $R^{25}$ is independently selected from the group consisting of hydrogen, and optionally substituted $C_1$-$C_6$alkyl. In a further embodiment of the aforementioned embodiments is a compound of Formula (Ia) wherein $R^2$ is —C(O)O$R^{25}$, and $R^{25}$ is hydrogen. In a further embodiment of the aforementioned embodiments is a compound of Formula (Ia) wherein $R^2$ is —C(O)O$R^{25}$, and $R^{25}$ is optionally substituted $C_1$-$C_6$alkyl. In a further embodiment of the aforementioned embodiments is a compound of Formula (Ia) wherein $R^2$ is —C(O)O$R^{25}$, and $R^{25}$ is unsubstituted $C_1$-$C_6$alkyl. In a further embodiment of the aforementioned embodiments is a compound of Formula (Ia) wherein $R^2$ is —C(O)O$R^{25}$, and $R^{25}$ is methyl. In a further embodiment of the aforementioned embodiments is a compound of Formula (Ia) wherein $R^2$ is —C(O)O$R^{25}$, and $R^{25}$ is ethyl.

In a further embodiment of the aforementioned embodiments is a compound of Formula (Ia) wherein $R^2$ is —C(O)N($R^{25}$)$R^{26}$. In a further embodiment of the aforementioned embodiments is a compound of Formula (Ia) wherein $R^2$ is —C(O)N($R^{25}$)$R^{26}$, and $R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —(C$_1$-C$_2$alkylene)-(heteroaryl). In a further embodiment of the aforementioned embodiments is a compound of Formula (Ia) wherein R$^2$ is —C(O)N(R$^{25}$)R$^{26}$, and R$^{25}$ and R$^{26}$ are each independently selected from the group consisting of hydrogen, and optionally substituted C$_1$-C$_6$alkyl. In a further embodiment of the aforementioned embodiments is a compound of Formula (Ia) wherein R$^2$ is —C(O)N(R$^{25}$)R$^{26}$, and R$^{25}$ and R$^{26}$ are hydrogen. In a further embodiment of the aforementioned embodiments is a compound of Formula (Ia) wherein R$^2$ is —C(O)N(R$^{25}$)R$^{26}$, and R$^{25}$ and R$^{26}$ are each independently optionally substituted C$_1$-C$_6$alkyl. In a further embodiment of the aforementioned embodiments is a compound of Formula (Ia) wherein R$^2$ is —C(O)N(R$^{25}$)R$^{26}$, R$^{25}$ is hydrogen, and R$^{26}$ is optionally substituted C$_1$-C$_6$alkyl. In a further embodiment of the aforementioned embodiments is a compound of Formula (Ia) wherein R$^2$ is —C(O)N(R$^{25}$)R$^{26}$, and R$^{25}$ and R$^{26}$ are each independently unsubstituted C$_1$-C$_6$alkyl. In a further embodiment of the aforementioned embodiments is a compound of Formula (Ia) wherein R$^2$ is —C(O)N(R$^{25}$)R$^{26}$, R$^{25}$ is hydrogen, and R$^{26}$ are methyl. In a further embodiment of the aforementioned embodiments is a compound of Formula (Ia) wherein R$^2$ is —C(O)N(R$^{25}$)R$^{26}$, and R$^{25}$ and R$^{26}$ are methyl. In a further embodiment of the aforementioned embodiments is a compound of Formula (Ia) wherein R$^2$ is —C(O)N(R$^{25}$)R$^{26}$, and R$^{25}$ and R$^{26}$ are ethyl.

In a further embodiment of the aforementioned embodiments is a compound of Formula (Ia) wherein R$^2$ is

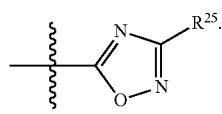

In a further embodiment of the aforementioned embodiments is a compound of Formula (Ia) wherein R$^2$ is

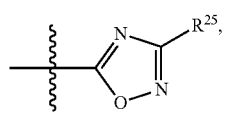

and R$^{25}$ is optionally substituted C$_1$-C$_6$alkyl. In a further embodiment of the aforementioned embodiments is a compound of Formula (Ia) wherein R$^2$ is

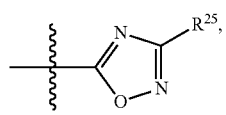

and R$^{25}$ is methyl. In a further embodiment of the aforementioned embodiments is a compound of Formula (Ia) wherein R$^2$ is

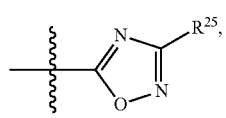

and R$^{25}$ is optionally substituted C$_1$-C$_6$alkyl. In a further embodiment of the aforementioned embodiments is a compound of Formula (Ia) wherein R$^2$ is

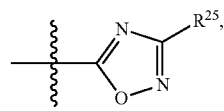

and R$^{25}$ is ethyl.

In a further embodiment of the aforementioned embodiments is a compound of Formula (Ia) wherein R$^2$ is

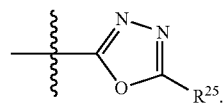

In a further embodiment of the aforementioned embodiments is a compound of Formula (Ia) wherein R$^2$ is

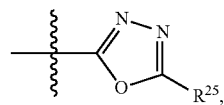

and R$^{25}$ is optionally substituted C$_1$-C$_6$alkyl. In a further embodiment of the aforementioned embodiments is a compound of Formula (Ia) wherein R$^2$ is

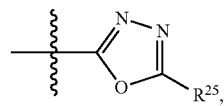

and R$^{25}$ is methyl. In a further embodiment of the aforementioned embodiments is a compound of Formula (Ia) wherein R$^2$ is

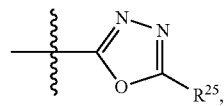

and R$^{25}$ is optionally substituted C$_1$-C$_6$alkyl. In a further embodiment of the aforementioned embodiments is a compound of Formula (Ia) wherein R$^2$ is

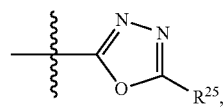

and R$^{25}$ is ethyl.

In a further embodiment of the aforementioned embodiments is a compound of Formula (Ia) wherein R$^1$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (Ia) wherein $R^1$ is hydrogen. In a further embodiment of the aforementioned embodiments is a compound of Formula (Ia) wherein $R^1$ is optionally substituted $C_1$-$C_6$alkyl. In a further embodiment of the aforementioned embodiments is a compound of Formula (Ia) wherein $R^1$ is methyl. In a further embodiment of the aforementioned embodiments is a compound of Formula (Ia) wherein $R^1$ is optionally substituted $C_2$-$C_6$alkenyl. In a further embodiment of the aforementioned embodiments is a compound of Formula (Ia) wherein $R^1$ is optionally substituted $C_2$-$C_6$alkynyl.

In a further embodiment of the aforementioned embodiments is a compound of Formula (Ia) wherein $R^1$ and $R^2$ together with the carbon atoms to which they are attached, form an optionally substituted $C_2$-$C_9$heterocycloalkyl ring or an optionally substituted heteroaryl ring. In a further embodiment of the aforementioned embodiments is a compound of Formula (Ia) wherein $R^1$ and $R^2$ together with the carbon atoms to which they are attached, form an optionally substituted $C_2$-$C_9$heterocycloalkyl ring. In a further embodiment of the aforementioned embodiments is a compound of Formula (Ia) wherein $R^1$ and $R^2$ together with the carbon atoms to which they are attached, form an optionally substituted heteroaryl ring.

In a further embodiment of the aforementioned embodiments is a compound of Formula (Ia) wherein $R^8$ is selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl). In a further embodiment of the aforementioned embodiments is a compound of Formula (Ia) wherein $R^8$ is selected from the group consisting of hydrogen, and optionally substituted $C_1$-$C_6$alkyl. In a further embodiment of the aforementioned embodiments is a compound of Formula (Ia) wherein $R^8$ is optionally substituted $C_1$-$C_6$alkyl. In a further embodiment of the aforementioned embodiments is a compound of Formula (Ia) wherein $R^8$ is methyl. In a further embodiment of the aforementioned embodiments is a compound of Formula (Ia) wherein $R^8$ is optionally substituted $C_1$-$C_6$alkyl. In a further embodiment of the aforementioned embodiments is a compound of Formula (Ia) wherein $R^8$ is ethyl. In a further embodiment of the aforementioned embodiments is a compound of Formula (Ia) wherein $R^8$ is optionally substituted $C_1$-$C_6$alkyl. In a further embodiment of the aforementioned embodiments is a compound of Formula (Ia) wherein $R^8$ is hydrogen.

In another embodiment of the aforementioned embodiments is a compound of Formula (Ia) wherein $R^{15}$ is —OC(=J)O$R^{16a}$. In another embodiment of the aforementioned embodiments is a compound of Formula (Ia) wherein $R^{15}$ is —N($R^{12}$)C(=J)O$R^{16a}$. In another embodiment of the aforementioned embodiments is a compound of Formula (Ia) wherein $R^{15}$ is —OC(=J)N(H)$R^{16a}$. In another embodiment of the aforementioned embodiments is a compound of Formula (Ia) wherein $R^{15}$ is —N($R^{12}$)C(=J)N(H)$R^{16a}$. In another embodiment of the aforementioned embodiments is a compound of Formula (Ia) wherein $R^{15}$ is —OC(=J)N(H)($C_2$-$C_6$alkyl)$R^{30}$. In another embodiment of the aforementioned embodiments is a compound of Formula (Ia) wherein $R^{15}$ is —N($R^{12}$)C(=J)O($C_2$-$C_6$alkyl)$R^{30}$. In another embodiment of the aforementioned embodiments is a compound of Formula (Ia) wherein $R^{15}$ is —N($R^{12}$)C(=J)N(H)($C_2$-$C_6$alkyl)$R^{30}$. In another embodiment of the aforementioned embodiments is a compound of Formula (Ia) wherein $R^{15}$ is —OC(=J)O($C_2$-$C_6$alkyl)$R^{30}$. In another embodiment of the aforementioned embodiments is a compound of Formula (Ia) wherein $R^{15}$ is —C(=J)$R^{31}$. In another embodiment of the aforementioned embodiments is a compound of Formula (Ia) wherein $R^{15}$ is —OC(=J)$R^{31}$.

In another embodiment of the aforementioned embodiments is a compound of Formula (Ia) wherein $R^{15}$ is —N($R^{12}$)C(=J)$R^{31}$. In another embodiment of the aforementioned embodiments is a compound of Formula (Ia) wherein $R^{15}$ is —O($C_2$-$C_6$alkyl)$R^{30}$. In another embodiment of the aforementioned embodiments is a compound of Formula (Ia) wherein $R^{15}$ is —N($R^{12}$)($C_2$-$C_6$alkyl)$R^{30}$. In another embodiment of the aforementioned embodiments is a compound of Formula (Ia) wherein $R^{15}$ is —OS(=O)$_v R^{31}$. In another embodiment of the aforementioned embodiments is a compound of Formula (Ia) wherein $R^{15}$ is —N($R^{12}$)S(=O)$_v R^{31}$. In another embodiment of the aforementioned embodiments is a compound of Formula (Ia) wherein $R^{15}$ is —OS(=O)$_v$($C_2$-$C_6$alkyl)$R^{30}$. In another embodiment of the aforementioned embodiments is a compound of Formula (Ia) wherein $R^{15}$ is —N($R^{12}$)S(=O)$_v$($C_2$-$C_6$alkyl)$R^{30}$. In a further embodiment of the aforementioned embodiments is a compound of Formula (Ia) wherein $R^{30}$ is $R^{16a}$. In a further embodiment of the aforementioned embodiments is a compound of Formula (Ia) wherein $R^{30}$ is $R^{16b}$. In a further embodiment of the aforementioned embodiments is a compound of Formula (Ia) wherein $R^{30}$ is $R^{16c}$. In a further embodiment of the aforementioned embodiments is a compound of Formula (Ia) wherein $R^{31}$ is $R^{16a}$. In a further embodiment of the aforementioned embodiments is a compound of Formula (Ia) wherein $R^{31}$ is $R^{16b}$. In a further embodiment of the aforementioned embodiments is a compound of Formula (Ia) wherein J is O. In a further embodiment of the aforementioned embodiments is a compound of Formula (Ia) wherein J is S. In a further embodiment of the aforementioned embodiments is a compound of Formula (Ia) wherein J is N($R^{12}$).

In another embodiment of the aforementioned embodiments is a compound of Formula (Ia) wherein $R^{16a}$ is

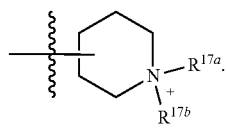

In another embodiment of the aforementioned embodiments is a compound of Formula (Ia) wherein $R^{16a}$ is

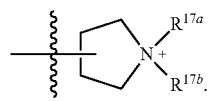

In another embodiment of the aforementioned embodiments is a compound of Formula (Ia) wherein $R^{16a}$ is

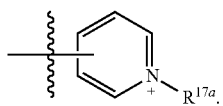

In another embodiment of the aforementioned embodiments is a compound of Formula (Ia) wherein $R^{16b}$ is

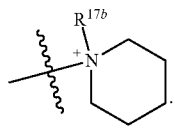

In another embodiment of the aforementioned embodiments is a compound of Formula (Ia) wherein $R^{16b}$ is

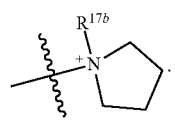

In another embodiment of the aforementioned embodiments is a compound of Formula (Ia) wherein $R^{16b}$ is

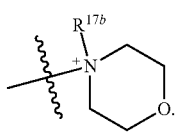

In another embodiment of the aforementioned embodiments is a compound of Formula (Ia) wherein $R^{16b}$ is

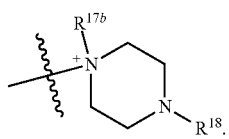

In another embodiment of the aforementioned embodiments is a compound of Formula (Ia) wherein $R^{16b}$ is

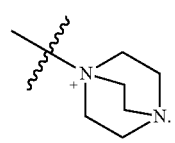

In another embodiment of the aforementioned embodiments is a compound of Formula (Ia) wherein $R^{16b}$ is

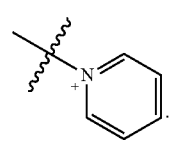

In another embodiment of the aforementioned embodiments is a compound of Formula (Ia) wherein $R^{16b}$ is

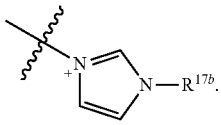

In another embodiment of the aforementioned embodiments is a compound of Formula (Ia) wherein $R^{16c}$ is

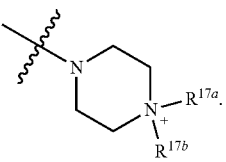

In another embodiment is a compound of Formula (Ia) wherein $R^{16c}$ is

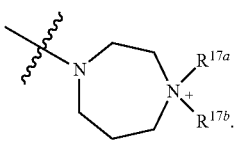

In a further embodiment of the aforementioned embodiments is a compound of Formula (Ia) wherein $R^{17a}$ is methyl. In a further embodiment of the aforementioned embodiments is a compound of Formula (Ia) wherein $R^{17a}$ is ethyl. In a further embodiment of the aforementioned embodiments is a compound of Formula (Ia) wherein $R^{17b}$ is methyl optionally substituted with phenyl, —C(=O)OH or —S(=O)$_2$OH. In a further embodiment of the aforementioned embodiments is a compound of Formula (Ia) wherein $R^{17a}$ is ethyl optionally substituted with phenyl, —C(=O)OH or —S(=O)$_2$OH.

In another embodiment of the aforementioned embodiments is a compound of Formula (Ia) wherein n is 0. In another embodiment of the aforementioned embodiments is a compound of Formula (Ia) wherein n is 1. In another embodiment of the aforementioned embodiments is a compound of Formula (Ia) wherein n is 1 and $R^{11}$ is $C_1$-$C_6$alkyl. In another embodiment of the aforementioned embodiments is a compound of Formula (Ia) wherein n is 1 and $R^{11}$ is $C_1$-$C_6$haloalkyl.

In another embodiment is a compound of Formula (Ia) wherein $R^{15}$ is —OC(=J)O$R^{16a}$, —N($R^{12}$)C(=J)O$R^{16a}$, —OC(=J)N(H)$R^{16a}$, —N($R^{12}$)C(=J)N(H)$R^{16a}$, —OC(=J)N(H)($C_1$-$C_6$alkyl)$R^{31}$, —N($R^{12}$)C(=J)O($C_1$-$C_6$alkyl)$R^{31}$, —N($R^{12}$)C(=J)N(H)($C_1$-$C_6$alkyl)$R^{31}$, —OC(=J)O($C_1$-$C_6$alkyl)$R^{31}$, —C(=J)$R^{31}$, —OC(=J)$R^{31}$, —N($R^{12}$)C(=J)$R^{31}$, —O($C_1$-$C_6$alkyl)$R^{31}$, —N($R^{12}$)($C_1$-$C_6$alkyl)$R^{31}$, —OS(=O)$_v$$R^{31}$, —N($R^{12}$)S(=O)$_v$$R^{31}$, —OS(=O)$_v$($C_1$-$C_6$alkyl)$R^{31}$, or —N($R^{12}$)S(=O)$_v$($C_1$-$C_6$alkyl)$R^{31}$.

In some embodiments provided herein, the compound of Formula (I) has the structure of Formula (Ib), or a pharmaceutically acceptable salt or solvate thereof:

Formula (Ib)

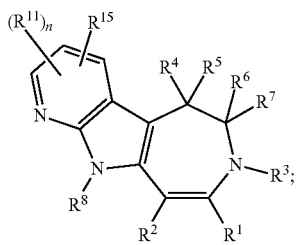

wherein:

R¹ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

R² is selected from the group consisting of —CN, —C(=O)OR²⁵, —C(=O)N(R²⁵)R²⁶,

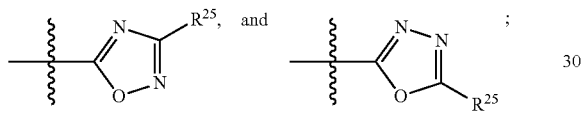

or R¹ and R² together with the carbon atoms to which they are attached, form an optionally substituted $C_2$-$C_9$heterocycloalkyl ring or an optionally substituted heteroaryl ring;

R³ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_{10}$cycloalkyl, optionally substituted aryl, optionally substituted —($C_1$-$C_2$alkylene)-(aryl), optionally substituted heteroaryl, optionally substituted $C_2$-$C_9$heterocycloalkyl, optionally substituted —($C_1$-$C_2$alkylene)-(heteroaryl), —C(=O)R²⁰, —C(=O)OR²⁰, —S(=O)₂R²⁰, —C(=O)N(R²¹)R²², —C(=O)N(R²¹)S(=O)₂R²⁴, —C(=O)N(R²³)N(R²¹)R²², —C(=O)N(R²³)N(R²¹)S(=O)₂R²⁴, —N(R²³)C(=O)R²⁰, —N(R²³)C(=O)N(R²¹)R²², —N(R²³)C(=O)N(R²¹)S(=O)₂R²⁴, —N(R²⁰)C(=O)N(R²³)N(R²¹)R²², —N(R²⁰)C(=O)N(R²³)N(R²¹)S(=O)₂R²⁴, —N(R²³)C(=O)OR²⁰, —P(=O)OR²⁰, and —P(=O)(OR¹⁹)OR²⁰;

R⁴ and R⁵ are each independently selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl; or R⁴ and R⁵ together with the carbon atom to which they are attached, form an optionally substituted $C_3$-$C_6$cycloalkyl ring or an optionally substituted $C_2$-$C_7$heterocycloalkyl ring;

R⁶ is selected from the group consisting of hydrogen, halogen, optionally substituted $C_1$-$C_6$alkyl, optionally substituted $C_2$-$C_6$alkenyl, optionally substituted $C_2$-$C_6$alkynyl, and —C(=O)N(R²⁷)R²⁸;

R⁷ is selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl;

R⁸ is selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl);

each R¹¹ is independently selected from the group consisting of halogen, —CN, amino, alkylamino, $C_1$-$C_6$alkyl, $C_1$-$C_6$haloalkyl, $C_1$-$C_6$alkoxy, $C_1$-$C_6$haloalkoxy, $C_3$-$C_8$cycloalkyl, $C_2$-$C_9$heterocycloalkyl, aryl, heteroaryl, —C(=O)OR¹², —C(=O)N(R¹³)R¹⁴;

each R¹² is independently selected from the group consisting of hydrogen and $C_1$-$C_6$alkyl;

each R¹³ and R¹⁴ are each independently selected from the group consisting of hydrogen and $C_1$-$C_6$alkyl; or R¹³ and R¹⁴ together with the nitrogen atom to which they are attached, form an optionally substituted $C_2$-$C_9$heterocycloalkyl ring;

R¹⁵ is —OC(=J)OR¹⁶ᵃ, —N(R¹²)C(=J)OR¹⁶ᵃ, —OC(=J)N(H)R¹⁶ᵃ, —N(R¹²)C(=J)N(H)R¹⁶ᵃ, —OC(=J)N(H)($C_2$-$C_6$alkyl)R³⁰, —N(R¹²)C(=J)O($C_2$-$C_6$alkyl)R³⁰, —N(R¹²)C(=J)N(H)($C_2$-$C_6$alkyl)R³⁰, —OC(=J)O($C_2$-$C_6$alkyl)R³⁰, —C(=J)R³¹, —OC(=J)R³¹, —N(R¹²)C(=J)R³¹, —O($C_2$-$C_6$alkyl)R³⁰, —N(R¹²)($C_2$-$C_6$alkyl)R³⁰, —OS(=O)ᵥR³¹, —N(R¹²)S(=O)ᵥR³¹, —OS(=O)ᵥ($C_2$-$C_6$alkyl)R³⁰, or —N(R¹²)S(=O)ᵥ($C_2$-$C_6$alkyl)R³⁰;

R³⁰ is R¹⁶ᵃ, R¹⁶ᵇ, or R¹⁶ᶜ;

R³¹ is R¹⁶ᵃ or R¹⁶ᶜ;

J is O, S, or N(R¹²);

R¹⁶ᵃ is

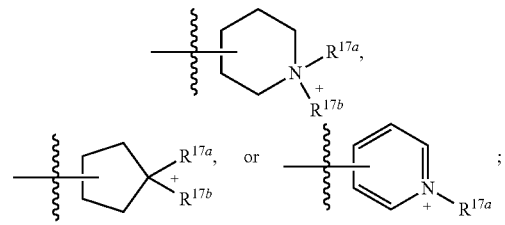

R¹⁶ᵇ is

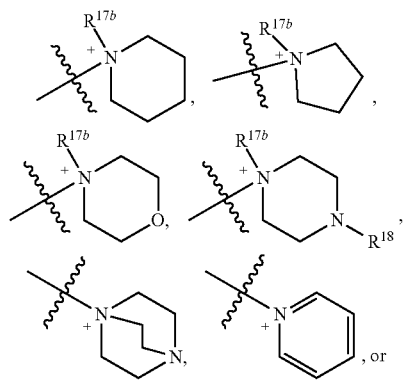

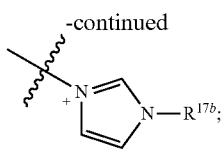

$R^{16c}$ is

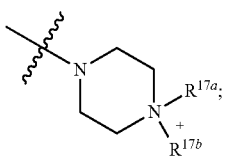

$R^{17a}$ is $C_1$-$C_6$alkyl;
$R^{17b}$ is $C_1$-$C_6$alkyl optionally substituted with phenyl, —C(=O)OH or —S(=O)$_2$OH;
$R^{18}$ is hydrogen, —OH, —(C$_0$-C$_6$alkyl)-C(=O)OH, or $C_1$-$C_6$alkyl;
n is 0, 1, or 2;
v is 1 or 2;
$R^{19}$, $R^{20}$, and $R^{23}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —(C$_1$-$C_2$alkylene)-(aryl), optionally substituted $C_2$-$C_9$heterocycloalkyl, optionally substituted heteroaryl, and optionally substituted —(C$_1$-$C_2$alkylene)-(heteroaryl);
$R^{21}$ and $R^{22}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —(C$_1$-$C_2$alkylene)-(aryl), optionally substituted $C_2$-$C_9$heterocycloalkyl, optionally substituted heteroaryl, and optionally substituted —(C$_1$-$C_2$alkylene)-(heteroaryl); or $R^{21}$ and $R^{22}$ together with the nitrogen atom to which they are attached, form an optionally substituted $C_2$-$C_9$heterocycloalkyl ring;
$R^{24}$ is selected from the group consisting of optionally substituted $C_1$-$C_6$alkyl, optionally substituted $C_2$-$C_6$alkenyl, optionally substituted $C_2$-$C_6$alkynyl, optionally substituted $C_3$-$C_5$ cycloalkyl, optionally substituted aryl optionally substituted —(C$_1$-$C_2$alkylene)-(aryl), optionally substituted $C_2$-$C_9$heterocycloalkyl, optionally substituted heteroaryl, and optionally substituted —(C$_1$-$C_2$alkylene)-(heteroaryl); and
$R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —(C$_1$-$C_2$alkylene)-(aryl), optionally substituted $C_2$-$C_9$heterocycloalkyl, optionally substituted heteroaryl, and optionally substituted —(C$_1$-$C_2$alkylene)-(heteroaryl);
$R^{27}$ and $R^{28}$ are each independently selected from the group consisting of hydrogen, optionally substituted $C_1$-$C_6$alkyl, optionally substituted $C_3$-$C_8$cycloalkyl, optionally substituted aryl, optionally substituted —(C$_1$-$C_2$alkylene)-(aryl), optionally substituted $C_2$-$C_9$heterocycloalkyl, optionally substituted heteroaryl, and optionally substituted —(C$_1$-$C_2$alkylene)-(heteroaryl); or $R^{27}$ and $R^{28}$ together with the nitrogen atom to which they are attached, form an optionally substituted $C_2$-$C_9$heterocycloalkyl ring.

In one embodiment is a compound of Formula (Ib) wherein $R^4$ and $R^5$ are each independently selected from the group consisting of hydrogen, halogen, and optionally substituted $C_1$-$C_6$alkyl. In another embodiment is a compound of Formula (Ib) wherein $R^4$ and $R^5$ are each independently selected from the group consisting of hydrogen and optionally substituted $C_1$-$C_6$alkyl. In another embodiment is a compound of Formula (Ib) wherein $R^4$ and $R^5$ are each hydrogen. In another embodiment is a compound of Formula (Ib) wherein $R^4$ and $R^5$ are each independently optionally substituted $C_1$-$C_6$alkyl. In another embodiment is a compound of Formula (Ib) wherein $R^4$ and $R^5$ are each methyl. In another embodiment is a compound of Formula (Ib) wherein $R^4$ and $R^5$ form an optionally substituted $C_3$-$C_6$cycloalkyl ring or an optionally substituted $C_2$-$C_7$heterocycloalkyl ring. In some embodiments is a compound of Formula (Ib) wherein $R^4$ and $R^5$ form an optionally substituted $C_3$-$C_6$cycloalkyl ring. In some embodiments is a compound of Formula (Ib) wherein $R^4$ and $R^5$ form an optionally substituted $C_2$-$C_7$heterocycloalkyl ring.

In another embodiment is a compound of Formula (Ib) wherein $R^6$ and $R^7$ are each independently selected from the group consisting of hydrogen, halogen, and optionally substituted $C_1$-$C_6$alkyl. In another embodiment is a compound of Formula (Ib) wherein $R^6$ and $R^7$ are each independently selected from the group consisting of hydrogen and optionally substituted $C_1$-$C_6$alkyl. In another embodiment is a compound of Formula (Ib) wherein $R^6$ and $R^7$ are each independently optionally substituted $C_1$-$C_6$alkyl. In another embodiment is a compound of Formula (Ib) wherein $R^6$ and $R^7$ are each methyl. In another embodiment is a compound of Formula (Ib) wherein $R^6$ and $R^7$ are each hydrogen.

In another embodiment is a compound of Formula (Ib) wherein $R^6$ and $R^7$ are hydrogen, $R^4$ and $R^5$ are independently optionally substituted $C_1$-$C_6$alkyl, $R^3$ is —C(O)R$^{20}$, and $R^{20}$ is optionally substituted aryl. In another embodiment is a compound of Formula (Ib) wherein $R^6$ and $R^7$ are hydrogen, $R^4$ and $R^5$ are independently optionally substituted $C_1$-$C_6$alkyl, $R^3$ is —C(O)R$^{20}$, and $R^{20}$ is optionally substituted heteroaryl. In another embodiment is a compound of Formula (Ib) wherein $R^6$ and $R^7$ are hydrogen, $R^4$ and $R^5$ are methyl, $R^3$ is —C(O)R$^{20}$, and $R^{20}$ is optionally substituted aryl. In another embodiment is a compound of Formula (Ib) wherein $R^6$ and $R^7$ are hydrogen, $R^4$ and $R^5$ are methyl, $R^3$ is —C(O)R$^{20}$, and $R^{20}$ is optionally substituted heteroaryl.

In another embodiment is a compound of Formula (Ib) wherein $R^6$ and $R^7$ are hydrogen, $R^4$ and $R^5$ are independently optionally substituted $C_1$-$C_6$alkyl, $R^3$ is —S(O)$_2$R$^{20}$, and $R^{20}$ is optionally substituted aryl. In another embodiment is a compound of Formula (Ib) wherein $R^6$ and $R^7$ are hydrogen, $R^4$ and $R^5$ are independently optionally substituted $C_1$-$C_6$alkyl, $R^3$ is —S(O)$_2$R$^{20}$, and $R^{20}$ is optionally substituted heteroaryl. In another embodiment is a compound of Formula (Ib) wherein $R^6$ and $R^7$ are hydrogen, $R^4$ and $R^5$ are methyl, $R^3$ is —S(O)$_2$R$^{20}$, and $R^{20}$ is optionally substituted aryl. In another embodiment is a compound of Formula (Ib) wherein $R^6$ and $R^7$ are hydrogen, $R^4$ and $R^5$ are methyl, $R^3$ is —S(O)$_2$R$^{20}$, and $R^{20}$ is optionally substituted heteroaryl.

In another embodiment is a compound of Formula (Ib) wherein $R^6$ and $R^7$ are hydrogen, $R^4$ and $R^5$ are independently optionally substituted $C_1$-$C_6$alkyl, $R^3$ is —C(O)N($R^{21}$)$R^{22}$, $R^{21}$ is hydrogen and $R^{22}$ is optionally substituted aryl. In another embodiment is a compound of Formula (Ib) wherein $R^6$ and $R^7$ are hydrogen, $R^4$ and $R^5$ are independently optionally substituted $C_1$-$C_6$alkyl, $R^3$ is —C(O)N($R^{21}$)$R^{22}$, $R^{21}$ is hydrogen and $R^{22}$ is optionally substituted heteroaryl. In another embodiment is a compound of Formula (Ib) wherein $R^6$ and $R^7$ are hydrogen, $R^4$ and $R^5$ are methyl, $R^3$ is —C(O)N($R^{21}$)$R^{22}$, $R^{21}$ is hydrogen and $R^{22}$ is optionally substituted aryl. In another embodiment is a compound of Formula (Ib) wherein $R^6$ and $R^7$ are hydrogen, $R^4$ and $R^5$ are methyl, $R^3$ is —C(O)N($R^{21}$)$R^{22}$, $R^{21}$ is hydrogen and $R^{22}$ is optionally substituted heteroaryl.

In a further embodiment of the aforementioned embodiments is a compound of Formula (Ib) wherein $R^2$ is selected from the group consisting of —CN, —C(O)O$R^{25}$, —C(O)N($R^{25}$)$R^{26}$,

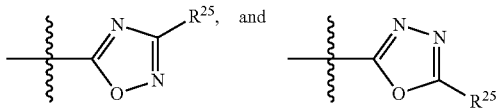

In a further embodiment of the aforementioned embodiments is a compound of Formula (Ib) wherein $R^2$ is —CN.

In a further embodiment of the aforementioned embodiments is a compound of Formula (Ib) wherein $R^2$ is —C(O)O$R^{25}$. In a further embodiment of the aforementioned embodiments is a compound of Formula (Ib) wherein $R^2$ is —C(O)O$R^{25}$, and $R^{25}$ is independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (Ib) wherein $R^2$ is —C(O)O$R^{25}$, and $R^{25}$ is independently selected from the group consisting of hydrogen, and optionally substituted $C_1$-$C_6$alkyl. In a further embodiment of the aforementioned embodiments is a compound of Formula (Ib) wherein $R^2$ is —C(O)O$R^{25}$, and $R^{25}$ is hydrogen. In a further embodiment of the aforementioned embodiments is a compound of Formula (Ib) wherein $R^2$ is —C(O)O$R^{25}$, and $R^{25}$ is optionally substituted $C_1$-$C_6$alkyl. In a further embodiment of the aforementioned embodiments is a compound of Formula (Ib) wherein $R^2$ is —C(O)O$R^{25}$, and $R^{25}$ is unsubstituted $C_1$-$C_6$alkyl. In a further embodiment of the aforementioned embodiments is a compound of Formula (Ib) wherein $R^2$ is —C(O)O$R^{25}$, and $R^{25}$ is methyl. In a further embodiment of the aforementioned embodiments is a compound of Formula (Ib) wherein $R^2$ is —C(O)O$R^{25}$, and $R^{25}$ is ethyl.

In a further embodiment of the aforementioned embodiments is a compound of Formula (Ib) wherein $R^2$ is —C(O)N($R^{25}$)$R^{26}$. In a further embodiment of the aforementioned embodiments is a compound of Formula (Ib) wherein $R^2$ is —C(O)N($R^{25}$)$R^{26}$, and $R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (Ib) wherein $R^2$ is —C(O)N($R^{25}$)$R^{26}$, and $R^{25}$ and $R^{26}$ are each independently selected from the group consisting of hydrogen, and optionally substituted $C_1$-$C_6$alkyl. In a further embodiment of the aforementioned embodiments is a compound of Formula (Ib) wherein $R^2$ is —C(O)N($R^{25}$)$R^{26}$, and $R^{25}$ and $R^{26}$ are hydrogen. In a further embodiment of the aforementioned embodiments is a compound of Formula (Ib) wherein $R^2$ is —C(O)N($R^{25}$)$R^{26}$, and $R^{25}$ and $R^{26}$ are each independently optionally substituted $C_1$-$C_6$alkyl. In a further embodiment of the aforementioned embodiments is a compound of Formula (Ib) wherein $R^2$ is —C(O)N($R^{25}$)$R^{26}$, $R^{25}$ is hydrogen, and $R^{26}$ is optionally substituted $C_1$-$C_6$alkyl. In a further embodiment of the aforementioned embodiments is a compound of Formula (Ib) wherein $R^2$ is —C(O)N($R^{25}$)$R^{26}$, and $R^{25}$ and $R^{26}$ are each independently unsubstituted $C_1$-$C_6$alkyl. In a further embodiment of the aforementioned embodiments is a compound of Formula (Ib) wherein $R^2$ is —C(O)N($R^{25}$)$R^{26}$, $R^{25}$ is hydrogen, and $R^{26}$ are methyl. In a further embodiment of the aforementioned embodiments is a compound of Formula (Ib) wherein $R^2$ is —C(O)N($R^{25}$)$R^{26}$, and $R^{25}$ and $R^{26}$ are methyl. In a further embodiment of the aforementioned embodiments is a compound of Formula (Ib) wherein $R^2$ is —C(O)N($R^{25}$)$R^{26}$, and $R^{25}$ and $R^{26}$ are ethyl.

In a further embodiment of the aforementioned embodiments is a compound of Formula (Ib) wherein $R^2$ is

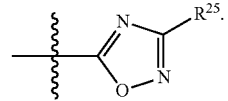

In a further embodiment of the aforementioned embodiments is a compound of Formula (Ib) wherein $R^2$ is

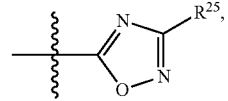

and $R^{25}$ is optionally substituted $C_1$-$C_6$alkyl. In a further embodiment of the aforementioned embodiments is a compound of Formula (Ib) wherein $R^2$ is

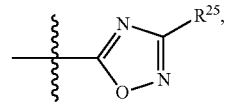

and $R^{25}$ is methyl. In a further embodiment of the aforementioned embodiments is a compound of Formula (Ib) wherein $R^2$ is

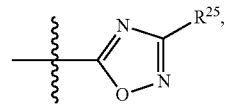

and $R^{25}$ is optionally substituted $C_1$-$C_6$alkyl. In a further embodiment of the aforementioned embodiments is a compound of Formula (Ib) wherein $R^2$ is

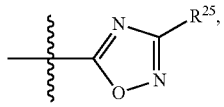

and $R^{25}$ is ethyl.

In a further embodiment of the aforementioned embodiments is a compound of Formula (Ib) wherein $R^2$ is

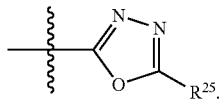

In a further embodiment of the aforementioned embodiments is a compound of Formula (Ib) wherein $R^2$ is

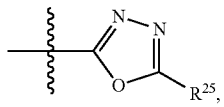

and $R^{25}$ is optionally substituted $C_1$-$C_6$alkyl. In a further embodiment of the aforementioned embodiments is a compound of Formula (Ib) wherein $R^2$ is

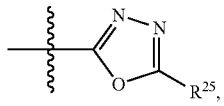

and $R^{25}$ is methyl. In a further embodiment of the aforementioned embodiments is a compound of Formula (Ib) wherein $R^2$ is

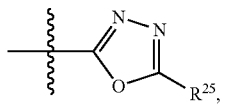

and $R^{25}$ is optionally substituted $C_1$-$C_6$alkyl. In a further embodiment of the aforementioned embodiments is a compound of Formula (Ib) wherein $R^2$ is

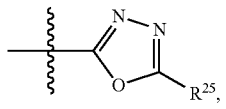

and $R^{25}$ is ethyl.

In a further embodiment of the aforementioned embodiments is a compound of Formula (Ib) wherein $R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (Ib) wherein $R^1$ is hydrogen. In a further embodiment of the aforementioned embodiments is a compound of Formula (Ib) wherein $R^1$ is optionally substituted $C_1$-$C_6$alkyl. In a further embodiment of the aforementioned embodiments is a compound of Formula (Ib) wherein $R^1$ is methyl. In a further embodiment of the aforementioned embodiments is a compound of Formula (Ib) wherein $R^1$ is optionally substituted $C_2$-$C_6$alkenyl. In a further embodiment of the aforementioned embodiments is a compound of Formula (Ib) wherein $R^1$ is optionally substituted $C_2$-$C_6$alkynyl.

In a further embodiment of the aforementioned embodiments is a compound of Formula (Ib) wherein $R^1$ and $R^2$ together with the carbon atoms to which they are attached, form an optionally substituted $C_2$-$C_9$heterocycloalkyl ring or an optionally substituted heteroaryl ring. In a further embodiment of the aforementioned embodiments is a compound of Formula (Ib) wherein $R^1$ and $R^2$ together with the carbon atoms to which they are attached, form an optionally substituted $C_2$-$C_9$heterocycloalkyl ring. In a further embodiment of the aforementioned embodiments is a compound of Formula (Ib) wherein $R^1$ and $R^2$ together with the carbon atoms to which they are attached, form an optionally substituted heteroaryl ring.

In a further embodiment of the aforementioned embodiments is a compound of Formula (Ib) wherein $R^8$ is selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl). In a further embodiment of the aforementioned embodiments is a compound of Formula (Ib) wherein $R^8$ is selected from the group consisting of hydrogen, and optionally substituted $C_1$-$C_6$alkyl. In a further embodiment of the aforementioned embodiments is a compound of Formula (Ib) wherein $R^8$ is optionally substituted $C_1$-$C_6$alkyl. In a further embodiment of the aforementioned embodiments is a compound of Formula (Ib) wherein $R^8$ is methyl. In a further embodiment of the aforementioned embodiments is a compound of Formula (Ib) wherein $R^8$ is optionally substituted $C_1$-$C_6$alkyl. In a further embodiment of the aforementioned embodiments is a compound of Formula (Ib) wherein $R^8$ is ethyl. In a further embodiment of the aforementioned embodiments is a compound of Formula (Ib) wherein $R^8$ is optionally substituted $C_1$-$C_6$alkyl. In a further embodiment of the aforementioned embodiments is a compound of Formula (Ib) wherein $R^8$ is hydrogen.

In another embodiment of the aforementioned embodiments is a compound of Formula (Ib) wherein $R^{15}$ is —OC(=J)OR$^{16a}$. In another embodiment of the aforementioned embodiments is a compound of Formula (Ib) wherein $R^{15}$ is —N(R$^{12}$)C(=J)OR$^{16a}$. In another embodiment of the aforementioned embodiments is a compound of Formula (Ib) wherein $R^{15}$ is —OC(=J)N(H)R$^{16a}$ In another embodiment of the aforementioned embodiments is a compound of Formula (Ib) wherein $R^{15}$ is —N(R$^{12}$)C(=J)N(H)R$^{16a}$. In another embodiment of the aforementioned embodiments is a compound of Formula (Ib) wherein $R^{15}$ is —OC(=J)N(H)($C_2$-$C_6$alkyl)R$^{30}$. In another embodiment of the aforementioned embodiments is a compound of Formula (Ib) wherein $R^{15}$ is —N($R^{12}$)C(=J)O($C_2$-$C_6$alkyl)$R^{30}$. In another embodiment of the aforementioned embodiments is a compound of Formula (Ib) wherein $R^{15}$ is —N($R^{12}$)C(=J)N(H)($C_2$-$C_6$alkyl)$R^{30}$. In another embodiment of the aforementioned embodiments is a compound of Formula (Ib) wherein $R^{15}$ is —OC(=J)O($C_2$-$C_6$alkyl)$R^{30}$. In another embodiment of the aforementioned embodiments is a compound of Formula (Ib) wherein $R^{15}$ is —C(=J)$R^{31}$. In another embodiment of the aforementioned embodiments is a compound of Formula (Ib) wherein $R^{15}$ is —OC(=J)$R^{31}$. In another embodiment of the aforementioned embodiments is a compound of Formula (Ib) wherein $R^{15}$ is —N($R^{12}$)C(=J)$R^{31}$. In another embodiment of the aforementioned embodiments is a compound of Formula (Ib) wherein $R^{15}$ is —O($C_2$-$C_6$alkyl)$R^{30}$. In another embodiment of the aforementioned embodiments is a compound of Formula (Ib) wherein $R^{15}$ is —N($R^{12}$)($C_2$-$C_6$alkyl)$R^{30}$. In another embodiment of the aforementioned embodiments is a compound of Formula (Ib) wherein $R^{15}$ is —OS(=O)$_v$$R^{31}$. In another embodiment of the aforementioned embodiments is a compound of Formula (Ib) wherein $R^{15}$ is —N($R^{12}$)S(=O)$_v$$R^{31}$. In another embodiment of the aforementioned embodiments is a compound of Formula (Ib) wherein $R^{15}$ is —OS(=O)$_v$($C_2$-$C_6$alkyl)$R^{30}$. In another embodiment of the aforementioned embodiments is a compound of Formula (Ib) wherein $R^{15}$ is —N($R^{12}$)S(=O)$_v$($C_2$-$C_6$alkyl)$R^{30}$. In a further embodiment of the aforementioned embodiments is a compound of Formula (Ib) wherein $R^{30}$ is $R^{16a}$. In a further embodiment of the aforementioned embodiments is a compound of Formula (Ib) wherein $R^{30}$ is $R^{16b}$. In a further embodiment of the aforementioned embodiments is a compound of Formula (Ib) wherein $R^{30}$ is $R^{16c}$. In a further embodiment of the aforementioned embodiments is a compound of Formula (Ib) wherein $R^{31}$ is $R^{16a}$. In a further embodiment of the aforementioned embodiments is a compound of Formula (Ib) wherein $R^{31}$ is $R^{16b}$. In a further embodiment of the aforementioned embodiments is a compound of Formula (Ib) wherein J is O. In a further embodiment of the aforementioned embodiments is a compound of Formula (Ib) wherein J is S. In a further embodiment of the aforementioned embodiments is a compound of Formula (Ib) wherein J is N($R^{12}$).

In another embodiment of the aforementioned embodiments is a compound of Formula (Ib) wherein $R^{16a}$ is

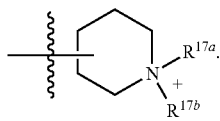

In another embodiment of the aforementioned embodiments is a compound of Formula (Ib) wherein $R^{16a}$ is

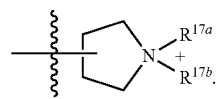

In another embodiment of the aforementioned embodiments is a compound of Formula (Ib) wherein $R^{16a}$ is

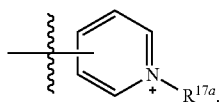

In another embodiment of the aforementioned embodiments is a compound of Formula (Ib) wherein $R^{16b}$ is

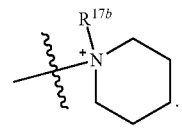

In another embodiment of the aforementioned embodiments is a compound of Formula (Ib) wherein $R^{16b}$ is

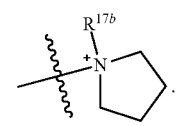

In another embodiment of the aforementioned embodiments is a compound of Formula (Ib) wherein $R^{16b}$ is

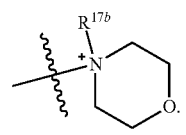

In another embodiment of the aforementioned embodiments is a compound of Formula (Ib) wherein $R^{16b}$ is

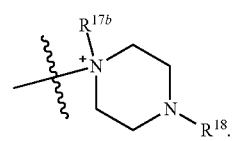

In another embodiment of the aforementioned embodiments is a compound of Formula (Ib) wherein $R^{16b}$ is

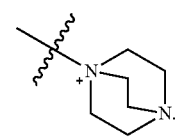 [SMILES: *[N+]12CCN(CC1)CC2]

In another embodiment of the aforementioned embodiments is a compound of Formula (Ib) wherein $R^{16b}$ is

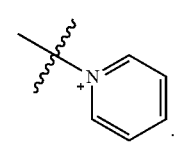 [SMILES: *[n+]1ccccc1]

In another embodiment of the aforementioned embodiments is a compound of Formula (Ib) wherein $R^{16b}$ is

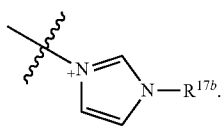

In another embodiment of the aforementioned embodiments is a compound of Formula (Ib) wherein $R^{16c}$ is

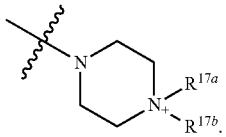

In another embodiment is a compound of Formula (Ib) wherein $R^{16c}$ is

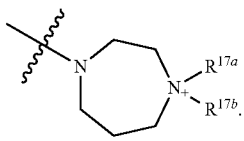

In a further embodiment of the aforementioned embodiments is a compound of Formula (Ib) wherein $R^{17a}$ is methyl. In a further embodiment of the aforementioned embodiments is a compound of Formula (Ib) wherein $R^{17a}$ is ethyl. In a further embodiment of the aforementioned embodiments is a compound of Formula (Ib) wherein $R^{17b}$ is methyl optionally substituted with phenyl, —C(=O)OH or —S(=O)$_2$OH. In a further embodiment of the aforementioned embodiments is a compound of Formula (Ib) wherein $R^{17a}$ is ethyl optionally substituted with phenyl, —C(=O)OH or —S(=O)$_2$OH.

In another embodiment of the aforementioned embodiments is a compound of Formula (Ib) wherein n is 0. In another embodiment of the aforementioned embodiments is a compound of Formula (Ib) wherein n is 1. In another embodiment of the aforementioned embodiments is a compound of Formula (Ib) wherein n is 1 and $R^{11}$ is $C_1$-$C_6$alkyl. In another embodiment of the aforementioned embodiments is a compound of Formula (Ib) wherein n is 1 and $R^{11}$ is $C_1$-$C_6$haloalkyl.

In another embodiment is a compound of Formula (Ib) wherein $R^{15}$ is —OC(=J)OR$^{16a}$, —N(R$^{12}$)C(=J)OR$^{16a}$, —OC(=J)N(H)R$^{16a}$, —N(R$^{12}$)C(=J)N(H)R$^{16a}$, —OC(=J)N(H)(C$_1$-C$_6$alkyl)R$^{31}$, —N(R$^{12}$)C(=J)O(C$_1$-C$_6$alkyl)R$^{31}$, —N(R$^{12}$)C(=J)N(H)(C$_1$-C$_6$alkyl)R$^{31}$, —OC(=J)O(C$_1$-C$_6$alkyl)R$^{31}$, —C(=J)R$^{31}$, —OC(=J)R$^{31}$, —N(R$^{12}$)C(=J)R$^{31}$, —O(C$_1$-C$_6$alkyl)R$^{31}$, —N(R$^{12}$)(C$_1$-C$_6$alkyl)R$^{31}$, —OS(=O)$_v$R$^{31}$, —N(R$^{12}$)S(=O)$_v$R$^{31}$, —OS(=O)$_v$(C$_1$-C$_6$alkyl)R$^{31}$, or —N(R$^{12}$)S(=O)$_v$(C$_1$-C$_6$alkyl)R$^{31}$.

In some embodiments provided herein, the compound of Formula (I) has the structure of Formula (Ic), or a pharmaceutically acceptable salt or solvate thereof:

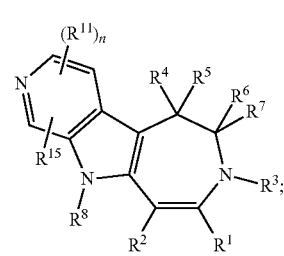

Formula (Ic)

wherein:
$R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R^2$ is selected from the group consisting of —CN, —C(=O)OR$^{25}$, —C(=O)N(R$^{25}$)R$^{26}$,

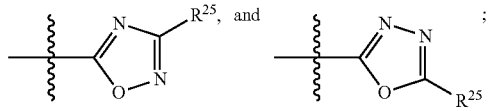

or $R^1$ and $R^2$ together with the carbon atoms to which they are attached, form an optionally substituted $C_2$-$C_9$heterocycloalkyl ring or an optionally substituted heteroaryl ring;

$R^3$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_{10}$cycloalkyl, optionally substituted aryl, optionally substituted —($C_1$-$C_2$alkylene)-(aryl), optionally substituted heteroaryl, optionally substituted $C_2$-$C_9$heterocycloalkyl, optionally substituted —($C_1$-$C_2$alkylene)-(heteroaryl), —C(=O)R$^{20}$, —C(=O)OR$^{20}$, —S(=O)$_2$R$^{20}$, —C(=O)N(R$^{21}$)R$^{22}$, —C(=O)N(R$^{21}$)S(=O)$_2$R$^{24}$, —C(=O)N(R$^{23}$)N(R$^{21}$)R$^{22}$, —C(=O)N(R$^{23}$)N(R$^{21}$)S(=O)$_2$R$^{24}$, —N(R$^{23}$)C(=O)R$^{20}$, —N(R$^{23}$)C(=O)N(R$^{21}$)R$^{22}$, —N(R$^{23}$)C(=O)N(R$^{21}$)S(=O)$_2$R$^{24}$, —N(R$^{20}$)C(=O)N(R$^{23}$)N(R$^{21}$)R$^{22}$, —N(R$^{20}$)C(=O)N(R$^{23}$)N(R$^{21}$)S(=O)$_2$R$^{24}$, —N(R$^{23}$)C(=O)OR$^{20}$, —P(=O)OR$^{20}$, and —P(=O)(OR$^{19}$)OR$^{20}$;

$R^4$ and $R^5$ are each independently selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl; or $R^4$ and $R^5$ together with the carbon atom to which they are attached, form an optionally substituted $C_3$-$C_6$cycloalkyl ring or an optionally substituted $C_2$-$C_7$heterocycloalkyl ring;

$R^6$ is selected from the group consisting of hydrogen, halogen, optionally substituted $C_1$-$C_6$alkyl, optionally substituted $C_2$-$C_6$alkenyl, optionally substituted $C_2$-$C_6$alkynyl, and —C(=O)N(R$^{27}$)R$^{28}$;

$R^7$ is selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl;

$R^8$ is selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl);

each $R^{11}$ is independently selected from the group consisting of halogen, —CN, amino, alkylamino, $C_1$-$C_6$alkyl, $C_1$-$C_6$haloalkyl, $C_1$-$C_6$alkoxy, $C_1$-$C_6$haloalkoxy, $C_3$-$C_8$cycloalkyl, $C_2$-$C_9$heterocycloalkyl, aryl, heteroaryl, —C(=O)OR$^{12}$, —C(=O)N(R$^{13}$)R$^{14}$;

each $R^{12}$ is independently selected from the group consisting of hydrogen and $C_1$-$C_6$alkyl;

each $R^{13}$ and $R^{14}$ are each independently selected from the group consisting of hydrogen and $C_1$-$C_6$alkyl; or $R^{13}$ and $R^{14}$ together with the nitrogen atom to which they are attached, form an optionally substituted $C_2$-$C_9$heterocycloalkyl ring;

$R^{15}$ is —OC(=J)OR$^{16a}$, —N(R$^{12}$)C(=J)OR$^{16a}$, —OC(=J)N(H)R$^{16a}$, —N(R$^{12}$)C(=J)N(H)R$^{16a}$, —OC(=J)N(H)(C$_2$-$C_6$alkyl)R$^{30}$, —N(R$^{12}$)C(=J)O(C$_2$-$C_6$alkyl)R$^{30}$, —N(R$^{12}$)C(=J)N(H)(C$_2$-$C_6$alkyl)R$^{30}$, —OC(=J)O(C$_2$-$C_6$alkyl)R$^{30}$, —C(=J)R$^{31}$, —OC(=J)R$^{31}$, —N(R$^{12}$)C(=J)R$^{31}$, —O(C$_2$-$C_6$alkyl)R$^{30}$, —N(R$^{12}$)(C$_2$-$C_6$alkyl)R$^{30}$, —OS(=O)$_v$R$^{31}$, —N(R$^{12}$)S(=O)$_v$R$^{31}$, —OS(=O)$_v$(C$_2$-$C_6$alkyl)R$^{30}$, or —N(R$^{12}$)S(=O)$_v$(C$_2$-$C_6$alkyl)R$^{30}$;

$R^{30}$ is $R^{16a}$, $R^{16b}$, or $R^{16c}$;

$R^{31}$ is $R^{16a}$ or $R^{16c}$;

J is O, S, or N(R$^{12}$);

$R^{16a}$ is

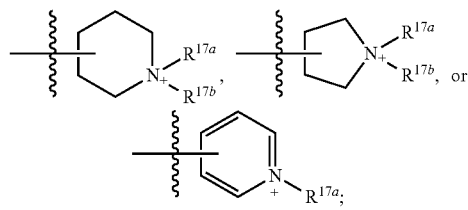

$R^{16b}$ is

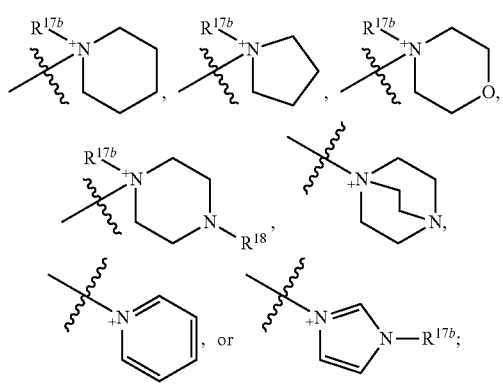

$R^{16c}$ is

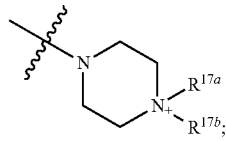

$R^{17a}$ is $C_1$-$C_6$alkyl;

$R^{17b}$ is $C_1$-$C_6$alkyl optionally substituted with phenyl, —C(=O)OH or —S(=O)$_2$OH;

$R^{18}$ is hydrogen, —OH, —(C$_0$-$C_6$alkyl)-C(=O)OH, or $C_1$-$C_6$alkyl;

n is 0, 1, or 2;

v is 1 or 2;

$R^{19}$, $R^{20}$, and $R^{23}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R^{21}$ and $R^{22}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{21}$ and $R^{22}$ together with the nitrogen atom to which they are attached, form an optionally substituted $C_2$-$C_9$heterocycloalkyl ring;

$R^{24}$ is selected from the group consisting of optionally substituted $C_1$-$C_6$alkyl, optionally substituted $C_2$-$C_6$alkenyl, optionally substituted $C_2$-$C_6$alkynyl, optionally substituted $C_3$-$C_8$ cycloalkyl, optionally substituted aryl optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); and $R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R^{27}$ and $R^{28}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{27}$ and $R^{28}$ together with the nitrogen atom to which they are attached, form an optionally substituted $C_2$-$C_9$heterocycloalkyl ring.

In one embodiment is a compound of Formula (Ic) wherein $R^4$ and $R^5$ are each independently selected from the group consisting of hydrogen, halogen, and optionally substituted $C_1$-$C_6$alkyl. In another embodiment is a compound of Formula (Ic) wherein $R^4$ and $R^5$ are each independently selected from the group consisting of hydrogen and optionally substituted $C_1$-$C_6$alkyl. In another embodiment is a compound of Formula (Ic) wherein $R^4$ and $R^5$ are each hydrogen. In another embodiment is a compound of Formula (Ic) wherein $R^4$ and $R^5$ are each independently optionally substituted $C_1$-$C_6$alkyl. In another embodiment is a compound of Formula (Ic) wherein $R^4$ and $R^5$ are each methyl. In another embodiment is a compound of Formula (Ic) wherein $R^4$ and $R^5$ form an optionally substituted $C_3$-$C_6$cycloalkyl ring or an optionally substituted $C_2$-$C_7$heterocycloalkyl ring. In some embodiments is a compound of Formula (Ic) wherein $R^4$ and $R^5$ form an optionally substituted $C_3$-$C_6$cycloalkyl ring. In some embodiments is a compound of Formula (Ic) wherein $R^4$ and $R^5$ form an optionally substituted $C_2$-$C_7$heterocycloalkyl ring.

In another embodiment is a compound of Formula (Ic) wherein $R^6$ and $R^7$ are each independently selected from the group consisting of hydrogen, halogen, and optionally substituted $C_1$-$C_6$alkyl. In another embodiment is a compound of Formula (Ic) wherein $R^6$ and $R^7$ are each independently selected from the group consisting of hydrogen and optionally substituted $C_1$-$C_6$alkyl. In another embodiment is a compound of Formula (Ic) wherein $R^6$ and $R^7$ are each independently optionally substituted $C_1$-$C_6$alkyl. In another embodiment is a compound of Formula (Ic) wherein $R^6$ and $R^7$ are each methyl. In another embodiment is a compound of Formula (Ic) wherein $R^6$ and $R^7$ are each hydrogen.

In another embodiment is a compound of Formula (Ic) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted aryl. In another embodiment is a compound of Formula (Ic) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted heteroaryl. In another embodiment is a compound of Formula (Ic) wherein $R^6$ and $R^7$ are hydrogen, $R^4$ and $R^5$ are methyl, $R^3$ is —C(O)$R^{20}$, and $R^{20}$ is optionally substituted aryl. In another embodiment is a compound of Formula (Ic) wherein $R^6$ and $R^7$ are hydrogen, $R^4$ and $R^5$ are methyl, $R^3$ is —C(O)$R^{20}$, and $R^{20}$ is optionally substituted heteroaryl.

In another embodiment is a compound of Formula (Ic) wherein $R^6$ and $R^7$ are hydrogen, $R^4$ and $R^5$ are independently optionally substituted $C_1$-$C_6$alkyl, $R^3$ is —S(O)$_2$$R^{20}$, and $R^{20}$ is optionally substituted aryl. In another embodiment is a compound of Formula (Ic) wherein $R^6$ and $R^7$ are hydrogen, $R^4$ and $R^5$ are independently optionally substituted $C_1$-$C_6$alkyl, $R^3$ is —S(O)$_2$$R^{20}$, and $R^{20}$ is optionally substituted heteroaryl. In another embodiment is a compound of Formula (Ic) wherein $R^6$ and $R^7$ are hydrogen, $R^4$ and $R^5$ are methyl, $R^3$ is —S(O)$_2$$R^{20}$, and $R^{20}$ is optionally substituted aryl. In another embodiment is a compound of Formula (Ic) wherein $R^6$ and $R^7$ are hydrogen, $R^4$ and $R^5$ are methyl, $R^3$ is —S(O)$_2$$R^{20}$, and $R^{20}$ is optionally substituted heteroaryl.

In another embodiment is a compound of Formula (Ic) wherein $R^6$ and $R^7$ are hydrogen, $R^4$ and $R^5$ are independently optionally substituted $C_1$-$C_6$alkyl, $R^3$ is —C(O)N($R^{21}$)$R^{22}$, $R^{21}$ is hydrogen and $R^{22}$ is optionally substituted aryl. In another embodiment is a compound of Formula (Ic) wherein $R^6$ and $R^7$ are hydrogen, $R^4$ and $R^5$ are independently optionally substituted $C_1$-$C_6$alkyl, $R^3$ is —C(O)N($R^{21}$)$R^{22}$, $R^{21}$ is hydrogen and $R^{22}$ is optionally substituted heteroaryl. In another embodiment is a compound of Formula (Ic) wherein $R^6$ and $R^7$ are hydrogen, $R^4$ and $R^5$ are methyl, $R^3$ is —C(O)N($R^{21}$)$R^{22}$, $R^{21}$ is hydrogen and $R^{22}$ is optionally substituted aryl. In another embodiment is a compound of Formula (Ic) wherein $R^6$ and $R^7$ are hydrogen, $R^4$ and $R^5$ are methyl, $R^3$ is —C(O)N($R^{21}$)$R^{22}$, $R^{21}$ is hydrogen and $R^{22}$ is optionally substituted heteroaryl.

In a further embodiment of the aforementioned embodiments is a compound of Formula (Ic) wherein $R^2$ is selected from the group consisting of —CN, —C(O)O$R^{25}$, —C(O)N($R^{25}$)$R^{26}$,

[chemical structures shown]

In a further embodiment of the aforementioned embodiments is a compound of Formula (Ic) wherein $R^2$ is —CN.

In a further embodiment of the aforementioned embodiments is a compound of Formula (Ic) wherein $R^2$ is —C(O)O$R^{25}$. In a further embodiment of the aforementioned embodiments is a compound of Formula (Ic) wherein $R^2$ is —C(O)O$R^{25}$, and $R^{25}$ is independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (Ic) wherein $R^2$ is —C(O)O$R^{25}$, and $R^{25}$ is independently selected from the group consisting of hydrogen, and optionally substituted $C_1$-$C_6$alkyl. In a further embodiment of the aforementioned embodiments is a compound of Formula (Ic) wherein $R^2$ is —C(O)O$R^{25}$, and $R^{25}$ is hydrogen. In a further embodiment of the aforementioned embodiments is a compound of Formula (Ic) wherein $R^2$ is —C(O)O$R^{25}$, and $R^{25}$ is optionally substituted $C_1$-$C_6$alkyl. In a further embodiment of the aforementioned embodiments is a compound of Formula (Ic) wherein $R^2$ is —C(O)O$R^{25}$, and $R^{25}$ is unsubstituted $C_1$-$C_6$alkyl. In a further embodiment of the aforementioned embodiments is a compound of Formula (Ic) wherein $R^2$ is —C(O)O$R^{25}$, and $R^{25}$ is methyl. In a further embodiment of the aforementioned embodiments is a compound of Formula (Ic) wherein $R^2$ is —C(O)O$R^{25}$, and $R^{25}$ is ethyl.

In a further embodiment of the aforementioned embodiments is a compound of Formula (Ic) wherein $R^2$ is —C(O)N($R^{25}$)$R^{26}$. In a further embodiment of the aforementioned embodiments is a compound of Formula (Ic) wherein $R^2$ is —C(O)N($R^{25}$)$R^{26}$, and $R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (Ic) wherein $R^2$ is —C(O)N($R^{25}$)$R^{26}$, and $R^{25}$ and $R^{26}$ are each independently selected from the group consisting of hydrogen, and optionally substituted $C_1$-$C_6$alkyl. In a further embodiment of the aforementioned embodiments is a compound of Formula (Ic) wherein $R^2$ is —C(O)N($R^{25}$)$R^{26}$, and $R^{25}$ and $R^{26}$ are hydrogen. In a further embodiment of the aforementioned embodiments is a compound of Formula (Ic) wherein $R^2$ is —C(O)N($R^{25}$)$R^{26}$, and $R^{25}$ and $R^{26}$ are each independently optionally substituted $C_1$-$C_6$alkyl. In a further embodiment of the aforementioned embodiments is a compound of Formula (Ic) wherein $R^2$ is —C(O)N($R^{25}$)$R^{26}$, $R^{25}$ is hydrogen, and $R^{26}$ is optionally substituted $C_1$-$C_6$alkyl. In a further embodiment of the aforementioned embodiments is a compound of Formula (Ic) wherein $R^2$ is —C(O)N($R^{25}$)$R^{26}$, and $R^{25}$ and $R^{26}$ are each independently unsubstituted $C_1$-$C_6$alkyl. In a further embodiment of the aforementioned embodiments is a compound of Formula (Ic) wherein $R^2$ is —C(O)N($R^{25}$)$R^{26}$, $R^{25}$ is hydrogen, and $R^{26}$ are methyl. In a further embodiment of the aforementioned embodiments is a compound of Formula (Ic) wherein $R^2$ is —C(O)N($R^{25}$)$R^{26}$, and $R^{25}$ and $R^{26}$ are methyl. In a further embodiment of the aforementioned embodiments is a compound of Formula (Ic) wherein $R^2$ is —C(O)N($R^{25}$)$R^{26}$, and $R^{25}$ and $R^{26}$ are ethyl.

In a further embodiment of the aforementioned embodiments is a compound of Formula (Ic) wherein $R^2$ is

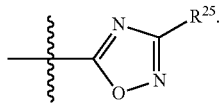

In a further embodiment of the aforementioned embodiments is a compound of Formula (Ic) wherein $R^2$ is

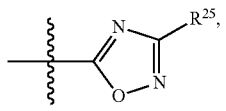

and $R^{25}$ is optionally substituted $C_1$-$C_6$alkyl. In a further embodiment of the aforementioned embodiments is a compound of Formula (Ic) wherein $R^2$ is

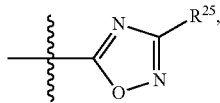

and $R^{25}$ is methyl. In a further embodiment of the aforementioned embodiments is a compound of Formula (Ic) wherein $R^2$ is

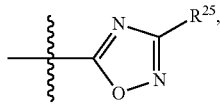

and $R^{25}$ is optionally substituted $C_1$-$C_6$alkyl. In a further embodiment of the aforementioned embodiments is a compound of Formula (Ic) wherein $R^2$ is

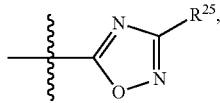

and $R^{25}$ is ethyl.

In a further embodiment of the aforementioned embodiments is a compound of Formula (Ic) wherein $R^2$ is

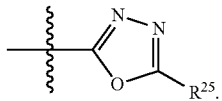

In a further embodiment of the aforementioned embodiments is a compound of Formula (Ic) wherein $R^2$ is

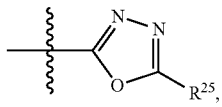

and $R^{25}$ is optionally substituted $C_1$-$C_6$alkyl. In a further embodiment of the aforementioned embodiments is a compound of Formula (Ic) wherein $R^2$ is

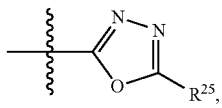

and $R^{25}$ is methyl. In a further embodiment of the aforementioned embodiments is a compound of Formula (Ic) wherein $R^2$ is

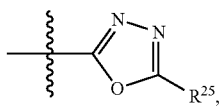

and $R^{25}$ is optionally substituted $C_1$-$C_6$alkyl. In a further embodiment of the aforementioned embodiments is a compound of Formula (Ic) wherein $R^2$ is

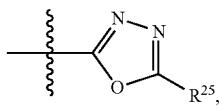

and $R^{25}$ is ethyl.

In a further embodiment of the aforementioned embodiments is a compound of Formula (Ic) wherein $R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (Ic) wherein $R^1$ is hydrogen. In a further embodiment of the aforementioned embodiments is a compound of Formula (Ic) wherein $R^1$ is optionally substituted $C_1$-$C_6$alkyl. In a further embodiment of the aforementioned embodiments is a compound of Formula (Ic) wherein $R^1$ is methyl. In a further embodiment of the aforementioned embodiments is a compound of Formula (Ic) wherein $R^1$ is optionally substituted $C_2$-$C_6$alkenyl. In a further embodiment of the aforementioned embodiments is a compound of Formula (Ic) wherein $R^1$ is optionally substituted $C_2$-$C_6$alkynyl.

In a further embodiment of the aforementioned embodiments is a compound of Formula (Ic) wherein $R^1$ and $R^2$ together with the carbon atoms to which they are attached, form an optionally substituted $C_2$-$C_9$heterocycloalkyl ring or an optionally substituted heteroaryl ring. In a further embodiment of the aforementioned embodiments is a compound of Formula (Ic) wherein $R^1$ and $R^2$ together with the carbon atoms to which they are attached, form an optionally substituted $C_2$-$C_9$heterocycloalkyl ring. In a further embodiment of the aforementioned embodiments is a compound of Formula (Ic) wherein $R^1$ and $R^2$ together with the carbon atoms to which they are attached, form an optionally substituted heteroaryl ring.

In a further embodiment of the aforementioned embodiments is a compound of Formula (Ic) wherein $R^8$ is selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl). In a further embodiment of the aforementioned embodiments is a compound of Formula (Ic) wherein $R^8$ is selected from the group consisting of hydrogen, and optionally substituted $C_1$-$C_6$alkyl. In a further embodiment of the aforementioned embodiments is a compound of Formula (Ic) wherein $R^8$ is optionally substituted $C_1$-$C_6$alkyl. In a further embodiment of the aforementioned embodiments is a compound of Formula (Ic) wherein $R^8$ is methyl. In a further embodiment of the aforementioned embodiments is a compound of Formula (Ic) wherein $R^8$ is optionally substituted $C_1$-$C_6$alkyl. In a further embodiment of the aforementioned embodiments is a compound of Formula (Ic) wherein $R^8$ is ethyl. In a further embodiment of the aforementioned embodiments is a compound of Formula (Ic) wherein $R^8$ is optionally substituted $C_1$-$C_6$alkyl. In a further embodiment of the aforementioned embodiments is a compound of Formula (Ic) wherein $R^8$ is hydrogen.

In another embodiment of the aforementioned embodiments is a compound of Formula (Ic) wherein $R^{15}$ is —OC(=J)OR$^{16a}$. In another embodiment of the aforementioned embodiments is a compound of Formula (Ic) wherein $R^{15}$ is —N(R$^{12}$)C(=J)OR$^{16a}$. In another embodiment of the aforementioned embodiments is a compound of Formula (Ic) wherein $R^{15}$ is —OC(=J)N(H)R$^{16a}$ In another embodiment of the aforementioned embodiments is a compound of Formula (Ic) wherein $R^{15}$ is —N(R$^{12}$)C(=J)N(H)R$^{16a}$. In another embodiment of the aforementioned embodiments is a compound of Formula (Ic) wherein $R^{15}$ is —OC(=J)N(H)($C_2$-$C_6$alkyl)R$^{30}$. In another embodiment of the aforementioned embodiments is a compound of Formula (Ic) wherein $R^{15}$ is —N(R$^{12}$)C(=J)O($C_2$-$C_6$alkyl)R$^{30}$. In another embodiment of the aforementioned embodiments is a compound of Formula (Ic) wherein $R^{15}$ is —N(R$^{12}$)C(=J)N(H)($C_2$-$C_6$alkyl)R$^{30}$. In another embodiment of the aforementioned embodiments is a compound of Formula (Ic) wherein $R^{15}$ is —OC(=J)O($C_2$-$C_6$alkyl)R$^{30}$. In another embodiment of the aforementioned embodiments is a compound of Formula (Ic) wherein $R^{15}$ is —C(=J)R$^{31}$. In another embodiment of the aforementioned embodiments is a compound of Formula (Ic) wherein $R^{15}$ is —OC(=J)R$^{31}$. In another embodiment of the aforementioned embodiments is a compound of Formula (Ic) wherein $R^{15}$ is —N(R$^{12}$)C(=J)R$^{31}$. In another embodiment of the aforementioned embodiments is a compound of Formula (Ic) wherein $R^{15}$ is —O($C_2$-$C_6$alkyl)R$^{30}$. In another embodiment of the aforementioned embodiments is a compound of Formula (Ic) wherein $R^{15}$ is —N(R$^{12}$)($C_2$-$C_6$alkyl)R$^{30}$. In another embodiment of the aforementioned embodiments is a compound of Formula (Ic) wherein $R^{15}$ is —OS(=O)$_v$R$^{31}$. In another embodiment of the aforementioned embodiments is a compound of Formula (Ic) wherein $R^{15}$ is —N(R$^{12}$)S(=O)$_v$R$^{31}$. In another embodiment of the aforementioned embodiments is a compound of Formula (Ic) wherein $R^{15}$ is —OS(=O)$_v$($C_2$-$C_6$alkyl)R$^{30}$. In another embodiment of the aforementioned embodiments is a compound of Formula (Ic) wherein $R^{15}$ is —N(R$^{12}$)S(=O)$_v$($C_2$-$C_6$alkyl)R$^{30}$. In a further embodiment of the aforementioned embodiments is a compound of Formula (Ic) wherein $R^{30}$ is $R^{16a}$. In a further embodiment of the aforementioned embodiments is a compound of Formula (Ic) wherein $R^{30}$ is $R^{16b}$. In a further embodiment of the aforementioned embodiments is a compound of Formula (Ic) wherein $R^{30}$ is $R^{16c}$. In a further embodiment of the aforementioned embodiments is a compound of Formula (Ic) wherein $R^{31}$ is $R^{16a}$. In a further embodiment of the aforementioned embodiments is a compound of Formula (Ic) wherein $R^{31}$ is $R^{16b}$. In a further embodiment of the aforementioned embodiments is a compound of Formula (Ic) wherein J is O. In a further embodiment of the aforementioned embodiments is a compound of Formula (Ic) wherein J is S. In a further embodiment of the aforementioned embodiments is a compound of Formula (Ic) wherein J is N(R$^{12}$).

In another embodiment of the aforementioned embodiments is a compound of Formula (Ic) wherein $R^{16a}$ is

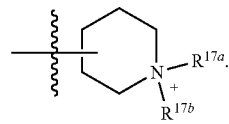

In another embodiment of the aforementioned embodiments is a compound of Formula (Ic) wherein $R^{16a}$ is

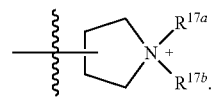

In another embodiment of the aforementioned embodiments is a compound of Formula (Ic) wherein $R^{16a}$ is

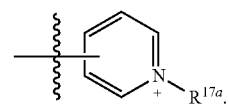

In another embodiment of the aforementioned embodiments is a compound of Formula (Ic) wherein $R^{16b}$ is

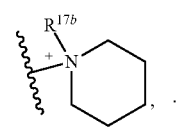

In another embodiment of the aforementioned embodiments is a compound of Formula (Ic) wherein $R^{16b}$ is

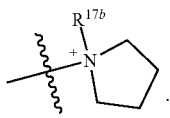

In another embodiment of the aforementioned embodiments is a compound of Formula (Ic) wherein $R^{16b}$ is

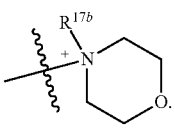

In another embodiment of the aforementioned embodiments is a compound of Formula (Ic) wherein $R^{16b}$ is

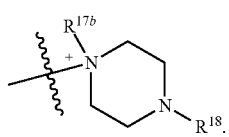

In another embodiment of the aforementioned embodiments is a aforementioned embodiments is a compound of Formula (Ic) wherein $R^{16b}$ is

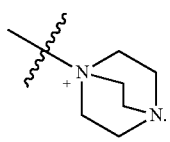

In another embodiment of the aforementioned embodiments is a compound of Formula (Ic) wherein $R^{16b}$ is

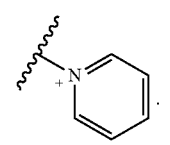

In wherein $R^{16b}$ is

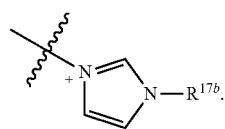

In another embodiment of the aforementioned embodiments is a compound of Formula (Ic) wherein $R^{16c}$ is

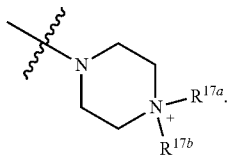

In another embodiment is a compound of Formula (Ic) wherein $R^{16c}$ is

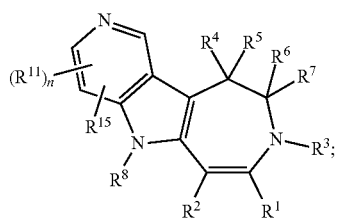

In a further embodiment of the aforementioned embodiments is a compound of Formula (Ic) wherein $R^{17a}$ is methyl. In a further embodiment of the aforementioned embodiments is a compound of Formula (Ic) wherein $R^{17a}$ is ethyl. In a further embodiment of the aforementioned embodiments is a compound of Formula (Ic) wherein $R^{17b}$ is methyl optionally substituted with phenyl, —C(=O)OH or —S(=O)$_2$OH. In a further embodiment of the aforementioned embodiments is a compound of Formula (Ic) wherein $R^{17a}$ is ethyl optionally substituted with phenyl, —C(=O)OH or —S(=O)$_2$OH.

In another embodiment of the aforementioned embodiments is a compound of Formula (Ic) wherein n is 0. In another embodiment of the aforementioned embodiments is a compound of Formula (Ic) wherein n is 1. In another embodiment of the aforementioned embodiments is a compound of Formula (Ic) wherein n is 1 and $R^{11}$ is $C_1$-$C_6$alkyl. In another embodiment of the aforementioned embodiments is a compound of Formula (Ic) wherein n is 1 and $R^{11}$ is $C_1$-$C_6$haloalkyl.

In another embodiment is a compound of Formula (Ic) wherein $R^{15}$ is —OC(=J)OR$^{16a}$, —N(R$^{12}$)C(=J)OR$^{16a}$, —OC(=J)N(H)R$^{16a}$, —N(R$^{12}$)C(=J)N(H)R$^{16a}$, —OC(=J)N(H)(C$_1$-C$_6$alkyl)R$^{31}$, —N(R$^{12}$)C(=J)O(C$_1$-C$_6$alkyl)R$^{31}$, —N(R$^{12}$)C(=J)N(H)(C$_1$-C$_6$alkyl)R$^{31}$, —OC(=J)O(C$_1$-C$_6$alkyl)R$^{31}$, —C(=J)R$^{31}$, —OC(=J)R$^{31}$, —N(R$^{12}$)C(=J)R$^{31}$, —O(C$_1$-C$_6$alkyl)R$^{31}$, —N(R$^{12}$)(C$_1$-C$_6$alkyl)R$^{31}$, —OS(=O)$_v$R$^{31}$, —N(R$^{12}$)S(=O)$_v$R$^{31}$, —OS(=O)$_v$(C$_1$-C$_6$alkyl)R$^{31}$, or —N(R$^{12}$)S(=O)$_v$(C$_1$-C$_6$alkyl)R$^{31}$.

In some embodiments provided herein, the compound of Formula (I) has the structure of Formula (Id), or a pharmaceutically acceptable salt or solvate thereof:

Formula (Id)

wherein:
$R^1$ is selected from the group consisting of hydrogen, optionally substituted $C_1$-$C_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

R$^2$ is selected from the group consisting of —CN, —C(=O)OR$^{25}$, —C(=O)N(R$^{25}$)R$^{26}$,

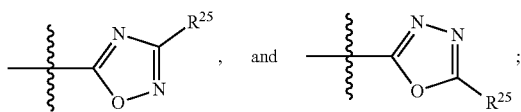

or R$^1$ and R$^2$ together with the carbon atoms to which they are attached, form an optionally substituted C$_2$-C$_9$heterocycloalkyl ring or an optionally substituted heteroaryl ring;

R$^3$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_{10}$cycloalkyl, optionally substituted aryl, optionally substituted —(C$_1$-C$_2$alkylene)-(aryl), optionally substituted heteroaryl, optionally substituted C$_2$-C$_9$heterocycloalkyl, optionally substituted —(C$_1$-C$_2$alkylene)-(heteroaryl), —C(=O)R$^{20}$, —C(=O)OR$^{20}$, —S(=O)$_2$R$^{20}$, —C(=O)N(R$^{21}$)R$^{22}$, —C(=O)N(R$^{21}$)S(=O)$_2$R$^{24}$, —C(=O)N(R$^{23}$)N(R$^{21}$)R$^{22}$, —C(=O)N(R$^{23}$)N(R$^{21}$)S(=O)$_2$R$^{24}$, —N(R$^{23}$)C(=O)R$^{20}$, —N(R$^{23}$)C(=O)N(R$^{21}$)R$^{22}$, —N(R$^{23}$)C(=O)N(R$^{21}$)S(=O)$_2$R$^{24}$, —N(R$^{20}$)C(=O)N(R$^{23}$)N(R$^{21}$)R$^{22}$, —N(R$^{20}$)C(=O)N(R$^{23}$)N(R$^{21}$)S(=O)$_2$R$^{24}$, —N(R$^{23}$)C(=O)OR$^{20}$, —P(=O)OR$^{20}$, and —P(=O)(OR$^{19}$)OR$^{20}$;

R$^4$ and R$^5$ are each independently selected from the group consisting of hydrogen, halogen, optionally substituted C$_1$-C$_6$alkyl, optionally substituted C$_1$-C$_6$alkoxy, optionally substituted C$_2$-C$_6$alkenyl, and optionally substituted C$_2$-C$_6$alkynyl; or R$^4$ and R$^5$ together with the carbon atom to which they are attached, form an optionally substituted C$_3$-C$_6$cycloalkyl ring or an optionally substituted C$_2$-C$_7$heterocycloalkyl ring;

R$^6$ is selected from the group consisting of hydrogen, halogen, optionally substituted C$_1$-C$_6$alkyl, optionally substituted C$_2$-C$_6$alkenyl, optionally substituted C$_2$-C$_6$alkynyl, and —C(=O)N(R$^{27}$)R$^{28}$;

R$^7$ is selected from the group consisting of hydrogen, halogen, optionally substituted C$_1$-C$_6$alkyl, optionally substituted C$_1$-C$_6$alkoxy, optionally substituted C$_2$-C$_6$alkenyl, and optionally substituted C$_2$-C$_6$alkynyl;

R$^8$ is selected from the group consisting of hydrogen, optionally substituted C$_1$-C$_6$alkyl, optionally substituted C$_3$-C$_8$cycloalkyl, optionally substituted aryl, optionally substituted —(C$_1$-C$_2$alkylene)-(aryl), optionally substituted heteroaryl, optionally substituted C$_2$-C$_9$heterocycloalkyl, and optionally substituted —(C$_1$-C$_2$alkylene)-(heteroaryl);

each R$^{11}$ is independently selected from the group consisting of halogen, —CN, amino, alkylamino, C$_1$-C$_6$alkyl, C$_1$-C$_6$haloalkyl, C$_1$-C$_6$alkoxy, C$_1$-C$_6$haloalkoxy, C$_3$-C$_8$cycloalkyl, C$_2$-C$_9$heterocycloalkyl, aryl, heteroaryl, —C(=O)OR$^{12}$, —C(=O)N(R$^{13}$)R$^{14}$;

each R$^{12}$ is independently selected from the group consisting of hydrogen and C$_1$-C$_6$alkyl;

each R$^{13}$ and R$^{14}$ are each independently selected from the group consisting of hydrogen and C$_1$-C$_6$alkyl; or R$^{13}$ and R$^{14}$ together with the nitrogen atom to which they are attached, form an optionally substituted C$_2$-C$_9$heterocycloalkyl ring;

R$^{15}$ is —OC(=J)OR$^{16a}$, —N(R$^{12}$)C(=J)OR$^{16a}$, —OC(=J)N(H)R$^{16a}$, —N(R$^{12}$)C(=J)N(H)R$^{16a}$, —OC(=J)N(H)(C$_2$-C$_6$alkyl)R$^{30}$, —N(R$^{12}$)C(=J)O(C$_2$-C$_6$alkyl)R$^{30}$, —N(R$^{12}$)C(=J)N(H)(C$_2$-C$_6$alkyl)R$^{30}$, —OC(=J)O(C$_2$-C$_6$alkyl)R$^{30}$, —C(=J)R$^{31}$, —OC(=J)R$^{31}$, —N(R$^{12}$)C(=J)R$^{31}$, —O(C$_2$-C$_6$alkyl)R$^{30}$, —N(R$^{12}$)(C$_2$-C$_6$alkyl)R$^{30}$, —OS(=O)$_v$R$^{31}$, —N(R$^{12}$)S(=O)$_v$R$^{31}$, —OS(=O)$_v$(C$_2$-C$_6$alkyl)R$^{30}$, or —N(R$^{12}$)S(=O)$_v$(C$_2$-C$_6$alkyl)R$^{30}$;

R$^{30}$ is R$^{16a}$, R$^{16b}$, or R$^{16c}$;
R$^{31}$ is R$^{16a}$ or R$^{16c}$;
J is O, S, or N(R$^{12}$);
R$^{16a}$ is

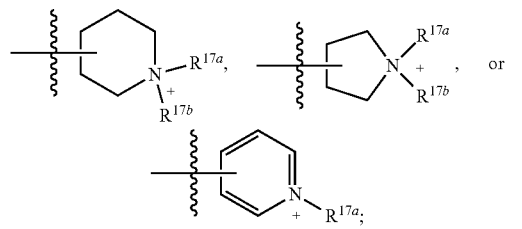

R$^{16b}$ is

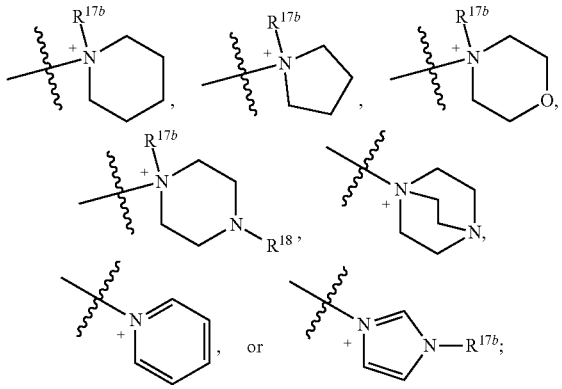

R$^{16c}$ is

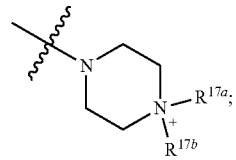

R$^{17a}$ is C$_1$-C$_6$alkyl;
R$^{17b}$ is C$_1$-C$_6$alkyl optionally substituted with phenyl, —C(=O)OH or —S(=O)$_2$OH;
R$^{18}$ is hydrogen, —OH, —(C$_0$-C$_6$alkyl)-C(=O)OH, or C$_1$-C$_6$alkyl;

n is 0, 1, or 2;

v is 1 or 2;

$R^{19}$, $R^{20}$, and $R^{23}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R^{21}$ and $R^{22}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{21}$ and $R^{22}$ together with the nitrogen atom to which they are attached, form an optionally substituted $C_2$-$C_9$heterocycloalkyl ring;

$R^{24}$ is selected from the group consisting of optionally substituted $C_1$-$C_6$alkyl, optionally substituted $C_2$-$C_6$alkenyl, optionally substituted $C_2$-$C_6$alkynyl, optionally substituted $C_3$-$C_8$ cycloalkyl, optionally substituted aryl optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); and $R^{25}$ and $R^{26}$ are each independently selected from the group consisting of hydrogen, optionally substituted $C_1$-$C_6$alkyl, optionally substituted $C_2$-$C_9$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R^{27}$ and $R^{28}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{27}$ and $R^{28}$ together with the nitrogen atom to which they are attached, form an optionally substituted $C_2$-$C_9$heterocycloalkyl ring.

In another embodiment is a compound of Formula (Id) wherein $R^4$ and $R^5$ are each independently selected from the group consisting of hydrogen, halogen, and optionally substituted $C_1$-$C_6$alkyl. In another embodiment is a compound of Formula (Id) wherein $R^4$ and $R^5$ are each independently selected from the group consisting of hydrogen and optionally substituted $C_1$-$C_6$alkyl. In another embodiment is a compound of Formula (Id) wherein $R^4$ and $R^5$ are each hydrogen. In another embodiment is a compound of Formula (Id) wherein $R^4$ and $R^5$ are each independently optionally substituted $C_1$-$C_6$alkyl. In another embodiment is a compound of Formula (Id) wherein $R^4$ and $R^5$ are each methyl. In another embodiment is a compound of Formula (Id) wherein $R^4$ and $R^5$ form an optionally substituted $C_3$-$C_6$cycloalkyl ring or an optionally substituted $C_2$-$C_7$heterocycloalkyl ring. In some embodiments is a compound of Formula (Id) wherein $R^4$ and $R^5$ form an optionally substituted $C_3$-$C_6$cycloalkyl ring. In some embodiments is a compound of Formula (Id) wherein $R^4$ and $R^5$ form an optionally substituted $C_2$-$C_7$heterocycloalkyl ring.

In another embodiment is a compound of Formula (Id) wherein $R^6$ and $R^7$ are each independently selected from the group consisting of hydrogen, halogen, and optionally substituted $C_1$-$C_6$alkyl. In another embodiment is a compound of Formula (Id) wherein $R^6$ and $R^7$ are each independently selected from the group consisting of hydrogen and optionally substituted $C_1$-$C_6$alkyl. In another embodiment is a compound of Formula (Id) wherein $R^6$ and $R^7$ are each independently optionally substituted $C_1$-$C_6$alkyl. In another embodiment is a compound of Formula (Id) wherein $R^6$ and $R^7$ are each methyl. In another embodiment is a compound of Formula (Id) wherein $R^6$ and $R^7$ are each hydrogen.

In another embodiment is a compound of Formula (Id) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted aryl. In another embodiment is a compound of Formula (Id) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted heteroaryl. In another embodiment is a compound of Formula (Id) wherein $R^6$ and $R^7$ are hydrogen, $R^4$ and $R^5$ are methyl, $R^3$ is —C(O)$R^{20}$, and $R^{20}$ is optionally substituted aryl. In another embodiment is a compound of Formula (Id) wherein $R^6$ and $R^7$ are hydrogen, $R^4$ and $R^5$ are methyl, $R^3$ is —C(O)$R^{20}$, and $R^{20}$ is optionally substituted heteroaryl.

In another embodiment is a compound of Formula (Id) wherein $R^6$ and $R^7$ are hydrogen, $R^4$ and $R^5$ are independently optionally substituted $C_1$-$C_6$alkyl, $R^3$ is —S(O)$_2$$R^{20}$, and $R^{20}$ is optionally substituted aryl. In another embodiment is a compound of Formula (Id) wherein $R^6$ and $R^7$ are hydrogen, $R^4$ and $R^5$ are independently optionally substituted $C_1$-$C_6$alkyl, $R^3$ is —S(O)$_2$$R^{20}$, and $R^{20}$ is optionally substituted heteroaryl. In another embodiment is a compound of Formula (Id) wherein $R^6$ and $R^7$ are hydrogen, $R^4$ and $R^5$ are methyl, $R^3$ is —S(O)$_2$$R^{20}$, and $R^{20}$ is optionally substituted aryl. In another embodiment is a compound of Formula (Id) wherein $R^6$ and $R^7$ are hydrogen, $R^4$ and $R^5$ are methyl, $R^3$ is —S(O)$_2$$R^{20}$, and $R^{20}$ is optionally substituted heteroaryl.

In another embodiment is a compound of Formula (Id) wherein $R^6$ and $R^7$ are hydrogen, $R^4$ and $R^5$ are independently optionally substituted $C_1$-$C_6$alkyl, $R^3$ is —C(O)N($R^{21}$)$R^{22}$, $R^{21}$ is hydrogen and $R^{22}$ is optionally substituted aryl. In another embodiment is a compound of Formula (Id) wherein $R^6$ and $R^7$ are hydrogen, $R^4$ and $R^5$ are independently optionally substituted $C_1$-$C_6$alkyl, $R^3$ is —C(O)N($R^{21}$)$R^{22}$, $R^{21}$ is hydrogen and $R^{22}$ is optionally substituted heteroaryl. In another embodiment is a compound of Formula (Id) wherein $R^6$ and $R^7$ are hydrogen, $R^4$ and $R^5$ are methyl, $R^3$ is —C(O)N($R^{21}$)$R^{22}$, $R^{21}$ is hydrogen and $R^{22}$ is optionally substituted aryl. In another embodiment is a compound of Formula (Id) wherein $R^6$ and $R^7$ are hydrogen, $R^4$ and $R^5$ are methyl, $R^3$ is —C(O)N($R^{21}$)$R^{22}$, $R^{21}$ is hydrogen and $R^{22}$ is optionally substituted heteroaryl.

In a further embodiment of the aforementioned embodiments is a compound of Formula (Id) wherein $R^2$ is selected from the group consisting of —CN, —C(O)O$R^{25}$, —C(O)N($R^{25}$)$R^{26}$,

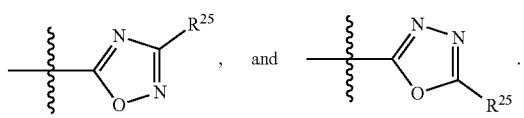

In a further embodiment of the aforementioned embodiments is a compound of Formula (Id) wherein $R^2$ is —CN.

In a further embodiment of the aforementioned embodiments is a compound of Formula (Id) wherein $R^2$ is —C(O)OR$^{25}$. In a further embodiment of the aforementioned embodiments is a compound of Formula (Id) wherein $R^2$ is —C(O)OR$^{25}$, and $R^{25}$ is independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (Id) wherein $R^2$ is —C(O)OR$^{25}$, and $R^{25}$ is independently selected from the group consisting of hydrogen, and optionally substituted $C_1$-$C_6$alkyl. In a further embodiment of the aforementioned embodiments is a compound of Formula (Id) wherein $R^2$ is —C(O)OR$^{25}$, and $R^{25}$ is hydrogen. In a further embodiment of the aforementioned embodiments is a compound of Formula (Id) wherein $R^2$ is —C(O)OR$^{25}$, and $R^{25}$ is optionally substituted $C_1$-$C_6$alkyl. In a further embodiment of the aforementioned embodiments is a compound of Formula (Id) wherein $R^2$ is —C(O)OR$^{25}$, and $R^{25}$ is unsubstituted $C_1$-$C_6$alkyl. In a further embodiment of the aforementioned embodiments is a compound of Formula (Id) wherein $R^2$ is —C(O)OR$^{25}$, and $R^{25}$ is methyl. In a further embodiment of the aforementioned embodiments is a compound of Formula (Id) wherein $R^2$ is —C(O)OR$^{25}$, and $R^{25}$ is ethyl.

In a further embodiment of the aforementioned embodiments is a compound of Formula (Id) wherein $R^2$ is —C(O)N(R$^{25}$)R$^{26}$. In a further embodiment of the aforementioned embodiments is a compound of Formula (Id) wherein $R^2$ is —C(O)N(R$^{25}$)R$^{26}$, and $R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (Id) wherein $R^2$ is —C(O)N(R$^{25}$)R$^{26}$, and $R^{25}$ and $R^{26}$ are each independently selected from the group consisting of hydrogen, and optionally substituted $C_1$-$C_6$alkyl. In a further embodiment of the aforementioned embodiments is a compound of Formula (Id) wherein $R^2$ is —C(O)N(R$^{25}$)R$^{26}$, and $R^{25}$ and $R^{26}$ are hydrogen. In a further embodiment of the aforementioned embodiments is a compound of Formula (Id) wherein $R^2$ is —C(O)N(R$^{25}$)R$^{26}$, and $R^{25}$ and $R^{26}$ are each independently optionally substituted $C_1$-$C_6$alkyl. In a further embodiment of the aforementioned embodiments is a compound of Formula (Id) wherein $R^2$ is —C(O)N(R$^{25}$)R$^{26}$, $R^{25}$ is hydrogen, and $R^{26}$ is optionally substituted $C_1$-$C_6$alkyl. In a further embodiment of the aforementioned embodiments is a compound of Formula (Id) wherein $R^2$ is —C(O)N(R$^{25}$)R$^{26}$, and $R^{25}$ and $R^{26}$ are each independently unsubstituted $C_1$-$C_6$alkyl. In a further embodiment of the aforementioned embodiments is a compound of Formula (Id) wherein $R^2$ is —C(O)N(R$^{25}$)R$^{26}$, $R^{25}$ is hydrogen, and $R^{26}$ are methyl. In a further embodiment of the aforementioned embodiments is a compound of Formula (Id) wherein $R^2$ is —C(O)N(R$^{25}$)R$^{26}$, and $R^{25}$ and $R^{26}$ are methyl. In a further embodiment of the aforementioned embodiments is a compound of Formula (Id) wherein $R^2$ is —C(O)N(R$^{25}$)R$^{26}$, and $R^{25}$ and $R^{26}$ are ethyl.

In a further embodiment of the aforementioned embodiments is a compound of Formula (Id) wherein $R^2$ is

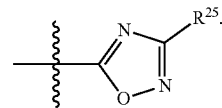

In a further embodiment of the aforementioned embodiments is a compound of Formula (Id) wherein $R^2$ is

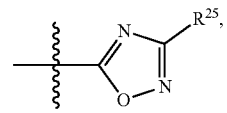

and $R^{25}$ is optionally substituted $C_1$-$C_6$alkyl. In a further embodiment of the aforementioned embodiments is a compound of Formula (Id) wherein $R^2$ is

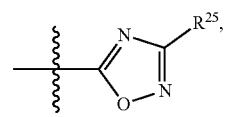

and $R^{25}$ is methyl. In a further embodiment of the aforementioned embodiments is a compound of Formula (Id) wherein $R^2$ is

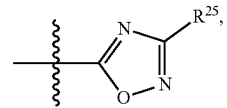

and $R^{25}$ is optionally substituted $C_1$-$C_6$alkyl. In a further embodiment of the aforementioned embodiments is a compound of Formula (Id) wherein $R^2$ is

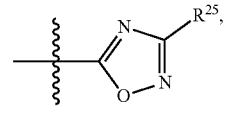

and $R^{25}$ is ethyl.

In a further embodiment of the aforementioned embodiments is a compound of Formula (Id) wherein $R^2$ is

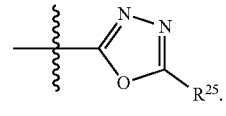

In a further embodiment of the aforementioned embodiments is a compound of Formula (Id) wherein $R^2$ is and $R^{25}$ is optionally substituted $C_1$-$C_6$alkyl. In a further embodiment of the aforementioned embodiments is a compound of Formula (Id) wherein $R^2$ is and $R^{25}$ is methyl. In a further embodiment of the aforementioned embodiments is a compound of Formula (Id) wherein $R^2$ is and $R^{25}$ is optionally substituted $C_1$-$C_6$alkyl. In a further embodiment of the aforementioned embodiments is a compound of Formula (Id) wherein $R^2$ is and $R^{25}$ is ethyl.

In a further embodiment of the aforementioned embodiments is a compound of Formula (Id) wherein $R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (Id) wherein $R^1$ is hydrogen. In a further embodiment of the aforementioned embodiments is a compound of Formula (Id) wherein $R^1$ is optionally substituted $C_1$-$C_6$alkyl. In a further embodiment of the aforementioned embodiments is a compound of Formula (Id) wherein $R^1$ is methyl. In a further embodiment of the aforementioned embodiments is a compound of Formula (Id) wherein $R^1$ is optionally substituted $C_2$-$C_6$alkenyl. In a further embodiment of the aforementioned embodiments is a compound of Formula (Id) wherein $R^1$ is optionally substituted $C_2$-$C_6$alkynyl.

In a further embodiment of the aforementioned embodiments is a compound of Formula (Id) wherein $R^1$ and $R^2$ together with the carbon atoms to which they are attached, form an optionally substituted $C_2$-$C_9$heterocycloalkyl ring or an optionally substituted heteroaryl ring. In a further embodiment of the aforementioned embodiments is a compound of Formula (Id) wherein $R^1$ and $R^2$ together with the carbon atoms to which they are attached, form an optionally substituted $C_2$-$C_9$heterocycloalkyl ring. In a further embodiment of the aforementioned embodiments is a compound of Formula (Id) wherein $R^1$ and $R^2$ together with the carbon atoms to which they are attached, form an optionally substituted heteroaryl ring.

In a further embodiment of the aforementioned embodiments is a compound of Formula (Id) wherein $R^8$ is selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl). In a further embodiment of the aforementioned embodiments is a compound of Formula (Id) wherein $R^8$ is selected from the group consisting of hydrogen, and optionally substituted $C_1$-$C_6$alkyl. In a further embodiment of the aforementioned embodiments is a compound of Formula (Id) wherein $R^8$ is optionally substituted $C_1$-$C_6$alkyl. In a further embodiment of the aforementioned embodiments is a compound of Formula (Id) wherein $R^8$ is methyl. In a further embodiment of the aforementioned embodiments is a compound of Formula (Id) wherein $R^8$ is optionally substituted $C_1$-$C_6$alkyl. In a further embodiment of the aforementioned embodiments is a compound of Formula (Id) wherein $R^8$ is ethyl. In a further embodiment of the aforementioned embodiments is a compound of Formula (Id) wherein $R^8$ is optionally substituted $C_1$-$C_6$alkyl. In a further embodiment of the aforementioned embodiments is a compound of Formula (Id) wherein $R^8$ is hydrogen.

In another embodiment of the aforementioned embodiments is a compound of Formula (Id) wherein $R^{15}$ is —OC(=J)OR$^{16a}$. In another embodiment of the aforementioned embodiments is a compound of Formula (Id) wherein $R^{15}$ is —N(R$^{12}$)C(=J)OR$^{16a}$. In another embodiment of the aforementioned embodiments is a compound of Formula (Id) wherein $R^{15}$ is —OC(=J)N(H)R$^{16a}$. In another embodiment of the aforementioned embodiments is a compound of Formula (Id) wherein $R^{15}$ is —N(R$^{12}$)C(=J)N(H)R$^{16a}$. In another embodiment of the aforementioned embodiments is a compound of Formula (Id) wherein $R^{15}$ is —OC(=J)N(H)(C$_2$-C$_6$alkyl)R$^{30}$. In another embodiment of the aforementioned embodiments is a compound of Formula (Id) wherein $R^{15}$ is —N(R$^{12}$)C(=J)O(C$_2$-C$_6$alkyl)R$^{30}$. In another embodiment of the aforementioned embodiments is a compound of Formula (Id) wherein $R^{15}$ is —N(R$^{12}$)C(=J)N(H)(C$_2$-C$_6$alkyl)R$^{30}$. In another embodiment of the aforementioned embodiments is a compound of Formula (Id) wherein $R^{15}$ is —OC(=J)O(C$_2$-C$_6$alkyl)R$^{30}$. In another embodiment of the aforementioned embodiments is a compound of Formula (Id) wherein $R^{15}$ is —C(=J)R$^{31}$. In another embodiment of the aforementioned embodiments is a compound of Formula (Id) wherein $R^{15}$ is —OC(=J)R$^{31}$. In another embodiment of the aforementioned embodiments is a compound of Formula (Id) wherein $R^{15}$ is —N(R$^{12}$)C(=J)R$^{31}$. In another embodiment of the aforementioned embodiments is a compound of Formula (Id) wherein $R^{15}$ is —O(C$_2$-C$_6$alkyl)R$^{30}$. In another embodiment of the aforementioned embodiments is a compound of Formula (Id) wherein $R^{15}$ is —N(R$^{12}$)(C$_2$-C$_6$alkyl)R$^{30}$. In another embodiment of the aforementioned embodiments is a compound of Formula (Id) wherein $R^{15}$ is —OS(=O)$_v$R$^{31}$. In another embodiment of the aforementioned embodiments is a compound of Formula (Id) wherein $R^{15}$ is —N(R$^{12}$)S(=O)$_v$R$^{31}$. In another embodiment of the aforementioned embodiments is a compound of Formula (Id) wherein $R^{15}$ is —OS(=O)$_v$(C$_2$-C$_6$alkyl)R$^{30}$. In another embodiment of the aforementioned embodiments is a compound of Formula (Id) wherein $R^{15}$ is —N($R^{12}$)S(=O)$_v$(C$_2$-C$_6$alkyl)$R^{30}$. In a further embodiment of the aforementioned embodiments is a compound of Formula (Id) wherein $R^{30}$ is $R^{16a}$. In a further embodiment of the aforementioned embodiments is a compound of Formula (Id) wherein $R^{30}$ is $R^{16b}$. In a further embodiment of the aforementioned embodiments is a compound of Formula (Id) wherein $R^{30}$ is $R^{16c}$. In a further embodiment of the aforementioned embodiments is a compound of Formula (Id) wherein $R^{31}$ is $R^{16a}$. In a further embodiment of the aforementioned embodiments is a compound of Formula (Id) wherein $R^{31}$ is $R^{16b}$. In a further embodiment of the aforementioned embodiments is a compound of Formula (Id) wherein J is O. In a further embodiment of the aforementioned embodiments is a compound of Formula (Id) wherein J is S. In a further embodiment of the aforementioned embodiments is a compound of Formula (Id) wherein J is N($R^{12}$).

In another embodiment of the aforementioned embodiments is a compound of Formula (Id) wherein $R^{16a}$ is

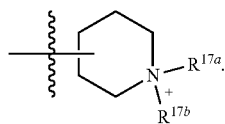

In another embodiment of the aforementioned embodiments is a compound of Formula (Id) wherein $R^{16a}$ is

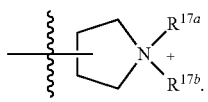

In another embodiment of the aforementioned embodiments is a compound of Formula (Id) wherein $R^{16a}$ is

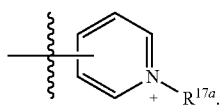

In another embodiment of the aforementioned embodiments is a compound of Formula (Id) wherein $R^{16b}$ is

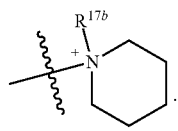

In another embodiment of the aforementioned embodiments is a compound of Formula (Id) wherein $R^{16b}$ is

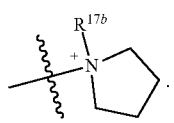

In another embodiment of the aforementioned embodiments is a compound of Formula (Id) wherein $R^{16b}$ is

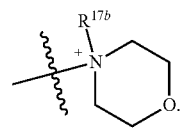

In another embodiment of the aforementioned embodiments is a compound of Formula (Id) wherein $R^{16b}$ is

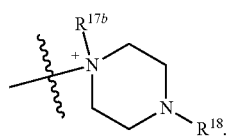

In another embodiment of the aforementioned embodiments is a compound of Formula (Id) wherein $R^{16b}$ is

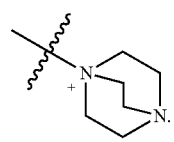

In another embodiment of the aforementioned embodiments is a compound of Formula (Id) wherein $R^{16b}$ is

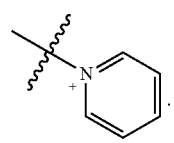

In another embodiment of the aforementioned embodiments is a compound of Formula (Id) wherein $R^{16b}$ is

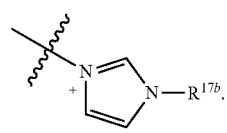

In another embodiment of the aforementioned embodiments is a compound of Formula (Id) wherein $R^{16c}$ is

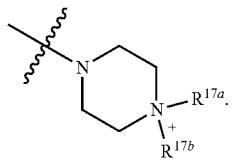

In another embodiment is a compound of Formula (Id) wherein $R^{16c}$ is

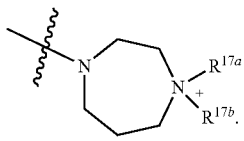

In a further embodiment of the aforementioned embodiments is a compound of Formula (Id) wherein $R^{17a}$ is methyl. In a further embodiment of the aforementioned embodiments is a compound of Formula (Id) wherein $R^{17a}$ is ethyl. In a further embodiment of the aforementioned embodiments is a compound of Formula (Id) wherein $R^{17b}$ is methyl optionally substituted with phenyl, —C(=O)OH or —S(=O)$_2$OH. In a further embodiment of the aforementioned embodiments is a compound of Formula (Id) wherein $R^{17a}$ is ethyl optionally substituted with phenyl, —C(=O)OH or —S(=O)$_2$OH.

In another embodiment of the aforementioned embodiments is a compound of Formula (Id) wherein n is 0. In another embodiment of the aforementioned embodiments is a compound of Formula (Id) wherein n is 1. In another embodiment of the aforementioned embodiments is a compound of Formula (Id) wherein n is 1 and $R^{11}$ is $C_1$-$C_6$alkyl. In another embodiment of the aforementioned embodiments is a compound of Formula (Id) wherein n is 1 and $R^{11}$ is $C_1$-$C_6$haloalkyl.

In another embodiment is a compound of Formula (Id) wherein $R^{15}$ is —OC(=J)OR$^{16a}$, —N(R$^{12}$)C(=J)OR$^{16a}$, —OC(=J)N(H)R$^{16a}$, —N(R$^{12}$)C(=J)N(H)R$^{16a}$, —OC(=J)N(H)(C$_1$-C$_6$alkyl)R$^{31}$, —N(R$^{12}$)C(=J)O(C$_1$-C$_6$alkyl)R$^{31}$, —N(R$^{12}$)C(=J)N(H)(C$_1$-C$_6$alkyl)R$^{31}$, —OC(=J)O(C$_1$-C$_6$alkyl)R$^{31}$, —C(=J)R$^{31}$, —OC(=J)R$^{31}$, —N(R$^{12}$)C(=J)R$^{31}$, —O(C$_1$-C$_6$alkyl)R$^{31}$, —N(R$^{12}$)(C$_1$-C$_6$alkyl)R$^{31}$, —OS(=O)$_x$R$^{31}$, —N(R$^{12}$)S(=O)$_x$R$^{31}$, —OS(=O)$_x$(C$_1$-C$_6$alkyl)R$^{31}$, or —N(R$^{12}$)S(=O)$_x$(C$_1$-C$_6$alkyl)R$^{31}$.

In some embodiments provided herein, the compound of Formula (I) has the structure of Formula (Ie), or a pharmaceutically acceptable salt or solvate thereof:

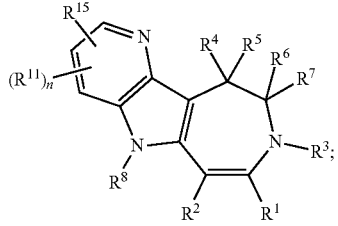

Formula (Ie)

wherein:
$R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);
$R^2$ is selected from the group consisting of —CN, —C(=O)OR$^{25}$, —C(=O)N(R$^{25}$)R$^{26}$,

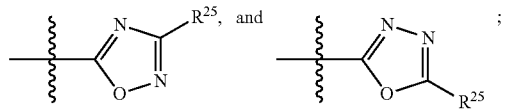

or $R^1$ and $R^2$ together with the carbon atoms to which they are attached, form an optionally substituted $C_2$-$C_9$heterocycloalkyl ring or an optionally substituted heteroaryl ring;
$R^3$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_{10}$cycloalkyl, optionally substituted aryl, optionally substituted —($C_1$-$C_2$alkylene)-(aryl), optionally substituted heteroaryl, optionally substituted $C_2$-$C_9$heterocycloalkyl, optionally substituted —($C_1$-$C_2$alkylene)-(heteroaryl), —C(=O)R$^{20}$, —C(=O)OR$^{20}$, —S(=O)$_2$R$^{20}$, —C(=O)N(R$^{21}$)R$^{22}$, —C(=O)N(R$^{21}$)S(=O)$_2$R$^{24}$, —C(=O)N(R$^{23}$)N(R$^{21}$)R$^{22}$, —C(=O)N(R$^{23}$)N(R$^{21}$)S(=O)$_2$R$^{24}$, —N(R$^{23}$)C(=O)R$^{20}$, —N(R$^{23}$)C(=O)N(R$^{21}$)R$^{22}$, —N(R$^{23}$)C(=O)N(R$^{21}$)S(=O)$_2$R$^{24}$, —N(R$^{20}$)C(=O)N(R$^{23}$)N(R$^{21}$)R$^{22}$, —N(R$^{20}$)C(=O)N(R$^{23}$)N(R$^{21}$)S(=O)$_2$R$^{24}$, —N(R$^{23}$)C(=O)OR$^{20}$, —P(=O)OR$^{20}$, and —P(=O)(OR$^{19}$)OR$^{20}$;
$R^4$ and $R^5$ are each independently selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl; or $R^4$ and $R^5$ together with the carbon atom to which they are attached, form an optionally substituted $C_3$-$C_6$cycloalkyl ring or an optionally substituted $C_2$-$C_7$heterocycloalkyl ring;
$R^6$ is selected from the group consisting of hydrogen, halogen, optionally substituted $C_1$-$C_6$alkyl, optionally substituted $C_2$-$C_6$alkenyl, optionally substituted $C_2$-$C_6$alkynyl, and —C(=O)N(R$^{27}$)R$^{28}$;
$R^7$ is selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl;
$R^8$ is selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl);
each $R^{11}$ is independently selected from the group consisting of halogen, —CN, amino, alkylamino, $C_1$-$C_6$alkyl, $C_1$-$C_6$haloalkyl, $C_1$-$C_6$alkoxy, $C_1$-$C_6$haloalkoxy, $C_3$-$C_8$cycloalkyl, $C_2$-$C_9$heterocycloalkyl, aryl, heteroaryl, —C(=O)OR$^{12}$, —C(=O)N(R$^{13}$)R$^{14}$;
each $R^{12}$ is independently selected from the group consisting of hydrogen and $C_1$-$C_6$alkyl;
each $R^{13}$ and $R^{14}$ are each independently selected from the group consisting of hydrogen and $C_1$-$C_6$alkyl; or $R^{13}$ and $R^{14}$ together with the nitrogen atom to which they are attached, form an optionally substituted $C_2$-$C_9$heterocycloalkyl ring;
$R^{15}$ is —OC(=J)OR$^{16a}$, —N(R$^{12}$)C(=J)OR$^{16a}$, —OC(=J)N(H)R$^{16a}$, —N(R$^{12}$)C(=J)N(H)R$^{16a}$, —OC(=J)N(H)(C$_2$-C$_6$alkyl)R$^{30}$, —N(R$^{12}$)C(=J)O(C$_2$-C$_6$alkyl)R$^{30}$, —N(R$^{12}$)C(=J)N(H)(C$_2$-C$_6$alkyl)R$^{30}$, —OC(=J)O(C$_2$-

$C_6$alkyl)$R^{30}$, —C(=J)$R^{31}$, —OC(=J)$R^{31}$, —N($R^{12}$)C(=J)$R^{31}$, —O($C_2$-$C_6$alkyl)$R^{30}$, —N($R^{12}$)($C_2$-$C_6$alkyl)$R^{30}$, —OS(=O)$_v$$R^{31}$, —N($R^{12}$)S(=O)$_v$$R^{31}$, —OS(=O)$_v$($C_2$-$C_6$alkyl)$R^{30}$, or —N($R^{12}$)S(=O)$_v$($C_2$-$C_6$alkyl)$R^{30}$;

$R^{30}$ is $R^{16a}$, $R^{16b}$, or $R^{16c}$;
$R^{31}$ is $R^{16a}$ or $R^{16c}$;
J is O, S, or N($R^{12}$);
$R^{16a}$ is

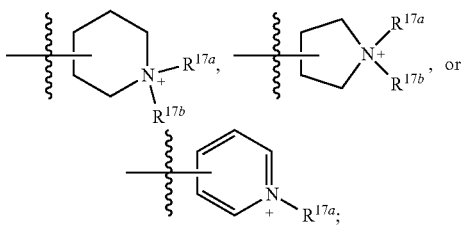

$R^{16b}$ is

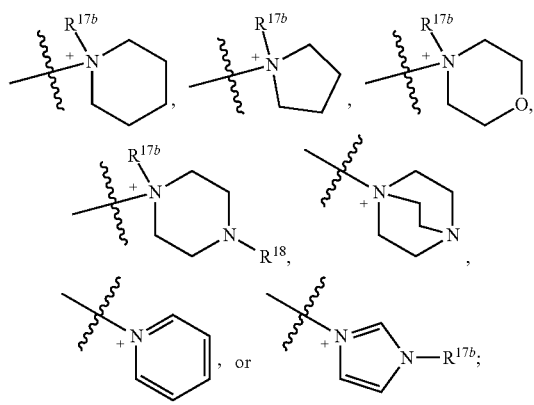

$R^{16c}$ is

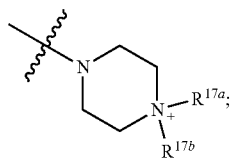

$R^{17a}$ is $C_1$-$C_6$alkyl;
$R^{17b}$ is $C_1$-$C_6$alkyl optionally substituted with phenyl, —C(=O)OH or —S(=O)$_2$OH;
$R^{18}$ is hydrogen, —OH, —($C_0$-$C_6$alkyl)—C(=O)OH, or $C_1$-$C_6$alkyl;
n is 0, 1, or 2;
v is 1 or 2;
$R^{19}$, $R^{20}$, and $R^{23}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R^{21}$ and $R^{22}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{21}$ and $R^{22}$ together with the nitrogen atom to which they are attached, form an optionally substituted $C_2$-$C_9$heterocycloalkyl ring;

$R^{24}$ is selected from the group consisting of optionally substituted $C_1$-$C_6$alkyl, optionally substituted $C_2$-$C_6$alkenyl, optionally substituted $C_2$-$C_6$alkynyl, optionally substituted $C_3$-$C_5$ cycloalkyl, optionally substituted aryl optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); and $R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R^{27}$ and $R^{28}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{27}$ and $R^{28}$ together with the nitrogen atom to which they are attached, form an optionally substituted $C_2$-$C_9$heterocycloalkyl ring.

In one embodiment is a compound of Formula (Ie) wherein $R^4$ and $R^5$ are each independently selected from the group consisting of hydrogen, halogen, and optionally substituted $C_1$-$C_6$alkyl. In another embodiment is a compound of Formula (Ie) wherein $R^4$ and $R^5$ are each independently selected from the group consisting of hydrogen and optionally substituted $C_1$-$C_6$alkyl. In another embodiment is a compound of Formula (Ie) wherein $R^4$ and $R^5$ are each hydrogen. In another embodiment is a compound of Formula (Ie) wherein $R^4$ and $R^5$ are each independently optionally substituted $C_1$-$C_6$alkyl. In another embodiment is a compound of Formula (Ie) wherein $R^4$ and $R^5$ are each methyl. In another embodiment is a compound of Formula (Ie) wherein $R^4$ and $R^5$ form an optionally substituted $C_3$-$C_6$cycloalkyl ring or an optionally substituted $C_2$-$C_7$heterocycloalkyl ring. In some embodiments is a compound of Formula (Ie) wherein $R^4$ and $R^5$ form an optionally substituted $C_3$-$C_6$cycloalkyl ring. In some embodiments is a compound of Formula (Ie) wherein $R^4$ and $R^5$ form an optionally substituted $C_2$-$C_7$heterocycloalkyl ring.

In another embodiment is a compound of Formula (Ie) wherein $R^6$ and $R^7$ are each independently selected from the group consisting of hydrogen, halogen, and optionally substituted $C_1$-$C_6$alkyl. In another embodiment is a compound of Formula (Ie) wherein $R^6$ and $R^7$ are each independently selected from the group consisting of hydrogen and optionally substituted $C_1$-$C_6$alkyl. In another embodiment is a compound of Formula (Ie) wherein $R^6$ and $R^7$ are each independently optionally substituted $C_1$-$C_6$alkyl. In another embodiment is a compound of Formula (Ie) wherein $R^6$ and $R^7$ are each methyl. In another embodiment is a compound of Formula (Ie) wherein $R^6$ and $R^7$ are each hydrogen.

In another embodiment is a compound of Formula (Ie) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted aryl. In another embodiment is a compound of Formula (Ie) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted heteroaryl. In another embodiment is a compound of Formula (Ie) wherein $R^6$ and $R^7$ are hydrogen, $R^4$ and $R^5$ are methyl, $R^3$ is —C(O)$R^{20}$, and $R^{20}$ is optionally substituted aryl. In another embodiment is a compound of Formula (Ie) wherein $R^6$ and $R^7$ are hydrogen, $R^4$ and $R^5$ are methyl, $R^3$ is —C(O)$R^{20}$, and $R^{20}$ is optionally substituted heteroaryl.

In another embodiment is a compound of Formula (Ie) wherein $R^6$ and $R^7$ are hydrogen, $R^4$ and $R^5$ are independently optionally substituted $C_1$-$C_6$alkyl, $R^3$ is —S(O)$_2$$R^{20}$, and $R^{20}$ is optionally substituted aryl. In another embodiment is a compound of Formula (Ie) wherein $R^6$ and $R^7$ are hydrogen, $R^4$ and $R^5$ are independently optionally substituted $C_1$-$C_6$alkyl, $R^3$ is —S(O)$_2$$R^{20}$, and $R^{20}$ is optionally substituted heteroaryl. In another embodiment is a compound of Formula (Ie) wherein $R^6$ and $R^7$ are hydrogen, $R^4$ and $R^5$ are methyl, $R^3$ is —S(O)$_2$$R^{20}$, and $R^{20}$ is optionally substituted aryl. In another embodiment is a compound of Formula (Ie) wherein $R^6$ and $R^7$ are hydrogen, $R^4$ and $R^5$ are methyl, $R^3$ is —S(O)$_2$$R^{20}$, and $R^{20}$ is optionally substituted heteroaryl.

In another embodiment is a compound of Formula (Ie) wherein $R^6$ and $R^7$ are hydrogen, $R^4$ and $R^5$ are independently optionally substituted $C_1$-$C_6$alkyl, $R^3$ is —C(O)N($R^{21}$)$R^{22}$, $R^{21}$ is hydrogen and $R^{22}$ is optionally substituted aryl. In another embodiment is a compound of Formula (Ie) wherein $R^6$ and $R^7$ are hydrogen, $R^4$ and $R^5$ are independently optionally substituted $C_1$-$C_6$alkyl, $R^3$ is —C(O)N($R^{21}$)$R^{22}$, $R^{21}$ is hydrogen and $R^{22}$ is optionally substituted heteroaryl. In another embodiment is a compound of Formula (Ie) wherein $R^6$ and $R^7$ are hydrogen, $R^4$ and $R^5$ are methyl, $R^3$ is —C(O)N($R^{21}$)$R^{22}$, $R^{21}$ is hydrogen and $R^{22}$ is optionally substituted aryl. In another embodiment is a compound of Formula (Ie) wherein $R^6$ and $R^7$ are hydrogen, $R^4$ and $R^5$ are methyl, $R^3$ is —C(O)N($R^{21}$)$R^{22}$, $R^{21}$ is hydrogen and $R^{22}$ is optionally substituted heteroaryl.

In a further embodiment of the aforementioned embodiments is a compound of Formula (Ie) wherein $R^2$ is selected from the group consisting of —CN, —C(O)O$R^{25}$, —C(O)N($R^{25}$)$R^{26}$,

[chemical structures]

In a further embodiment of the aforementioned embodiments is a compound of Formula (Ie) wherein $R^2$ is —CN.

In a further embodiment of the aforementioned embodiments is a compound of Formula (Ie) wherein $R^2$ is —C(O)O$R^{25}$. In a further embodiment of the aforementioned embodiments is a compound of Formula (Ie) wherein $R^2$ is —C(O)O$R^{25}$, and $R^{25}$ is independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (Ie) wherein $R^2$ is —C(O)O$R^{25}$, and $R^{25}$ is independently selected from the group consisting of hydrogen, and optionally substituted $C_1$-$C_6$alkyl. In a further embodiment of the aforementioned embodiments is a compound of Formula (Ie) wherein $R^2$ is —C(O)O$R^{25}$, and $R^{25}$ is hydrogen. In a further embodiment of the aforementioned embodiments is a compound of Formula (Ie) wherein $R^2$ is —C(O)O$R^{25}$, and $R^{25}$ is optionally substituted $C_1$-$C_6$alkyl. In a further embodiment of the aforementioned embodiments is a compound of Formula (Ie) wherein $R^2$ is —C(O)O$R^{25}$, and $R^{25}$ is unsubstituted $C_1$-$C_6$alkyl. In a further embodiment of the aforementioned embodiments is a compound of Formula (Ie) wherein $R^2$ is —C(O)O$R^{25}$, and $R^{25}$ is methyl. In a further embodiment of the aforementioned embodiments is a compound of Formula (Ie) wherein $R^2$ is —C(O)O$R^{25}$, and $R^{25}$ is ethyl.

In a further embodiment of the aforementioned embodiments is a compound of Formula (Ie) wherein $R^2$ is —C(O)N($R^{25}$)$R^{26}$. In a further embodiment of the aforementioned embodiments is a compound of Formula (Ie) wherein $R^2$ is —C(O)N($R^{25}$)$R^{26}$, and $R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (Ie) wherein $R^2$ is —C(O)N($R^{25}$)$R^{26}$, and $R^{25}$ and $R^{26}$ are each independently selected from the group consisting of hydrogen, and optionally substituted $C_1$-$C_6$alkyl. In a further embodiment of the aforementioned embodiments is a compound of Formula (Ie) wherein $R^2$ is —C(O)N($R^{25}$)$R^{26}$, and $R^{25}$ and $R^{26}$ are hydrogen. In a further embodiment of the aforementioned embodiments is a compound of Formula (Ie) wherein $R^2$ is —C(O)N($R^{25}$)$R^{26}$, and $R^{25}$ and $R^{26}$ are each independently optionally substituted $C_1$-$C_6$alkyl. In a further embodiment of the aforementioned embodiments is a compound of Formula (Ie) wherein $R^2$ is —C(O)N($R^{25}$)$R^{26}$, $R^{25}$ is hydrogen, and $R^{26}$ is optionally substituted $C_1$-$C_6$alkyl. In a further embodiment of the aforementioned embodiments is a compound of Formula (Ie) wherein $R^2$ is —C(O)N($R^{25}$)$R^{26}$, and $R^{25}$ and $R^{26}$ are each independently unsubstituted $C_1$-$C_6$alkyl. In a further embodiment of the aforementioned embodiments is a compound of Formula (Ie) wherein $R^2$ is —C(O)N($R^{25}$)$R^{26}$, $R^{25}$ is hydrogen, and $R^{26}$ are methyl. In a further embodiment of the aforementioned embodiments is a compound of Formula (Ie) wherein $R^2$ is —C(O)N($R^{25}$)$R^{26}$, and $R^{25}$ and $R^{26}$ are methyl. In a further embodiment of the aforementioned embodiments is a compound of Formula (Ie) wherein $R^2$ is —C(O)N($R^{25}$)$R^{26}$, and $R^{25}$ and $R^{26}$ are ethyl.

In a further embodiment of the aforementioned embodiments is a compound of Formula (Ie) wherein $R^2$ is

[chemical structure]

In a further embodiment of the aforementioned embodiments is a compound of Formula (Ie) wherein $R^2$ is

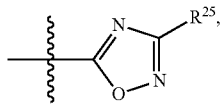

and $R^{25}$ is optionally substituted $C_1$-$C_6$alkyl. In a further embodiment of the aforementioned embodiments is a compound of Formula (Ie) wherein $R^2$ is

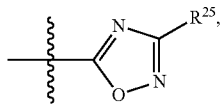

and $R^{25}$ is methyl. In a further embodiment of the aforementioned embodiments is a compound of Formula (Ie) wherein $R^2$ is

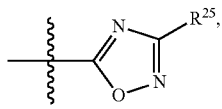

and $R^{25}$ is optionally substituted $C_1$-$C_6$alkyl. In a further embodiment of the aforementioned embodiments is a compound of Formula (Ie) wherein $R^2$ is

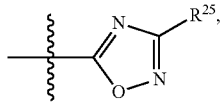

and $R^{25}$ is ethyl.

In a further embodiment of the aforementioned embodiments is a compound of Formula (Ie) wherein $R^2$ is

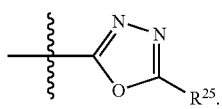

In a further embodiment of the aforementioned embodiments is a compound of Formula (Ie) wherein $R^2$ is

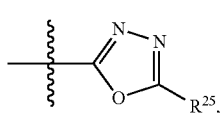

and $R^{25}$ is optionally substituted $C_1$-$C_6$alkyl. In a further embodiment of the aforementioned embodiments is a compound of Formula (Ie) wherein $R^2$ is

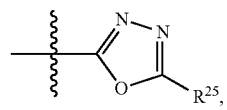

and $R^{25}$ is methyl. In a further embodiment of the aforementioned embodiments is a compound of Formula (Ie) wherein $R^2$ is

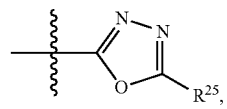

and $R^{25}$ is optionally substituted $C_1$-$C_6$alkyl. In a further embodiment of the aforementioned embodiments is a compound of Formula (Ie) wherein $R^2$ is

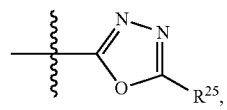

and $R^{25}$ is ethyl.

In a further embodiment of the aforementioned embodiments is a compound of Formula (Ie) wherein $R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (Ie) wherein $R^1$ is hydrogen. In a further embodiment of the aforementioned embodiments is a compound of Formula (Ie) wherein $R^1$ is optionally substituted $C_1$-$C_6$alkyl. In a further embodiment of the aforementioned embodiments is a compound of Formula (Ie) wherein $R^1$ is methyl. In a further embodiment of the aforementioned embodiments is a compound of Formula (Ie) wherein $R^1$ is optionally substituted $C_2$-$C_6$alkenyl. In a further embodiment of the aforementioned embodiments is a compound of Formula (Ie) wherein $R^1$ is optionally substituted $C_2$-$C_6$alkynyl.

In a further embodiment of the aforementioned embodiments is a compound of Formula (Ie) wherein $R^1$ and $R^2$ together with the carbon atoms to which they are attached, form an optionally substituted $C_2$-$C_9$heterocycloalkyl ring or an optionally substituted heteroaryl ring. In a further embodiment of the aforementioned embodiments is a compound of Formula (Ie) wherein $R^1$ and $R^2$ together with the carbon atoms to which they are attached, form an optionally substituted $C_2$-$C_9$heterocycloalkyl ring. In a further embodiment of the aforementioned embodiments is a compound of Formula (Ie) wherein $R^1$ and $R^2$ together with the carbon atoms to which they are attached, form an optionally substituted heteroaryl ring.

In a further embodiment of the aforementioned embodiments is a compound of Formula (Ie) wherein $R^8$ is selected from the group consisting of hydrogen, optionally substituted $C_1$-$C_6$alkyl, optionally substituted $C_3$-$C_8$cycloalkyl, optionally substituted aryl, optionally substituted —($C_1$-

$C_2$alkylene)-(aryl), optionally substituted heteroaryl, optionally substituted $C_2$-$C_9$heterocycloalkyl, and optionally substituted —($C_1$-$C_2$alkylene)-(heteroaryl). In a further embodiment of the aforementioned embodiments is a compound of Formula (Ie) wherein $R^8$ is selected from the group consisting of hydrogen, and optionally substituted $C_1$-$C_6$alkyl. In a further embodiment of the aforementioned embodiments is a compound of Formula (Ie) wherein $R^8$ is optionally substituted $C_1$-$C_6$alkyl. In a further embodiment of the aforementioned embodiments is a compound of Formula (Ie) wherein $R^8$ is methyl. In a further embodiment of the aforementioned embodiments is a compound of Formula (Ie) wherein $R^8$ is optionally substituted $C_1$-$C_6$alkyl. In a further embodiment of the aforementioned embodiments is a compound of Formula (Ie) wherein $R^8$ is ethyl. In a further embodiment of the aforementioned embodiments is a compound of Formula (Ie) wherein $R^8$ is optionally substituted $C_1$-$C_6$alkyl. In a further embodiment of the aforementioned embodiments is a compound of Formula (Ie) wherein $R^8$ is hydrogen.

In another embodiment of the aforementioned embodiments is a compound of Formula (Ie) wherein $R^{15}$ is —OC(=J)O$R^{16a}$. In another embodiment of the aforementioned embodiments is a compound of Formula (Ie) wherein $R^{15}$ is —N($R^{12}$)C(=J)O$R^{16a}$. In another embodiment of the aforementioned embodiments is a compound of Formula (Ie) wherein $R^{15}$ is —OC(=J)N(H)$R^{16a}$. In another embodiment of the aforementioned embodiments is a compound of Formula (Ie) wherein $R^{15}$ is —N($R^{12}$)C(=J)N(H)$R^{16a}$. In another embodiment of the aforementioned embodiments is a compound of Formula (Ie) wherein $R^{15}$ is —OC(=J)N(H)($C_2$-$C_6$alkyl)$R^{30}$. In another embodiment of the aforementioned embodiments is a compound of Formula (Ie) wherein $R^{15}$ is —N($R^{12}$)C(=J)O($C_2$-$C_6$alkyl)$R^{30}$. In another embodiment of the aforementioned embodiments is a compound of Formula (Ie) wherein $R^{15}$ is —N($R^{12}$)C(=J)N(H)($C_2$-$C_6$alkyl)$R^{30}$. In another embodiment of the aforementioned embodiments is a compound of Formula (Ie) wherein $R^{15}$ is —OC(=J)O($C_2$-$C_6$alkyl)$R^{30}$. In another embodiment of the aforementioned embodiments is a compound of Formula (Ie) wherein $R^{15}$ is —C(=J)$R^{31}$. In another embodiment of the aforementioned embodiments is a compound of Formula (Ie) wherein $R^{15}$ is —OC(=J)$R^{31}$. In another embodiment of the aforementioned embodiments is a compound of Formula (Ie) wherein $R^{15}$ is —N($R^{12}$)C(=J)$R^{31}$. In another embodiment of the aforementioned embodiments is a compound of Formula (Ie) wherein $R^{15}$ is —O($C_2$-$C_6$alkyl)$R^{30}$. In another embodiment of the aforementioned embodiments is a compound of Formula (Ie) wherein $R^{15}$ is —N($R^{12}$)($C_2$-$C_6$alkyl)$R^{30}$. In another embodiment of the aforementioned embodiments is a compound of Formula (Ie) wherein $R^{15}$ is —OS(=O)$_v$$R^{31}$. In another embodiment of the aforementioned embodiments is a compound of Formula (Ie) wherein $R^{15}$ is —N($R^{12}$)S(=O)$_v$$R^{31}$. In another embodiment of the aforementioned embodiments is a compound of Formula (Ie) wherein $R^{15}$ is —OS(=O)$_v$($C_2$-$C_6$alkyl)$R^{30}$. In another embodiment of the aforementioned embodiments is a compound of Formula (Ie) wherein $R^{15}$ is —N($R^{12}$)S(=O)$_v$($C_2$-$C_6$alkyl)$R^{30}$. In a further embodiment of the aforementioned embodiments is a compound of Formula (Ie) wherein $R^{30}$ is $R^{16a}$. In a further embodiment of the aforementioned embodiments is a compound of Formula (Ie) wherein $R^{30}$ is $R^{16b}$. In a further embodiment of the aforementioned embodiments is a compound of Formula (Ie) wherein $R^{30}$ is $R^{16c}$. In a further embodiment of the aforementioned embodiments is a compound of Formula (Ie) wherein $R^{31}$ is $R^{16a}$. In a further embodiment of the aforementioned embodiments is a compound of Formula (Ie) wherein $R^{31}$ is $R^{16b}$. In a further embodiment of the aforementioned embodiments is a compound of Formula (Ie) wherein J is O. In a further embodiment of the aforementioned embodiments is a compound of Formula (Ie) wherein J is S. In a further embodiment of the aforementioned embodiments is a compound of Formula (Ie) wherein J is N($R^{12}$).

In another embodiment of the aforementioned embodiments is a compound of Formula (Ie) wherein $R^{16a}$ is In another embodiment of the aforementioned embodiments is a compound of Formula (Ie) wherein $R^{16a}$ is In another embodiment of the aforementioned embodiments is a compound of Formula (Ie) wherein $R^{16a}$ is In another embodiment of the aforementioned embodiments is a compound of Formula (Ie) wherein $R^{16b}$ is In another embodiment of the aforementioned embodiments is a compound of Formula (Ie) wherein $R^{16b}$ is In another embodiment of the aforementioned embodiments is a compound of Formula (Ie) wherein $R^{16b}$ is In another embodiment of the aforementioned embodiments is a compound of Formula (Ie) wherein $R^{16b}$ is

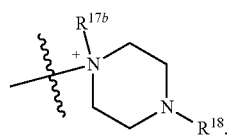

In another embodiment of the aforementioned embodiments is a compound of Formula (Ie) wherein $R^{16b}$ is

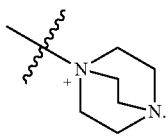

In another embodiment of the aforementioned embodiments is a compound of Formula (Ie) wherein $R^{16b}$ is

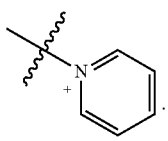

In another embodiment of the aforementioned embodiments is a compound of Formula (Ie) wherein $R^{16b}$ is

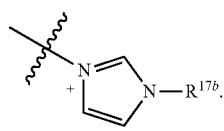

In another embodiment of the aforementioned embodiments is a compound of Formula (Ie) wherein $R^{16c}$ is

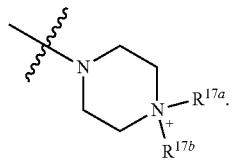

In another embodiment is a compound of Formula (Ie) wherein $R^{16c}$ is

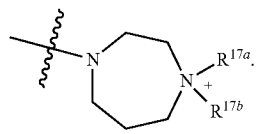

In a further embodiment of the aforementioned embodiments is a compound of Formula (Ie) wherein $R^{17a}$ is methyl. In a further embodiment of the aforementioned embodiments is a compound of Formula (Ie) wherein $R^{17a}$ is ethyl. In a further embodiment of the aforementioned embodiments is a compound of Formula (Ie) wherein $R^{17b}$ is methyl optionally substituted with phenyl, —C(=O)OH or —S(=O)$_2$OH. In a further embodiment of the aforementioned embodiments is a compound of Formula (Ie) wherein $R^{17a}$ is ethyl optionally substituted with phenyl, —C(=O)OH or —S(=O)$_2$OH.

In another embodiment of the aforementioned embodiments is a compound of Formula (Ie) wherein n is 0. In another embodiment of the aforementioned embodiments is a compound of Formula (Ie) wherein n is 1. In another embodiment of the aforementioned embodiments is a compound of Formula (Ie) wherein n is 1 and $R^{11}$ is $C_1$-$C_6$alkyl. In another embodiment of the aforementioned embodiments is a compound of Formula (Ie) wherein n is 1 and $R^{11}$ is $C_1$-$C_6$haloalkyl.

In another embodiment is a compound of Formula (Ie) wherein $R^{15}$ is —OC(=J)OR$^{16a}$, —N(R$^{12}$)C(=J)OR$^{16a}$, —OC(=J)N(H)R$^{16a}$, —N(R$^{12}$)C(=J)N(H)R$^{16a}$, —OC(=J)N(H)(C$_1$-C$_6$alkyl)R$^{31}$, —N(R$^{12}$)C(=J)O(C$_1$-C$_6$alkyl)R$^{31}$, —N(R$^{12}$)C(=J)N(H)(C$_1$-C$_6$alkyl)R$^{31}$, —OC(=J)O(C$_1$-C$_6$alkyl)R$^{31}$, —C(=J)R$^{31}$, —OC(=J)R$^{31}$, —N(R$^{12}$)C(=J)R$^{31}$, —O(C$_1$-C$_6$alkyl)R$^{31}$, —N(R$^{12}$)(C$_1$-C$_6$alkyl)R$^{31}$, —OS(=O)$_v$R$^{31}$, —N(R$^{12}$)S(=O)$_v$R$^{31}$, —OS(=O)$_v$(C$_1$-C$_6$alkyl)R$^{31}$, or —N(R$^{12}$)S(=O)$_v$(C$_1$-C$_6$alkyl)R$^{31}$.

In some embodiments provided herein, the compound of Formula (I) has the structure of Formula (If), or a pharmaceutically acceptable salt or solvate thereof:

Formula (If)

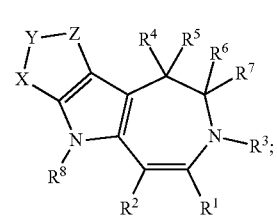

wherein:

—X—Y—Z— is selected from

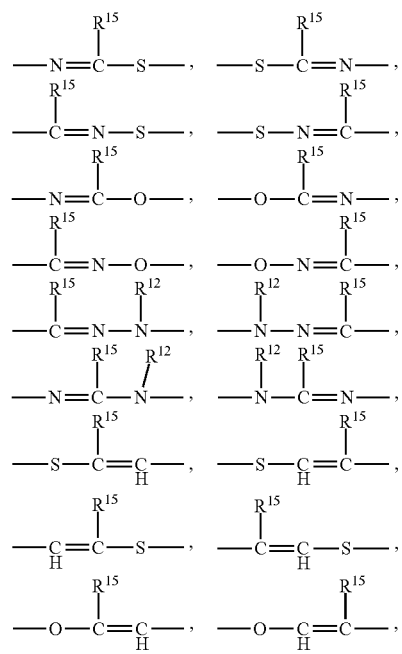

93

-continued

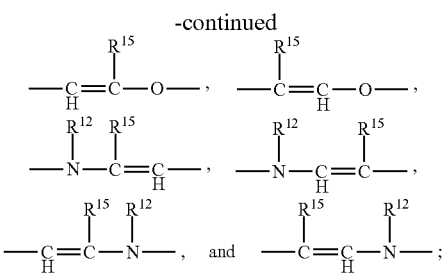

R$^1$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

R$^2$ is selected from the group consisting of —CN, —C(=O)OR$^{25}$, —C(=O)N(R$^{25}$)R$^{26}$,

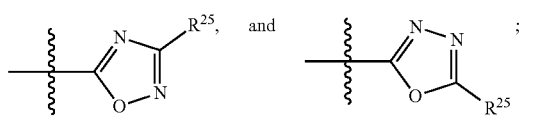

or R$^1$ and R$^2$ together with the carbon atoms to which they are attached, form an optionally substituted C$_2$-C$_9$heterocycloalkyl ring or an optionally substituted heteroaryl ring;

R$^3$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_{10}$cycloalkyl, optionally substituted aryl, optionally substituted —(C$_1$-C$_2$alkylene)-(aryl), optionally substituted heteroaryl, optionally substituted C$_2$-C$_9$heterocycloalkyl, optionally substituted —(C$_1$-C$_2$alkylene)-(heteroaryl), —C(=O)R$^{20}$, —C(=O)OR$^{20}$, —S(=O)$_2$R$^{20}$, —C(=O)N(R$^{21}$)R$^{22}$, —C(=O)N(R$^{21}$)S(=O)$_2$R$^{24}$, —C(=O)N(R$^{23}$)N(R$^{21}$)R$^{22}$, —C(=O)N(R$^{23}$)N(R$^{21}$)S(=O)$_2$R$^{24}$, —N(R$^{23}$)C(=O)R$^{20}$, —N(R$^{23}$)C(=O)N(R$^{21}$)R$^{22}$, —N(R$^{23}$)C(=O)N(R$^{21}$)S(=O)$_2$R$^{24}$, —N(R$^{20}$)C(=O)N(R$^{23}$)N(R$^{21}$)R$^{22}$, —N(R$^{20}$)C(=O)N(R$^{23}$)N(R$^{21}$)S(=O)$_2$R$^{24}$, —N(R$^{23}$)C(=O)OR$^{20}$, —P(=O)OR$^{20}$, and —P(=O)(OR$^{19}$)OR$^{20}$;

R$^4$ and R$^5$ are each independently selected from the group consisting of hydrogen, halogen, optionally substituted C$_1$-C$_6$alkyl, optionally substituted C$_1$-C$_6$alkoxy, optionally substituted C$_2$-C$_6$alkenyl, and optionally substituted C$_2$-C$_6$alkynyl; or R$^4$ and R$^5$ together with the carbon atom to which they are attached, form an optionally substituted C$_3$-C$_6$cycloalkyl ring or an optionally substituted C$_2$-C$_7$heterocycloalkyl ring;

R$^6$ is selected from the group consisting of hydrogen, halogen, optionally substituted C$_1$-C$_6$alkyl, optionally substituted C$_2$-C$_6$alkenyl, optionally substituted C$_2$-C$_6$alkynyl, and —C(=O)N(R$^{27}$)R$^{28}$;

R$^7$ is selected from the group consisting of hydrogen, halogen, optionally substituted C$_1$-C$_6$alkyl, optionally substituted C$_1$-C$_6$alkoxy, optionally substituted C$_2$-C$_6$alkenyl, and optionally substituted C$_2$-C$_6$alkynyl;

94

R$^8$ is selected from the group consisting of hydrogen, optionally substituted C$_1$-C$_6$alkyl, optionally substituted C$_3$-C$_8$cycloalkyl, optionally substituted aryl, optionally substituted —(C$_1$-C$_2$alkylene)-(aryl), optionally substituted heteroaryl, optionally substituted C$_2$-C$_9$heterocycloalkyl, and optionally substituted —(C$_1$-C$_2$alkylene)-(heteroaryl); each R$^{12}$ is independently selected from the group consisting of hydrogen and C$_1$-C$_6$alkyl;

R$^{15}$ is —OC(=J)OR$^{16a}$, —N(R$^{12}$)C(=J)OR$^{16a}$, —OC(=J)N(H)R$^{16a}$, —N(R$^{12}$)C(=J)N(H)R$^{16a}$, —OC(=J)N(H)(C$_2$-C$_6$alkyl)R$^{30}$, —N(R$^{12}$)C(=J)O(C$_2$-C$_6$alkyl)R$^{30}$, —N(R$^{12}$)C(=J)N(H)(C$_2$-C$_6$alkyl)R$^{30}$, —OC(=J)(C$_2$-C$_6$alkyl)R$^{30}$, —C(=J)R$^{31}$, —OC(=J)R$^{31}$, —N(R$^{12}$)C(=J)R$^{31}$, —O(C$_2$-C$_6$alkyl)R$^{30}$, —N(R$^{12}$)(C$_2$-C$_6$alkyl)R$^{30}$, —OS(=O)$_v$R$^{31}$, —N(R$^{12}$)S(=O)$_v$R$^{31}$, —OS(=O)$_v$(C$_2$-C$_6$alkyl)R$^{30}$, or —N(R$^{12}$)S(=O)$_v$(C$_2$-C$_6$alkyl)R$^{30}$;

R$^{30}$ is R$^{16a}$, R$^{16b}$, or R$^{16c}$;
R$^{31}$ is R$^{16a}$ or R$^{16c}$;
J is O, S, or N(R$^{12}$);
R$^{16a}$ is

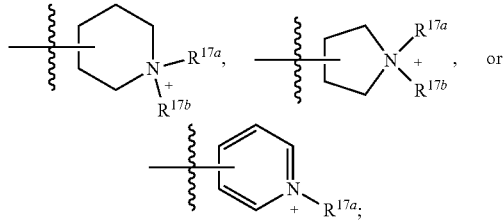

R$^{16b}$ is

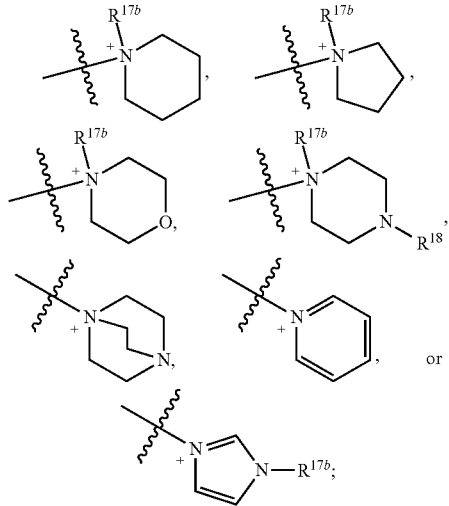

R$^{16c}$ is

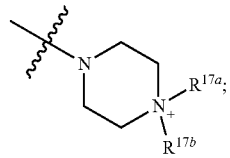

$R^{17a}$ is $C_1$-$C_6$alkyl;

$R^{17b}$ is $C_1$-$C_6$alkyl optionally substituted with phenyl, —C(═O)OH or —S(═O)$_2$OH;

$R^{18}$ is hydrogen, —OH, —($C_0$-$C_6$alkyl)-C(═O)OH, or $C_1$-$C_6$alkyl;

v is 1 or 2;

$R^{19}$, $R^{20}$, and $R^{23}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R^{21}$ and $R^{22}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{21}$ and $R^{22}$ together with the nitrogen atom to which they are attached, form an optionally substituted $C_2$-$C_9$heterocycloalkyl ring;

$R^{24}$ is selected from the group consisting of optionally substituted $C_1$-$C_6$alkyl, optionally substituted $C_2$-$C_6$alkenyl, optionally substituted $C_2$-$C_6$alkynyl, optionally substituted $C_3$-$C_8$ cycloalkyl, optionally substituted aryl optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); and $R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R^{27}$ and $R^{28}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{27}$ and $R^{28}$ together with the nitrogen atom to which they are attached, form an optionally substituted $C_2$-$C_9$heterocycloalkyl ring.

In one embodiment is a compound of Formula (If) wherein $R^4$ and $R^5$ are each independently selected from the group consisting of hydrogen, halogen, and optionally substituted $C_1$-$C_6$alkyl. In another embodiment is a compound of Formula (If) wherein $R^4$ and $R^5$ are each independently selected from the group consisting of hydrogen and optionally substituted $C_1$-$C_6$alkyl. In another embodiment is a compound of Formula (If) wherein $R^4$ and $R^5$ are each hydrogen. In another embodiment is a compound of Formula (If) wherein $R^4$ and $R^5$ are each independently optionally substituted $C_1$-$C_6$alkyl. In another embodiment is a compound of Formula (If) wherein $R^4$ and $R^5$ are each methyl. In another embodiment is a compound of Formula (If) wherein $R^4$ and $R^5$ form an optionally substituted $C_3$-$C_6$cycloalkyl ring or an optionally substituted $C_2$-$C_7$heterocycloalkyl ring. In some embodiments is a compound of Formula (If) wherein $R^4$ and $R^5$ form an optionally substituted $C_3$-$C_6$cycloalkyl ring. In some embodiments is a compound of Formula (If) wherein $R^4$ and $R^5$ form an optionally substituted $C_2$-$C_7$heterocycloalkyl ring.

In another embodiment is a compound of Formula (If) wherein $R^6$ and $R^7$ are each independently selected from the group consisting of hydrogen, halogen, and optionally substituted $C_1$-$C_6$alkyl. In another embodiment is a compound of Formula (If) wherein $R^6$ and $R^7$ are each independently selected from the group consisting of hydrogen and optionally substituted $C_1$-$C_6$alkyl. In another embodiment is a compound of Formula (If) wherein $R^6$ and $R^7$ are each independently optionally substituted $C_1$-$C_6$alkyl. In another embodiment is a compound of Formula (If) wherein $R^6$ and $R^7$ are each methyl. In another embodiment is a compound of Formula (If) wherein $R^6$ and $R^7$ are each hydrogen.

In another embodiment is a compound of Formula (If) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted aryl. In another embodiment is a compound of Formula (If) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted heteroaryl. In another embodiment is a compound of Formula (If) wherein $R^6$ and $R^7$ are hydrogen, $R^4$ and $R^5$ are methyl, $R^3$ is —C(O)$R^{20}$, and $R^{20}$ is optionally substituted aryl. In another embodiment is a compound of Formula (If) wherein $R^6$ and $R^7$ are hydrogen, $R^4$ and $R^5$ are methyl, $R^3$ is —C(O)$R^{20}$, and $R^{20}$ is optionally substituted heteroaryl.

In another embodiment is a compound of Formula (If) wherein $R^6$ and $R^7$ are hydrogen, $R^4$ and $R^5$ are independently optionally substituted $C_1$-$C_6$alkyl, $R^3$ is —S(O)$_2$$R^{20}$, and $R^{20}$ is optionally substituted aryl. In another embodiment is a compound of Formula (If) wherein $R^6$ and $R^7$ are hydrogen, $R^4$ and $R^5$ are independently optionally substituted $C_1$-$C_6$alkyl, $R^3$ is —S(O)$_2$$R^{20}$, and $R^{20}$ is optionally substituted heteroaryl. In another embodiment is a compound of Formula (If) wherein $R^6$ and $R^7$ are hydrogen, $R^4$ and $R^5$ are methyl, $R^3$ is —S(O)$_2$$R^{20}$, and $R^{20}$ is optionally substituted aryl. In another embodiment is a compound of Formula (If) wherein $R^6$ and $R^7$ are hydrogen, $R^4$ and $R^5$ are methyl, $R^3$ is —S(O)$_2$$R^{20}$, and $R^{20}$ is optionally substituted heteroaryl.

In another embodiment is a compound of Formula (If) wherein $R^6$ and $R^7$ are hydrogen, $R^4$ and $R^5$ are independently optionally substituted $C_1$-$C_6$alkyl, $R^3$ is —C(O)N($R^{21}$)$R^{22}$, $R^{21}$ is hydrogen and $R^{22}$ is optionally substituted aryl. In another embodiment is a compound of Formula (If) wherein $R^6$ and $R^7$ are hydrogen, $R^4$ and $R^5$ are independently optionally substituted $C_1$-$C_6$alkyl, $R^3$ is —C(O)N($R^{21}$)$R^{22}$, $R^{21}$ is hydrogen and $R^{22}$ is optionally substituted heteroaryl. In another embodiment is a compound of Formula (If) wherein $R^6$ and $R^7$ are hydrogen, $R^4$ and $R^5$ are methyl, $R^3$ is —C(O)N($R^{21}$)$R^{22}$, $R^{21}$ is hydrogen and $R^{22}$ is optionally substituted aryl. In another embodiment is a compound of Formula (If) wherein $R^6$ and $R^7$ are hydrogen, $R^4$ and $R^5$ are methyl, $R^3$ is —C(O)N($R^{21}$)$R^{22}$, $R^{21}$ is hydrogen and $R^{22}$ is optionally substituted heteroaryl.

In a further embodiment of the aforementioned embodiments is a compound of Formula (If) wherein $R^2$ is selected from the group consisting of —CN, —C(O)O$R^{25}$, —C(O)N($R^{25}$)$R^{26}$,

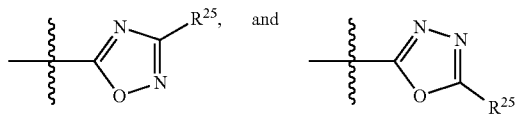

In a further embodiment of the aforementioned embodiments is a compound of Formula (If) wherein $R^2$ is —CN.

In a further embodiment of the aforementioned embodiments is a compound of Formula (If) wherein $R^2$ is —C(O)OR$^{25}$. In a further embodiment of the aforementioned embodiments is a compound of Formula (If) wherein $R^2$ is —C(O)OR$^{25}$, and $R^{25}$ is independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (If) wherein $R^2$ is —C(O)OR$^{25}$, and $R^{25}$ is independently selected from the group consisting of hydrogen, and optionally substituted $C_1$-$C_6$alkyl. In a further embodiment of the aforementioned embodiments is a compound of Formula (If) wherein $R^2$ is —C(O)OR$^{25}$, and $R^{25}$ is hydrogen. In a further embodiment of the aforementioned embodiments is a compound of Formula (If) wherein $R^2$ is —C(O)OR$^{25}$, and $R^{25}$ is optionally substituted $C_1$-$C_6$alkyl. In a further embodiment of the aforementioned embodiments is a compound of Formula (If) wherein $R^2$ is —C(O)OR$^{25}$, and $R^{25}$ is unsubstituted $C_1$-$C_6$alkyl. In a further embodiment of the aforementioned embodiments is a compound of Formula (If) wherein $R^2$ is —C(O)OR$^{25}$, and $R^{25}$ is methyl. In a further embodiment of the aforementioned embodiments is a compound of Formula (If) wherein $R^2$ is —C(O)OR$^{25}$, and $R^{25}$ is ethyl.

In a further embodiment of the aforementioned embodiments is a compound of Formula (If) wherein $R^2$ is —C(O)N($R^{25}$)$R^{26}$. In a further embodiment of the aforementioned embodiments is a compound of Formula (If) wherein $R^2$ is —C(O)N($R^{25}$)$R^{26}$, and $R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (If) wherein $R^2$ is —C(O)N($R^{25}$)$R^{26}$, and $R^{25}$ and $R^{26}$ are each independently selected from the group consisting of hydrogen, and optionally substituted $C_1$-$C_6$alkyl. In a further embodiment of the aforementioned embodiments is a compound of Formula (If) wherein $R^2$ is —C(O)N($R^{25}$)$R^{26}$, and $R^{25}$ and $R^{26}$ are hydrogen. In a further embodiment of the aforementioned embodiments is a compound of Formula (If) wherein $R^2$ is —C(O)N($R^{25}$)$R^{26}$, and $R^{25}$ and $R^{26}$ are each independently optionally substituted $C_1$-$C_6$alkyl. In a further embodiment of the aforementioned embodiments is a compound of Formula (If) wherein $R^2$ is —C(O)N($R^{25}$)$R^{26}$, $R^{25}$ is hydrogen, and $R^{26}$ is optionally substituted $C_1$-$C_6$alkyl. In a further embodiment of the aforementioned embodiments is a compound of Formula (If) wherein $R^2$ is —C(O)N($R^{25}$)$R^{26}$, and $R^{25}$ and $R^{26}$ are each independently unsubstituted $C_1$-$C_6$alkyl. In a further embodiment of the aforementioned embodiments is a compound of Formula (If) wherein $R^2$ is —C(O)N($R^{25}$)$R^{26}$, $R^{25}$ is hydrogen, and $R^{26}$ are methyl. In a further embodiment of the aforementioned embodiments is a compound of Formula (If) wherein $R^2$ is —C(O)N($R^{25}$)$R^{26}$, and $R^{25}$ and $R^{26}$ are methyl. In a further embodiment of the aforementioned embodiments is a compound of Formula (If) wherein $R^2$ is —C(O)N($R^{25}$)$R^{26}$, and $R^{25}$ and $R^{26}$ are ethyl.

In a further embodiment of the aforementioned embodiments is a compound of Formula (If) wherein $R^2$ is

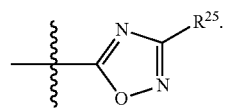

In a further embodiment of the aforementioned embodiments is a compound of Formula (If) wherein $R^2$ is

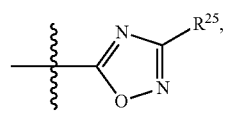

and $R^{25}$ is optionally substituted $C_1$-$C_6$alkyl. In a further embodiment of the aforementioned embodiments is a compound of Formula (If) wherein $R^2$ is

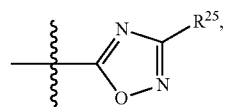

and $R^{25}$ is methyl. In a further embodiment of the aforementioned embodiments is a compound of Formula (If) wherein $R^2$ is

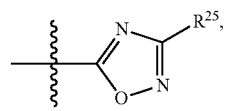

and $R^{25}$ is optionally substituted $C_1$-$C_6$alkyl. In a further embodiment of the aforementioned embodiments is a compound of Formula (If) wherein $R^2$ is

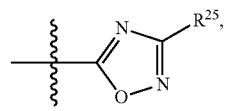

and $R^{25}$ is ethyl.

In a further embodiment of the aforementioned embodiments is a compound of Formula (If) wherein $R^2$ is

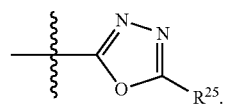

In a further embodiment of the aforementioned embodiments is a compound of Formula (If) wherein $R^2$ is

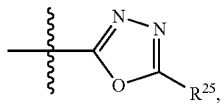

and $R^{25}$ is optionally substituted $C_1$-$C_6$alkyl. In a further embodiment of the aforementioned embodiments is a compound of Formula (If) wherein $R^2$ is

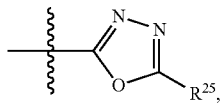

and $R^{25}$ is methyl. In a further embodiment of the aforementioned embodiments is a compound of Formula (If) wherein $R^2$ is

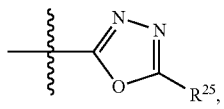

and $R^{25}$ is optionally substituted $C_1$-$C_6$alkyl. In a further embodiment of the aforementioned embodiments is a compound of Formula (If) wherein $R^2$ is

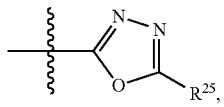

and $R^{25}$ is ethyl.

In a further embodiment of the aforementioned embodiments is a compound of Formula (If) wherein $R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (If) wherein $R^1$ is hydrogen. In a further embodiment of the aforementioned embodiments is a compound of Formula (If) wherein $R^1$ is optionally substituted $C_1$-$C_6$alkyl. In a further embodiment of the aforementioned embodiments is a compound of Formula (If) wherein $R^1$ is methyl. In a further embodiment of the aforementioned embodiments is a compound of Formula (If) wherein $R^1$ is optionally substituted $C_2$-$C_6$alkenyl. In a further embodiment of the aforementioned embodiments is a compound of Formula (If) wherein $R^1$ is optionally substituted $C_2$-$C_6$alkynyl.

In a further embodiment of the aforementioned embodiments is a compound of Formula (If) wherein $R^1$ and $R^2$ together with the carbon atoms to which they are attached, form an optionally substituted $C_2$-$C_9$heterocycloalkyl ring or an optionally substituted heteroaryl ring. In a further embodiment of the aforementioned embodiments is a compound of Formula (If) wherein $R^1$ and $R^2$ together with the carbon atoms to which they are attached, form an optionally substituted $C_2$-$C_9$heterocycloalkyl ring. In a further embodiment of the aforementioned embodiments is a compound of Formula (If) wherein $R^1$ and $R^2$ together with the carbon atoms to which they are attached, form an optionally substituted heteroaryl ring.

In a further embodiment of the aforementioned embodiments is a compound of Formula (If) wherein $R^8$ is selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl). In a further embodiment of the aforementioned embodiments is a compound of Formula (If) wherein $R^8$ is selected from the group consisting of hydrogen, and optionally substituted $C_1$-$C_6$alkyl. In a further embodiment of the aforementioned embodiments is a compound of Formula (If) wherein $R^8$ is optionally substituted $C_1$-$C_6$alkyl. In a further embodiment of the aforementioned embodiments is a compound of Formula (If) wherein $R^8$ is methyl. In a further embodiment of the aforementioned embodiments is a compound of Formula (If) wherein $R^8$ is optionally substituted $C_1$-$C_6$alkyl. In a further embodiment of the aforementioned embodiments is a compound of Formula (If) wherein $R^8$ is ethyl. In a further embodiment of the aforementioned embodiments is a compound of Formula (If) wherein $R^8$ is optionally substituted $C_1$-$C_6$alkyl. In a further embodiment of the aforementioned embodiments is a compound of Formula (If) wherein $R^8$ is hydrogen.

In another embodiment of the aforementioned embodiments is a compound of Formula (If) wherein $R^{15}$ is —OC(=J)OR$^{16a}$. In another embodiment of the aforementioned embodiments is a compound of Formula (If) wherein $R^{15}$ is —N(R$^{12}$)C(=J)OR$^{16a}$. In another embodiment of the aforementioned embodiments is a compound of Formula (If) wherein $R^{15}$ is —OC(=J)N(H)R$^{16a}$ In another embodiment of the aforementioned embodiments is a compound of Formula (If) wherein $R^{15}$ is —N(R$^{12}$)C(=J)N(H)R$^{16a}$. In another embodiment of the aforementioned embodiments is a compound of Formula (If) wherein $R^{15}$ is —OC(=J)N(H)(C$_2$-C$_6$alkyl)R$^{30}$. In another embodiment of the aforementioned embodiments is a compound of Formula (If) wherein $R^{15}$ is —N(R$^{12}$)C(=J)O(C$_2$-C$_6$alkyl)R$^{30}$. In another embodiment of the aforementioned embodiments is a compound of Formula (If) wherein $R^{15}$ is —N(R$^{12}$)C(=J)N(H)(C$_2$-C$_6$alkyl)R$^{30}$. In another embodiment of the aforementioned embodiments is a compound of Formula (If) wherein $R^{15}$ is —OC(=J)O(C$_2$-C$_6$alkyl)R$^{30}$. In another embodiment of the aforementioned embodiments is a compound of Formula (If) wherein $R^{15}$ is —C(=J)R$^{31}$. In another embodiment of the aforementioned embodiments is a compound of Formula (If) wherein $R^{15}$ is —OC(=J)R$^{31}$. In another embodiment of the aforementioned embodiments is a compound of Formula (If) wherein $R^{15}$ is —N(R$^{12}$)C(=J)R$^{31}$. In another embodiment of the aforementioned embodiments is a compound of Formula (If) wherein $R^{15}$ is —O(C$_2$-C$_6$alkyl)R$^{30}$. In another embodiment of the aforementioned embodiments is a compound of Formula (If) wherein $R^{15}$ is —N(R$^{12}$)(C$_2$-C$_6$alkyl)R$^{30}$. In another embodiment of the aforementioned embodiments is a compound of Formula (If) wherein $R^{15}$ is —OS(=O)$_v$R$^{31}$. In another embodiment of the aforementioned embodiments is a compound of Formula (If) wherein $R^{15}$ is —N(R$^{12}$)S(=O)$_v$R$^{31}$. In another embodiment of the aforementioned embodiments is a compound of Formula (If) wherein R$^{15}$ is —OS(=O)$_v$(C$_2$-C$_6$alkyl)R$^{30}$. In another embodiment of the aforementioned embodiments is a compound of Formula (If) wherein R$^{15}$ is —N(R$^{12}$)S(=O)$_v$(C$_2$-C$_6$alkyl)R$^{30}$. In a further embodiment of the aforementioned embodiments is a compound of Formula (If) wherein R$^{30}$ is R$^{16a}$. In a further embodiment of the aforementioned embodiments is a compound of Formula (If) wherein R$^{30}$ is R$^{16b}$. In a further embodiment of the aforementioned embodiments is a compound of Formula (If) wherein R$^{30}$ is R$^{16c}$. In a further embodiment of the aforementioned embodiments is a compound of Formula (If) wherein R$^{31}$ is R$^{16a}$. In a further embodiment of the aforementioned embodiments is a compound of Formula (If) wherein R$^{31}$ is R$^{16b}$. In a further embodiment of the aforementioned embodiments is a compound of Formula (If) wherein J is O. In a further embodiment of the aforementioned embodiments is a compound of Formula (If) wherein J is S. In a further embodiment of the aforementioned embodiments is a compound of Formula (If) wherein J is N(R$^{12}$).

In another embodiment of the aforementioned embodiments is a compound of Formula (If) wherein R$^{16a}$ is

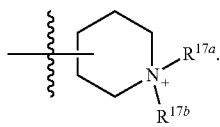

In another embodiment of the aforementioned embodiments is a compound of Formula (If) wherein R$^{16a}$ is

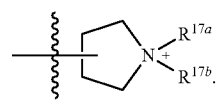

In another embodiment of the aforementioned embodiments is a compound of Formula (If) wherein R$^{16a}$ is

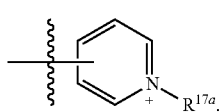

In another embodiment of the aforementioned embodiments is a compound of Formula (If) wherein R$^{16b}$ is

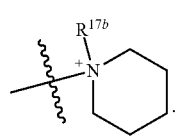

In another embodiment of the aforementioned embodiments is a compound of Formula (If) wherein R$^{16b}$ is

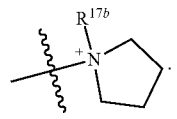

In another embodiment of the aforementioned embodiments is a compound of Formula (If) wherein R$^{16b}$ is

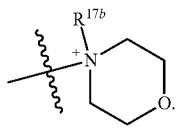

In another embodiment of the aforementioned embodiments is a compound of Formula (If) wherein R$^{16b}$ is

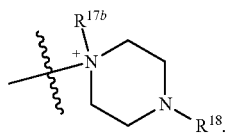

In another embodiment of the aforementioned embodiments is a compound of Formula (If) wherein R$^{16b}$ is

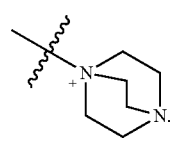

In another embodiment of the aforementioned embodiments is a compound of Formula (If) wherein R$^{16b}$ is

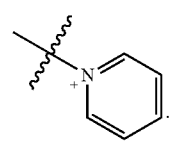

In another embodiment of the aforementioned embodiments is a compound of Formula (If) wherein R$^{16b}$ is

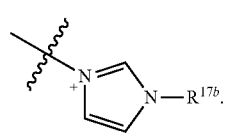

In another embodiment of the aforementioned embodiments is a compound of Formula (If) wherein R$^{16c}$ is

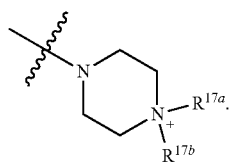

In another embodiment is a compound of Formula (If) wherein $R^{16c}$ is

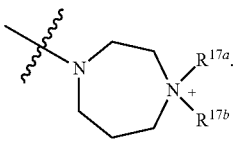

In a further embodiment of the aforementioned embodiments is a compound of Formula (If) wherein $R^{17a}$ is methyl. In a further embodiment of the aforementioned embodiments is a compound of Formula (If) wherein $R^{17a}$ is ethyl. In a further embodiment of the aforementioned embodiments is a compound of Formula (If) wherein $R^{17b}$ is methyl optionally substituted with phenyl, —C(=O)OH or —S(=O)$_2$OH. In a further embodiment of the aforementioned embodiments is a compound of Formula (If) wherein $R^{17a}$ is ethyl optionally substituted with phenyl, —C(=O)OH or —S(=O)$_2$OH.

In another embodiment is a compound of Formula (If) wherein $R^{15}$ is —OC(=J)OR$^{16a}$, —N(R$^{12}$)C(=J)OR$^{16a}$, —OC(=J)N(H)R$^{16a}$, —N(R$^{12}$)C(=J)N(H)R$^{16a}$, —OC(=J)N(H)(C$_1$-C$_6$alkyl)R$^{31}$, —N(R$^{12}$)C(=J)O(C$_1$-C$_6$alkyl)R$^{31}$, —N(R$^{12}$)C(=J)N(H)(C$_1$-C$_6$alkyl)R$^{31}$, —OC(=J)O(C$_1$-C$_6$alkyl)R$^{31}$, —C(=J)R$^{31}$, —OC(=J)R$^{31}$, —N(R$^{12}$)C(=J)R$^{31}$, —O(C$_1$-C$_6$alkyl)R$^{31}$, —N(R$^{12}$)(C$_1$-C$_6$alkyl)R$^{31}$, —OS(=O)$_v$R$^{31}$, —N(R$^{12}$)S(=O)$_v$R$^{31}$, —OS(=O)$_v$(C$_1$-C$_6$alkyl)R$^{31}$, or —N(R$^{12}$)S(=O)$_v$(C$_1$-C$_6$alkyl)R$^{31}$.

In yet another aspect, provided herein is a compound having the structure of Formula (II), or a pharmaceutically acceptable salt or solvate thereof:

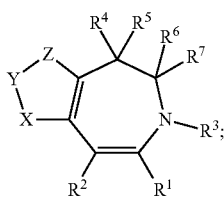

Formula (II)

wherein:
—X—Y—Z— is selected from

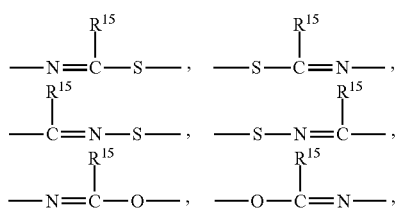

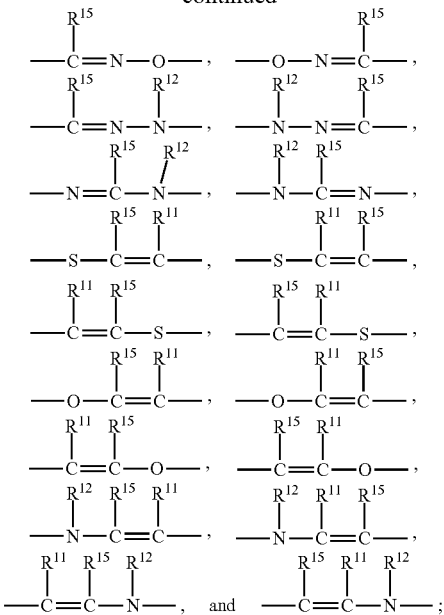

$R^1$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

$R^2$ is selected from the group consisting of —CN, —C(=O)OR$^{25}$, —C(=O)N(R$^{25}$)R$^{26}$,

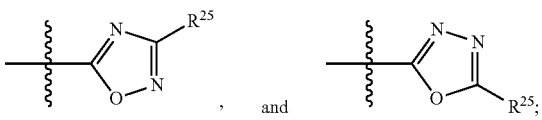

or $R^1$ and $R^2$ together with the carbon atoms to which they are attached, form an optionally substituted C$_2$-C$_9$heterocycloalkyl ring or an optionally substituted heteroaryl ring;

$R^3$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_{10}$cycloalkyl, optionally substituted aryl, optionally substituted —(C$_1$-C$_2$alkylene)-(aryl), optionally substituted heteroaryl, optionally substituted C$_2$-C$_9$heterocycloalkyl, optionally substituted —(C$_1$-C$_2$alkylene)-(heteroaryl), —C(=O)R$^{20}$, —C(=O)OR$^{20}$, —S(=O)$_2$R$^{20}$, —C(=O)N(R$^{21}$)R$^{22}$, —C(=O)N(R$^{21}$)S(=O)$_2$R$^{24}$, —C(=O)N(R$^{23}$)N(R$^{21}$)R$^{22}$, —C(=O)N(R$^{23}$)N(R$^{21}$)S(=O)$_2$R$^{24}$, —N(R$^{23}$)C(=O)R$^{20}$, —N(R$^{23}$)C(=O)N(R$^{21}$)R$^{22}$, —N(R$^{23}$)C(=O)N(R$^{21}$)S(=O)$_2$R$^{24}$, —N(R$^{20}$)C(=O)N(R$^{23}$)N(R$^{21}$)R$^{22}$, —N(R$^{20}$)C(=O)N(R$^{23}$)N(R$^{21}$)S(=O)$_2$R$^{24}$, —N(R$^{23}$)C(=O)OR$^{20}$, —P(=O)OR$^{20}$, and —P(=O)(OR$^{19}$)OR$^{20}$;

$R^4$ and $R^5$ are each independently selected from the group consisting of hydrogen, halogen, optionally substituted C$_1$-C$_6$alkyl, optionally substituted C$_1$-C$_6$alkoxy, optionally substituted C$_2$-C$_6$alkenyl, and optionally substituted C$_2$-C$_6$alkynyl; or R$^4$ and R$^5$ together with the carbon atom to which they are attached, form an optionally substituted C$_3$-C$_6$cycloalkyl ring or an optionally substituted C$_2$-C$_7$heterocycloalkyl ring;

R$^6$ is selected from the group consisting of hydrogen, halogen, optionally substituted C$_1$-C$_6$alkyl, optionally substituted C$_2$-C$_6$alkenyl, optionally substituted C$_2$-C$_6$alkynyl, and —C(=O)N(R$^{27}$)R$^{28}$;

R$^7$ is selected from the group consisting of hydrogen, halogen, optionally substituted C$_1$-C$_6$alkyl, optionally substituted C$_1$-C$_6$alkoxy, optionally substituted C$_2$-C$_6$alkenyl, and optionally substituted C$_2$-C$_6$alkynyl;

R$^{11}$ is selected from the group consisting of hydrogen, halogen, —CN, amino, alkylamino, C$_1$-C$_6$alkyl, C$_1$-C$_6$haloalkyl, C$_1$-C$_6$alkoxy, C$_1$-C$_6$haloalkoxy, C$_3$-C$_8$cycloalkyl, C$_2$-C$_9$heterocycloalkyl, aryl, heteroaryl, —C(=O)OR$^{12}$, —C(=O)N(R$^{13}$)R$^{14}$;

each R$^{12}$ is independently selected from the group consisting of hydrogen and C$_1$-C$_6$alkyl;

R$^{13}$ and R$^{14}$ are independently selected from the group consisting of hydrogen and C$_1$-C$_6$alkyl; or R$^{13}$ and R$^{14}$ together with the nitrogen atom to which they are attached, form an optionally substituted C$_2$-C$_9$heterocycloalkyl ring;

R$^{15}$ is —OC(=J)OR$^{16a}$, —N(R$^{12}$)C(=J)OR$^{16a}$, —OC(=J)N(H)R$^{16a}$, —N(R$^{12}$)C(=J)N(H)R$^{16a}$, —OC(=J)N(H)(C$_2$-C$_6$alkyl)R$^{30}$, —N(R$^{12}$)C(=J)O(C$_2$-C$_6$alkyl)R$^{30}$, —N(R$^{12}$)C(=J)N(H)(C$_2$-C$_6$alkyl)R$^{30}$, —OC(=J)O(C$_2$-C$_6$alkyl)R$^{30}$, —C(=J)R$^{31}$, —OC(=J)R$^{31}$, —N(R$^{12}$)C(=J)R$^{31}$, —O(C$_2$-C$_6$alkyl)R$^{30}$, —N(R$^{12}$)(C$_2$-C$_6$alkyl)R$^{30}$, —OS(=O)$_v$R$^{31}$, —N(R$^{12}$)S(=O)$_v$R$^{31}$, —OS(=O)$_v$(C$_2$-C$_6$alkyl)R$^{30}$, or —N(R$^{12}$)S(=O)$_v$(C$_2$-C$_6$alkyl)R$^{30}$;

R$^{30}$ is R$^{16a}$, R$^{16b}$, or R$^{16c}$;
R$^{31}$ is R$^{16a}$ or R$^{16c}$;
J is O, S, or N(R$^{12}$);
R$^{16a}$ is

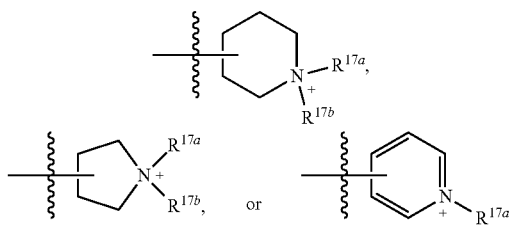

R$^{16b}$ is

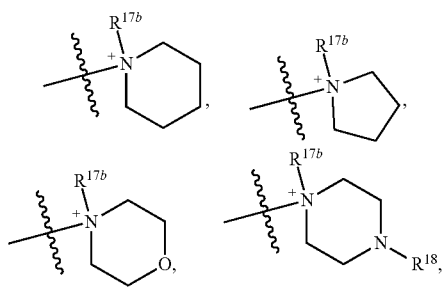

R$^{16c}$ is

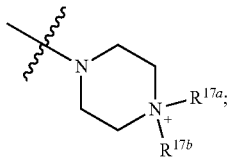

R$^{17a}$ is C$_1$-C$_6$alkyl;
R$^{17b}$ is C$_1$-C$_6$alkyl optionally substituted with phenyl, —C(=O)OH or —S(=O)$_2$OH;
R$^{18}$ is hydrogen, —OH, —(C$_0$-C$_6$alkyl)-C(=O)OH, or C$_1$-C$_6$alkyl;
v is 1 or 2;
R$^{19}$, R$^{20}$, and R$^{23}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);
R$^{21}$ and R$^{22}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl); or R$^{21}$ and R$^{22}$ together with the nitrogen atom to which they are attached, form an optionally substituted C$_2$-C$_9$heterocycloalkyl ring;
R$^{24}$ is selected from the group consisting of optionally substituted C$_1$-C$_6$alkyl, optionally substituted C$_2$-C$_6$alkenyl, optionally substituted C$_2$-C$_6$alkynyl, optionally substituted C$_3$-C$_5$ cycloalkyl, optionally substituted aryl optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl); and
R$^{25}$ and R$^{26}$ are each independently selected from the group consisting of hydrogen, optionally substituted C$_1$-C$_6$alkyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

$R^{27}$ and $R^{28}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{27}$ and $R^{28}$ together with the nitrogen atom to which they are attached, form an optionally substituted $C_2$-$C_9$heterocycloalkyl ring.

In one embodiment is a compound of Formula (II) wherein —X—Y—Z— is

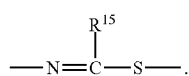

In another embodiment is a compound of Formula (II) wherein —X—Y—Z— is

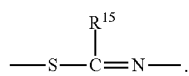

In another embodiment is a compound of Formula (II) wherein —X—Y—Z— is

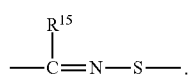

In another embodiment is a compound of Formula (II) wherein —X—Y—Z— is

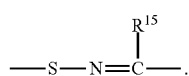

In another embodiment is a compound of Formula (II) wherein —X—Y—Z— is

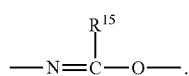

In another embodiment is a compound of Formula (II) wherein —X—Y—Z— is

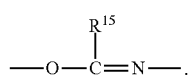

In another embodiment is a compound of Formula (II) wherein —X—Y—Z— is

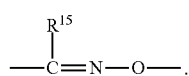

In another embodiment is a compound of Formula (II) wherein —X—Y—Z— is

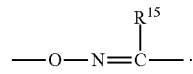

In another embodiment is a compound of Formula (II) wherein —X—Y—Z— is

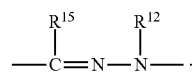

In another embodiment is a compound of Formula (II) wherein —X—Y—Z— is

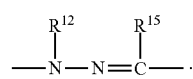

In another embodiment is a compound of Formula (II) wherein —X—Y—Z— is

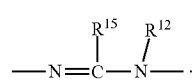

In another embodiment is a compound of Formula (II) wherein —X—Y—Z— is

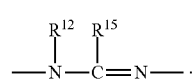

In another embodiment is a compound of Formula (II) wherein —X—Y—Z— is

In another embodiment is a compound of Formula (II) wherein —X—Y—Z— is

In another embodiment is a compound of Formula (II) wherein —X—Y—Z— is

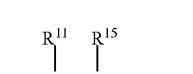

In another embodiment is a compound of Formula (II) wherein —X—Y—Z— is

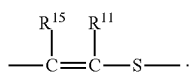

in another embodiment is a compound of Formula (II) wherein —X—Y—Z— is

In another embodiment is a compound of Formula (II) wherein —X—Y—Z— is

In another embodiment is a compound of Formula (II) wherein —X—Y—Z— is

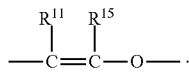

In another embodiment is a compound of Formula (II) wherein —X—Y—Z— is

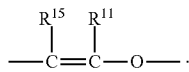

In another embodiment is a compound of Formula (II) wherein —X—Y—Z— is

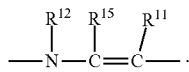

In another embodiment is a compound of Formula (II) wherein —X—Y—Z— is

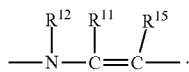

In another embodiment is a compound of Formula (II) wherein —X—Y—Z— is

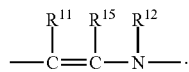

In another embodiment is a compound of Formula (II) wherein —X—Y—Z— is

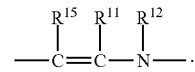

In another embodiment is a compound of Formula (II) wherein $R^4$ and $R^5$ are each independently selected from the group consisting of hydrogen, halogen, and optionally substituted $C_1$-$C_6$alkyl. In another embodiment is a compound of Formula (II) wherein $R^4$ and $R^5$ are each independently selected from the group consisting of hydrogen and optionally substituted $C_1$-$C_6$alkyl. In another embodiment is a compound of Formula (II) wherein $R^4$ and $R^5$ are each hydrogen. In another embodiment is a compound of Formula (II) wherein $R^4$ and $R^5$ are each independently optionally substituted $C_1$-$C_6$alkyl. In another embodiment is a compound of Formula (II) wherein $R^4$ and $R^5$ are each methyl. In another embodiment is a compound of Formula (II) wherein $R^4$ and $R^5$ form an optionally substituted $C_3$-$C_6$cycloalkyl ring or an optionally substituted $C_2$-$C_7$heterocycloalkyl ring. In some embodiments is a compound of Formula (II) wherein $R^4$ and $R^5$ form an optionally substituted $C_3$-$C_6$cycloalkyl ring. In some embodiments is a compound of Formula (II) wherein $R^4$ and $R^5$ form an optionally substituted $C_2$-$C_7$heterocycloalkyl ring.

In another embodiment is a compound of Formula (II) wherein $R^6$ and $R^7$ are each independently selected from the group consisting of hydrogen, halogen, and optionally substituted $C_1$-$C_6$alkyl. In another embodiment is a compound of Formula (II) wherein $R^6$ and $R^7$ are each independently selected from the group consisting of hydrogen and optionally substituted $C_1$-$C_6$alkyl. In another embodiment is a compound of Formula (II) wherein $R^6$ and $R^7$ are each independently optionally substituted $C_1$-$C_6$alkyl. In another embodiment is a compound of Formula (II) wherein $R^6$ and $R^7$ are each methyl. In another embodiment is a compound of Formula (II) wherein $R^6$ and $R^7$ are each hydrogen.

In another embodiment is a compound of Formula (II) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted aryl. In another embodiment is a compound of Formula (II) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted heteroaryl. In another embodiment is a compound of Formula (II) wherein $R^6$ and $R^7$ are hydrogen, $R^4$ and $R^5$ are methyl, $R^3$ is —C(O)$R^{20}$, and $R^{20}$ is optionally substituted aryl. In another embodiment is a compound of Formula (II) wherein $R^6$ and $R^7$ are hydrogen, $R^4$ and $R^5$ are methyl, $R^3$ is —C(O)$R^{20}$, and $R^{20}$ is optionally substituted heteroaryl.

In another embodiment is a compound of Formula (II) wherein $R^6$ and $R^7$ are hydrogen, $R^4$ and $R^5$ are independently optionally substituted $C_1$-$C_6$alkyl, $R^3$ is —S(O)$_2$$R^{20}$, and $R^{20}$ is optionally substituted aryl. In another embodiment is a compound of Formula (II) wherein $R^6$ and $R^7$ are hydrogen, $R^4$ and $R^5$ are independently optionally substituted $C_1$-$C_6$alkyl, $R^3$ is —S(O)$_2$$R^{20}$, and $R^{20}$ is optionally substituted heteroaryl. In another embodiment is a compound of Formula (II) wherein $R^6$ and $R^7$ are hydrogen, $R^4$ and $R^5$ are methyl, $R^3$ is —S(O)$_2$$R^{20}$, and $R^{20}$ is optionally substituted aryl. In another embodiment is a compound of Formula (II) wherein $R^6$ and $R^7$ are hydrogen, $R^4$ and $R^5$ are methyl, $R^3$ is —S(O)$_2$$R^{20}$, and $R^{20}$ is optionally substituted heteroaryl.

In another embodiment is a compound of Formula (II) wherein $R^6$ and $R^7$ are hydrogen, $R^4$ and $R^5$ are independently optionally substituted $C_1$-$C_6$alkyl, $R^3$ is —C(O)N($R^{21}$)$R^{22}$, $R^{21}$ is hydrogen and $R^{22}$ is optionally substituted aryl. In another embodiment is a compound of Formula (II) wherein $R^6$ and $R^7$ are hydrogen, $R^4$ and $R^5$ are independently optionally substituted $C_1$-$C_6$alkyl, $R^3$ is —C(O)N($R^{21}$)$R^{22}$, $R^{21}$ is hydrogen and $R^{22}$ is optionally substituted heteroaryl. In another embodiment is a compound of Formula (II) wherein $R^6$ and $R^7$ are hydrogen, $R^4$ and $R^5$ are methyl, $R^3$ is —C(O)N($R^{21}$)$R^{22}$, $R^{21}$ is hydrogen and $R^{22}$ is optionally substituted aryl. In another embodiment is a compound of Formula (II) wherein $R^6$ and $R^7$ are hydrogen, $R^4$ and $R^5$ are methyl, $R^3$ is —C(O)N($R^{21}$)$R^{22}$, $R^{21}$ is hydrogen and $R^{22}$ is optionally substituted heteroaryl.

In a further embodiment of the aforementioned embodiments is a compound of Formula (II) wherein $R^2$ is selected from the group consisting of —CN, —C(O)O$R^{25}$, —C(O)N($R^{25}$)$R^{26}$,

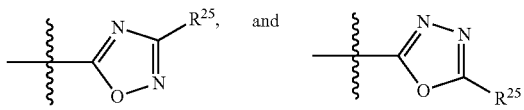

In a further embodiment of the aforementioned embodiments is a compound of Formula (II) wherein $R^2$ is —CN.

In a further embodiment of the aforementioned embodiments is a compound of Formula (II) wherein $R^2$ is —C(O)O$R^{25}$. In a further embodiment of the aforementioned embodiments is a compound of Formula (II) wherein $R^2$ is —C(O)O$R^{25}$, and $R^{25}$ is independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (II) wherein $R^2$ is —C(O)O$R^{25}$, and $R^{25}$ is independently selected from the group consisting of hydrogen, and optionally substituted $C_1$-$C_6$alkyl. In a further embodiment of the aforementioned embodiments is a compound of Formula (II) wherein $R^2$ is —C(O)O$R^{25}$, and $R^{25}$ is hydrogen. In a further embodiment of the aforementioned embodiments is a compound of Formula (II) wherein $R^2$ is —C(O)O$R^{25}$, and $R^{25}$ is optionally substituted $C_1$-$C_6$alkyl. In a further embodiment of the aforementioned embodiments is a compound of Formula (II) wherein $R^2$ is —C(O)O$R^{25}$, and $R^{25}$ is unsubstituted $C_1$-$C_6$alkyl. In a further embodiment of the aforementioned embodiments is a compound of Formula (II) wherein $R^2$ is —C(O)O$R^{25}$, and $R^{25}$ is methyl. In a further embodiment of the aforementioned embodiments is a compound of Formula (II) wherein $R^2$ is —C(O)O$R^{25}$, and $R^{25}$ is ethyl.

In a further embodiment of the aforementioned embodiments is a compound of Formula (II) wherein $R^2$ is —C(O)N($R^{25}$)$R^{26}$. In a further embodiment of the aforementioned embodiments is a compound of Formula (II) wherein $R^2$ is —C(O)N($R^{25}$)$R^{26}$, and $R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (II) wherein $R^2$ is —C(O)N($R^{25}$)$R^{26}$, and $R^{25}$ and $R^{26}$ are each independently selected from the group consisting of hydrogen, and optionally substituted $C_1$-$C_6$alkyl. In a further embodiment of the aforementioned embodiments is a compound of Formula (II) wherein $R^2$ is —C(O)N($R^{25}$)$R^{26}$, and $R^{25}$ and $R^{26}$ are hydrogen. In a further embodiment of the aforementioned embodiments is a compound of Formula (II) wherein $R^2$ is —C(O)N($R^{25}$)$R^{26}$, and $R^{25}$ and $R^{26}$ are each independently optionally substituted $C_1$-$C_6$alkyl. In a further embodiment of the aforementioned embodiments is a compound of Formula (II) wherein $R^2$ is —C(O)N($R^{25}$)$R^{26}$, $R^{25}$ is hydrogen, and $R^{26}$ is optionally substituted $C_1$-$C_6$alkyl. In a further embodiment of the aforementioned embodiments is a compound of Formula (II) wherein $R^2$ is —C(O)N($R^{25}$)$R^{26}$, and $R^{25}$ and $R^{26}$ are each independently unsubstituted $C_1$-$C_6$alkyl. In a further embodiment of the aforementioned embodiments is a compound of Formula (II) wherein $R^2$ is —C(O)N($R^{25}$)$R^{26}$, $R^{25}$ is hydrogen, and $R^{26}$ are methyl. In a further embodiment of the aforementioned embodiments is a compound of Formula (II) wherein $R^2$ is —C(O)N($R^{25}$)$R^{26}$, and $R^{25}$ and $R^{26}$ are methyl. In a further embodiment of the aforementioned embodiments is a compound of Formula (II) wherein $R^2$ is —C(O)N($R^{25}$)$R^{26}$, and $R^{25}$ and $R^{26}$ are ethyl.

In a further embodiment of the aforementioned embodiments is a compound of Formula (II) wherein $R^2$ is

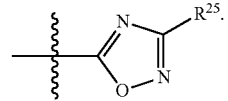

In a further embodiment of the aforementioned embodiments is a compound of Formula (II) wherein $R^2$ is

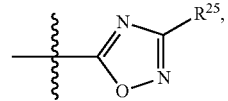

and $R^{25}$ is optionally substituted $C_1$-$C_6$alkyl. In a further embodiment of the aforementioned embodiments is a compound of Formula (II) wherein $R^2$ is

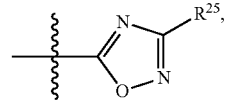

and $R^{25}$ is methyl. In a further embodiment of the aforementioned embodiments is a compound of Formula (II) wherein $R^2$ is

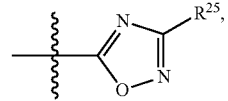

and $R^{25}$ is optionally substituted $C_1$-$C_6$alkyl. In a further embodiment of the aforementioned embodiments is a compound of Formula (II) wherein $R^2$ is

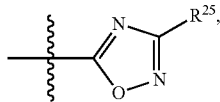

and $R^{25}$ is ethyl.

In a further embodiment of the aforementioned embodiments is a compound of Formula (II) wherein $R^2$ is

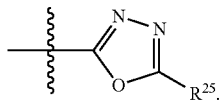

In a further embodiment of the aforementioned embodiments is a compound of Formula (II) wherein $R^2$ is

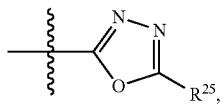

and $R^{25}$ is optionally substituted $C_1$-$C_6$alkyl. In a further embodiment of the aforementioned embodiments is a compound of Formula (II) wherein $R^2$ is

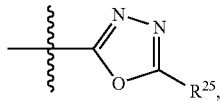

and $R^{25}$ is methyl. In a further embodiment of the aforementioned embodiments is a compound of Formula (II) wherein $R^2$ is

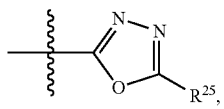

and $R^{25}$ is optionally substituted $C_1$-$C_6$alkyl. In a further embodiment of the aforementioned embodiments is a compound of Formula (II) wherein $R^2$ is

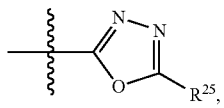

and $R^{25}$ is ethyl.

In a further embodiment of the aforementioned embodiments is a compound of Formula (II) wherein $R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (II) wherein $R^1$ is hydrogen. In a further embodiment of the aforementioned embodiments is a compound of Formula (II) wherein $R^1$ is optionally substituted $C_1$-$C_6$alkyl. In a further embodiment of the aforementioned embodiments is a compound of Formula (II) wherein $R^1$ is methyl. In a further embodiment of the aforementioned embodiments is a compound of Formula (II) wherein $R^1$ is optionally substituted $C_2$-$C_6$alkenyl. In a further embodiment of the aforementioned embodiments is a compound of Formula (II) wherein $R^1$ is optionally substituted $C_2$-$C_6$alkynyl.

In a further embodiment of the aforementioned embodiments is a compound of Formula (II) wherein $R^1$ and $R^2$ together with the carbon atoms to which they are attached, form an optionally substituted $C_2$-$C_9$heterocycloalkyl ring or an optionally substituted heteroaryl ring.

In a further embodiment of the aforementioned embodiments is a compound of Formula (II) wherein $R^1$ and $R^2$ together with the carbon atoms to which they are attached, form an optionally substituted $C_2$-$C_9$heterocycloalkyl ring. In a further embodiment of the aforementioned embodiments is a compound of Formula (II) wherein $R^1$ and $R^2$ together with the carbon atoms to which they are attached, form an optionally substituted heteroaryl ring.

In another embodiment of the aforementioned embodiments is a compound of Formula (II) wherein $R^{15}$ is —OC(=J)OR$^{16a}$. In another embodiment of the aforementioned embodiments is a compound of Formula (II) wherein $R^{15}$ is —N(R$^{12}$)C(=J)OR$^{16a}$. In another embodiment of the aforementioned embodiments is a compound of Formula (II) wherein $R^{15}$ is —OC(=J)N(H)R$^{16a}$ In another embodiment of the aforementioned embodiments is a compound of Formula (II) wherein $R^{15}$ is —N(R$^{12}$)C(=J)N(H)R$^{16a}$. In another embodiment of the aforementioned embodiments is a compound of Formula (II) wherein $R^{15}$ is —OC(=J)N(H)(C$_2$-C$_6$alkyl)R$^{30}$. In another embodiment of the aforementioned embodiments is a compound of Formula (II) wherein $R^{15}$ is —N(R$^{12}$)C(=J)O(C$_2$-C$_6$alkyl)R$^{30}$. In another embodiment of the aforementioned embodiments is a compound of Formula (II) wherein $R^{15}$ is —N(R$^{12}$)C(=J)N(H)(C$_2$-C$_6$alkyl)R$^{30}$. In another embodiment of the aforementioned embodiments is a compound of Formula (II) wherein $R^{15}$ is —OC(=J)O(C$_2$-C$_6$alkyl)R$^{30}$. In another embodiment of the aforementioned embodiments is a compound of Formula (II) wherein $R^{15}$ is —C(=J)R$^{31}$. In another embodiment of the aforementioned embodiments is a compound of Formula (II) wherein $R^{15}$ is —OC(=J)R$^{31}$. In another embodiment of the aforementioned embodiments is a compound of Formula (II) wherein $R^{15}$ is —N(R$^{12}$)C(=J)R$^{31}$. In another embodiment of the aforementioned embodiments is a compound of Formula (II) wherein $R^{15}$ is —O(C$_2$-C$_6$alkyl)R$^{30}$. In another embodiment of the aforementioned embodiments is a compound of Formula (II) wherein $R^{15}$ is —N(R$^{12}$)(C$_2$-C$_6$alkyl)R$^{30}$. In another embodiment of the aforementioned embodiments is a compound of Formula (II) wherein $R^{15}$ is —OS(=O)$_v$R$^{31}$. In another embodiment of the aforementioned embodiments is a compound of Formula (II) wherein $R^{15}$ is —N(R$^{12}$)S(=O)$_v$R$^{31}$. In another embodiment of the aforementioned embodiments is a compound of Formula (II) wherein $R^{15}$ is —OS(=O)$_v$(C$_2$-C$_6$alkyl)R$^{30}$. In another embodiment of the aforementioned embodiments is a compound of Formula (II) wherein $R^{15}$ is —N(R$^{12}$)S(=O)$_v$(C$_2$-

$C_6$alkyl)$R^{30}$. In a further embodiment of the aforementioned embodiments is a compound of Formula (II) wherein $R^{30}$ is $R^{16a}$. In a further embodiment of the aforementioned embodiments is a compound of Formula (II) wherein $R^{30}$ is $R^{16b}$. In a further embodiment of the aforementioned embodiments is a compound of Formula (II) wherein $R^{30}$ is $R^{16c}$. In a further embodiment of the aforementioned embodiments is a compound of Formula (II) wherein $R^{31}$ is $R^{16a}$. In a further embodiment of the aforementioned embodiments is a compound of Formula (II) wherein $R^{31}$ is $R^{16b}$. In a further embodiment of the aforementioned embodiments is a compound of Formula (II) wherein J is O. In a further embodiment of the aforementioned embodiments is a compound of Formula (II) wherein J is S. In a further embodiment of the aforementioned embodiments is a compound of Formula (II) wherein J is $N(R^{12})$.

In another embodiment of the aforementioned embodiments is a compound of Formula (II) wherein $R^{16a}$ is

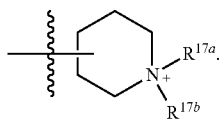

In another embodiment of the aforementioned embodiments is a compound of Formula (II) wherein $R^{16a}$ is

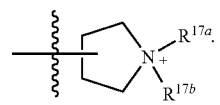

In another embodiment of the aforementioned embodiments is a compound of Formula (II) wherein $R^{16a}$ is

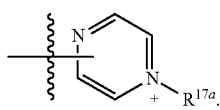

In another embodiment of the aforementioned embodiments is a compound of Formula (II) wherein $R^{16b}$ is

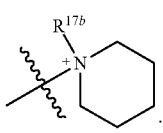

In another embodiment of the aforementioned embodiments is a compound of Formula (II) wherein $R^{16b}$ is

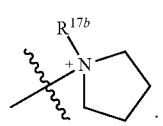

In another embodiment of the aforementioned embodiments is a compound of Formula (II) wherein $R^{16b}$ is

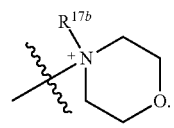

In another embodiment of the aforementioned embodiments is a compound of Formula (II) wherein $R^{16b}$ is

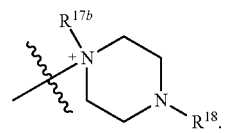

In another embodiment of the aforementioned embodiments is a compound of Formula (II) wherein $R^{16b}$ is

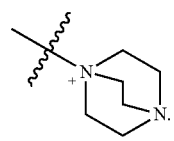

In another embodiment of the aforementioned embodiments is a compound of Formula (II) wherein $R^{16b}$ is

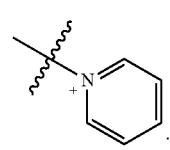

In another embodiment of the aforementioned embodiments is a compound of Formula (II) wherein $R^{16b}$ is

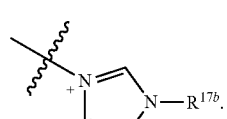

In another embodiment of the aforementioned embodiments is a compound of Formula (II) wherein $R^{16c}$ is

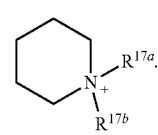

In another embodiment is a compound of Formula (II) wherein $R^{16c}$ is

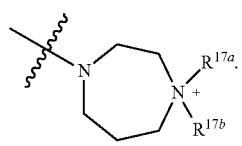

In a further embodiment of the aforementioned embodiments is a compound of Formula (II) wherein $R^{17a}$ is methyl. In a further embodiment of the aforementioned embodiments is a compound of Formula (II) wherein $R^{17a}$ is ethyl. In a further embodiment of the aforementioned embodiments is a compound of Formula (II) wherein $R^{17b}$ is methyl optionally substituted with phenyl, —C(=O)OH or —S(=O)$_2$OH. In a further embodiment of the aforementioned embodiments is a compound of Formula (II) wherein $R^{17a}$ is ethyl optionally substituted with phenyl, —C(=O)OH or —S(=O)$_2$OH.

In another embodiment is a compound of Formula (II) wherein $R^{15}$ is —OC(=J)OR$^{16a}$, —N(R$^{12}$)C(=J)OR$^{16a}$, —OC(=J)N(H)R$^{16a}$, —N(R$^{12}$)C(=J)N(H)R$^{16a}$, —OC(=J)N(H)(C$_1$-C$_6$alkyl)R$^{31}$, —N(R$^{12}$)C(=J)O(C$_1$-C$_6$alkyl)R$^{31}$, —N(R$^{12}$)C(=J)N(H)(C$_1$-C$_6$alkyl)R$^{31}$, —OC(=J)O(C$_1$-C$_6$alkyl)R$^{31}$, —C(=J)R$^{31}$, —OC(=J)R$^{31}$, —N(R$^{12}$)C(=J)R$^{31}$, —O(C$_1$-C$_6$alkyl)R$^{31}$, —N(R$^{12}$)(C$_1$-C$_6$alkyl)R$^{31}$, —OS(=O)$_v$R$^{31}$, —N(R$^{12}$)S(=O)$_v$R$^{31}$, —OS(=O)$_v$(C$_1$-C$_6$alkyl)R$^{31}$, or —N(R$^{12}$)S(=O)$_v$(C$_1$-C$_6$alkyl)R$^{31}$.

In some embodiments provided herein, the compound of Formula (II) has the structure of Formula (IIa), or a pharmaceutically acceptable salt or solvate thereof:

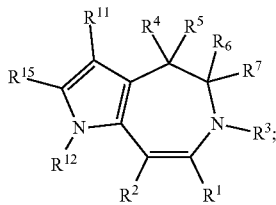

Formula (IIa)

wherein:
R$^1$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

R$^2$ is selected from the group consisting of —CN, —C(=O)OR$^{25}$, —C(=O)N(R$^{25}$)R$^{26}$,

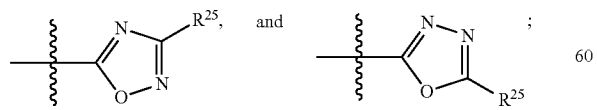

or R$^1$ and R$^2$ together with the carbon atoms to which they are attached, form an optionally substituted C$_2$-C$_9$heterocycloalkyl ring or an optionally substituted heteroaryl ring;

R$^3$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_{10}$cycloalkyl, optionally substituted aryl, optionally substituted —(C$_1$-C$_2$alkylene)-(aryl), optionally substituted heteroaryl, optionally substituted C$_2$-C$_9$heterocycloalkyl, optionally substituted —(C$_1$-C$_2$alkylene)-(heteroaryl), —C(=O)R$^{20}$, —C(=O)OR$^{20}$, —S(=O)$_2$R$^{20}$, —C(=O)N(R$^{21}$)R$^{22}$, —C(=O)N(R$^{21}$)S(=O)$_2$R$^{24}$, —C(=O)N(R$^{23}$)N(R$^{21}$)R$^{22}$, —C(=O)N(R$^{23}$)N(R$^{21}$)S(=O)$_2$R$^{24}$, —N(R$^{23}$)C(=O)R$^{20}$, —N(R$^{23}$)C(=O)N(R$^{21}$)R$^{22}$, —N(R$^{23}$)C(=O)N(R$^{21}$)S(=O)$_2$R$^{24}$, —N(R$^{20}$)C(=O)N(R$^{23}$)N(R$^{21}$)R$^{22}$, —N(R$^{20}$)C(=O)N(R$^{23}$)N(R$^{21}$)S(=O)$_2$R$^{24}$, —N(R$^{23}$)C(=O)OR$^{20}$, —P(=O)OR$^{20}$, and —P(=O)(OR$^{19}$)OR$^{20}$;

R$^4$ and R$^5$ are each independently selected from the group consisting of hydrogen, halogen, optionally substituted C$_1$-C$_6$alkyl, optionally substituted C$_1$-C$_6$alkoxy, optionally substituted C$_2$-C$_6$alkenyl, and optionally substituted C$_2$-C$_6$alkynyl; or R$^4$ and R$^5$ together with the carbon atom to which they are attached, form an optionally substituted C$_3$-C$_6$cycloalkyl ring or an optionally substituted C$_2$-C$_7$heterocycloalkyl ring;

R$^6$ is selected from the group consisting of hydrogen, halogen, optionally substituted C$_1$-C$_6$alkyl, optionally substituted C$_2$-C$_6$alkenyl, optionally substituted C$_2$-C$_6$alkynyl, and —C(=O)N(R$^{27}$)R$^{28}$;

R$^7$ is selected from the group consisting of hydrogen, halogen, optionally substituted C$_1$-C$_6$alkyl, optionally substituted C$_1$-C$_6$alkoxy, optionally substituted C$_2$-C$_6$alkenyl, and optionally substituted C$_2$-C$_6$alkynyl;

R$^{11}$ is selected from the group consisting of hydrogen, halogen, —CN, amino, alkylamino, C$_1$-C$_6$alkyl, C$_1$-C$_6$haloalkyl, C$_1$-C$_6$alkoxy, C$_1$-C$_6$haloalkoxy, C$_3$-C$_8$cycloalkyl, C$_2$-C$_9$heterocycloalkyl, aryl, heteroaryl, —C(=O)OR$^{12}$, —C(=O)N(R$^{13}$)R$^{14}$;

each R$^{12}$ is independently selected from the group consisting of hydrogen and C$_1$-C$_6$alkyl;

R$^{13}$ and R$^{14}$ are independently selected from the group consisting of hydrogen and C$_1$-C$_6$alkyl; or R$^{13}$ and R$^{14}$ together with the nitrogen atom to which they are attached, form an optionally substituted C$_2$-C$_9$heterocycloalkyl ring;

R$^{15}$ is —OC(=J)OR$^{16a}$, —N(R$^{12}$)C(=J)OR$^{16a}$, —OC(=J)N(H)R$^{16a}$, —N(R$^{12}$)C(=J)N(H)R$^{16a}$, —OC(=J)N(H)(C$_2$-C$_6$alkyl)R$^{30}$, —N(R$^{12}$)C(=J)O(C$_2$-C$_6$alkyl)R$^{30}$, —N(R$^{12}$)C(=J)N(H)(C$_2$-C$_6$alkyl)R$^{30}$, —OC(=J)O(C$_2$-C$_6$alkyl)R$^{30}$, —C(=J)R$^{31}$, —OC(=J)R$^{31}$, —N(R$^{12}$)C(=J)R$^{31}$, —O(C$_2$-C$_6$alkyl)R$^{30}$, —N(R$^{12}$)(C$_2$-C$_6$alkyl)R$^{30}$, —OS(=O)$_v$R$^{31}$, —N(R$^{12}$)S(=O)$_v$R$^{31}$, —OS(=O)$_v$(C$_2$-C$_6$alkyl)R$^{30}$, or —N(R$^{12}$)S(=O)$_v$(C$_2$-C$_6$alkyl)R$^{30}$;

R$^{30}$ is R$^{16a}$, R$^{16b}$, or R$^{16c}$;
R$^{31}$ is R$^{16a}$ or R$^{16c}$;
J is O, S, or N(R$^{12}$);
R$^{16a}$ is

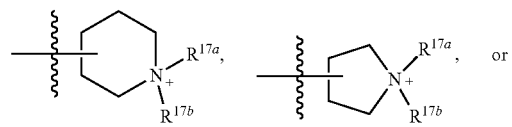

or

119

-continued

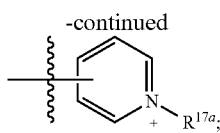

R$^{16b}$ is

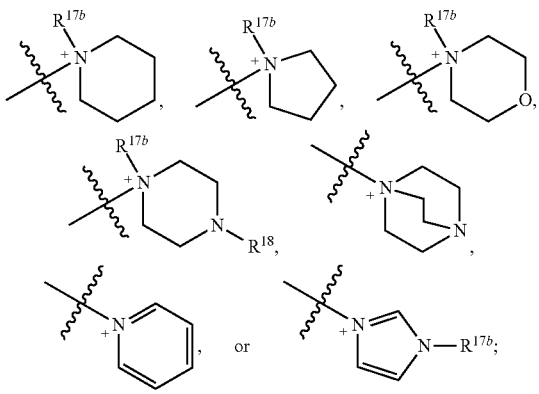

R$^{16c}$ is

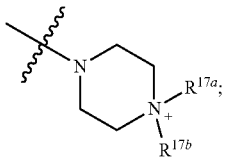

R$^{17a}$ is C$_1$-C$_6$alkyl;
R$^{17b}$ is C$_1$-C$_6$alkyl optionally substituted with phenyl, —C(=O)OH or —S(=O)$_2$OH;
R$^{18}$ is hydrogen, —OH, —(C$_0$-C$_6$alkyl)-C(=O)OH, or C$_1$-C$_6$alkyl;
v is 1 or 2;
R$^{19}$, R$^{20}$, and R$^{23}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);
R$^{21}$ and R$^{22}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl); or R$^{21}$ and R$^{22}$ together with the nitrogen atom to which they are attached, form an optionally substituted C$_2$-C$_9$heterocycloalkyl ring;
R$^{24}$ is selected from the group consisting of optionally substituted C$_1$-C$_6$alkyl, optionally substituted C$_2$-C$_6$alkenyl, optionally substituted C$_2$-C$_6$alkynyl, optionally substituted C$_3$-C$_5$ cycloalkyl, optionally substituted aryl optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl); and
R$^{25}$ and R$^{26}$ are each independently selected from the group consisting of hydrogen, optionally substituted C$_1$-C$_6$alkyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);
R$^{27}$ and R$^{28}$ are each independently selected from the group consisting of hydrogen, optionally substituted C$_1$-C$_6$alkyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl); or R$^{27}$ and R$^{28}$ together with the nitrogen atom to which they are attached, form an optionally substituted C$_2$-C$_9$heterocycloalkyl ring.

In one embodiment is a compound of Formula (IIa) wherein R$^4$ and R$^5$ are each independently selected from the group consisting of hydrogen, halogen, and optionally substituted C$_1$-C$_6$alkyl. In another embodiment is a compound of Formula (IIa) wherein R$^4$ and R$^5$ are each independently selected from the group consisting of hydrogen and optionally substituted C$_1$-C$_6$alkyl. In another embodiment is a compound of Formula (IIa) wherein R$^4$ and R$^5$ are each hydrogen. In another embodiment is a compound of Formula (IIa) wherein R$^4$ and R$^5$ are each independently optionally substituted C$_1$-C$_6$alkyl. In another embodiment is a compound of Formula (IIa) wherein R$^4$ and R$^5$ are each methyl. In another embodiment is a compound of Formula (IIa) wherein R$^4$ and R$^5$ form an optionally substituted C$_3$-C$_6$cycloalkyl ring or an optionally substituted C$_2$-C$_7$heterocycloalkyl ring. In some embodiments is a compound of Formula (IIa) wherein R$^4$ and R$^5$ form an optionally substituted C$_3$-C$_6$cycloalkyl ring. In some embodiments is a compound of Formula (IIa) wherein R$^4$ and R$^5$ form an optionally substituted C$_2$-C$_7$heterocycloalkyl ring.

In another embodiment is a compound of Formula (IIa) wherein R$^6$ and R$^7$ are each independently selected from the group consisting of hydrogen, halogen, and optionally substituted C$_1$-C$_6$alkyl. In another embodiment is a compound of Formula (IIa) wherein R$^6$ and R$^7$ are each independently selected from the group consisting of hydrogen and optionally substituted C$_1$-C$_6$alkyl. In another embodiment is a compound of Formula (IIa) wherein R$^6$ and R$^7$ are each independently optionally substituted C$_1$-C$_6$alkyl. In another embodiment is a compound of Formula (IIa) wherein R$^6$ and R$^7$ are each methyl. In another embodiment is a compound of Formula (IIa) wherein R$^6$ and R$^7$ are each hydrogen.

In another embodiment is a compound of Formula (IIa) wherein R$^6$ and R$^7$ are hydrogen, R$^4$ and R$^5$ are independently optionally substituted C$_1$-C$_6$alkyl, R$^3$ is —C(O)R$^{20}$, and R$^{20}$ is optionally substituted aryl. In another embodiment is a compound of Formula (IIa) wherein R$^6$ and R$^7$ are hydrogen, R$^4$ and R$^5$ are independently optionally substituted C$_1$-C$_6$alkyl, R$^3$ is —C(O)R$^{20}$, and R$^{20}$ is optionally substituted heteroaryl. In another embodiment is a compound of Formula (IIa) wherein R$^6$ and R$^7$ are hydrogen, R$^4$ and R$^5$ are methyl, R$^3$ is —C(O)R$^{20}$, and R$^{20}$ is optionally substituted aryl. In another embodiment is a compound of Formula (IIa) wherein $R^6$ and $R^7$ are hydrogen, $R^4$ and $R^5$ are methyl, $R^3$ is —C(O)$R^{20}$, and $R^{20}$ is optionally substituted heteroaryl.

In another embodiment is a compound of Formula (IIa) wherein $R^6$ and $R^7$ are hydrogen, $R^4$ and $R^5$ are independently optionally substituted $C_1$-$C_6$alkyl, $R^3$ is —S(O)$_2R^{20}$, and $R^{20}$ is optionally substituted aryl. In another embodiment is a compound of Formula (IIa) wherein $R^6$ and $R^7$ are hydrogen, $R^4$ and $R^5$ are independently optionally substituted $C_1$-$C_6$alkyl, $R^3$ is —S(O)$_2R^{20}$, and $R^{20}$ is optionally substituted heteroaryl. In another embodiment is a compound of Formula (IIa) wherein $R^6$ and $R^7$ are hydrogen, $R^4$ and $R^5$ are methyl, $R^3$ is —S(O)$_2R^{20}$, and $R^{20}$ is optionally substituted aryl. In another embodiment is a compound of Formula (IIa) wherein $R^6$ and $R^7$ are hydrogen, $R^4$ and $R^5$ are methyl, $R^3$ is —S(O)$_2R^{20}$, and $R^{20}$ is optionally substituted heteroaryl.

In another embodiment is a compound of Formula (IIa) wherein $R^6$ and $R^7$ are hydrogen, $R^4$ and $R^5$ are independently optionally substituted $C_1$-$C_6$alkyl, $R^3$ is —C(O)N($R^{21}$)$R^{22}$, $R^{21}$ is hydrogen and $R^{22}$ is optionally substituted aryl. In another embodiment is a compound of Formula (IIa) wherein $R^6$ and $R^7$ are hydrogen, $R^4$ and $R^5$ are independently optionally substituted $C_1$-$C_6$alkyl, $R^3$ is —C(O)N($R^{21}$)$R^{22}$, $R^{21}$ is hydrogen and $R^{22}$ is optionally substituted heteroaryl. In another embodiment is a compound of Formula (IIa) wherein $R^6$ and $R^7$ are hydrogen, $R^4$ and $R^5$ are methyl, $R^3$ is —C(O)N($R^{21}$)$R^{22}$, $R^{21}$ is hydrogen and $R^{22}$ is optionally substituted aryl. In another embodiment is a compound of Formula (IIa) wherein $R^6$ and $R^7$ are hydrogen, $R^4$ and $R^5$ are methyl, $R^3$ is —C(O)N($R^{21}$)$R^{22}$, $R^{21}$ is hydrogen and $R^{22}$ is optionally substituted heteroaryl.

In a further embodiment of the aforementioned embodiments is a compound of Formula (IIa) wherein $R^2$ is selected from the group consisting of —CN, —C(O)O$R^{25}$, —C(O)N($R^{25}$)$R^{26}$,

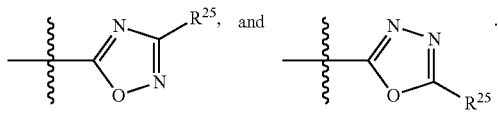

In a further embodiment of the aforementioned embodiments is a compound of Formula (IIa) wherein $R^2$ is —CN.

In a further embodiment of the aforementioned embodiments is a compound of Formula (IIa) wherein $R^2$ is —C(O)O$R^{25}$. In a further embodiment of the aforementioned embodiments is a compound of Formula (IIa) wherein $R^2$ is —C(O)O$R^{25}$, and $R^{25}$ is independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IIa) wherein $R^2$ is —C(O)O$R^{25}$, and $R^{25}$ is independently selected from the group consisting of hydrogen, and optionally substituted $C_1$-$C_6$alkyl. In a further embodiment of the aforementioned embodiments is a compound of Formula (IIa) wherein $R^2$ is —C(O)O$R^{25}$, and $R^{25}$ is hydrogen. In a further embodiment of the aforementioned embodiments is a compound of Formula (IIa) wherein $R^2$ is —C(O)O$R^{25}$, and $R^{25}$ is optionally substituted $C_1$-$C_6$alkyl. In a further embodiment of the aforementioned embodiments is a compound of Formula (IIa) wherein $R^2$ is —C(O)O$R^{25}$, and $R^{25}$ is unsubstituted $C_1$-$C_6$alkyl. In a further embodiment of the aforementioned embodiments is a compound of Formula (IIa) wherein $R^2$ is —C(O)O$R^{25}$, and $R^{25}$ is methyl. In a further embodiment of the aforementioned embodiments is a compound of Formula (IIa) wherein $R^2$ is —C(O)O$R^{25}$, and $R^{25}$ is ethyl.

In a further embodiment of the aforementioned embodiments is a compound of Formula (IIa) wherein $R^2$ is —C(O)N($R^{25}$)$R^{26}$. In a further embodiment of the aforementioned embodiments is a compound of Formula (IIa) wherein $R^2$ is —C(O)N($R^{25}$)$R^{26}$, and $R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IIa) wherein $R^2$ is —C(O)N($R^{25}$)$R^{26}$, and $R^{25}$ and $R^{26}$ are each independently selected from the group consisting of hydrogen, and optionally substituted $C_1$-$C_6$alkyl. In a further embodiment of the aforementioned embodiments is a compound of Formula (IIa) wherein $R^2$ is —C(O)N($R^{25}$)$R^{26}$, and $R^{25}$ and $R^{26}$ are hydrogen. In a further embodiment of the aforementioned embodiments is a compound of Formula (IIa) wherein $R^2$ is —C(O)N($R^{25}$)$R^{26}$, and $R^{25}$ and $R^{26}$ are each independently optionally substituted $C_1$-$C_6$alkyl. In a further embodiment of the aforementioned embodiments is a compound of Formula (IIa) wherein $R^2$ is —C(O)N($R^{25}$)$R^{26}$, $R^{25}$ is hydrogen, and $R^{26}$ is optionally substituted $C_1$-$C_6$alkyl. In a further embodiment of the aforementioned embodiments is a compound of Formula (IIa) wherein $R^2$ is —C(O)N($R^{25}$)$R^{26}$, and $R^{25}$ and $R^{26}$ are each independently unsubstituted $C_1$-$C_6$alkyl. In a further embodiment of the aforementioned embodiments is a compound of Formula (IIa) wherein $R^2$ is —C(O)N($R^{25}$)$R^{26}$, $R^{25}$ is hydrogen, and $R^{26}$ are methyl. In a further embodiment of the aforementioned embodiments is a compound of Formula (IIa) wherein $R^2$ is —C(O)N($R^{25}$)$R^{26}$, and $R^{25}$ and $R^{26}$ are methyl. In a further embodiment of the aforementioned embodiments is a compound of Formula (IIa) wherein $R^2$ is —C(O)N($R^{25}$)$R^{26}$, and $R^{25}$ and $R^{26}$ are ethyl.

In a further embodiment of the aforementioned embodiments is a compound of Formula (IIa) wherein $R^2$ is

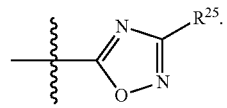

In a further embodiment of the aforementioned embodiments is a compound of Formula (IIa) wherein $R^2$ is

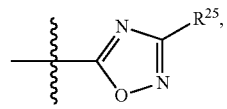

and $R^{25}$ is optionally substituted $C_1$-$C_6$alkyl. In a further embodiment of the aforementioned embodiments is a compound of Formula (IIa) wherein $R^2$ is

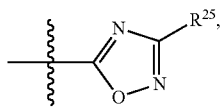

and $R^{25}$ is methyl. In a further embodiment of the aforementioned embodiments is a compound of Formula (IIa) wherein $R^2$ is

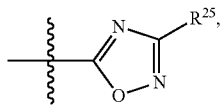

and $R^{25}$ is optionally substituted $C_1$-$C_6$alkyl. In a further embodiment of the aforementioned embodiments is a compound of Formula (IIa) wherein $R^2$ is

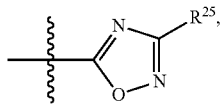

and $R^{25}$ is ethyl.

In a further embodiment of the aforementioned embodiments is a compound of Formula (Ia) wherein $R^2$ is

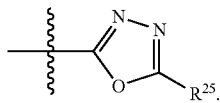

In a further embodiment of the aforementioned embodiments is a compound of Formula (IIa) wherein $R^2$ is

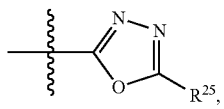

and $R^{25}$ is optionally substituted $C_1$-$C_6$alkyl. In a further embodiment of the aforementioned embodiments is a compound of Formula (IIa) wherein $R^2$ is

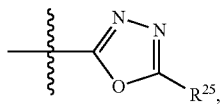

and $R^{25}$ is methyl. In a further embodiment of the aforementioned embodiments is a compound of Formula (IIa) wherein $R^2$ is

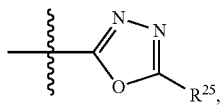

and $R^{25}$ is optionally substituted $C_1$-$C_6$alkyl. In a further embodiment of the aforementioned embodiments is a compound of Formula (IIa) wherein $R^2$ is

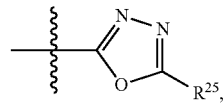

and $R^{25}$ is ethyl.

In a further embodiment of the aforementioned embodiments is a compound of Formula (IIa) wherein $R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IIa) wherein $R^1$ is hydrogen. In a further embodiment of the aforementioned embodiments is a compound of Formula (IIa) wherein $R^1$ is optionally substituted $C_1$-$C_6$alkyl. In a further embodiment of the aforementioned embodiments is a compound of Formula (IIa) wherein $R^1$ is methyl. In a further embodiment of the aforementioned embodiments is a compound of Formula (IIa) wherein $R^1$ is optionally substituted $C_2$-$C_6$alkenyl. In a further embodiment of the aforementioned embodiments is a compound of Formula (IIa) wherein $R^1$ is optionally substituted $C_2$-$C_6$alkynyl.

In a further embodiment of the aforementioned embodiments is a compound of Formula (IIa) wherein $R^1$ and $R^2$ together with the carbon atoms to which they are attached, form an optionally substituted $C_2$-$C_9$heterocycloalkyl ring or an optionally substituted heteroaryl ring. In a further embodiment of the aforementioned embodiments is a compound of Formula (IIa) wherein $R^1$ and $R^2$ together with the carbon atoms to which they are attached, form an optionally substituted $C_2$-$C_9$heterocycloalkyl ring. In a further embodiment of the aforementioned embodiments is a compound of Formula (IIa) wherein $R^1$ and $R^2$ together with the carbon atoms to which they are attached, form an optionally substituted heteroaryl ring.

In another embodiment of the aforementioned embodiments is a compound of Formula (IIa) wherein $R^{15}$ is —OC(=J)O$R^{16a}$. In another embodiment of the aforementioned embodiments is a compound of Formula (IIa) wherein $R^{15}$ is —N($R^{12}$)C(=J)O$R^{16a}$. In another embodiment of the aforementioned embodiments is a compound of Formula (IIa) wherein $R^{15}$ is —OC(=J)N(H)$R^{16a}$. In another embodiment of the aforementioned embodiments is a compound of Formula (IIa) wherein $R^{15}$ is —N($R^{12}$)C(=J)N(H)$R^{16a}$. In another embodiment of the aforementioned embodiments is a compound of Formula (IIa) wherein $R^{15}$ is —OC(=J)N(H)($C_2$-$C_6$alkyl)$R^{30}$. In another embodiment of the aforementioned embodiments is a compound of Formula (IIa) wherein $R^{15}$ is —N($R^{12}$)C(=J)O($C_2$-$C_6$alkyl)$R^{30}$. In another embodiment of the aforementioned embodiments is a compound of Formula (IIa) wherein $R^{15}$ is —N($R^{12}$)C(=J)N(H)($C_2$-$C_6$alkyl)$R^{30}$. In another embodiment of the aforementioned embodiments is a compound of Formula (IIa) wherein $R^{15}$ is —OC(=J)O($C_2$-$C_6$alkyl)$R^{30}$. In another embodiment of the aforementioned embodiments is a compound of Formula (IIa) wherein $R^{15}$ is —C(=J)$R^{31}$. In another embodiment of the aforementioned embodiments is a compound of Formula (IIa) wherein $R^{15}$ is —OC(=J)$R^{31}$. In another embodiment of the aforementioned embodiments is a compound of Formula (IIa) wherein $R^{15}$ is —N($R^{12}$)C(=J)$R^{31}$. In another embodiment of the aforementioned embodiments is a compound of Formula (IIa) wherein $R^{15}$ is —O($C_2$-$C_6$alkyl)$R^{30}$. In another embodiment of the aforementioned embodiments is a compound of Formula (IIa) wherein $R^{15}$ is —N($R^{12}$)($C_2$-$C_6$alkyl)$R^{30}$. In another embodiment of the aforementioned embodiments is a compound of Formula (IIa) wherein $R^{15}$ is —OS(=O)$_v$$R^{31}$. In another embodiment of the aforementioned embodiments is a compound of Formula (IIa) wherein $R^{15}$ is —N($R^{12}$)S(=O)$_v$$R^{31}$. In another embodiment of the aforementioned embodiments is a compound of Formula (IIa) wherein $R^{15}$ is —OS(=O)$_v$($C_2$-$C_6$alkyl)$R^{30}$. In another embodiment of the aforementioned embodiments is a compound of Formula (IIa) wherein $R^{15}$ is —N($R^{12}$)S(=O)$_v$($C_2$-$C_6$alkyl)$R^{30}$. In a further embodiment of the aforementioned embodiments is a compound of Formula (IIa) wherein $R^{30}$ is $R^{16a}$. In a further embodiment of the aforementioned embodiments is a compound of Formula (IIa) wherein $R^{30}$ is $R^{16b}$. In a further embodiment of the aforementioned embodiments is a compound of Formula (IIa) wherein $R^{30}$ is $R^{16c}$. In a further embodiment of the aforementioned embodiments is a compound of Formula (IIa) wherein $R^{31}$ is $R^{16a}$. In a further embodiment of the aforementioned embodiments is a compound of Formula (IIa) wherein $R^{31}$ is $R^{16b}$. In a further embodiment of the aforementioned embodiments is a compound of Formula (IIa) wherein J is O. In a further embodiment of the aforementioned embodiments is a compound of Formula (IIa) wherein J is S. In a further embodiment of the aforementioned embodiments is a compound of Formula (IIa) wherein J is N($R^{12}$).

In another embodiment of the aforementioned embodiments is a compound of Formula (IIa) wherein $R^{16a}$ is In another embodiment of the aforementioned embodiments is a compound of Formula (IIa) wherein $R^{16a}$ is In another embodiment of the aforementioned embodiments is a compound of Formula (IIa) wherein $R^{16a}$ is In another embodiment of the aforementioned embodiments is a compound of Formula (IIa) wherein $R^{16b}$ is In another embodiment of the aforementioned embodiments is a compound of Formula (IIa) wherein $R^{16b}$ is In another embodiment of the aforementioned embodiments is a compound of Formula (IIa) wherein $R^{16b}$ is In another embodiment of the aforementioned embodiments is a compound of Formula (IIa) wherein $R^{16b}$ is In another embodiment of the aforementioned embodiments is a compound of Formula (IIa) wherein $R^{16b}$ is In another embodiment of the aforementioned embodiments is a compound of Formula (IIa) wherein $R^{16b}$ is In another embodiment of the aforementioned embodiments is a compound of Formula (IIa) wherein $R^{16b}$ is

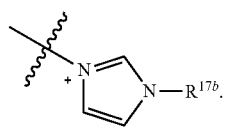

In another embodiment of the aforementioned embodiments is a compound of Formula (IIa) wherein $R^{16c}$ is

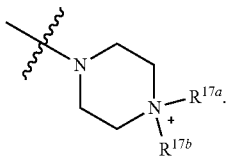

In another embodiment is a compound of Formula (IIa) wherein $R^{16c}$ is

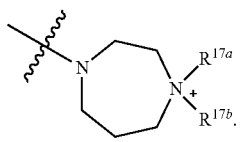

In a further embodiment of the aforementioned embodiments is a compound of Formula (IIa) wherein $R^{17a}$ is methyl. In a further embodiment of the aforementioned embodiments is a compound of Formula (IIa) wherein $R^{17a}$ is ethyl. In a further embodiment of the aforementioned embodiments is a compound of Formula (IIa) wherein $R^{17b}$ is methyl optionally substituted with phenyl, —C(=O)OH or —S(=O)$_2$OH. In a further embodiment of the aforementioned embodiments is a compound of Formula (IIa) wherein $R^{17a}$ is ethyl optionally substituted with phenyl, —C(=O)OH or —S(=O)$_2$OH.

In another embodiment is a compound of Formula (IIa) wherein $R^{15}$ is —OC(=J)OR$^{16a}$, —N(R$^{12}$)C(=J)OR$^{16a}$, —OC(=J)N(H)R$^{16a}$, —N(R$^{12}$)C(=J)N(H)R$^{16a}$, —OC(=J)N(H)(C$_1$-C$_6$alkyl)R$^{31}$, —N(R$^{12}$)C(=J)O(C$_1$-C$_6$alkyl)R$^{31}$, —N(R$^{12}$)C(=J)N(H)(C$_1$-C$_6$alkyl)R$^{31}$, —OC(=J)O(C$_1$-C$_6$alkyl)R$^{31}$, —C(=J)R$^{31}$, —OC(=J)R$^{31}$, —N(R$^{12}$)C(=J)R$^{31}$, —O(C$_1$-C$_6$alkyl)R$^{31}$, —N(R$^{12}$)(C$_1$-C$_6$alkyl)R$^{31}$, —OS(=O)$_v$R$^{31}$, —N(R$^{12}$)S(=O)$_v$R$^{31}$, —OS(=O)$_v$(C$_1$-C$_6$alkyl)R$^{31}$, or —N(R$^{12}$)S(=O)$_v$(C$_1$-C$_6$alkyl)R$^{31}$.

In some embodiments provided herein, the compound of Formula (II) has the structure of Formula (IIb), or a pharmaceutically acceptable salt or solvate thereof:

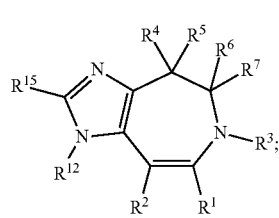

Formula (IIb)

wherein:
$R^1$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

$R^2$ is selected from the group consisting of —CN, —C(=O)OR$^{25}$, —C(=O)N(R$^{25}$)R$^{26}$,

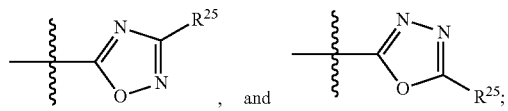

, and or $R^1$ and $R^2$ together with the carbon atoms to which they are attached, form an optionally substituted C$_2$-C$_9$heterocycloalkyl ring or an optionally substituted heteroaryl ring;

$R^3$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_{10}$cycloalkyl, optionally substituted aryl, optionally substituted —(C$_1$-C$_2$alkylene)-(aryl), optionally substituted heteroaryl, optionally substituted C$_2$-C$_9$heterocycloalkyl, optionally substituted —(C$_1$-C$_2$alkylene)-(heteroaryl), —C(=O)R$^{20}$, —C(=O)OR$^{20}$, —S(=O)$_2$R$^{20}$, —C(=O)N(R$^{21}$)R$^{22}$, —C(=O)N(R$^{21}$)S(=O)$_2$R$^{24}$, —C(=O)N(R$^{23}$)N(R$^{21}$)R$^{22}$, —C(=O)N(R$^{23}$)N(R$^{21}$)S(=O)$_2$R$^{24}$, —N(R$^{23}$)C(=O)R$^{20}$, —N(R$^{23}$)C(=O)N(R$^{21}$)R$^{22}$, —N(R$^{23}$)C(=O)N(R$^{21}$)S(=O)$_2$R$^{24}$, —N(R$^{20}$)C(=O)N(R$^{23}$)N(R$^{21}$)R$^{22}$, —N(R$^{20}$)C(=O)N(R$^{23}$)N(R$^{21}$)S(=O)$_2$R$^{24}$, —N(R$^{23}$)C(=O)OR$^{20}$, —P(=O)OR$^{20}$, and —P(=O)(OR$^{19}$)OR$^{20}$;

$R^4$ and $R^5$ are each independently selected from the group consisting of hydrogen, halogen, optionally substituted C$_1$-C$_6$alkyl, optionally substituted C$_1$-C$_6$alkoxy, optionally substituted C$_2$-C$_6$alkenyl, and optionally substituted C$_2$-C$_6$alkynyl; or $R^4$ and $R^5$ together with the carbon atom to which they are attached, form an optionally substituted C$_3$-C$_6$cycloalkyl ring or an optionally substituted C$_2$-C$_7$heterocycloalkyl ring;

$R^6$ is selected from the group consisting of hydrogen, halogen, optionally substituted C$_1$-C$_6$alkyl, optionally substituted C$_2$-C$_6$alkenyl, optionally substituted C$_2$-C$_6$alkynyl, and —C(=O)N(R$^{27}$)R$^{28}$;

$R^7$ is selected from the group consisting of hydrogen, halogen, optionally substituted C$_1$-C$_6$alkyl, optionally substituted C$_1$-C$_6$alkoxy, optionally substituted C$_2$-C$_6$alkenyl, and optionally substituted C$_2$-C$_6$alkynyl;

each $R^{12}$ is independently selected from the group consisting of hydrogen and C$_1$-C$_6$alkyl;

$R^{15}$ is —OC(=J)OR$^{16a}$, —N(R$^{12}$)C(=J)OR$^{16a}$, —OC(=J)N(H)R$^{16a}$, —N(R$^{12}$)C(=J)N(H)R$^{16a}$, —OC(=J)N(H)(C$_2$-C$_6$alkyl)R$^{30}$, —N(R$^{12}$)C(=J)O(C$_2$-C$_6$alkyl)R$^{30}$, —N(R$^{12}$)C(=J)N(H)(C$_2$-C$_6$alkyl)R$^{30}$, —OC(=J)O(C$_2$-C$_6$alkyl)R$^{30}$, —C(=J)R$^{31}$, —OC(=J)R$^{31}$, —N(R$^{12}$)C(=J)R$^{31}$, —O(C$_2$-C$_6$alkyl)R$^{30}$, —N(R$^{12}$)(C$_2$-C$_6$alkyl)R$^{30}$, —OS(=O)$_v$R$^{31}$, —N(R$^{12}$)S(=O)$_v$R$^{31}$, —OS(=O)$_v$(C$_2$-C$_6$alkyl)R$^{30}$, or —N(R$^{12}$)S(=O)$_v$(C$_2$-C$_6$alkyl)R$^{30}$;

$R^{30}$ is $R^{16a}$, $R^{16b}$, or $R^{16c}$;
$R^{31}$ is $R^{16a}$ or $R^{16c}$;
J is O, S, or N(R$^{12}$);

$R^{16a}$ is

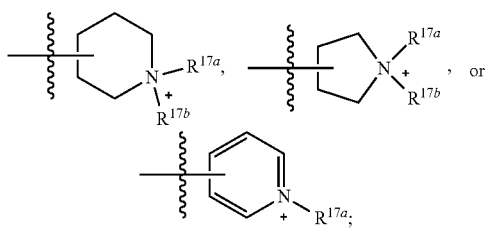

$R^{16b}$ is

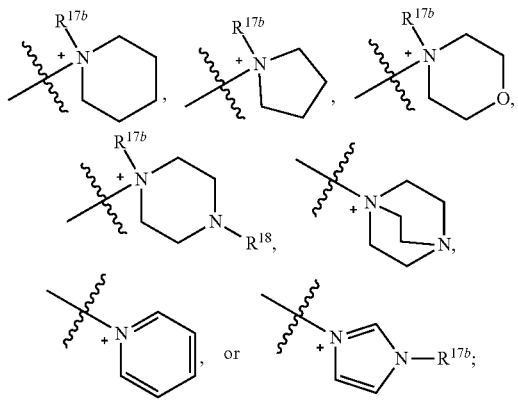

$R^{16c}$ is

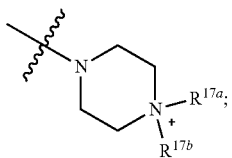

$R^{17a}$ is $C_1$-$C_6$alkyl;
$R^{17b}$ is $C_1$-$C_6$alkyl optionally substituted with phenyl, —C(=O)OH or —S(=O)$_2$OH;
$R^{18}$ is hydrogen, —OH, —($C_0$-$C_6$alkyl)-C(=O)OH, or $C_1$-$C_6$alkyl;
v is 1 or 2;
$R^{19}$, $R^{20}$, and $R^{23}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);
$R^{21}$ and $R^{22}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{21}$ and $R^{22}$ together with the nitrogen atom to which they are attached, form an optionally substituted $C_2$-$C_9$heterocycloalkyl ring;
$R^{24}$ is selected from the group consisting of optionally substituted $C_1$-$C_6$alkyl, optionally substituted $C_2$-$C_6$alkenyl, optionally substituted $C_2$-$C_6$alkynyl, optionally substituted $C_3$-$C_8$ cycloalkyl, optionally substituted aryl optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); and
$R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);
$R^{27}$ and $R^{28}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{27}$ and $R^{28}$ together with the nitrogen atom to which they are attached, form an optionally substituted $C_2$-$C_9$heterocycloalkyl ring.

In one embodiment is a compound of Formula (IIb) wherein $R^4$ and $R^5$ are each independently selected from the group consisting of hydrogen, halogen, and optionally substituted $C_1$-$C_6$alkyl. In another embodiment is a compound of Formula (IIb) wherein $R^4$ and $R^5$ are each independently selected from the group consisting of hydrogen and optionally substituted $C_1$-$C_6$alkyl. In another embodiment is a compound of Formula (IIb) wherein $R^4$ and $R^5$ are each hydrogen. In another embodiment is a compound of Formula (IIb) wherein $R^4$ and $R^5$ are each independently optionally substituted $C_1$-$C_6$alkyl. In another embodiment is a compound of Formula (IIb) wherein $R^4$ and $R^5$ are each methyl. In another embodiment is a compound of Formula (IIb) wherein $R^4$ and $R^5$ form an optionally substituted $C_3$-$C_6$cycloalkyl ring or an optionally substituted $C_2$-$C_7$heterocycloalkyl ring. In some embodiments is a compound of Formula (IIb) wherein $R^4$ and $R^5$ form an optionally substituted $C_3$-$C_6$cycloalkyl ring. In some embodiments is a compound of Formula (IIb) wherein $R^4$ and $R^5$ form an optionally substituted $C_2$-$C_7$heterocycloalkyl ring.

In another embodiment is a compound of Formula (IIb) wherein $R^6$ and $R^7$ are each independently selected from the group consisting of hydrogen, halogen, and optionally substituted $C_1$-$C_6$alkyl. In another embodiment is a compound of Formula (IIb) wherein $R^6$ and $R^7$ are each independently selected from the group consisting of hydrogen and optionally substituted $C_1$-$C_6$alkyl. In another embodiment is a compound of Formula (IIb) wherein $R^6$ and $R^7$ are each independently optionally substituted $C_1$-$C_6$alkyl. In another embodiment is a compound of Formula (IIb) wherein $R^6$ and $R^7$ are each methyl. In another embodiment is a compound of Formula (IIb) wherein $R^6$ and $R^7$ are each hydrogen.

In another embodiment is a compound of Formula (IIb) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted aryl. In another embodiment is a compound of Formula (IIb) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted heteroaryl. In another embodiment is a compound of Formula (IIb) wherein $R^6$ and $R^7$ are hydrogen, $R^4$ and $R^5$ are methyl, $R^3$ is —C(O)$R^{20}$, and $R^{20}$ is optionally substituted aryl. In another embodiment is a compound of Formula (IIb) wherein $R^6$ and $R^7$ are hydrogen, $R^4$ and $R^5$ are methyl, $R^3$ is —C(O)$R^{20}$, and $R^{20}$ is optionally substituted heteroaryl.

In another embodiment is a compound of Formula (IIb) wherein $R^6$ and $R^7$ are hydrogen, $R^4$ and $R^5$ are independently optionally substituted $C_1$-$C_6$alkyl, $R^3$ is —S(O)$_2R^{20}$, and $R^{20}$ is optionally substituted aryl. In another embodiment is a compound of Formula (IIb) wherein $R^6$ and $R^7$ are hydrogen, $R^4$ and $R^5$ are independently optionally substituted $C_1$-$C_6$alkyl, $R^3$ is —S(O)$_2R^{20}$, and $R^{20}$ is optionally substituted heteroaryl. In another embodiment is a compound of Formula (IIb) wherein $R^6$ and $R^7$ are hydrogen, $R^4$ and $R^5$ are methyl, $R^3$ is —S(O)$_2R^{20}$, and $R^{20}$ is optionally substituted aryl. In another embodiment is a compound of Formula (IIb) wherein $R^6$ and $R^7$ are hydrogen, $R^4$ and $R^5$ are methyl, $R^3$ is —S(O)$_2R^{20}$, and $R^{20}$ is optionally substituted heteroaryl.

In another embodiment is a compound of Formula (IIb) wherein $R^6$ and $R^7$ are hydrogen, $R^4$ and $R^5$ are independently optionally substituted $C_1$-$C_6$alkyl, $R^3$ is —C(O)N($R^{21}$)$R^{22}$, $R^{21}$ is hydrogen and $R^{22}$ is optionally substituted aryl. In another embodiment is a compound of Formula (IIb) wherein $R^6$ and $R^7$ are hydrogen, $R^4$ and $R^5$ are independently optionally substituted $C_1$-$C_6$alkyl, $R^3$ is —C(O)N($R^{21}$)$R^{22}$, $R^{21}$ is hydrogen and $R^{22}$ is optionally substituted heteroaryl. In another embodiment is a compound of Formula (IIb) wherein $R^6$ and $R^7$ are hydrogen, $R^4$ and $R^5$ are methyl, $R^3$ is —C(O)N($R^{21}$)$R^{22}$, $R^{21}$ is hydrogen and $R^{22}$ is optionally substituted aryl. In another embodiment is a compound of Formula (IIb) wherein $R^6$ and $R^7$ are hydrogen, $R^4$ and $R^5$ are methyl, $R^3$ is —C(O)N($R^{21}$)$R^{22}$, $R^{21}$ is hydrogen and $R^{22}$ is optionally substituted heteroaryl.

In a further embodiment of the aforementioned embodiments is a compound of Formula (IIb) wherein $R^2$ is selected from the group consisting of —CN, —C(O)O$R^{25}$, C(O)N($R^{25}$)$R^{26}$,

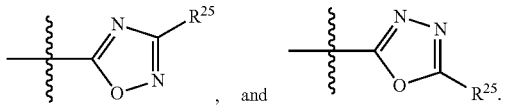
, and

In a further embodiment of the aforementioned embodiments is a compound of Formula (IIb) wherein $R^2$ is —CN.

In a further embodiment of the aforementioned embodiments is a compound of Formula (IIb) wherein $R^2$ is —C(O)O$R^{25}$. In a further embodiment of the aforementioned embodiments is a compound of Formula (IIb) wherein $R^2$ is —C(O)O$R^{25}$, and $R^{25}$ is independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IIb) wherein $R^2$ is —C(O)O$R^{25}$, and $R^{25}$ is independently selected from the group consisting of hydrogen, and optionally substituted $C_1$-$C_6$alkyl. In a further embodiment of the aforementioned embodiments is a compound of Formula (IIb) wherein $R^2$ is —C(O)O$R^{25}$, and $R^{25}$ is hydrogen. In a further embodiment of the aforementioned embodiments is a compound of Formula (IIb) wherein $R^2$ is —C(O)O$R^{25}$, and $R^{25}$ is optionally substituted $C_1$-$C_6$alkyl. In a further embodiment of the aforementioned embodiments is a compound of Formula (IIb) wherein $R^2$ is —C(O)O$R^{25}$, and $R^{25}$ is unsubstituted $C_1$-$C_6$alkyl. In a further embodiment of the aforementioned embodiments is a compound of Formula (IIb) wherein $R^2$ is —C(O)O$R^{25}$, and $R^{25}$ is methyl. In a further embodiment of the aforementioned embodiments is a compound of Formula (IIb) wherein $R^2$ is —C(O)O$R^{25}$, and $R^{25}$ is ethyl.

In a further embodiment of the aforementioned embodiments is a compound of Formula (IIb) wherein $R^2$ is —C(O)N($R^{25}$)$R^{26}$. In a further embodiment of the aforementioned embodiments is a compound of Formula (IIb) wherein $R^2$ is —C(O)N($R^{25}$)$R^{26}$, and $R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IIb) wherein $R^2$ is —C(O)N($R^{25}$)$R^{26}$, and $R^{25}$ and $R^{26}$ are each independently selected from the group consisting of hydrogen, and optionally substituted $C_1$-$C_6$alkyl. In a further embodiment of the aforementioned embodiments is a compound of Formula (IIb) wherein $R^2$ is —C(O)N($R^{25}$)$R^{26}$, and $R^{25}$ and $R^{26}$ are hydrogen. In a further embodiment of the aforementioned embodiments is a compound of Formula (IIb) wherein $R^2$ is —C(O)N($R^{25}$)$R^{26}$, and $R^{25}$ and $R^{26}$ are each independently optionally substituted $C_1$-$C_6$alkyl. In a further embodiment of the aforementioned embodiments is a compound of Formula (IIb) wherein $R^2$ is —C(O)N($R^{25}$)$R^{26}$, $R^{25}$ is hydrogen, and $R^{26}$ is optionally substituted $C_1$-$C_6$alkyl. In a further embodiment of the aforementioned embodiments is a compound of Formula (IIb) wherein $R^2$ is —C(O)N($R^{25}$)$R^{26}$, and $R^{25}$ and $R^{26}$ are each independently unsubstituted $C_1$-$C_6$alkyl. In a further embodiment of the aforementioned embodiments is a compound of Formula (IIb) wherein $R^2$ is —C(O)N($R^{25}$)$R^{26}$, $R^{25}$ is hydrogen, and $R^{26}$ are methyl. In a further embodiment of the aforementioned embodiments is a compound of Formula (IIb) wherein $R^2$ is —C(O)N($R^{25}$)$R^{26}$, and $R^{25}$ and $R^{26}$ are methyl. In a further embodiment of the aforementioned embodiments is a compound of Formula (IIb) wherein $R^2$ is —C(O)N($R^{25}$)$R^{26}$, and $R^{25}$ and $R^{26}$ are ethyl.

In a further embodiment of the aforementioned embodiments is a compound of Formula (IIb) wherein $R^2$ is

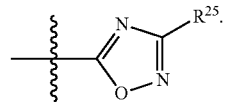

In a further embodiment of the aforementioned embodiments is a compound of Formula (IIb) wherein $R^2$ is

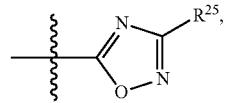

and $R^{25}$ is optionally substituted $C_1$-$C_6$alkyl. In a further embodiment of the aforementioned embodiments is a compound of Formula (IIb) wherein $R^2$ is

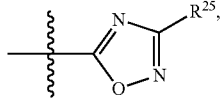

and $R^{25}$ is methyl. In a further embodiment of the aforementioned embodiments is a compound of Formula (IIb) wherein $R^2$ is

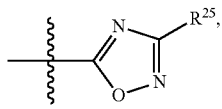

and $R^{25}$ is optionally substituted $C_1$-$C_6$alkyl. In a further embodiment of the aforementioned embodiments is a compound of Formula (IIb) wherein $R^2$ is

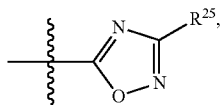

and $R^{25}$ is ethyl.

In a further embodiment of the aforementioned embodiments is a compound of Formula (IIb) wherein $R^2$ is

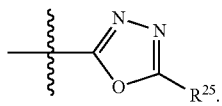

In a further embodiment of the aforementioned embodiments is a compound of Formula (IIb) wherein $R^2$ is

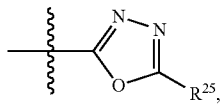

and $R^{25}$ is optionally substituted $C_1$-$C_6$alkyl. In a further embodiment of the aforementioned embodiments is a compound of Formula (IIb) wherein $R^2$ is

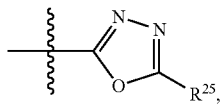

and $R^{25}$ is methyl. In a further embodiment of the aforementioned embodiments is a compound of Formula (IIb) wherein $R^2$ is

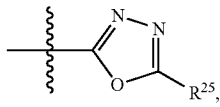

and $R^{25}$ is optionally substituted $C_1$-$C_6$alkyl. In a further embodiment of the aforementioned embodiments is a compound of Formula (IIb) wherein $R^2$ is

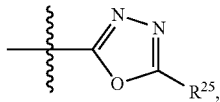

and $R^{25}$ is ethyl.

In a further embodiment of the aforementioned embodiments is a compound of Formula (IIb) wherein $R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IIb) wherein $R^1$ is hydrogen. In a further embodiment of the aforementioned embodiments is a compound of Formula (IIb) wherein $R^1$ is optionally substituted $C_1$-$C_6$alkyl. In a further embodiment of the aforementioned embodiments is a compound of Formula (IIb) wherein $R^1$ is methyl. In a further embodiment of the aforementioned embodiments is a compound of Formula (IIb) wherein $R^1$ is optionally substituted $C_2$-$C_6$alkenyl. In a further embodiment of the aforementioned embodiments is a compound of Formula (IIb) wherein $R^1$ is optionally substituted $C_2$-$C_6$alkynyl.

In a further embodiment of the aforementioned embodiments is a compound of Formula (IIb) wherein $R^1$ and $R^2$ together with the carbon atoms to which they are attached, form an optionally substituted $C_2$-$C_9$heterocycloalkyl ring or an optionally substituted heteroaryl ring. In a further embodiment of the aforementioned embodiments is a compound of Formula (IIb) wherein $R^1$ and $R^2$ together with the carbon atoms to which they are attached, form an optionally substituted $C_2$-$C_9$heterocycloalkyl ring. In a further embodiment of the aforementioned embodiments is a compound of Formula (IIb) wherein $R^1$ and $R^2$ together with the carbon atoms to which they are attached, form an optionally substituted heteroaryl ring.

In another embodiment of the aforementioned embodiments is a compound of Formula (IIb) wherein $R^{15}$ is —OC(=J)OR$^{16a}$. In another embodiment of the aforementioned embodiments is a compound of Formula (IIb) wherein $R^{15}$ is —N($R^{12}$)C(=J)OR$^{16a}$. In another embodiment of the aforementioned embodiments is a compound of Formula (IIb) wherein $R^{15}$ is —OC(=J)N(H)R$^{16a}$. In another embodiment of the aforementioned embodiments is a compound of Formula (IIb) wherein $R^{15}$ is —N($R^{12}$)C(=J)N(H)R$^{16a}$. In another embodiment of the aforementioned embodiments is a compound of Formula (IIb) wherein $R^{15}$ is —OC(=J)N(H)($C_2$-$C_6$alkyl)R$^{30}$. In another embodiment of the aforementioned embodiments is a compound of Formula (IIb) wherein $R^{15}$ is —N($R^{12}$)C(=J)O($C_2$-$C_6$alkyl)R$^{30}$. In another embodiment of the aforementioned embodiments is a compound of Formula (IIb) wherein $R^{15}$ is —$N(R^{12})C(=J)N(H)(C_2\text{-}C_6\text{alkyl})R^{30}$. In another embodiment of the aforementioned embodiments is a compound of Formula (IIb) wherein $R^{15}$ is —$OC(=J)O(C_2\text{-}C_6\text{alkyl})R^{30}$. In another embodiment of the aforementioned embodiments is a compound of Formula (IIb) wherein $R^{15}$ is —$C(=J)R^{31}$. In another embodiment of the aforementioned embodiments is a compound of Formula (IIb) wherein $R^{15}$ is —$OC(=J)R^{31}$. In another embodiment of the aforementioned embodiments is a compound of Formula (IIb) wherein $R^{15}$ is —$N(R^{12})C(=J)R^{31}$. In another embodiment of the aforementioned embodiments is a compound of Formula (IIb) wherein $R^{15}$ is —$O(C_2\text{-}C_6\text{alkyl})R^{30}$. In another embodiment of the aforementioned embodiments is a compound of Formula (IIb) wherein $R^{15}$ is —$N(R^{12})(C_2\text{-}C_6\text{alkyl})R^{30}$. In another embodiment of the aforementioned embodiments is a compound of Formula (IIb) wherein $R^{15}$ is —$OS(=O)_vR^{31}$. In another embodiment of the aforementioned embodiments is a compound of Formula (IIb) wherein $R^{15}$ is —$N(R^{12})S(=O)_vR^{31}$. In another embodiment of the aforementioned embodiments is a compound of Formula (IIb) wherein $R^{15}$ is —$OS(=O)_v(C_2\text{-}C_6\text{alkyl})R^{30}$. In another embodiment of the aforementioned embodiments is a compound of Formula (IIb) wherein $R^{15}$ is —$N(R^{12})S(=O)_v(C_2\text{-}C_6\text{alkyl})R^{30}$. In a further embodiment of the aforementioned embodiments is a compound of Formula (IIb) wherein $R^{30}$ is $R^{16a}$. In a further embodiment of the aforementioned embodiments is a compound of Formula (IIb) wherein $R^{30}$ is $R^{16b}$. In a further embodiment of the aforementioned embodiments is a compound of Formula (IIb) wherein $R^{30}$ is $R^{16c}$. In a further embodiment of the aforementioned embodiments is a compound of Formula (IIb) wherein $R^{31}$ is $R^{16a}$. In a further embodiment of the aforementioned embodiments is a compound of Formula (IIb) wherein $R^{31}$ is $R^{16b}$. In a further embodiment of the aforementioned embodiments is a compound of Formula (IIb) wherein J is O. In a further embodiment of the aforementioned embodiments is a compound of Formula (IIb) wherein J is S. In a further embodiment of the aforementioned embodiments is a compound of Formula (IIb) wherein J is $N(R^{12})$.

In another embodiment of the aforementioned embodiments is a compound of Formula (IIb) wherein $R^{16a}$ is

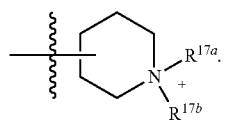

In another embodiment of the aforementioned embodiments is a compound of Formula (IIb) wherein $R^{16a}$ is

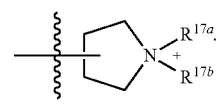

In another embodiment of the aforementioned embodiments is a compound of Formula (IIb) wherein $R^{16a}$ is

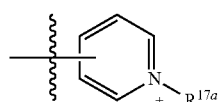

In another embodiment of the aforementioned embodiments is a compound of Formula (IIb) wherein $R^{16b}$ is

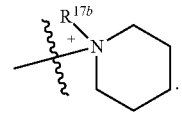

In another embodiment of the aforementioned embodiments is a compound of Formula (IIb) wherein $R^{16b}$ is

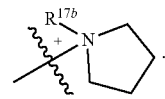

In another embodiment of the aforementioned embodiments is a compound of Formula (IIb) wherein $R^{16b}$ is

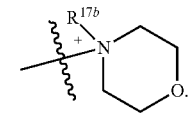

In another embodiment of the aforementioned embodiments is a compound of Formula (IIb) wherein $R^{16b}$ is

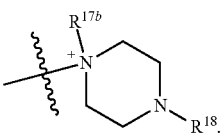

In another embodiment of the aforementioned embodiments is a compound of Formula (IIb) wherein $R^{16b}$ is

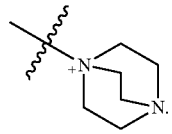

In another embodiment of the aforementioned embodiments is a compound of Formula (IIb) wherein $R^{16b}$ is

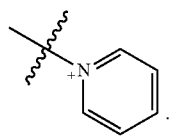

In another embodiment of the aforementioned embodiments is a compound of Formula (IIb) wherein $R^{16b}$ is

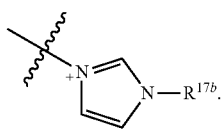

In another embodiment of the aforementioned embodiments is a compound of Formula (IIb) wherein $R^{16c}$ is

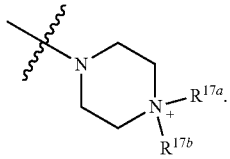

In another embodiment is a compound of Formula (IIb) wherein $R^{16c}$ is

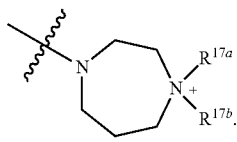

In a further embodiment of the aforementioned embodiments is a compound of Formula (IIb) wherein $R^{17a}$ is methyl. In a further embodiment of the aforementioned embodiments is a compound of Formula (IIb) wherein $R^{17a}$ is ethyl. In a further embodiment of the aforementioned embodiments is a compound of Formula (IIb) wherein $R^{17b}$ is methyl optionally substituted with phenyl, —C(=O)OH or —S(=O)$_2$OH. In a further embodiment of the aforementioned embodiments is a compound of Formula (IIb) wherein $R^{17a}$ is ethyl optionally substituted with phenyl, —C(=O)OH or —S(=O)$_2$OH.

In another embodiment is a compound of Formula (IIb) wherein $R^{15}$ is —OC(=J)OR$^{16a}$, —N(R$^{12}$)C(=J)OR$^{16a}$, —OC(=J)N(H)R$^{16a}$, —N(R$^{12}$)C(=J)N(H)R$^{16a}$, —OC(=J)N(H)(C$_1$-C$_6$alkyl)R$^{31}$, —N(R$^{12}$)C(=J)O(C$_1$-C$_6$alkyl)R$^{31}$, —N(R$^{12}$)C(=J)N(H)(C$_1$-C$_6$alkyl)R$^{31}$, —OC(=J)O(C$_1$-C$_6$alkyl)R$^{31}$, —C(=J)R$^{31}$, —OC(=J)R$^{31}$, —N(R$^{12}$)C(=J)R$^{31}$, —O(C$_1$-C$_6$alkyl)R$^{31}$, —N(R$^{12}$)(C$_1$-C$_6$alkyl)R$^{31}$, —OS(=O)$_v$R$^{31}$, —N(R$^{12}$)S(=O)$_v$R$^{31}$, —OS(=O)$_v$(C$_1$-C$_6$alkyl)R$^{31}$, or —N(R$^{12}$)S(=O)$_v$(C$_1$-C$_6$alkyl)R$^{31}$.

In some embodiments provided herein, the compound of Formula (II) has the structure of Formula (IIc), or a pharmaceutically acceptable salt or solvate thereof:

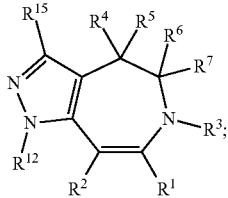

Formula (IIc)

wherein:
$R^1$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

$R^2$ is selected from the group consisting of —CN, —C(=O)OR$^{25}$, —C(=O)N(R$^{25}$)R$^{26}$,

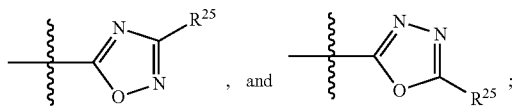

or $R^1$ and $R^2$ together with the carbon atoms to which they are attached, form an optionally substituted C$_2$-C$_9$heterocycloalkyl ring or an optionally substituted heteroaryl ring;

$R^3$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_{10}$cycloalkyl, optionally substituted aryl, optionally substituted —(C$_1$-C$_2$alkylene)-(aryl), optionally substituted heteroaryl, optionally substituted C$_2$-C$_9$heterocycloalkyl, optionally substituted —(C$_1$-C$_2$alkylene)-(heteroaryl), —C(=O)R$^{20}$, —C(=O)OR$^{20}$, —S(=O)$_2$R$^{20}$, —C(=O)N(R$^{21}$)R$^{22}$, —C(=O)N(R$^{21}$)S(=O)$_2$R$^{24}$, —C(=O)N(R$^{23}$)N(R$^{21}$)R$^{22}$, —C(=O)N(R$^{23}$)N(R$^{21}$)S(=O)$_2$R$^{24}$, —N(R$^{23}$)C(=O)R$^{20}$, —N(R$^{23}$)C(=O)N(R$^{21}$)R$^{22}$, —N(R$^{23}$)C(=O)N(R$^{21}$)S(=O)$_2$R$^{24}$, —N(R$^{20}$)C(=O)N(R$^{23}$)N(R$^{21}$)R$^{22}$, —N(R$^{20}$)C(=O)N(R$^{23}$)N(R$^{21}$)S(=O)$_2$R$^{24}$, —N(R$^{23}$)C(=O)OR$^{20}$, —P(=O)OR$^{20}$, and —P(=O)(OR$^{19}$)OR$^{20}$;

$R^4$ and $R^5$ are each independently selected from the group consisting of hydrogen, halogen, optionally substituted C$_1$-C$_6$alkyl, optionally substituted C$_1$-C$_6$alkoxy, optionally substituted C$_2$-C$_6$alkenyl, and optionally substituted C$_2$-C$_6$alkynyl; or $R^4$ and $R^5$ together with the carbon atom to which they are attached, form an optionally substituted C$_3$-C$_6$cycloalkyl ring or an optionally substituted C$_2$-C$_7$heterocycloalkyl ring;

$R^6$ is selected from the group consisting of hydrogen, halogen, optionally substituted C$_1$-C$_6$alkyl, optionally substituted C$_2$-C$_6$alkenyl, optionally substituted C$_2$-C$_6$alkynyl, and —C(=O)N(R$^{27}$)R$^{28}$;

$R^7$ is selected from the group consisting of hydrogen, halogen, optionally substituted C$_1$-C$_6$alkyl, optionally substituted C$_1$-C$_6$alkoxy, optionally substituted C$_2$-C$_6$alkenyl, and optionally substituted C$_2$-C$_6$alkynyl;

each $R^{12}$ is independently selected from the group consisting of hydrogen and C$_1$-C$_6$alkyl;

$R^{15}$ is —OC(=J)OR$^{16a}$, —N(R$^{12}$)C(=J)OR$^{16a}$, —OC(=J)N(H)R$^{16a}$, —N(R$^{12}$)C(=J)N(H)R$^{16a}$, —OC(=J)N(H)(C$_2$-C$_6$alkyl)R$^{30}$, —N(R$^{12}$)C(=J)O(C$_2$-C$_6$alkyl)R$^{30}$, —N(R$^{12}$)C(=J)N(H)(C$_2$-C$_6$alkyl)R$^{30}$, —OC(=J)O(C$_2$-C$_6$alkyl)R$^{30}$, —C(=J)R$^{31}$, —OC(=J)R$^{31}$, —N(R$^{12}$)C(=J)R$^{31}$, —O(C$_2$-C$_6$alkyl)R$^{30}$, —N(R$^{12}$)(C$_2$-C$_6$alkyl)R$^{30}$, —OS(=O)$_v$R$^{31}$, —N(R$^{12}$)S(=O)$_v$R$^{31}$, —OS(=O)$_v$(C$_2$-C$_6$alkyl)R$^{30}$, or —N(R$^{12}$)S(=O)$_v$(C$_2$-C$_6$alkyl)R$^{30}$;

$R^{30}$ is $R^{16a}$, $R^{16b}$, or $R^{16c}$;
$R^{31}$ is $R^{16a}$ or $R^{16c}$;
J is O, S, or N(R$^{12}$);

$R^{16a}$ is

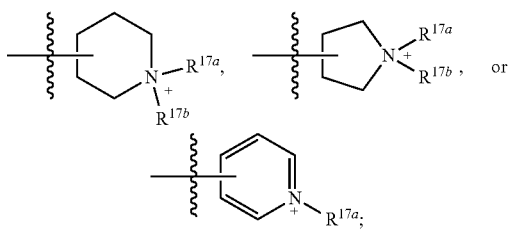

$R^{16b}$ is

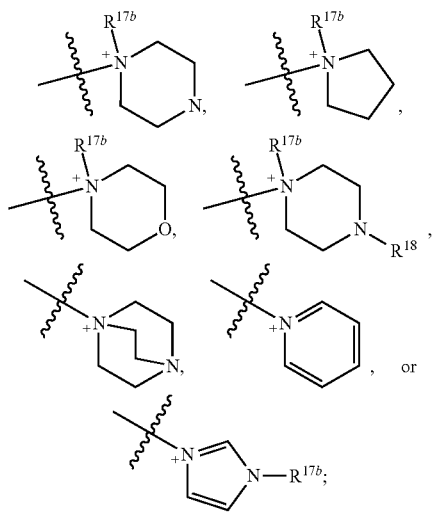

$R^{16c}$ is

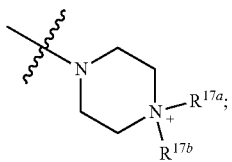

$R^{17a}$ is $C_1$-$C_6$alkyl;
$R^{17b}$ is $C_1$-$C_6$alkyl optionally substituted with phenyl, —C(=O)OH or —S(=O)$_2$OH;
$R^{18}$ is hydrogen, —OH, —($C_0$-$C_6$alkyl)-C(=O)OH, or $C_1$-$C_6$alkyl;
v is 1 or 2;
$R^{19}$, $R^{20}$, and $R^{23}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);
$R^{21}$ and $R^{22}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{21}$ and $R^{22}$ together with the nitrogen atom to which they are attached, form an optionally substituted $C_2$-$C_9$heterocycloalkyl ring;
$R^{24}$ is selected from the group consisting of optionally substituted $C_1$-$C_6$alkyl, optionally substituted $C_2$-$C_6$alkenyl, optionally substituted $C_2$-$C_6$alkynyl, optionally substituted $C_3$-$C_5$ cycloalkyl, optionally substituted aryl optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); and
$R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);
$R^{27}$ and $R^{28}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{27}$ and $R^{28}$ together with the nitrogen atom to which they are attached, form an optionally substituted $C_2$-$C_9$heterocycloalkyl ring.

In one embodiment is a compound of Formula (IIc) wherein $R^4$ and $R^5$ are each independently selected from the group consisting of hydrogen, halogen, and optionally substituted $C_1$-$C_6$alkyl. In another embodiment is a compound of Formula (IIc) wherein $R^4$ and $R^5$ are each independently selected from the group consisting of hydrogen and optionally substituted $C_1$-$C_6$alkyl. In another embodiment is a compound of Formula (IIc) wherein $R^4$ and $R^5$ are each hydrogen. In another embodiment is a compound of Formula (IIc) wherein $R^4$ and $R^5$ are each independently optionally substituted $C_1$-$C_6$alkyl. In another embodiment is a compound of Formula (IIc) wherein $R^4$ and $R^5$ are each methyl. In another embodiment is a compound of Formula (IIc) wherein $R^4$ and $R^5$ form an optionally substituted $C_3$-$C_6$cycloalkyl ring or an optionally substituted $C_2$-$C_7$heterocycloalkyl ring. In some embodiments is a compound of Formula (IIc) wherein $R^4$ and $R^5$ form an optionally substituted $C_3$-$C_6$cycloalkyl ring. In some embodiments is a compound of Formula (IIc) wherein $R^4$ and $R^5$ form an optionally substituted $C_2$-$C_7$heterocycloalkyl ring.

In another embodiment is a compound of Formula (IIc) wherein $R^6$ and $R^7$ are each independently selected from the group consisting of hydrogen, halogen, and optionally substituted $C_1$-$C_6$alkyl. In another embodiment is a compound of Formula (IIc) wherein $R^6$ and $R^7$ are each independently selected from the group consisting of hydrogen and optionally substituted $C_1$-$C_6$alkyl. In another embodiment is a compound of Formula (IIc) wherein $R^6$ and $R^7$ are each independently optionally substituted $C_1$-$C_6$alkyl. In another embodiment is a compound of Formula (IIc) wherein $R^6$ and $R^7$ are each methyl. In another embodiment is a compound of Formula (IIc) wherein $R^6$ and $R^7$ are each hydrogen.

In another embodiment is a compound of Formula (IIc) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted aryl. In another embodiment is a compound of Formula (IIc) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted heteroaryl. In another embodiment is a compound of Formula (IIc) wherein $R^6$ and $R^7$ are hydrogen, $R^4$ and $R^5$ are methyl, $R^3$ is —C(O)$R^{20}$, and $R^{20}$ is optionally substituted aryl. In another embodiment is a compound of Formula (IIc) wherein $R^6$ and $R^7$ are hydrogen, $R^4$ and $R^5$ are methyl, $R^3$ is —C(O)$R^{20}$, and $R^{20}$ is optionally substituted heteroaryl.

In another embodiment is a compound of Formula (IIc) wherein $R^6$ and $R^7$ are hydrogen, $R^4$ and $R^5$ are independently optionally substituted $C_1$-$C_6$alkyl, $R^3$ is —S(O)$_2R^{20}$, and $R^{20}$ is optionally substituted aryl. In another embodiment is a compound of Formula (IIc) wherein $R^6$ and $R^7$ are hydrogen, $R^4$ and $R^5$ are independently optionally substituted $C_1$-$C_6$alkyl, $R^3$ is —S(O)$_2R^{20}$, and $R^{20}$ is optionally substituted heteroaryl. In another embodiment is a compound of Formula (IIc) wherein $R^6$ and $R^7$ are hydrogen, $R^4$ and $R^5$ are methyl, $R^3$ is —S(O)$_2R^{20}$, and $R^{20}$ is optionally substituted aryl. In another embodiment is a compound of Formula (IIc) wherein $R^6$ and $R^7$ are hydrogen, $R^4$ and $R^5$ are methyl, $R^3$ is —S(O)$_2R^{20}$, and $R^{20}$ is optionally substituted heteroaryl.

In another embodiment is a compound of Formula (IIc) wherein $R^6$ and $R^7$ are hydrogen, $R^4$ and $R^5$ are independently optionally substituted $C_1$-$C_6$alkyl, $R^3$ is —C(O)N($R^{21}$)$R^{22}$, $R^{21}$ is hydrogen and $R^{22}$ is optionally substituted aryl. In another embodiment is a compound of Formula (IIc) wherein $R^6$ and $R^7$ are hydrogen, $R^4$ and $R^5$ are independently optionally substituted $C_1$-$C_6$alkyl, $R^3$ is —C(O)N($R^{21}$)$R^{22}$, $R^{21}$ is hydrogen and $R^{22}$ is optionally substituted heteroaryl. In another embodiment is a compound of Formula (IIc) wherein $R^6$ and $R^7$ are hydrogen, $R^4$ and $R^5$ are methyl, $R^3$ is —C(O)N($R^{21}$)$R^{22}$, $R^{21}$ is hydrogen and $R^{22}$ is optionally substituted aryl. In another embodiment is a compound of Formula (IIc) wherein $R^6$ and $R^7$ are hydrogen, $R^4$ and $R^5$ are methyl, $R^3$ is —C(O)N($R^{21}$)$R^{22}$, $R^{21}$ is hydrogen and $R^{22}$ is optionally substituted heteroaryl.

In a further embodiment of the aforementioned embodiments is a compound of Formula (IIc) wherein $R^2$ is selected from the group consisting of —CN, —C(O)O$R^{25}$, —C(O)N($R^{25}$)$R^{26}$,

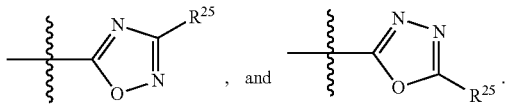

In a further embodiment of the aforementioned embodiments is a compound of Formula (IIc) wherein $R^2$ is —CN.

In a further embodiment of the aforementioned embodiments is a compound of Formula (IIc) wherein $R^2$ is —C(O)OR$^{25}$. In a further embodiment of the aforementioned embodiments is a compound of Formula (IIc) wherein $R^2$ is —C(O)OR$^{25}$, and $R^{25}$ is independently selected from the group consisting of hydrogen, optionally substituted $C_1$-$C_6$alkyl, optionally substituted $C_3$-$C_8$cycloalkyl, optionally substituted aryl, optionally substituted —(C$_1$-C$_2$alkylene)-(aryl), optionally substituted $C_2$-$C_9$heterocycloalkyl, optionally substituted heteroaryl, and optionally substituted —(C$_1$-C$_2$alkylene)-(heteroaryl). In a further embodiment of the aforementioned embodiments is a compound of Formula (IIc) wherein $R^2$ is —C(O)OR$^{25}$, and $R^{25}$ is independently selected from the group consisting of hydrogen, and optionally substituted $C_1$-$C_6$alkyl. In a further embodiment of the aforementioned embodiments is a compound of Formula (IIc) wherein $R^2$ is —C(O)OR$^{25}$, and $R^{25}$ is hydrogen. In a further embodiment of the aforementioned embodiments is a compound of Formula (IIc) wherein $R^2$ is —C(O)OR$^{25}$, and $R^{25}$ is optionally substituted $C_1$-$C_6$alkyl. In a further embodiment of the aforementioned embodiments is a compound of Formula (IIc) wherein $R^2$ is —C(O)OR$^{25}$, and $R^{25}$ is unsubstituted $C_1$-$C_6$alkyl. In a further embodiment of the aforementioned embodiments is a compound of Formula (IIc) wherein $R^2$ is —C(O)OR$^{25}$, and $R^{25}$ is methyl. In a further embodiment of the aforementioned embodiments is a compound of Formula (IIc) wherein $R^2$ is —C(O)OR$^{25}$, and $R^{25}$ is ethyl.

In a further embodiment of the aforementioned embodiments is a compound of Formula (IIc) wherein $R^2$ is —C(O)N($R^{25}$)$R^{26}$. In a further embodiment of the aforementioned embodiments is a compound of Formula (IIc) wherein $R^2$ is —C(O)N($R^{25}$)$R^{26}$, and $R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —(C$_1$-C$_2$alkylene)-(aryl), optionally substituted $C_2$-$C_9$heterocycloalkyl, optionally substituted heteroaryl, and optionally substituted —(C$_1$-C$_2$alkylene)-(heteroaryl). In a further embodiment of the aforementioned embodiments is a compound of Formula (IIc) wherein $R^2$ is —C(O)N($R^{25}$)$R^{26}$, and $R^{25}$ and $R^{26}$ are each independently selected from the group consisting of hydrogen, and optionally substituted $C_1$-$C_6$alkyl. In a further embodiment of the aforementioned embodiments is a compound of Formula (IIc) wherein $R^2$ is —C(O)N($R^{25}$)$R^{26}$, and $R^{25}$ and $R^{26}$ are hydrogen. In a further embodiment of the aforementioned embodiments is a compound of Formula (IIc) wherein $R^2$ is —C(O)N($R^{25}$)$R^{26}$, and $R^{25}$ and $R^{26}$ are each independently optionally substituted $C_1$-$C_6$alkyl. In a further embodiment of the aforementioned embodiments is a compound of Formula (IIc) wherein $R^2$ is —C(O)N($R^{25}$)$R^{26}$, $R^{25}$ is hydrogen, and $R^{26}$ is optionally substituted $C_1$-$C_6$alkyl. In a further embodiment of the aforementioned embodiments is a compound of Formula (IIc) wherein $R^2$ is —C(O)N($R^{25}$)$R^{26}$, and $R^{25}$ and $R^{26}$ are each independently unsubstituted $C_1$-$C_6$alkyl. In a further embodiment of the aforementioned embodiments is a compound of Formula (IIc) wherein $R^2$ is —C(O)N($R^{25}$)$R^{26}$, $R^{25}$ is hydrogen, and $R^{26}$ are methyl. In a further embodiment of the aforementioned embodiments is a compound of Formula (IIc) wherein $R^2$ is —C(O)N($R^{25}$)$R^{26}$, and $R^{25}$ and $R^{26}$ are methyl. In a further embodiment of the aforementioned embodiments is a compound of Formula (IIc) wherein $R^2$ is —C(O)N($R^{25}$)$R^{26}$, and $R^{25}$ and $R^{26}$ are ethyl.

In a further embodiment of the aforementioned embodiments is a compound of Formula (IIc) wherein $R^2$ is

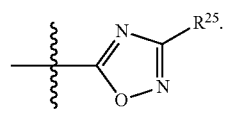

In a further embodiment of the aforementioned embodiments is a compound of Formula (IIc) wherein $R^2$ is

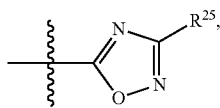

and $R^{25}$ is optionally substituted $C_1$-$C_6$alkyl. In a further embodiment of the aforementioned embodiments is a compound of Formula (IIc) wherein $R^2$ is

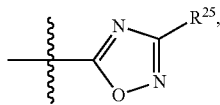

and $R^{25}$ is methyl. In a further embodiment of the aforementioned embodiments is a compound of Formula (IIc) wherein $R^2$ is

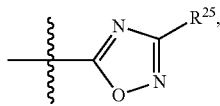

and $R^{25}$ is optionally substituted $C_1$-$C_6$alkyl. In a further embodiment of the aforementioned embodiments is a compound of Formula (IIc) wherein $R^2$ is

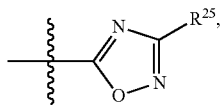

and $R^{25}$ is ethyl.

In a further embodiment of the aforementioned embodiments is a compound of Formula (IIc) wherein $R^2$ is

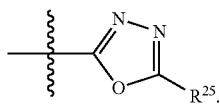

In a further embodiment of the aforementioned embodiments is a compound of Formula (IIc) wherein $R^2$ is

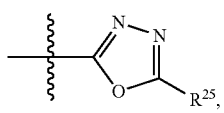

and $R^{25}$ is optionally substituted $C_1$-$C_6$alkyl. In a further embodiment of the aforementioned embodiments is a compound of Formula (IIc) wherein $R^2$ is

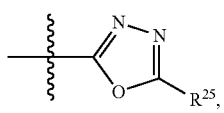

and $R^{25}$ is methyl. In a further embodiment of the aforementioned embodiments is a compound of Formula (IIc) wherein $R^2$ is

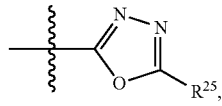

and $R^{25}$ is optionally substituted $C_1$-$C_6$alkyl. In a further embodiment of the aforementioned embodiments is a compound of Formula (IIc) wherein $R^2$ is

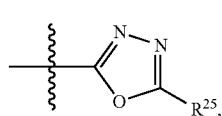

and $R^{25}$ is ethyl.

In a further embodiment of the aforementioned embodiments is a compound of Formula (IIc) wherein $R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IIc) wherein $R^1$ is hydrogen. In a further embodiment of the aforementioned embodiments is a compound of Formula (IIc) wherein $R^1$ is optionally substituted $C_1$-$C_6$alkyl. In a further embodiment of the aforementioned embodiments is a compound of Formula (IIc) wherein $R^1$ is methyl. In a further embodiment of the aforementioned embodiments is a compound of Formula (IIc) wherein $R^1$ is optionally substituted $C_2$-$C_6$alkenyl. In a further embodiment of the aforementioned embodiments is a compound of Formula (IIc) wherein $R^1$ is optionally substituted $C_2$-$C_6$alkynyl.

In a further embodiment of the aforementioned embodiments is a compound of Formula (IIc) wherein $R^1$ and $R^2$ together with the carbon atoms to which they are attached, form an optionally substituted $C_2$-$C_9$heterocycloalkyl ring or an optionally substituted heteroaryl ring. In a further embodiment of the aforementioned embodiments is a compound of Formula (IIc) wherein $R^1$ and $R^2$ together with the carbon atoms to which they are attached, form an optionally substituted $C_2$-$C_9$heterocycloalkyl ring. In a further embodiment of the aforementioned embodiments is a compound of Formula (IIc) wherein $R^1$ and $R^2$ together with the carbon atoms to which they are attached, form an optionally substituted heteroaryl ring.

In another embodiment of the aforementioned embodiments is a compound of Formula (IIc) wherein $R^{15}$ is —OC(=J)O$R^{16a}$. In another embodiment of the aforementioned embodiments is a compound of Formula (IIc) wherein $R^{15}$ is —N($R^{12}$)C(=J)O$R^{16a}$. In another embodiment of the aforementioned embodiments is a compound of Formula (IIc) wherein $R^{15}$ is —OC(=J)N(H)$R^{16a}$. In another embodiment of the aforementioned embodiments is a compound of Formula (IIc) wherein $R^{15}$ is —N($R^{12}$)C(=J)N(H)$R^{16a}$. In another embodiment of the aforementioned embodiments is a compound of Formula (IIc) wherein $R^{15}$ is —OC(=J)N(H)(C$_2$-C$_6$alkyl)R$^{30}$. In another embodiment of the aforementioned embodiments is a compound of Formula (IIc) wherein R$^{15}$ is —N(R$^{12}$)C(=J)O(C$_2$-C$_6$alkyl)R$^{30}$. In another embodiment of the aforementioned embodiments is a compound of Formula (IIc) wherein R$^{15}$ is —N(R$^{12}$)C(=J) N(H)(C$_2$-C$_6$alkyl)R$^{30}$. In another embodiment of the aforementioned embodiments is a compound of Formula (IIc) wherein R$^{15}$ is —OC(=J)O(C$_2$-C$_6$alkyl)R$^{30}$. In another embodiment of the aforementioned embodiments is a compound of Formula (IIc) wherein R$^{15}$ is —C(=J)R$^{31}$. In another embodiment of the aforementioned embodiments is a compound of Formula (IIc) wherein R$^{15}$ is —OC(=J)R$^{31}$. In another embodiment of the aforementioned embodiments is a compound of Formula (IIc) wherein R$^{15}$ is —N(R$^{12}$)C (=J)R$^{31}$. In another embodiment of the aforementioned embodiments is a compound of Formula (IIc) wherein R$^{15}$ is —O(C$_2$-C$_6$alkyl)R$^{30}$. In another embodiment of the aforementioned embodiments is a compound of Formula (IIc) wherein R$^{15}$ is —N(R$^{12}$)(C$_2$-C$_6$alkyl)R$^{30}$. In another embodiment of the aforementioned embodiments is a compound of Formula (IIc) wherein R$^{15}$ is —OS(=O)$_v$R$^{31}$. In another embodiment of the aforementioned embodiments is a compound of Formula (IIc) wherein R$^{15}$ is —N(R$^{12}$)S (=O)$_v$R$^{31}$. In another embodiment of the aforementioned embodiments is a compound of Formula (IIc) wherein R$^{15}$ is —OS(=O)$_v$(C$_2$-C$_6$alkyl)R$^{30}$. In another embodiment of the aforementioned embodiments is a compound of Formula (IIc) wherein R$^{15}$ is —N(R$^{12}$)S(=O)$_v$(C$_2$-C$_6$alkyl)R$^{30}$. In a further embodiment of the aforementioned embodiments is a compound of Formula (IIc) wherein R$^{30}$ is R$^{16a}$. In a further embodiment of the aforementioned embodiments is a compound of Formula (IIc) wherein R$^{30}$ is R$^{16b}$. In a further embodiment of the aforementioned embodiments is a compound of Formula (IIc) wherein R$^{30}$ is R$^{16c}$. In a further embodiment of the aforementioned embodiments is a compound of Formula (IIc) wherein R$^{31}$ is R$^{16a}$. In a further embodiment of the aforementioned embodiments is a compound of Formula (IIc) wherein R$^{31}$ is R$^{16b}$. In a further embodiment of the aforementioned embodiments is a compound of Formula (IIc) wherein J is O. In a further embodiment of the aforementioned embodiments is a compound of Formula (IIc) wherein J is S. In a further embodiment of the aforementioned embodiments is a compound of Formula (IIc) wherein J is N(R$^{12}$).

In another embodiment of the aforementioned embodiments is a compound of Formula (IIc) wherein R$^{16a}$ is

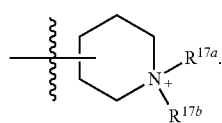

In another embodiment of the aforementioned embodiments is a compound of Formula (IIc) wherein R$^{16a}$ is

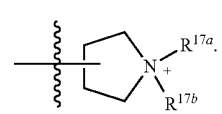

In another embodiment of the aforementioned embodiments is a compound of Formula (IIc) wherein R$^{16a}$ is

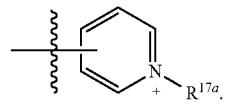

In another embodiment of the aforementioned embodiments is a compound of Formula (IIc) wherein R$^{16b}$ is

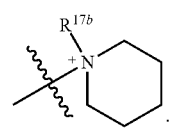

In another embodiment of the aforementioned embodiments is a compound of Formula (IIc) wherein R$^{16b}$ is

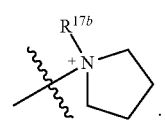

In another embodiment of the aforementioned embodiments is a compound of Formula (IIc) wherein R$^{16b}$ is

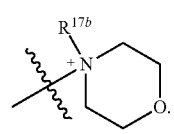

In another embodiment of the aforementioned embodiments is a compound of Formula (IIc) wherein R$^{16b}$ is

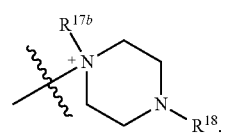

In another embodiment of the aforementioned embodiments is a compound of Formula (IIc) wherein R$^{16b}$ is

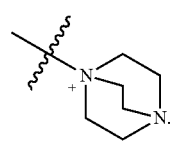

In another of Formula (IIc) aforementioned embodiments is a compound of Formula (IIc) wherein R$^{16b}$ is

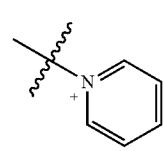

In another embodiment of the aforementioned embodiments is a compound of Formula (IIc) wherein $R^{16b}$ is

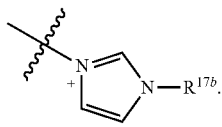

In another embodiment of the aforementioned embodiments is a compound of Formula (IIc) wherein $R^{16c}$ is

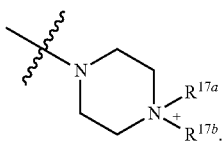

In another embodiment is a compound of Formula (IIc) wherein $R^{16c}$ is

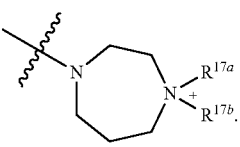

In a further embodiment of the aforementioned embodiments is a compound of Formula (IIc) wherein $R^{17a}$ is methyl. In a further embodiment of the aforementioned embodiments is a compound of Formula (IIc) wherein $R^{17a}$ is ethyl. In a further embodiment of the aforementioned embodiments is a compound of Formula (IIc) wherein $R^{17b}$ is methyl optionally substituted with phenyl, —C(=O)OH or —S(=O)$_2$OH. In a further embodiment of the aforementioned embodiments is a compound of Formula (IIc) wherein $R^{17a}$ is ethyl optionally substituted with phenyl, —C(=O)OH or —S(=O)$_2$OH.

In another embodiment is a compound of Formula (IIc) wherein $R^{15}$ is —OC(=J)OR$^{16a}$, —N(R$^{12}$)C(=J)OR$^{16a}$, —OC(=J)N(H)R$^{16a}$, —N(R$^{12}$)C(=J)N(H)R$^{16a}$, —OC(=J)N(H)(C$_1$-C$_6$alkyl)R$^{31}$, —N(R$^{12}$)C(=J)O(C$_1$-C$_6$alkyl)R$^{31}$, —N(R$^{12}$)C(=J)N(H)(C$_1$-C$_6$alkyl)R$^{31}$, —OC(=J)O(C$_1$-C$_6$alkyl)R$^{31}$, —C(=J)R$^{31}$, —OC(=J)R$^{31}$, —N(R$^{12}$)C(=J)R$^{31}$, —O(C$_1$-C$_6$alkyl)R$^{31}$, —N(R$^{12}$)(C$_1$-C$_6$alkyl)R$^{31}$, —OS(=O)$_v$R$^{31}$, —N(R$^{12}$)S(=O)$_v$R$^{31}$, —OS(=O)$_v$(C$_1$-C$_6$alkyl)R$^{31}$, or —N(R$^{12}$)S(=O)$_v$(C$_1$-C$_6$alkyl)R$^{31}$.

In another aspect, provided herein is a compound having the structure of Formula (III), or a pharmaceutically acceptable salt or solvate thereof:

Formula (III)

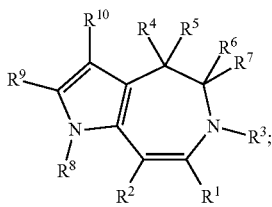

wherein:
$R^1$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

$R^2$ is selected from the group consisting of —CN, —C(=O)OR$^{25}$, —C(=O)N(R$^{25}$)R$^{26}$,

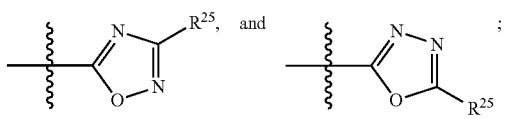

or $R^1$ and $R^2$ together with the carbon atoms to which they are attached, form an optionally substituted C$_2$-C$_9$heterocycloalkyl ring or an optionally substituted heteroaryl ring;

$R^3$ is —C(=O)R$^{20}$ or —S(=O)$_2$R$^{20}$;

$R^4$ and $R^5$ are each independently selected from the group consisting of hydrogen, halogen, optionally substituted C$_1$-C$_6$alkyl, optionally substituted C$_1$-C$_6$alkoxy, optionally substituted C$_2$-C$_6$alkenyl, and optionally substituted C$_2$-C$_6$alkynyl; or $R^4$ and $R^5$ together with the carbon atom to which they are attached, form an optionally substituted C$_3$-C$_6$cycloalkyl ring or an optionally substituted C$_2$-C$_7$heterocycloalkyl ring;

$R^6$ is selected from the group consisting of hydrogen, halogen, optionally substituted C$_1$-C$_6$alkyl, optionally substituted C$_2$-C$_6$alkenyl, optionally substituted C$_2$-C$_6$alkynyl, and —C(=O)N(R$^{27}$)R$^{28}$;

$R^7$ is selected from the group consisting of hydrogen, halogen, optionally substituted C$_1$-C$_6$alkyl, optionally substituted C$_1$-C$_6$alkoxy, optionally substituted C$_2$-C$_6$alkenyl, and optionally substituted C$_2$-C$_6$alkynyl;

$R^8$ is selected from the group consisting of hydrogen, optionally substituted C$_1$-C$_6$alkyl, optionally substituted C$_3$-C$_8$cycloalkyl, optionally substituted aryl, optionally substituted —(C$_1$-C$_2$alkylene)-(aryl), optionally substituted heteroaryl, optionally substituted C$_2$-C$_9$heterocycloalkyl, and optionally substituted —(C$_1$-C$_2$alkylene)-(heteroaryl);

$R^9$ and $R^{10}$ together with the carbon atoms to which they are attached, form a phenyl ring substituted with (R$^{11}$)$_n$; or $R^9$ and $R^{10}$ together with the carbon atoms to which they are attached, form a nitrogen containing 6-membered heteroaryl ring substituted with (R$^{11}$)$_n$; or $R^9$ and $R^{10}$ together with the carbon atoms to which they are attached, form a 5-membered heteroaryl ring substituted with (R$^{39}$)$_p$ and (R$^{12}$)$_q$;

each $R^{11}$ is independently selected from the group consisting of halogen, —CN, amino, alkylamino, C$_1$-C$_6$alkyl, C$_1$-C$_6$haloalkyl, C$_1$-C$_6$alkoxy, C$_1$-C$_6$haloalkoxy, C$_3$-C$_8$cycloalkyl, C$_2$-C$_9$heterocycloalkyl, aryl, heteroaryl, —C(=O)OR$^{12}$, —C(=O)N(R$^{13}$)R$^{14}$;

each $R^{12}$ is independently selected from the group consisting of hydrogen and C$_1$-C$_6$alkyl;

each $R^{13}$ and $R^{14}$ are each independently selected from the group consisting of hydrogen and C$_1$-C$_6$alkyl; or $R^{13}$ and $R^{14}$ together with the nitrogen atom to which they are attached, form an optionally substituted $C_2$-$C_9$heterocycloalkyl ring;

each $R^{39}$ is independently selected from the group consisting of hydrogen, halogen, —CN, amino, alkylamino, $C_1$-$C_6$alkyl, $C_1$-$C_6$haloalkyl, $C_1$-$C_6$alkoxy, $C_1$-$C_6$haloalkoxy, $C_3$-$C_8$cycloalkyl, $C_2$-$C_9$heterocycloalkyl, aryl, heteroaryl, —C(=O)OR$^{12}$, —C(=O)N(R$^{13}$)R$^{14}$;

n is 0, 1, 2, or 3;
p is 0, 1 or 2;
q is 0 or 1;
$R^{20}$ is selected from the group consisting of —R$^{34}$R$^{35}$ or —R$^{31}$;
$R^{34}$ is selected from the group consisting of optionally substituted $C_1$-$C_6$alkyl, optionally substituted $C_3$-$C_{10}$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl);
$R^{35}$ is —($C_1$-$C_6$alkyl)-R$^{30}$, —O($C_2$-$C_6$alkyl)-R$^{30}$, or —N(R$^{12}$)($C_2$-$C_6$alkyl)-R$^{30}$;
$R^{30}$ is $R^{36a}$, $R^{36b}$, or $R^{36c}$;
$R^{31}$ is $R^{36a}$ or $R^{36c}$;
$R^{36a}$ is

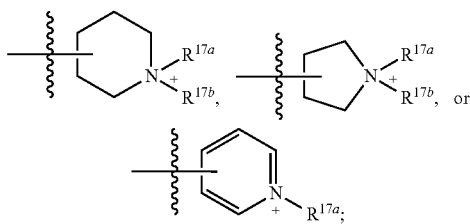

$R^{36b}$ is

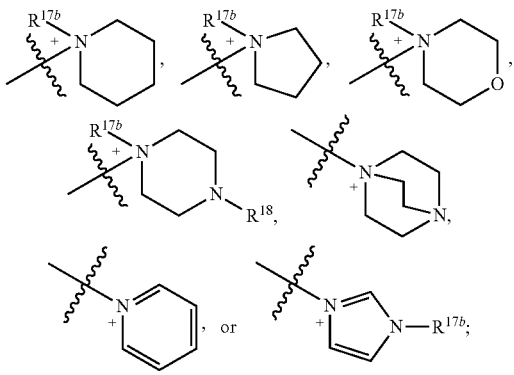

$R^{36c}$ is

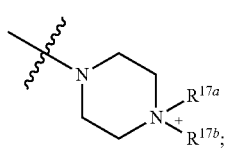

$R^{17a}$ is $C_1$-$C_6$alkyl;
$R^{17b}$ is $C_1$-$C_6$alkyl optionally substituted with phenyl, —C(=O)OH or —S(=O)$_2$OH;

$R^{18}$ is hydrogen, —OH, —($C_0$-$C_6$alkyl)-C(=O)OH, or $C_1$-$C_6$alkyl;

$R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); and $R^{27}$ and $R^{28}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{27}$ and $R^{28}$ together with the nitrogen atom to which they are attached, form an optionally substituted $C_2$-$C_9$heterocycloalkyl ring.

In one embodiment is a compound of Formula (III) wherein $R^4$ and $R^5$ are each independently selected from the group consisting of hydrogen, halogen, and optionally substituted $C_1$-$C_6$alkyl. In another embodiment is a compound of Formula (III) wherein $R^4$ and $R^5$ are each independently selected from the group consisting of hydrogen and optionally substituted $C_1$-$C_6$alkyl. In another embodiment is a compound of Formula (III) wherein $R^4$ and $R^5$ are each hydrogen. In another embodiment is a compound of Formula (III) wherein $R^4$ and $R^5$ are each independently optionally substituted $C_1$-$C_6$alkyl. In another embodiment is a compound of Formula (III) wherein $R^4$ and $R^5$ are each methyl. In another embodiment is a compound of Formula (III) wherein $R^4$ and $R^5$ form an optionally substituted $C_3$-$C_6$cycloalkyl ring or an optionally substituted $C_2$-$C_7$heterocycloalkyl ring. In some embodiments is a compound of Formula (III) wherein $R^4$ and $R^5$ form an optionally substituted $C_3$-$C_6$cycloalkyl ring. In some embodiments is a compound of Formula (III) wherein $R^4$ and $R^5$ form an optionally substituted $C_2$-$C_7$heterocycloalkyl ring.

In another embodiment is a compound of Formula (III) wherein $R^6$ and $R^7$ are each independently selected from the group consisting of hydrogen, halogen, and optionally substituted $C_1$-$C_6$alkyl. In another embodiment is a compound of Formula (III) wherein $R^6$ and $R^7$ are each independently selected from the group consisting of hydrogen and optionally substituted $C_1$-$C_6$alkyl. In another embodiment is a compound of Formula (III) wherein $R^6$ and $R^7$ are each independently optionally substituted $C_1$-$C_6$alkyl. In another embodiment is a compound of Formula (III) wherein $R^6$ and $R^7$ are each methyl. In another embodiment is a compound of Formula (III) wherein $R^6$ and $R^7$ are each hydrogen.

In another embodiment is a compound of Formula (III) wherein $R^6$ and $R^7$ are hydrogen, $R^4$ and $R^5$ are independently optionally substituted $C_1$-$C_6$alkyl, $R^3$ is —C(O)R$^{20}$, and $R^{20}$ is optionally substituted aryl. In another embodiment is a compound of Formula (III) wherein $R^6$ and $R^7$ are hydrogen, $R^4$ and $R^5$ are independently optionally substituted $C_1$-$C_6$alkyl, $R^3$ is —C(O)R$^{20}$, and $R^{20}$ is optionally substituted heteroaryl. In another embodiment is a compound of Formula (III) wherein $R^6$ and $R^7$ are hydrogen, $R^4$ and $R^5$ are methyl, $R^3$ is —C(O)R$^{20}$, and $R^{20}$ is optionally substituted aryl. In another embodiment is a compound of Formula (III) wherein $R^6$ and $R^7$ are hydrogen, $R^4$ and $R^5$ are methyl, $R^3$ is —C(O)$R^{20}$, and $R^{20}$ is optionally substituted heteroaryl.

In another embodiment is a compound of Formula (III) wherein $R^6$ and $R^7$ are hydrogen, $R^4$ and $R^5$ are independently optionally substituted $C_1$-$C_6$alkyl, $R^3$ is —S(O)$_2R^{20}$, and $R^{20}$ is optionally substituted aryl. In another embodiment is a compound of Formula (III) wherein $R^6$ and $R^7$ are hydrogen, $R^4$ and $R^5$ are independently optionally substituted $C_1$-$C_6$alkyl, $R^3$ is —S(O)$_2R^{20}$, and $R^{20}$ is optionally substituted heteroaryl. In another embodiment is a compound of Formula (III) wherein $R^6$ and $R^7$ are hydrogen, $R^4$ and $R^5$ are methyl, $R^3$ is —S(O)$_2R^{20}$, and $R^{20}$ is optionally substituted aryl. In another embodiment is a compound of Formula (III) wherein $R^6$ and $R^7$ are hydrogen, $R^4$ and $R^5$ are methyl, $R^3$ is —S(O)$_2R^{20}$, and $R^{20}$ is optionally substituted heteroaryl.

In a further embodiment of the aforementioned embodiments is a compound of Formula (III) wherein $R^2$ is selected from the group consisting of —CN, —C(O)O$R^{25}$, —C(O)N($R^{25}$)$R^{26}$,

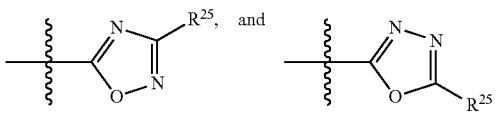

In a further embodiment of the aforementioned embodiments is a compound of Formula (III) wherein $R^2$ is —CN.

In a further embodiment of the aforementioned embodiments is a compound of Formula (III) wherein $R^2$ is —C(O)O$R^{25}$. In a further embodiment of the aforementioned embodiments is a compound of Formula (III) wherein $R^2$ is —C(O)O$R^{25}$, and $R^{25}$ is independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (III) wherein $R^2$ is —C(O)O$R^{25}$, and $R^{25}$ is independently selected from the group consisting of hydrogen, and optionally substituted $C_1$-$C_6$alkyl. In a further embodiment of the aforementioned embodiments is a compound of Formula (III) wherein $R^2$ is —C(O)O$R^{25}$, and $R^{25}$ is hydrogen. In a further embodiment of the aforementioned embodiments is a compound of Formula (III) wherein $R^2$ is —C(O)O$R^{25}$, and $R^{25}$ is optionally substituted $C_1$-$C_6$alkyl. In a further embodiment of the aforementioned embodiments is a compound of Formula (III) wherein $R^2$ is —C(O)O$R^{25}$, and $R^{25}$ is unsubstituted $C_1$-$C_6$alkyl. In a further embodiment of the aforementioned embodiments is a compound of Formula (III) wherein $R^2$ is —C(O)O$R^{25}$, and $R^{25}$ is methyl. In a further embodiment of the aforementioned embodiments is a compound of Formula (III) wherein $R^2$ is —C(O)O$R^{25}$, and $R^{25}$ is ethyl.

In a further embodiment of the aforementioned embodiments is a compound of Formula (III) wherein $R^2$ is —C(O)N($R^{25}$)$R^{26}$. In a further embodiment of the aforementioned embodiments is a compound of Formula (III) wherein $R^2$ is —C(O)N($R^{25}$)$R^{26}$, and $R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (III) wherein $R^2$ is —C(O)N($R^{25}$)$R^{26}$, and $R^{25}$ and $R^{26}$ are each independently selected from the group consisting of hydrogen, and optionally substituted $C_1$-$C_6$alkyl. In a further embodiment of the aforementioned embodiments is a compound of Formula (III) wherein $R^2$ is —C(O)N($R^{25}$)$R^{26}$, and $R^{25}$ and $R^{26}$ are hydrogen. In a further embodiment of the aforementioned embodiments is a compound of Formula (III) wherein $R^2$ is —C(O)N($R^{25}$)$R^{26}$, and $R^{25}$ and $R^{26}$ are each independently optionally substituted $C_1$-$C_6$alkyl. In a further embodiment of the aforementioned embodiments is a compound of Formula (III) wherein $R^2$ is —C(O)N($R^{25}$)$R^{26}$, $R^{25}$ is hydrogen, and $R^{26}$ is optionally substituted $C_1$-$C_6$alkyl. In a further embodiment of the aforementioned embodiments is a compound of Formula (III) wherein $R^2$ is —C(O)N($R^{25}$)$R^{26}$, and $R^{25}$ and $R^{26}$ are each independently unsubstituted $C_1$-$C_6$alkyl. In a further embodiment of the aforementioned embodiments is a compound of Formula (III) wherein $R^2$ is —C(O)N($R^{25}$)$R^{26}$, $R^{25}$ is hydrogen, and $R^{26}$ is methyl. In a further embodiment of the aforementioned embodiments is a compound of Formula (III) wherein $R^2$ is —C(O)N($R^{25}$)$R^{26}$, and $R^{25}$ and $R^{26}$ are methyl. In a further embodiment of the aforementioned embodiments is a compound of Formula (III) wherein $R^2$ is —C(O)N($R^{25}$)$R^{26}$, and $R^{25}$ and $R^{26}$ are ethyl.

In a further embodiment of the aforementioned embodiments is a compound of Formula (III) wherein $R^2$ is

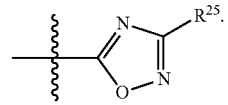

In a further embodiment of the aforementioned embodiments is a compound of Formula (III) wherein $R^2$ is

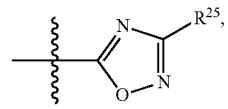

and $R^{25}$ is optionally substituted $C_1$-$C_6$alkyl. In a further embodiment of the aforementioned embodiments is a compound of Formula (III) wherein $R^2$ is

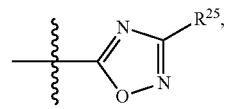

and $R^{25}$ is methyl. In a further embodiment of the aforementioned embodiments is a compound of Formula (III) wherein $R^2$ is

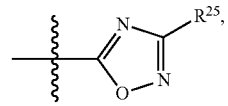

and $R^{25}$ is optionally substituted $C_1$-$C_6$alkyl. In a further embodiment of the aforementioned embodiments is a compound of Formula (III) wherein $R^2$ is

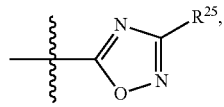

and $R^{25}$ is ethyl.

In a further embodiment of the aforementioned embodiments is a compound of Formula (III) wherein $R^2$ is

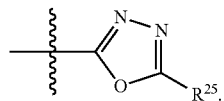

In a further embodiment of the aforementioned embodiments is a compound of Formula (III) wherein $R^2$ is

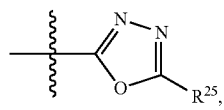

and $R^{25}$ is optionally substituted $C_1$-$C_6$alkyl. In a further embodiment of the aforementioned embodiments is a compound of Formula (III) wherein $R^2$ is

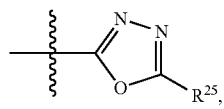

and $R^{25}$ is methyl. In a further embodiment of the aforementioned embodiments is a compound of Formula (III) wherein $R^2$ is

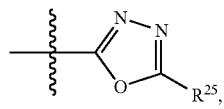

and $R^{25}$ is optionally substituted $C_1$-$C_6$alkyl. In a further embodiment of the aforementioned embodiments is a compound of Formula (III) wherein $R^2$ is

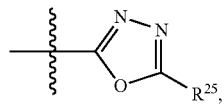

and $R^{25}$ is ethyl.

In a further embodiment of the aforementioned embodiments is a compound of Formula (III) wherein $R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (III) wherein $R^1$ is hydrogen. In a further embodiment of the aforementioned embodiments is a compound of Formula (III) wherein $R^1$ is optionally substituted $C_1$-$C_6$alkyl. In a further embodiment of the aforementioned embodiments is a compound of Formula (III) wherein $R^1$ is methyl. In a further embodiment of the aforementioned embodiments is a compound of Formula (III) wherein $R^1$ is optionally substituted $C_2$-$C_6$alkenyl. In a further embodiment of the aforementioned embodiments is a compound of Formula (III) wherein $R^1$ is optionally substituted $C_2$-$C_6$alkynyl.

In a further embodiment of the aforementioned embodiments is a compound of Formula (III) wherein $R^1$ and $R^2$ together with the carbon atoms to which they are attached, form an optionally substituted $C_2$-$C_9$heterocycloalkyl ring or an optionally substituted heteroaryl ring.

In a further embodiment of the aforementioned embodiments is a compound of Formula (III) wherein $R^1$ and $R^2$ together with the carbon atoms to which they are attached, form an optionally substituted $C_2$-$C_9$heterocycloalkyl ring. In a further embodiment of the aforementioned embodiments is a compound of Formula (III) wherein $R^1$ and $R^2$ together with the carbon atoms to which they are attached, form an optionally substituted heteroaryl ring.

In a further embodiment of the aforementioned embodiments is a compound of Formula (III) wherein $R^8$ is selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl). In a further embodiment of the aforementioned embodiments is a compound of Formula (III) wherein $R^8$ is selected from the group consisting of hydrogen, and optionally substituted $C_1$-$C_6$alkyl. In a further embodiment of the aforementioned embodiments is a compound of Formula (III) wherein $R^8$ is optionally substituted $C_1$-$C_6$alkyl. In a further embodiment of the aforementioned embodiments is a compound of Formula (III) wherein $R^8$ is methyl. In a further embodiment of the aforementioned embodiments is a compound of Formula (III) wherein $R^8$ is optionally substituted $C_1$-$C_6$alkyl. In a further embodiment of the aforementioned embodiments is a compound of Formula (III) wherein $R^8$ is ethyl. In a further embodiment of the aforementioned embodiments is a compound of Formula (III) wherein $R^8$ is optionally substituted $C_1$-$C_6$alkyl. In a further embodiment of the aforementioned embodiments is a compound of Formula (III) wherein $R^8$ is hydrogen.

In another embodiment of the aforementioned embodiments is a compound of Formula (III) wherein $R^{20}$ is —$R^{34}R^{35}$. In another embodiment of the aforementioned embodiments is a compound of Formula (III) wherein $R^{20}$ is —$R^{34}R^{35}$, and $R^{34}$ is optionally substituted $C_1$-$C_6$alkyl. In another embodiment of the aforementioned embodiments is a compound of Formula (III) wherein $R^{20}$ is —$R^{34}R^{35}$, and $R^{34}$ is optionally substituted $C_3$-$C_{10}$cycloalkyl. In another embodiment of the aforementioned embodiments is a compound of Formula (III) wherein $R^{20}$ is —$R^{34}R^{35}$, and $R^{34}$ is optionally substituted aryl. In another embodiment of the aforementioned embodiments is a compound of Formula (III) wherein $R^{20}$ is —$R^{34}R^{35}$, and $R^{34}$ is optionally substituted —(C$_1$-C$_2$alkylene)-(aryl). In another embodiment of the aforementioned embodiments is a compound of Formula (III) wherein R$^{20}$ is —R$^{34}$R$^{35}$, and R$^{34}$ is optionally substituted heteroaryl. In another embodiment of the aforementioned embodiments is a compound of Formula (III) wherein R$^{20}$ is —R$^{34}$R$^{35}$, and R$^{34}$ is optionally substituted C$_2$-C$_9$heterocycloalkyl. In another embodiment of the aforementioned embodiments is a compound of Formula (III) wherein R$^{20}$ is —R$^{34}$R$^{35}$, and R$^{34}$ is optionally substituted —(C$_1$-C$_2$alkylene)-(heteroaryl). In another embodiment of the aforementioned embodiments is a compound of Formula (III) wherein R$^{20}$ is —R$^{34}$R$^{35}$, and R$^{35}$ is —(C$_1$-C$_6$alkyl)-R$^{30}$. In another embodiment of the aforementioned embodiments is a compound of Formula (III) wherein R$^{20}$ is —R$^{34}$R$^{35}$, and R$^{35}$ is —O(C$_2$-C$_6$alkyl)-R$^{30}$. In another embodiment of the aforementioned embodiments is a compound of Formula (III) wherein R$^{20}$ is —R$^{34}$R$^{35}$, and R$^{35}$ is —N(R$^{12}$)(C$_2$-C$_6$alkyl)-R$^{30}$. In a further embodiment of the aforementioned embodiments is a compound of Formula (III) wherein R$^{30}$ is R$^{36a}$. In a further embodiment of the aforementioned embodiments is a compound of Formula (III) wherein R$^{30}$ is R$^{36b}$. In a further embodiment of the aforementioned embodiments is a compound of Formula (III) wherein R$^{30}$ is R$^{36c}$.

In another embodiment of the aforementioned embodiments is a compound of Formula (III) wherein R$^{20}$ is —R$^{31}$. In a further embodiment of the aforementioned embodiments is a compound of Formula (III) wherein R$^{31}$ is R$^{36a}$. In a further embodiment of the aforementioned embodiments is a compound of Formula (III) wherein R$^{31}$ is R$^{36c}$.

In another embodiment of the aforementioned embodiments is a compound of Formula (III) wherein R$^{36a}$ is

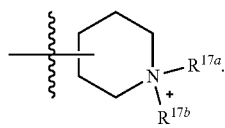

In another embodiment of the aforementioned embodiments is a compound of Formula (III) wherein R$^{36a}$ is

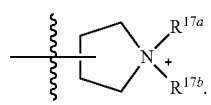

In another embodiment of the aforementioned embodiments is a compound of Formula (III) wherein R$^{36a}$ is

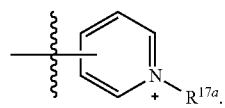

In another embodiment of the aforementioned embodiments is a compound of Formula (III) wherein R$^{36b}$ is

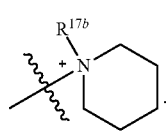

In another embodiment of the aforementioned embodiments is a compound of Formula (III) wherein R$^{36b}$ is

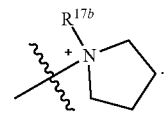

In another embodiment of the aforementioned embodiments is a compound of Formula (III) wherein R$^{36b}$ is

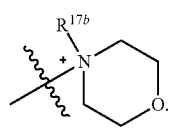

In another embodiment of the aforementioned embodiments is a compound of Formula (III) wherein R$^{36b}$ is

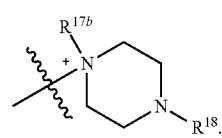

In another embodiment of the aforementioned embodiments is a compound of Formula (III) wherein R$^{36b}$ is

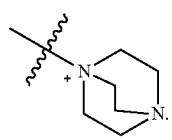 [SMILES: *[N+]12CCN(CC1)CC2]

In another embodiment of the aforementioned embodiments is a compound of Formula (III) wherein R$^{36b}$ is

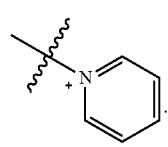

In another embodiment of the aforementioned embodiments is a compound of Formula (III) wherein R$^{36b}$ is

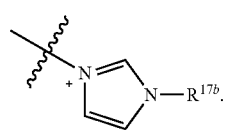

In another embodiment of the aforementioned embodiments is a compound of Formula (III) wherein R$^{36c}$ is

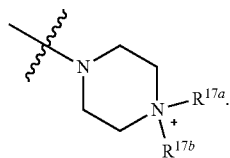

In another embodiment is a compound of Formula (III) wherein $R^{36c}$ is

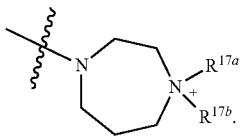

In a further embodiment of the aforementioned embodiments is a compound of Formula (III) wherein $R^{17a}$ is methyl. In a further embodiment of the aforementioned embodiments is a compound of Formula (III) wherein $R^{17a}$ is ethyl. In a further embodiment of the aforementioned embodiments is a compound of Formula (III) wherein $R^{17b}$ is methyl optionally substituted with phenyl, —C(=O)OH or —S(=O)$_2$OH. In a further embodiment of the aforementioned embodiments is a compound of Formula (III) wherein $R^{17a}$ is ethyl optionally substituted with phenyl, —C(=O)OH or —S(=O)$_2$OH.

In another embodiment of the aforementioned embodiments is a compound of Formula (III) wherein n is 0. In another embodiment of the aforementioned embodiments is a compound of Formula (III) wherein n is 1. In another embodiment of the aforementioned embodiments is a compound of Formula (III) wherein n is 1 and $R^{11}$ is $C_1$-$C_6$alkyl. In another embodiment of the aforementioned embodiments is a compound of Formula (III) wherein n is 1 and $R^{11}$ is $C_1$-$C_6$haloalkyl.

In some embodiments provided herein, the compound of Formula (III) has the structure of Formula (IIIa), or a pharmaceutically acceptable salt or solvate thereof:

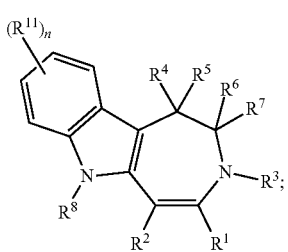

Formula (IIIa)

wherein:
$R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);
$R^2$ is selected from the group consisting of —CN, —C(=O)OR$^{25}$, —C(=O)N(R$^{25}$)R$^{26}$,

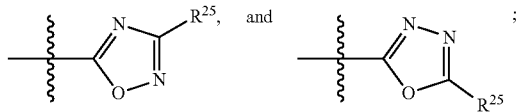

or $R^1$ and $R^2$ together with the carbon atoms to which they are attached, form an optionally substituted $C_2$-$C_9$heterocycloalkyl ring or an optionally substituted heteroaryl ring;
$R^3$ is —C(=O)R$^{20}$ or —S(=O)$_2$R$^{20}$;
$R^4$ and $R^5$ are each independently selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl; or $R^4$ and $R^5$ together with the carbon atom to which they are attached, form an optionally substituted $C_3$-$C_6$cycloalkyl ring or an optionally substituted $C_2$-$C_7$heterocycloalkyl ring;
$R^6$ is selected from the group consisting of hydrogen, halogen, optionally substituted $C_1$-$C_6$alkyl, optionally substituted $C_2$-$C_6$alkenyl, optionally substituted $C_2$-$C_6$alkynyl, and —C(=O)N(R$^{27}$)R$^{28}$;
$R^7$ is selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl;
$R^8$ is selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl);
each $R^{11}$ is independently selected from the group consisting of halogen, —CN, amino, alkylamino, $C_1$-$C_6$alkyl, $C_1$-$C_6$haloalkyl, $C_1$-$C_6$alkoxy, $C_1$-$C_6$haloalkoxy, $C_3$-$C_8$cycloalkyl, $C_2$-$C_9$heterocycloalkyl, aryl, heteroaryl, —C(=O)OR$^{12}$, —C(=O)N(R$^{13}$)R$^{14}$;
each $R^{12}$ is independently selected from the group consisting of hydrogen and $C_1$-$C_6$alkyl;
each $R^{13}$ and $R^{14}$ are each independently selected from the group consisting of hydrogen and $C_1$-$C_6$alkyl; or $R^{13}$ and $R^{14}$ together with the nitrogen atom to which they are attached, form an optionally substituted $C_2$-$C_9$heterocycloalkyl ring;
n is 0, 1, 2, or 3;
$R^{20}$ is selected from the group consisting of —R$^{34}$R$^{35}$ or —R$^{31}$;
$R^{34}$ is selected from the group consisting of optionally substituted $C_1$-$C_6$alkyl, optionally substituted $C_3$-$C_{10}$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl);
$R^{35}$ is —($C_1$-$C_6$alkyl)-R$^{30}$, —O($C_2$-$C_6$alkyl)-R$^{30}$, or —N(R$^{12}$)($C_2$-$C_6$alkyl)-R$^{30}$;
$R^{30}$ is $R^{36a}$, $R^{36b}$, or $R^{36c}$;
$R^{31}$ is $R^{36a}$ or $R^{36c}$;

$R^{36a}$ is

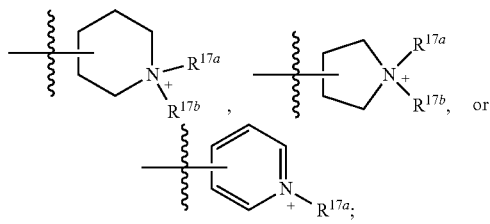

$R^{36b}$ is

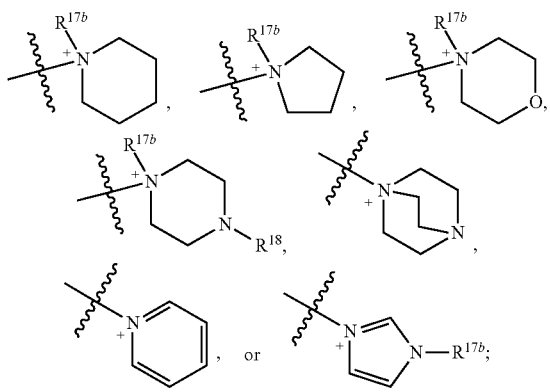

$R^{36c}$ is

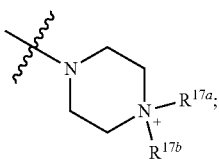

$R^{17a}$ is $C_1$-$C_6$alkyl;

$R^{17b}$ is $C_1$-$C_6$alkyl optionally substituted with phenyl, —C(=O)OH or —S(=O)$_2$OH;

$R^{18}$ is hydrogen, —OH, —(C$_0$-C$_6$alkyl)-C(=O)OH, or $C_1$-$C_6$alkyl;

$R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —(C$_1$-C$_2$alkylene)-(aryl), optionally substituted $C_2$-$C_9$heterocycloalkyl, optionally substituted heteroaryl, and optionally substituted —(C$_1$-C$_2$alkylene)-(heteroaryl); and $R^{27}$ and $R^{28}$ are each independently selected from the group consisting of hydrogen, optionally substituted $C_1$-$C_6$alkyl, optionally substituted $C_3$-$C_8$cycloalkyl, optionally substituted aryl, optionally substituted —(C$_1$-C$_2$alkylene)-(aryl), optionally substituted $C_2$-$C_9$heterocycloalkyl, optionally substituted heteroaryl, and optionally substituted —(C$_1$-C$_2$alkylene)-(heteroaryl); or $R^{27}$ and $R^{28}$ together with the nitrogen atom to which they are attached, form an optionally substituted $C_2$-$C_9$heterocycloalkyl ring.

In one embodiment is a compound of Formula (IIIa) wherein $R^4$ and $R^5$ are each independently selected from the group consisting of hydrogen, halogen, and optionally substituted $C_1$-$C_6$alkyl. In another embodiment is a compound of Formula (IIIa) wherein $R^4$ and $R^5$ are each independently selected from the group consisting of hydrogen and optionally substituted $C_1$-$C_6$alkyl. In another embodiment is a compound of Formula (IIIa) wherein $R^4$ and $R^5$ are each hydrogen. In another embodiment is a compound of Formula (IIIa) wherein $R^4$ and $R^5$ are each independently optionally substituted $C_1$-$C_6$alkyl. In another embodiment is a compound of Formula (IIIa) wherein $R^4$ and $R^5$ are each methyl. In another embodiment is a compound of Formula (IIIa) wherein $R^4$ and $R^5$ form an optionally substituted $C_3$-$C_6$cycloalkyl ring or an optionally substituted $C_2$-$C_7$heterocycloalkyl ring. In some embodiments is a compound of Formula (IIIa) wherein $R^4$ and $R^5$ form an optionally substituted $C_3$-$C_6$cycloalkyl ring. In some embodiments is a compound of Formula (IIIa) wherein $R^4$ and $R^5$ form an optionally substituted $C_2$-$C_7$heterocycloalkyl ring.

In another embodiment is a compound of Formula (IIIa) wherein $R^6$ and $R^7$ are each independently selected from the group consisting of hydrogen, halogen, and optionally substituted $C_1$-$C_6$alkyl. In another embodiment is a compound of Formula (IIIa) wherein $R^6$ and $R^7$ are each independently selected from the group consisting of hydrogen and optionally substituted $C_1$-$C_6$alkyl. In another embodiment is a compound of Formula (IIIa) wherein $R^6$ and $R^7$ are each independently optionally substituted $C_1$-$C_6$alkyl. In another embodiment is a compound of Formula (IIIa) wherein $R^6$ and $R^7$ are each methyl. In another embodiment is a compound of Formula (IIIa) wherein $R^6$ and $R^7$ are each hydrogen.

In another embodiment is a compound of Formula (IIIa) wherein $R^6$ and $R^7$ are hydrogen, $R^4$ and $R^5$ are independently optionally substituted $C_1$-$C_6$alkyl, $R^3$ is —C(O)R$^{20}$, and $R^{20}$ is optionally substituted aryl. In another embodiment is a compound of Formula (IIIa) wherein $R^6$ and $R^7$ are hydrogen, $R^4$ and $R^5$ are independently optionally substituted $C_1$-$C_6$alkyl, $R^3$ is —C(O)R$^{20}$, and $R^{20}$ is optionally substituted heteroaryl. In another embodiment is a compound of Formula (IIIa) wherein $R^6$ and $R^7$ are hydrogen, $R^4$ and $R^5$ are methyl, $R^3$ is —C(O)R$^{20}$, and $R^{20}$ is optionally substituted aryl. In another embodiment is a compound of Formula (IIIa) wherein $R^6$ and $R^7$ are hydrogen, $R^4$ and $R^5$ are methyl, $R^3$ is —C(O)R$^{20}$, and $R^{20}$ is optionally substituted heteroaryl.

In another embodiment is a compound of Formula (IIIa) wherein $R^6$ and $R^7$ are hydrogen, $R^4$ and $R^5$ are independently optionally substituted $C_1$-$C_6$alkyl, $R^3$ is —S(O)$_2$R$^{20}$, and $R^{20}$ is optionally substituted aryl. In another embodiment is a compound of Formula (IIIa) wherein $R^6$ and $R^7$ are hydrogen, $R^4$ and $R^5$ are independently optionally substituted $C_1$-$C_6$alkyl, $R^3$ is —S(O)$_2$R$^{20}$, and $R^{20}$ is optionally substituted heteroaryl. In another embodiment is a compound of Formula (IIIa) wherein $R^6$ and $R^7$ are hydrogen, $R^4$ and $R^5$ are methyl, $R^3$ is —S(O)$_2$R$^{20}$, and $R^{20}$ is optionally substituted aryl. In another embodiment is a compound of Formula (IIIa) wherein $R^6$ and $R^7$ are hydrogen, $R^4$ and $R^5$ are methyl, $R^3$ is —S(O)$_2$R$^{20}$, and $R^{20}$ is optionally substituted heteroaryl.

In a further embodiment of the aforementioned embodiments is a compound of Formula (IIIa) wherein $R^2$ is selected from the group consisting of —CN, —C(O)OR$^{25}$, —C(O)N(R$^{25}$)R$^{26}$,

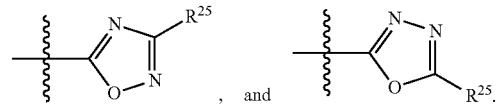

In a further embodiment of the aforementioned embodiments is a compound of Formula (IIIa) wherein $R^2$ is —CN.

In a further embodiment of the aforementioned embodiments is a compound of Formula (IIIa) wherein $R^2$ is —C(O)OR$^{25}$. In a further embodiment of the aforementioned embodiments is a compound of Formula (IIIa) wherein $R^2$ is —C(O)OR$^{25}$, and $R^{25}$ is independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IIIa) wherein $R^2$ is —C(O)OR$^{25}$, and $R^{25}$ is independently selected from the group consisting of hydrogen, and optionally substituted $C_1$-$C_6$alkyl. In a further embodiment of the aforementioned embodiments is a compound of Formula (IIIa) wherein $R^2$ is —C(O)OR$^{25}$, and $R^{25}$ is hydrogen. In a further embodiment of the aforementioned embodiments is a compound of Formula (IIIa) wherein $R^2$ is —C(O)OR$^{25}$, and $R^{25}$ is optionally substituted $C_1$-$C_6$alkyl. In a further embodiment of the aforementioned embodiments is a compound of Formula (IIIa) wherein $R^2$ is —C(O)OR$^{25}$, and $R^{25}$ is unsubstituted $C_1$-$C_6$alkyl. In a further embodiment of the aforementioned embodiments is a compound of Formula (IIIa) wherein $R^2$ is —C(O)OR$^{25}$, and $R^{25}$ is methyl. In a further embodiment of the aforementioned embodiments is a compound of Formula (IIIa) wherein $R^2$ is —C(O)OR$^{25}$, and $R^{25}$ is ethyl.

In a further embodiment of the aforementioned embodiments is a compound of Formula (IIIa) wherein $R^2$ is —C(O)N($R^{25}$)$R^{26}$. In a further embodiment of the aforementioned embodiments is a compound of Formula (IIIa) wherein $R^2$ is —C(O)N($R^{25}$)$R^{26}$, and $R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IIIa) wherein $R^2$ is —C(O)N($R^{25}$)$R^{26}$, and $R^{25}$ and $R^{26}$ are each independently selected from the group consisting of hydrogen, and optionally substituted $C_1$-$C_6$alkyl. In a further embodiment of the aforementioned embodiments is a compound of Formula (IIIa) wherein $R^2$ is —C(O)N($R^{25}$)$R^{26}$, and $R^{25}$ and $R^{26}$ are hydrogen. In a further embodiment of the aforementioned embodiments is a compound of Formula (IIIa) wherein $R^2$ is —C(O)N($R^{25}$)$R^{26}$, and $R^{25}$ and $R^{26}$ are each independently optionally substituted $C_1$-$C_6$alkyl. In a further embodiment of the aforementioned embodiments is a compound of Formula (IIIa) wherein $R^2$ is —C(O)N($R^{25}$)$R^{26}$, $R^{25}$ is hydrogen, and $R^{26}$ is optionally substituted $C_1$-$C_6$alkyl. In a further embodiment of the aforementioned embodiments is a compound of Formula (IIIa) wherein $R^2$ is —C(O)N($R^{25}$)$R^{26}$, and $R^{25}$ and $R^{26}$ are each independently unsubstituted $C_1$-$C_6$alkyl. In a further embodiment of the aforementioned embodiments is a compound of Formula (IIIa) wherein $R^2$ is —C(O)N($R^{25}$)$R^{26}$, $R^{25}$ is hydrogen, and $R^{26}$ are methyl. In a further embodiment of the aforementioned embodiments is a compound of Formula (IIIa) wherein $R^2$ is —C(O)N($R^{25}$)$R^{26}$, and $R^{25}$ and $R^{26}$ are methyl. In a further embodiment of the aforementioned embodiments is a compound of Formula (IIIa) wherein $R^2$ is —C(O)N($R^{25}$)$R^{26}$, and $R^{25}$ and $R^{26}$ are ethyl.

In a further embodiment of the aforementioned embodiments is a compound of Formula (IIIa) wherein $R^2$ is

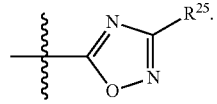

In a further embodiment of the aforementioned embodiments is a compound of Formula (IIIa) wherein $R^2$ is

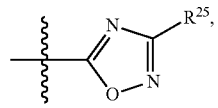

and $R^{25}$ is optionally substituted $C_1$-$C_6$alkyl. In a further embodiment of the aforementioned embodiments is a compound of Formula (IIIa) wherein $R^2$ is

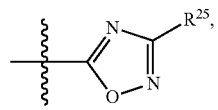

and $R^{25}$ is methyl. In a further embodiment of the aforementioned embodiments is a compound of Formula (IIIa) wherein $R^2$ is

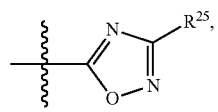

and $R^{25}$ is optionally substituted $C_1$-$C_6$alkyl. In a further embodiment of the aforementioned embodiments is a compound of Formula (IIIa) wherein $R^2$ is

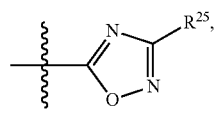

and $R^{25}$ is ethyl.

In a further embodiment of the aforementioned embodiments is a compound of Formula (IIIa) wherein $R^2$ is

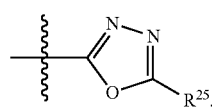

In a further embodiment of the aforementioned embodiments is a compound of Formula (IIIa) wherein $R^2$ is

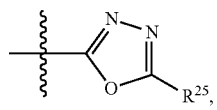

and $R^{25}$ is optionally substituted $C_1$-$C_6$alkyl. In a further embodiment of the aforementioned embodiments is a compound of Formula (IIIa) wherein $R^2$ is

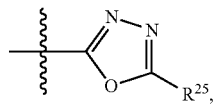

and $R^{25}$ is methyl. In a further embodiment of the aforementioned embodiments is a compound of Formula (IIIa) wherein $R^2$ is

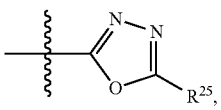

and $R^{25}$ is optionally substituted $C_1$-$C_6$alkyl. In a further embodiment of the aforementioned embodiments is a compound of Formula (IIIa) wherein $R^2$ is

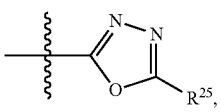

and $R^{25}$ is ethyl.

In a further embodiment of the aforementioned embodiments is a compound of Formula (IIIa) wherein $R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IIIa) wherein $R^1$ is hydrogen. In a further embodiment of the aforementioned embodiments is a compound of Formula (IIIa) wherein $R^1$ is optionally substituted $C_1$-$C_6$alkyl. In a further embodiment of the aforementioned embodiments is a compound of Formula (IIIa) wherein $R^1$ is methyl. In a further embodiment of the aforementioned embodiments is a compound of Formula (IIIa) wherein $R^1$ is optionally substituted $C_2$-$C_6$alkenyl. In a further embodiment of the aforementioned embodiments is a compound of Formula (IIIa) wherein $R^1$ is optionally substituted $C_2$-$C_6$alkynyl.

In a further embodiment of the aforementioned embodiments is a compound of Formula (IIIa) wherein $R^1$ and $R^2$ together with the carbon atoms to which they are attached, form an optionally substituted $C_2$-$C_9$heterocycloalkyl ring or an optionally substituted heteroaryl ring. In a further embodiment of the aforementioned embodiments is a compound of Formula (IIIa) wherein $R^1$ and $R^2$ together with the carbon atoms to which they are attached, form an optionally substituted $C_2$-$C_9$heterocycloalkyl ring. In a further embodiment of the aforementioned embodiments is a compound of Formula (IIIa) wherein $R^1$ and $R^2$ together with the carbon atoms to which they are attached, form an optionally substituted heteroaryl ring.

In a further embodiment of the aforementioned embodiments is a compound of Formula (IIIa) wherein $R^8$ is selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl). In a further embodiment of the aforementioned embodiments is a compound of Formula (IIIa) wherein $R^8$ is selected from the group consisting of hydrogen, and optionally substituted $C_1$-$C_6$alkyl. In a further embodiment of the aforementioned embodiments is a compound of Formula (IIIa) wherein $R^8$ is optionally substituted $C_1$-$C_6$alkyl. In a further embodiment of the aforementioned embodiments is a compound of Formula (IIIa) wherein $R^8$ is methyl. In a further embodiment of the aforementioned embodiments is a compound of Formula (IIIa) wherein $R^8$ is optionally substituted $C_1$-$C_6$alkyl. In a further embodiment of the aforementioned embodiments is a compound of Formula (IIIa) wherein $R^8$ is ethyl. In a further embodiment of the aforementioned embodiments is a compound of Formula (IIIa) wherein $R^8$ is optionally substituted $C_1$-$C_6$alkyl. In a further embodiment of the aforementioned embodiments is a compound of Formula (IIIa) wherein $R^8$ is hydrogen.

In another embodiment of the aforementioned embodiments is a compound of Formula (IIIa) wherein $R^{20}$ is —$R^{34}R^{35}$. In another embodiment of the aforementioned embodiments is a compound of Formula (IIIa) wherein $R^{20}$ is —$R^{34}R^{35}$, and $R^{34}$ is optionally substituted $C_1$-$C_6$alkyl.

In another embodiment of the aforementioned embodiments is a compound of Formula (IIIa) wherein $R^{20}$ is —$R^{34}R^{35}$, and $R^{34}$ is optionally substituted $C_3$-$C_{10}$cycloalkyl. In another embodiment of the aforementioned embodiments is a compound of Formula (IIIa) wherein $R^{20}$ is —$R^{34}R^{35}$, and $R^{34}$ is optionally substituted aryl. In another embodiment of the aforementioned embodiments is a compound of Formula (IIIa) wherein $R^{20}$ is —$R^{34}R^{35}$, and $R^{34}$ is optionally substituted —($C_1$-$C_2$alkylene)-(aryl). In another embodiment of the aforementioned embodiments is a compound of Formula (IIIa) wherein $R^{20}$ is —$R^{34}R^{35}$, and $R^{34}$ is optionally substituted heteroaryl. In another embodiment of the aforementioned embodiments is a compound of Formula (IIIa) wherein $R^{20}$ is —$R^{34}R^{35}$, and $R^{34}$ is optionally substituted $C_2$-$C_9$heterocycloalkyl. In another embodiment of the aforementioned embodiments is a compound of Formula (IIIa) wherein $R^{20}$ is —$R^{34}R^{35}$, and $R^{34}$ is optionally substituted —($C_1$-$C_2$alkylene)-(heteroaryl). In another embodiment of the aforementioned embodiments is a compound of Formula (IIIa) wherein $R^{20}$ is —$R^{34}R^{35}$, and $R^{35}$ is —($C_1$-$C_6$alkyl)-$R^{30}$. In another embodiment of the aforementioned embodiments is a compound of Formula (IIIa) wherein $R^{20}$ is —$R^{34}R^{35}$, and $R^{35}$ is —O($C_2$-$C_6$alkyl)-$R^{30}$. In another embodiment of the aforementioned embodiments is a compound of Formula (IIIa) wherein $R^{20}$ is —$R^{34}R^{35}$, and $R^{35}$ is —N($R^{12}$)($C_2$-$C_6$alkyl)-$R^{30}$. In a further embodiment of the aforementioned embodiments is a compound of Formula (IIIa) wherein $R^{30}$ is $R^{36a}$. In a further embodiment of the aforementioned embodiments is a compound of Formula (IIIa) wherein $R^{30}$ is $R^{36b}$. In a further embodiment of the aforementioned embodiments is a compound of Formula (IIIa) wherein $R^{30}$ is $R^{36c}$.

In another embodiment of the aforementioned embodiments is a compound of Formula (IIIa) wherein $R^{20}$ is —$R^{31}$. In a further embodiment of the aforementioned embodiments is a compound of Formula (IIIa) wherein $R^{31}$ is $R^{36a}$. In a further embodiment of the aforementioned embodiments is a compound of Formula (IIIa) wherein $R^{31}$ is $R^{36c}$.

In another embodiment of the aforementioned embodiments is a compound of Formula (IIIa) wherein $R^{36a}$ is

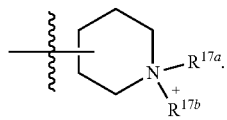

In another embodiment of the aforementioned embodiments is a compound of Formula (IIIa) wherein $R^{36a}$ is

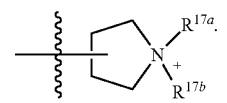

In another embodiment of the aforementioned embodiments is a compound of Formula (IIIa) wherein $R^{36a}$ is

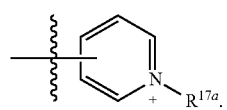

In another embodiment of the aforementioned embodiments is a compound of Formula (IIIa) wherein $R^{36b}$ is

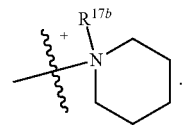

In another embodiment of the aforementioned embodiments is a compound of Formula (IIIa) wherein $R^{36b}$ is

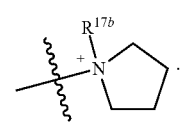

In another embodiment of the aforementioned embodiments is a compound of Formula (IIIa) wherein $R^{36b}$ is

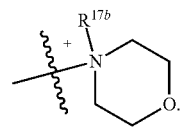

In another embodiment of the aforementioned embodiments is a compound of Formula (IIIa) wherein $R^{36b}$ is

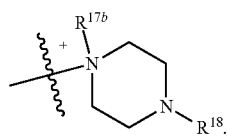

In another embodiment of the aforementioned embodiments is a compound of Formula (IIIa) wherein $R^{36b}$ is

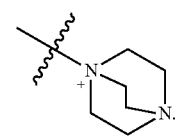

In another embodiment of the aforementioned embodiments is a compound of Formula (IIIa) wherein $R^{36b}$ is

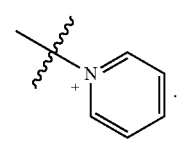

In another embodiment of the aforementioned embodiments is a compound of Formula (IIIa) wherein $R^{36b}$ is

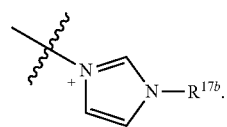

In another embodiment of the aforementioned embodiments is a compound of Formula (IIIa) wherein $R^{36c}$ is

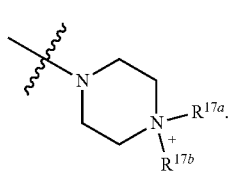

In another embodiment is a compound of Formula (IIIa) wherein $R^{36c}$ is

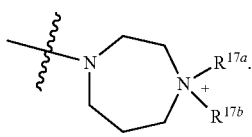

In a further embodiment of the aforementioned embodiments is a compound of Formula (IIIa) wherein $R^{17a}$ is methyl. In a further embodiment of the aforementioned embodiments is a compound of Formula (IIIa) wherein $R^{17a}$ is ethyl. In a further embodiment of the aforementioned embodiments is a compound of Formula (IIIa) wherein $R^{17b}$ is methyl optionally substituted with phenyl, —C(=O)OH or —S(=O)$_2$OH. In a further embodiment of the aforementioned embodiments is a compound of Formula (IIIa) wherein $R^{17a}$ is ethyl optionally substituted with phenyl, —C(=O)OH or —S(=O)$_2$OH.

In another embodiment of the aforementioned embodiments is a compound of Formula (IIIa) wherein n is 0. In another embodiment of the aforementioned embodiments is a compound of Formula (IIIa) wherein n is 1. In another embodiment of the aforementioned embodiments is a compound of Formula (IIIa) wherein n is 1 and $R^{11}$ is $C_1$-$C_6$alkyl. In another embodiment of the aforementioned embodiments is a compound of Formula (IIIa) wherein n is 1 and $R^{11}$ is $C_1$-$C_6$haloalkyl.

In some embodiments provided herein, the compound of Formula (III) has the structure of Formula (IIIb), or a pharmaceutically acceptable salt or solvate thereof:

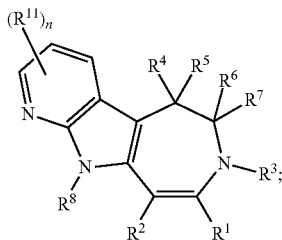

Formula (IIIb)

wherein:
$R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R^2$ is selected from the group consisting of —CN, —C(=O)OR$^{25}$, —C(=O)N(R$^{25}$)R$^{26}$,

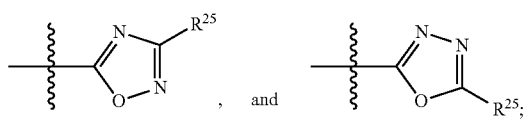

, and or $R^1$ and $R^2$ together with the carbon atoms to which they are attached, form an optionally substituted $C_2$-$C_9$heterocycloalkyl ring or an optionally substituted heteroaryl ring;

$R^3$ is —C(=O)R$^{20}$ or —S(=O)$_2$R$^{20}$;

$R^4$ and $R^5$ are each independently selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl; or $R^4$ and $R^5$ together with the carbon atom to which they are attached, form an optionally substituted $C_3$-$C_6$cycloalkyl ring or an optionally substituted $C_2$-$C_7$heterocycloalkyl ring;

$R^6$ is selected from the group consisting of hydrogen, halogen, optionally substituted $C_1$-$C_6$alkyl, optionally substituted $C_2$-$C_6$alkenyl, optionally substituted $C_2$-$C_6$alkynyl, and —C(=O)N(R$^{27}$)R$^{28}$;

$R^7$ is selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl;

$R^8$ is selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl);

each $R^{11}$ is independently selected from the group consisting of halogen, —CN, amino, alkylamino, $C_1$-$C_6$alkyl, $C_1$-$C_6$haloalkyl, $C_1$-$C_6$alkoxy, $C_1$-$C_6$haloalkoxy, $C_3$-$C_8$cycloalkyl, $C_2$-$C_9$heterocycloalkyl, aryl, heteroaryl, —C(=O)OR$^{12}$, —C(=O)N(R$^{13}$)R$^{14}$;

each $R^{12}$ is independently selected from the group consisting of hydrogen and $C_1$-$C_6$alkyl;

each $R^{13}$ and $R^{14}$ are each independently selected from the group consisting of hydrogen and $C_1$-$C_6$alkyl; or $R^{13}$ and $R^{14}$ together with the nitrogen atom to which they are attached, form an optionally substituted $C_2$-$C_9$heterocycloalkyl ring;

n is 0, 1, 2, or 3;

$R^{20}$ is selected from the group consisting of —R$^{34}$R$^{35}$ or —R$^{31}$;

$R^{34}$ is selected from the group consisting of optionally substituted $C_1$-$C_6$alkyl, optionally substituted $C_3$-$C_{10}$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl);

$R^{35}$ is —($C_1$-$C_6$alkyl)-R$^{30}$, —O($C_2$-$C_6$alkyl)-R$^{30}$, or —N(R$^{12}$)($C_2$-$C_6$alkyl)-R$^{30}$;

$R^{30}$ is $R^{36a}$, $R^{36b}$, or $R^{36c}$;

$R^{31}$ is $R^{36a}$ or $R^{36c}$;

$R^{36a}$ is

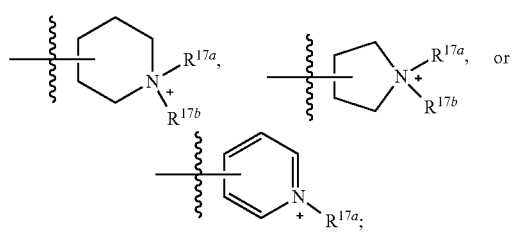

$R^{36b}$ is

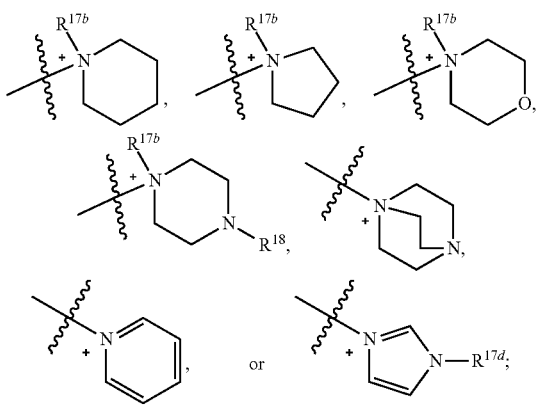

$R^{36c}$ is

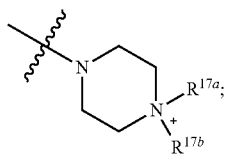

$R^{17a}$ is $C_1$-$C_6$alkyl;
$R^{17b}$ is $C_1$-$C_6$alkyl optionally substituted with phenyl, —C(=O)OH or —S(=O)$_2$OH;
$R^{18}$ is hydrogen, —OH, —($C_0$-$C_6$alkyl)-C(=O)OH, or $C_1$-$C_6$alkyl;
$R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); and
$R^{27}$ and $R^{28}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{27}$ and $R^{28}$ together with the nitrogen atom to which they are attached, form an optionally substituted $C_2$-$C_9$heterocycloalkyl ring.

In one embodiment is a compound of Formula (IIIb) wherein $R^4$ and $R^5$ are each independently selected from the group consisting of hydrogen, halogen, and optionally substituted $C_1$-$C_6$alkyl. In another embodiment is a compound of Formula (IIIb) wherein $R^4$ and $R^5$ are each independently selected from the group consisting of hydrogen and optionally substituted $C_1$-$C_6$alkyl. In another embodiment is a compound of Formula (IIIb) wherein $R^4$ and $R^5$ are each hydrogen. In another embodiment is a compound of Formula (IIIb) wherein $R^4$ and $R^5$ are each independently optionally substituted $C_1$-$C_6$alkyl. In another embodiment is a compound of Formula (IIIb) wherein $R^4$ and $R^5$ are each methyl. In another embodiment is a compound of Formula (IIIb) wherein $R^4$ and $R^5$ form an optionally substituted $C_3$-$C_6$cycloalkyl ring or an optionally substituted $C_2$-$C_7$heterocycloalkyl ring. In some embodiments is a compound of Formula (IIIb) wherein $R^4$ and $R^5$ form an optionally substituted $C_3$-$C_6$cycloalkyl ring. In some embodiments is a compound of Formula (IIIb) wherein $R^4$ and $R^5$ form an optionally substituted $C_2$-$C_7$heterocycloalkyl ring.

In another embodiment is a compound of Formula (IIIb) wherein $R^6$ and $R^7$ are each independently selected from the group consisting of hydrogen, halogen, and optionally substituted $C_1$-$C_6$alkyl. In another embodiment is a compound of Formula (IIIb) wherein $R^6$ and $R^7$ are each independently selected from the group consisting of hydrogen and optionally substituted $C_1$-$C_6$alkyl. In another embodiment is a compound of Formula (IIIb) wherein $R^6$ and $R^7$ are each independently optionally substituted $C_1$-$C_6$alkyl. In another embodiment is a compound of Formula (IIIb) wherein $R^6$ and $R^7$ are each methyl. In another embodiment is a compound of Formula (IIIb) wherein $R^6$ and $R^7$ are each hydrogen.

In another embodiment is a compound of Formula (IIIb) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted aryl. In another embodiment is a compound of Formula (IIIb) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted heteroaryl. In another embodiment is a compound of Formula (IIIb) wherein $R^6$ and $R^7$ are hydrogen, $R^4$ and $R^5$ are methyl, $R^3$ is —C(O)$R^{20}$, and $R^{20}$ is optionally substituted aryl. In another embodiment is a compound of Formula (IIIb) wherein $R^6$ and $R^7$ are hydrogen, $R^4$ and $R^5$ are methyl, $R^3$ is —C(O)$R^{20}$, and $R^{20}$ is optionally substituted heteroaryl.

In another embodiment is a compound of Formula (IIIb) wherein $R^6$ and $R^7$ are hydrogen, $R^4$ and $R^5$ are independently optionally substituted $C_1$-$C_6$alkyl, $R^3$ is —S(O)$_2R^{20}$, and $R^{20}$ is optionally substituted aryl. In another embodiment is a compound of Formula (IIIb) wherein $R^6$ and $R^7$ are hydrogen, $R^4$ and $R^5$ are independently optionally substituted $C_1$-$C_6$alkyl, $R^3$ is —S(O)$_2R^{20}$, and $R^{20}$ is optionally substituted heteroaryl. In another embodiment is a compound of Formula (IIIb) wherein $R^6$ and $R^7$ are hydrogen, $R^4$ and $R^5$ are methyl, $R^3$ is —S(O)$_2R^{20}$, and $R^{20}$ is optionally substituted aryl. In another embodiment is a compound of Formula (IIIb) wherein $R^6$ and $R^7$ are hydrogen, $R^4$ and $R^5$ are methyl, $R^3$ is —S(O)$_2R^{20}$, and $R^{20}$ is optionally substituted heteroaryl.

In a further embodiment of the aforementioned embodiments is a compound of Formula (IIIb) wherein $R^2$ is selected from the group consisting of —CN, —C(O)O$R^{25}$, —C(O)N($R^{25}$)$R^{26}$,

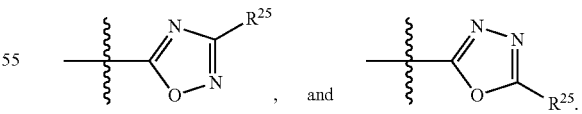

In a further embodiment of the aforementioned embodiments is a compound of Formula (IIIb) wherein $R^2$ is —CN.

In a further embodiment of the aforementioned embodiments is a compound of Formula (IIIb) wherein $R^2$ is —C(O)O$R^{25}$. In a further embodiment of the aforementioned embodiments is a compound of Formula (IIIb) wherein $R^2$ is —C(O)O$R^{25}$, and $R^{25}$ is independently selected from the group consisting of hydrogen, optionally substituted $C_1$-$C_6$alkyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl). In a further embodiment of the aforementioned embodiments is a compound of Formula (IIIb) wherein R$^2$ is —C(O)OR$^{25}$, and R$^{25}$ is independently selected from the group consisting of hydrogen, and optionally substituted C$_1$-C$_6$alkyl. In a further embodiment of the aforementioned embodiments is a compound of Formula (IIIb) wherein R$^2$ is —C(O)OR$^{25}$, and R$^{25}$ is hydrogen. In a further embodiment of the aforementioned embodiments is a compound of Formula (IIIb) wherein R$^2$ is —C(O)OR$^{25}$, and R$^{25}$ is optionally substituted C$_1$-C$_6$alkyl. In a further embodiment of the aforementioned embodiments is a compound of Formula (IIIb) wherein R$^2$ is —C(O)OR$^{25}$, and R$^{25}$ is unsubstituted C$_1$-C$_6$alkyl. In a further embodiment of the aforementioned embodiments is a compound of Formula (IIIb) wherein R$^2$ is —C(O)OR$^{25}$, and R$^{25}$ is methyl. In a further embodiment of the aforementioned embodiments is a compound of Formula (IIIb) wherein R$^2$ is —C(O)OR$^{25}$, and R$^{25}$ is ethyl.

In a further embodiment of the aforementioned embodiments is a compound of Formula (IIIb) wherein R$^2$ is —C(O)N(R$^{25}$)R$^{26}$. In a further embodiment of the aforementioned embodiments is a compound of Formula (IIIb) wherein R$^2$ is —C(O)N(R$^{25}$)R$^{26}$, and R$^{25}$ and R$^{26}$ are each independently selected from the group consisting of hydrogen, optionally substituted C$_1$-C$_6$alkyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl). In a further embodiment of the aforementioned embodiments is a compound of Formula (IIIb) wherein R$^2$ is —C(O)N(R$^{25}$)R$^{26}$, and R$^{25}$ and R$^{26}$ are each independently selected from the group consisting of hydrogen, and optionally substituted C$_1$-C$_6$alkyl. In a further embodiment of the aforementioned embodiments is a compound of Formula (IIIb) wherein R$^2$ is —C(O)N(R$^{25}$)R$^{26}$, and R$^{25}$ and R$^{26}$ are hydrogen. In a further embodiment of the aforementioned embodiments is a compound of Formula (IIIb) wherein R$^2$ is —C(O)N(R$^{25}$)R$^{26}$, and R$^{25}$ and R$^{26}$ are each independently optionally substituted C$_1$-C$_6$alkyl. In a further embodiment of the aforementioned embodiments is a compound of Formula (IIIb) wherein R$^2$ is —C(O)N(R$^{25}$)R$^{26}$, R$^{25}$ is hydrogen, and R$^{26}$ is optionally substituted C$_1$-C$_6$alkyl. In a further embodiment of the aforementioned embodiments is a compound of Formula (IIIb) wherein R$^2$ is —C(O)N(R$^{25}$)R$^{26}$, and R$^{25}$ and R$^{26}$ are each independently unsubstituted C$_1$-C$_6$alkyl. In a further embodiment of the aforementioned embodiments is a compound of Formula (IIIb) wherein R$^2$ is —C(O)N(R$^{25}$)R$^{26}$, R$^{25}$ is hydrogen, and R$^{26}$ are methyl. In a further embodiment of the aforementioned embodiments is a compound of Formula (IIIb) wherein R$^2$ is —C(O)N(R$^{25}$)R$^{26}$, and R$^{25}$ and R$^{26}$ are methyl. In a further embodiment of the aforementioned embodiments is a compound of Formula (IIIb) wherein R$^2$ is —C(O)N(R$^{25}$)R$^{26}$, and R$^{25}$ and R$^{26}$ are ethyl.

In a further embodiment of the aforementioned embodiments is a compound of Formula (IIIb) wherein R$^2$ is

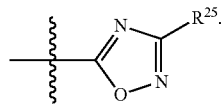

In a further embodiment of the aforementioned embodiments is a compound of Formula (IIIb) wherein R$^2$ is

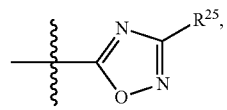

and R$^{25}$ is optionally substituted C$_1$-C$_6$alkyl. In a further embodiment of the aforementioned embodiments is a compound of Formula (IIIb) wherein R$^2$ is

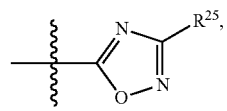

and R$^{25}$ is methyl. In a further embodiment of the aforementioned embodiments is a compound of Formula (IIIb) wherein R$^2$ is

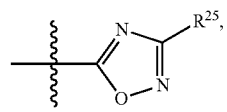

and R$^{25}$ is optionally substituted C$_1$-C$_6$alkyl. In a further embodiment of the aforementioned embodiments is a compound of Formula (IIIb) wherein R$^2$ is

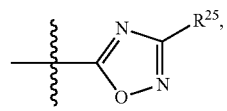

and R$^{25}$ is ethyl.

In a further embodiment of the aforementioned embodiments is a compound of Formula (IIIb) wherein R$^2$ is

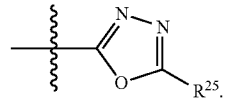

In a further embodiment of the aforementioned embodiments is a compound of Formula (IIIb) wherein R$^2$ is

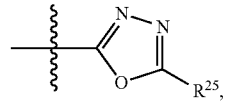

and R$^{25}$ is optionally substituted C$_1$-C$_6$alkyl. In a further embodiment of the aforementioned embodiments is a compound of Formula (IIIb) wherein R$^2$ is

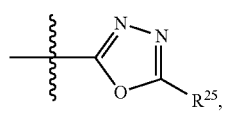

and $R^{25}$ is methyl. In a further embodiment of the aforementioned embodiments is a compound of Formula (IIIb) wherein $R^2$ is

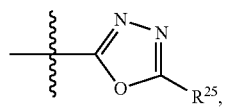

and $R^{25}$ is optionally substituted $C_1$-$C_6$alkyl. In a further embodiment of the aforementioned embodiments is a compound of Formula (IIIb) wherein $R^2$ is

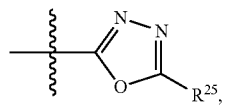

and $R^{25}$ is ethyl.

In a further embodiment of the aforementioned embodiments is a compound of Formula (IIIb) wherein $R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IIIb) wherein $R^1$ is hydrogen. In a further embodiment of the aforementioned embodiments is a compound of Formula (IIIb) wherein $R^1$ is optionally substituted $C_1$-$C_6$alkyl. In a further embodiment of the aforementioned embodiments is a compound of Formula (IIIb) wherein $R^1$ is methyl. In a further embodiment of the aforementioned embodiments is a compound of Formula (IIIb) wherein $R^1$ is optionally substituted $C_2$-$C_6$alkenyl. In a further embodiment of the aforementioned embodiments is a compound of Formula (IIIb) wherein $R^1$ is optionally substituted $C_2$-$C_6$alkynyl.

In a further embodiment of the aforementioned embodiments is a compound of Formula (IIIb) wherein $R^1$ and $R^2$ together with the carbon atoms to which they are attached, form an optionally substituted $C_2$-$C_9$heterocycloalkyl ring or an optionally substituted heteroaryl ring. In a further embodiment of the aforementioned embodiments is a compound of Formula (IIIb) wherein $R^1$ and $R^2$ together with the carbon atoms to which they are attached, form an optionally substituted $C_2$-$C_9$heterocycloalkyl ring. In a further embodiment of the aforementioned embodiments is a compound of Formula (IIIb) wherein $R^1$ and $R^2$ together with the carbon atoms to which they are attached, form an optionally substituted heteroaryl ring.

In a further embodiment of the aforementioned embodiments is a compound of Formula (IIIb) wherein $R^8$ is selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl). In a further embodiment of the aforementioned embodiments is a compound of Formula (IIIb) wherein $R^8$ is selected from the group consisting of hydrogen, and optionally substituted $C_1$-$C_6$alkyl. In a further embodiment of the aforementioned embodiments is a compound of Formula (IIIb) wherein $R^8$ is optionally substituted $C_1$-$C_6$alkyl. In a further embodiment of the aforementioned embodiments is a compound of Formula (IIIb) wherein $R^8$ is methyl. In a further embodiment of the aforementioned embodiments is a compound of Formula (IIIb) wherein $R^8$ is optionally substituted $C_1$-$C_6$alkyl. In a further embodiment of the aforementioned embodiments is a compound of Formula (IIIb) wherein $R^8$ is ethyl. In a further embodiment of the aforementioned embodiments is a compound of Formula (IIIb) wherein $R^8$ is optionally substituted $C_1$-$C_6$alkyl. In a further embodiment of the aforementioned embodiments is a compound of Formula (IIIb) wherein $R^8$ is hydrogen.

In another embodiment of the aforementioned embodiments is a compound of Formula (IIIb) wherein $R^{20}$ is —$R^{34}R^{35}$. In another embodiment of the aforementioned embodiments is a compound of Formula (IIIb) wherein $R^{20}$ is —$R^{34}R^{35}$, and $R^{34}$ is optionally substituted $C_1$-$C_6$alkyl.

In another embodiment of the aforementioned embodiments is a compound of Formula (IIIb) wherein $R^{20}$ is —$R^{34}R^{35}$, and $R^{34}$ is optionally substituted $C_3$-$C_{10}$cycloalkyl. In another embodiment of the aforementioned embodiments is a compound of Formula (IIIb) wherein $R^{20}$ is —$R^{34}R^{35}$, and $R^{34}$ is optionally substituted aryl. In another embodiment of the aforementioned embodiments is a compound of Formula (IIIb) wherein $R^{20}$ is —$R^{34}R^{35}$, and $R^{34}$ is optionally substituted —($C_1$-$C_2$alkylene)-(aryl). In another embodiment of the aforementioned embodiments is a compound of Formula (IIIb) wherein $R^{20}$ is —$R^{34}R^{35}$, and $R^{34}$ is optionally substituted heteroaryl. In another embodiment of the aforementioned embodiments is a compound of Formula (IIIb) wherein $R^{20}$ is —$R^{34}R^{35}$, and $R^{34}$ is optionally substituted $C_2$-$C_9$heterocycloalkyl. In another embodiment of the aforementioned embodiments is a compound of Formula (IIIb) wherein $R^{20}$ is —$R^{34}R^{35}$, and $R^{34}$ is optionally substituted —($C_1$-$C_2$alkylene)-(heteroaryl). In another embodiment of the aforementioned embodiments is a compound of Formula (IIIb) wherein $R^{20}$ is —$R^{34}R^{35}$, and $R^{35}$ is —($C_1$-$C_6$alkyl)-$R^{30}$. In another embodiment of the aforementioned embodiments is a compound of Formula (IIIb) wherein $R^{20}$ is —$R^{34}R^{35}$, and $R^{35}$ is —O($C_2$-$C_6$alkyl)-$R^{30}$. In another embodiment of the aforementioned embodiments is a compound of Formula (IIIb) wherein $R^{20}$ is —$R^{34}R^{35}$, and $R^{35}$ is —N($R^{12}$)($C_2$-$C_6$alkyl)-$R^{30}$. In a further embodiment of the aforementioned embodiments is a compound of Formula (IIIb) wherein $R^{30}$ is $R^{36a}$. In a further embodiment of the aforementioned embodiments is a compound of Formula (IIIb) wherein $R^{30}$ is $R^{36b}$. In a further embodiment of the aforementioned embodiments is a compound of Formula (IIIb) wherein $R^{30}$ is $R^{36c}$.

In another embodiment of the aforementioned embodiments is a compound of Formula (IIIb) wherein $R^{20}$ is —$R^{31}$. In a further embodiment of the aforementioned embodiments is a compound of Formula (IIIb) wherein $R^{31}$ is $R^{36a}$. In a further embodiment of the aforementioned embodiments is a compound of Formula (IIIb) wherein $R^{31}$ is $R^{36c}$.

In another embodiment of the aforementioned embodiments is a compound of Formula (IIIb) wherein $R^{36a}$ is

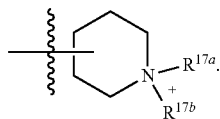

In another embodiment of the aforementioned embodiments is a compound of Formula (IIIb) wherein $R^{36a}$ is

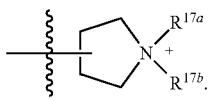

In another embodiment of the aforementioned embodiments is a compound of Formula (IIIb) wherein $R^{36a}$ is

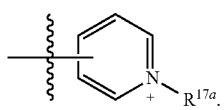

In another embodiment of the aforementioned embodiments is a compound of Formula (IIIb) wherein $R^{36b}$ is

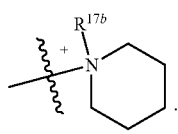

In another embodiment of the aforementioned embodiments is a compound of Formula (IIIb) wherein $R^{36b}$ is

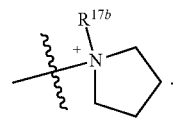

In another embodiment of the aforementioned embodiments is a compound of Formula (IIIb) wherein $R^{36b}$ is

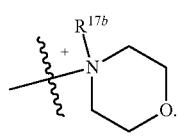

In another embodiment of the aforementioned embodiments is a compound of Formula (IIIb) wherein $R^{36b}$ is

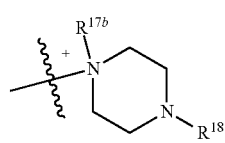

In another embodiment of the aforementioned embodiments is a compound of Formula (IIIb) wherein $R^{36b}$ is

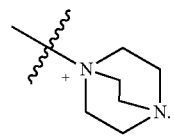

In another embodiment of the aforementioned embodiments is a compound of Formula (IIIb) wherein $R^{36b}$ is

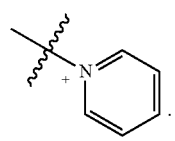

In another embodiment of the aforementioned embodiments is a compound of Formula (IIIb) wherein $R^{36b}$ is

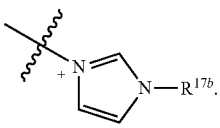

In another embodiment of the aforementioned embodiments is a compound of Formula (IIIb) wherein $R^{36c}$ is

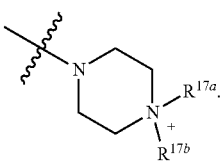

In another embodiment is a compound of Formula (IIIb) wherein $R^{36c}$ is

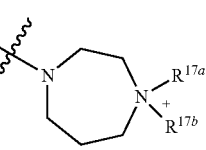

In a further embodiment of the aforementioned embodiments is a compound of Formula (IIIb) wherein $R^{17a}$ is methyl. In a further embodiment of the aforementioned embodiments is a compound of Formula (IIIb) wherein $R^{17a}$ is ethyl. In a further embodiment of the aforementioned embodiments is a compound of Formula (IIIb) wherein $R^{17b}$ is methyl optionally substituted with phenyl, —C(=O)OH or —S(=O)$_2$OH. In a further embodiment of the aforementioned embodiments is a compound of Formula (IIIb) wherein $R^{17a}$ is ethyl optionally substituted with phenyl, —C(=O)OH or —S(=O)$_2$OH.

In another embodiment of the aforementioned embodiments is a compound of Formula (IIIb) wherein n is 0. In another embodiment of the aforementioned embodiments is a compound of Formula (IIIb) wherein n is 1. In another embodiment of the aforementioned embodiments is a compound of Formula (IIIb) wherein n is 1 and $R^{11}$ is $C_1$-$C_6$alkyl. In another embodiment of the aforementioned embodiments is a compound of Formula (IIIb) wherein n is 1 and $R^{11}$ is $C_1$-$C_6$haloalkyl.

In some embodiments provided herein, the compound of Formula (III) has the structure of Formula (IIIc), or a pharmaceutically acceptable salt or solvate thereof:

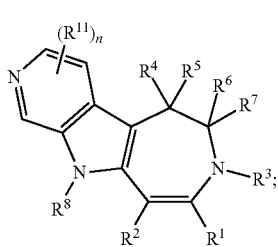

Formula (IIIc)

wherein:
- $R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);
- $R^2$ is selected from the group consisting of —CN, —C(=O)OR$^{25}$, —C(=O)N(R$^{25}$)R$^{26}$,

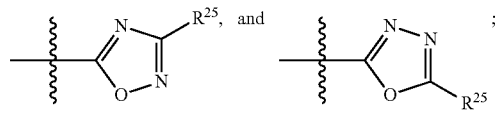

or $R^1$ and $R^2$ together with the carbon atoms to which they are attached, form an optionally substituted $C_2$-$C_9$heterocycloalkyl ring or an optionally substituted heteroaryl ring;
- $R^3$ is —C(=O)R$^{20}$ or —S(=O)$_2$R$^{20}$;
- $R^4$ and $R^5$ are each independently selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl; or $R^4$ and $R^5$ together with the carbon atom to which they are attached, form an optionally substituted $C_3$-$C_6$cycloalkyl ring or an optionally substituted $C_2$-$C_7$heterocycloalkyl ring;
- $R^6$ is selected from the group consisting of hydrogen, halogen, optionally substituted $C_1$-$C_6$alkyl, optionally substituted $C_2$-$C_6$alkenyl, optionally substituted $C_2$-$C_6$alkynyl, and —C(=O)N(R$^{27}$)R$^{28}$;
- $R^7$ is selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl;
- $R^8$ is selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl);
- each $R^{11}$ is independently selected from the group consisting of halogen, —CN, amino, alkylamino, $C_1$-$C_6$alkyl, $C_1$-$C_6$haloalkyl, $C_1$-$C_6$alkoxy, $C_1$-$C_6$haloalkoxy, $C_3$-$C_8$cycloalkyl, $C_2$-$C_9$heterocycloalkyl, aryl, heteroaryl, —C(=O)OR$^{12}$, —C(=O)N(R$^{13}$)R$^{14}$;
- each $R^{12}$ is independently selected from the group consisting of hydrogen and $C_1$-$C_6$alkyl;
- each $R^{13}$ and $R^{14}$ are each independently selected from the group consisting of hydrogen and $C_1$-$C_6$alkyl; or $R^{13}$ and $R^{14}$ together with the nitrogen atom to which they are attached, form an optionally substituted $C_2$-$C_9$heterocycloalkyl ring;
- n is 0, 1, 2, or 3;
- $R^{20}$ is selected from the group consisting of —R$^{34}$R$^{35}$ or —R$^{31}$;
- $R^{34}$ is selected from the group consisting of optionally substituted $C_1$-$C_6$alkyl, optionally substituted $C_3$-$C_{10}$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl);
- $R^{35}$ is —($C_1$-$C_6$alkyl)-R$^{30}$, —O($C_2$-$C_6$alkyl)-R$^{30}$, or —N(R$^{12}$)($C_2$-$C_6$alkyl)-R$^{30}$;
- $R^{30}$ is R$^{36a}$, R$^{36b}$, or R$^{36c}$;
- $R^{31}$ is R$^{36a}$ or R$^{36c}$;
- $R^{36a}$ is

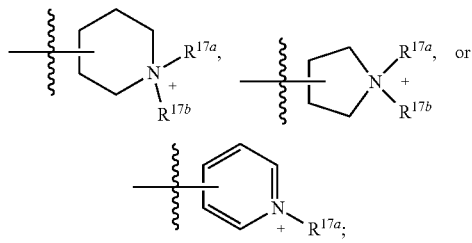

$R^{36b}$ is

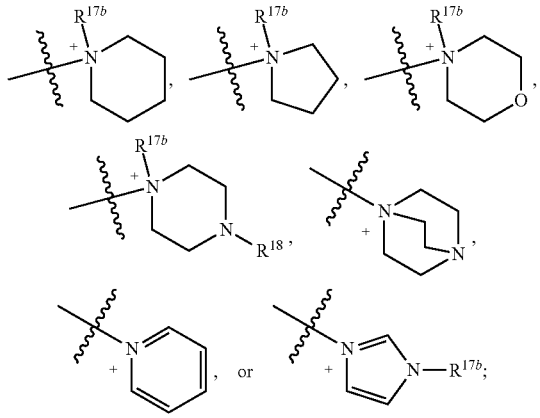

$R^{36c}$ is

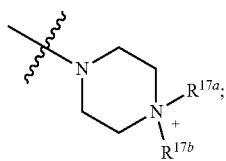

$R^{17a}$ is $C_1$-$C_6$alkyl;
$R^{17b}$ is $C_1$-$C_6$alkyl optionally substituted with phenyl, —C(=O)OH or —S(=O)$_2$OH;
$R^{18}$ is hydrogen, —OH, —($C_0$-$C_6$alkyl)-C(=O)OH, or $C_1$-$C_6$alkyl;
$R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); and
$R^{27}$ and $R^{28}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{27}$ and $R^{28}$ together with the nitrogen atom to which they are attached, form an optionally substituted $C_2$-$C_9$heterocycloalkyl ring.

In one embodiment is a compound of Formula (IIIc) wherein $R^4$ and $R^5$ are each independently selected from the group consisting of hydrogen, halogen, and optionally substituted $C_1$-$C_6$alkyl. In another embodiment is a compound of Formula (IIIc) wherein $R^4$ and $R^5$ are each independently selected from the group consisting of hydrogen and optionally substituted $C_1$-$C_6$alkyl. In another embodiment is a compound of Formula (IIIc) wherein $R^4$ and $R^5$ are each hydrogen. In another embodiment is a compound of Formula (IIIc) wherein $R^4$ and $R^5$ are each independently optionally substituted $C_1$-$C_6$alkyl. In another embodiment is a compound of Formula (IIIc) wherein $R^4$ and $R^5$ are each methyl. In another embodiment is a compound of Formula (IIIc) wherein $R^4$ and $R^5$ form an optionally substituted $C_3$-$C_6$cycloalkyl ring or an optionally substituted $C_2$-$C_7$heterocycloalkyl ring. In some embodiments is a compound of Formula (IIIc) wherein $R^4$ and $R^5$ form an optionally substituted $C_3$-$C_6$cycloalkyl ring. In some embodiments is a compound of Formula (IIIc) wherein $R^4$ and $R^5$ form an optionally substituted $C_2$-$C_7$heterocycloalkyl ring.

In another embodiment is a compound of Formula (IIIc) wherein $R^6$ and $R^7$ are each independently selected from the group consisting of hydrogen, halogen, and optionally substituted $C_1$-$C_6$alkyl. In another embodiment is a compound of Formula (IIIc) wherein $R^6$ and $R^7$ are each independently selected from the group consisting of hydrogen and optionally substituted $C_1$-$C_6$alkyl. In another embodiment is a compound of Formula (IIIc) wherein $R^6$ and $R^7$ are each independently optionally substituted $C_1$-$C_6$alkyl. In another embodiment is a compound of Formula (IIIc) wherein $R^6$ and $R^7$ are each methyl. In another embodiment is a compound of Formula (IIIc) wherein $R^6$ and $R^7$ are each hydrogen.

In another embodiment is a compound of Formula (IIIc) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted aryl. In another embodiment is a compound of Formula (IIIc) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted heteroaryl. In another embodiment is a compound of Formula (IIIc) wherein $R^6$ and $R^7$ are hydrogen, $R^4$ and $R^5$ are methyl, $R^3$ is —C(O)$R^{20}$, and $R^{20}$ is optionally substituted aryl. In another embodiment is a compound of Formula (IIIc) wherein $R^6$ and $R^7$ are hydrogen, $R^4$ and $R^5$ are methyl, $R^3$ is —C(O)$R^{20}$, and $R^{20}$ is optionally substituted heteroaryl.

In another embodiment is a compound of Formula (IIIc) wherein $R^6$ and $R^7$ are hydrogen, $R^4$ and $R^5$ are independently optionally substituted $C_1$-$C_6$alkyl, $R^3$ is —S(O)$_2$$R^{20}$, and $R^{20}$ is optionally substituted aryl. In another embodiment is a compound of Formula (IIIc) wherein $R^6$ and $R^7$ are hydrogen, $R^4$ and $R^5$ are independently optionally substituted $C_1$-$C_6$alkyl, $R^3$ is —S(O)$_2$$R^{20}$, and $R^{20}$ is optionally substituted heteroaryl. In another embodiment is a compound of Formula (IIIc) wherein $R^6$ and $R^7$ are hydrogen, $R^4$ and $R^5$ are methyl, $R^3$ is —S(O)$_2$$R^{20}$, and $R^{20}$ is optionally substituted aryl. In another embodiment is a compound of Formula (IIIc) wherein $R^6$ and $R^7$ are hydrogen, $R^4$ and $R^5$ are methyl, $R^3$ is —S(O)$_2$$R^{20}$, and $R^{20}$ is optionally substituted heteroaryl.

In a further embodiment of the aforementioned embodiments is a compound of Formula (IIIc) wherein $R^2$ is selected from the group consisting of —CN, —C(O)O$R^{25}$, —C(O)N($R^{25}$)$R^{26}$,

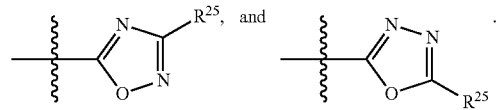

In a further embodiment of the aforementioned embodiments is a compound of Formula (IIIc) wherein $R^2$ is —CN.

In a further embodiment of the aforementioned embodiments is a compound of Formula (IIIc) wherein $R^2$ is —C(O)O$R^{25}$. In a further embodiment of the aforementioned embodiments is a compound of Formula (IIIc) wherein $R^2$ is —C(O)O$R^{25}$, and $R^{25}$ is independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IIIc) wherein $R^2$ is —C(O)O$R^{25}$, and $R^{25}$ is independently selected from the group consisting of hydrogen, and optionally substituted $C_1$-$C_6$alkyl. In a further embodiment of the aforementioned embodiments is a compound of Formula (IIIc) wherein $R^2$ is —C(O)O$R^{25}$, and $R^{25}$ is hydrogen. In a further embodiment of the aforementioned embodiments is a compound of Formula (IIIc) wherein $R^2$ is —C(O)O$R^{25}$, and $R^{25}$ is optionally substituted $C_1$-$C_6$alkyl. In a further embodiment of the aforementioned embodiments is a compound of Formula (IIIc) wherein $R^2$ is —C(O)O$R^{25}$, and $R^{25}$ is unsubstituted $C_1$-$C_6$alkyl. In a further embodiment of the aforementioned embodiments is a compound of Formula (IIIc)

wherein R² is —C(O)OR²⁵, and R²⁵ is methyl. In a further embodiment of the aforementioned embodiments is a compound of Formula (IIIc) wherein R² is —C(O)OR²⁵, and R²⁵ is ethyl.

In a further embodiment of the aforementioned embodiments is a compound of Formula (IIIc) wherein R² is —C(O)N(R²⁵)R²⁶. In a further embodiment of the aforementioned embodiments is a compound of Formula (IIIc) wherein R² is —C(O)N(R²⁵)R²⁶, and R²⁵ and R²⁶ are each independently selected from the group consisting of hydrogen, optionally substituted C₁-C₆alkyl, optionally substituted C₃-C₈cycloalkyl, optionally substituted aryl, optionally substituted —(C₁-C₂alkylene)-(aryl), optionally substituted C₂-C₉heterocycloalkyl, optionally substituted heteroaryl, and optionally substituted —(C₁-C₂alkylene)-(heteroaryl). In a further embodiment of the aforementioned embodiments is a compound of Formula (IIIc) wherein R² is —C(O)N(R²⁵)R²⁶, and R²⁵ and R²⁶ are each independently selected from the group consisting of hydrogen, and optionally substituted C₁-C₆alkyl. In a further embodiment of the aforementioned embodiments is a compound of Formula (IIIc) wherein R² is —C(O)N(R²⁵)R²⁶, and R²⁵ and R²⁶ are hydrogen. In a further embodiment of the aforementioned embodiments is a compound of Formula (IIIc) wherein R² is —C(O)N(R²⁵)R²⁶, and R²⁵ and R²⁶ are each independently optionally substituted C₁-C₆alkyl. In a further embodiment of the aforementioned embodiments is a compound of Formula (IIIc) wherein R² is —C(O)N(R²⁵)R²⁶, R²⁵ is hydrogen, and R²⁶ is optionally substituted C₁-C₆alkyl. In a further embodiment of the aforementioned embodiments is a compound of Formula (IIIc) wherein R² is —C(O)N(R²⁵)R²⁶, and R²⁵ and R²⁶ are each independently unsubstituted C₁-C₆alkyl. In a further embodiment of the aforementioned embodiments is a compound of Formula (IIIc) wherein R² is —C(O)N(R²⁵)R²⁶, R²⁵ is hydrogen, and R²⁶ are methyl. In a further embodiment of the aforementioned embodiments is a compound of Formula (IIIc) wherein R² is —C(O)N(R²⁵)R²⁶, and R²⁵ and R²⁶ are methyl. In a further embodiment of the aforementioned embodiments is a compound of Formula (IIIc) wherein R² is —C(O)N(R²⁵)R²⁶, and R²⁵ and R²⁶ are ethyl.

In a further embodiment of the aforementioned embodiments is a compound of Formula (IIIc) wherein R² is

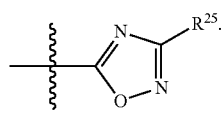

In a further embodiment of the aforementioned embodiments is a compound of Formula (IIIc) wherein R² is

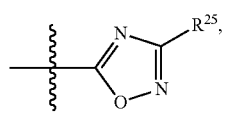

and R²⁵ is optionally substituted C₁-C₆alkyl. In a further embodiment of the aforementioned embodiments is a compound of Formula (IIIc) wherein R² is

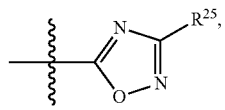

and R²⁵ is methyl. In a further embodiment of the aforementioned embodiments is a compound of Formula (IIIc) wherein R² is

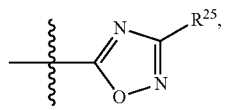

and R²⁵ is optionally substituted C₁-C₆alkyl. In a further embodiment of the aforementioned embodiments is a compound of Formula (IIIc) wherein R² is

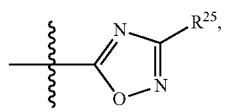

and R²⁵ is ethyl.

In a further embodiment of the aforementioned embodiments is a compound of Formula (IIIc) wherein R² is

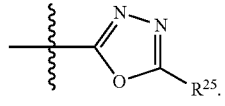

In a further embodiment of the aforementioned embodiments is a compound of Formula (IIIc) wherein R² is

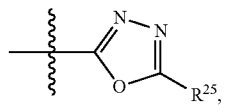

and R²⁵ is optionally substituted C₁-C₆alkyl. In a further embodiment of the aforementioned embodiments is a compound of Formula (IIIc) wherein R² is

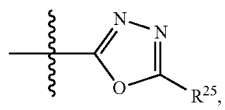

and R²⁵ is methyl. In a further embodiment of the aforementioned embodiments is a compound of Formula (IIIc) wherein R² is

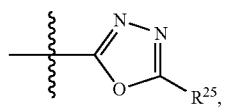

and $R^{25}$ is optionally substituted $C_1$-$C_6$alkyl. In a further embodiment of the aforementioned embodiments is a compound of Formula (IIIc) wherein $R^2$ is

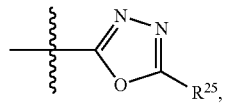

and $R^{25}$ is ethyl.

In a further embodiment of the aforementioned embodiments is a compound of Formula (IIIc) wherein $R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IIIc) wherein $R^1$ is hydrogen. In a further embodiment of the aforementioned embodiments is a compound of Formula (IIIc) wherein $R^1$ is optionally substituted $C_1$-$C_6$alkyl. In a further embodiment of the aforementioned embodiments is a compound of Formula (IIIc) wherein $R^1$ is methyl. In a further embodiment of the aforementioned embodiments is a compound of Formula (IIIc) wherein $R^1$ is optionally substituted $C_2$-$C_6$alkenyl. In a further embodiment of the aforementioned embodiments is a compound of Formula (IIIc) wherein $R^1$ is optionally substituted $C_2$-$C_6$alkynyl.

In a further embodiment of the aforementioned embodiments is a compound of Formula (IIIc) wherein $R^1$ and $R^2$ together with the carbon atoms to which they are attached, form an optionally substituted $C_2$-$C_9$heterocycloalkyl ring or an optionally substituted heteroaryl ring. In a further embodiment of the aforementioned embodiments is a compound of Formula (IIIc) wherein $R^1$ and $R^2$ together with the carbon atoms to which they are attached, form an optionally substituted $C_2$-$C_9$heterocycloalkyl ring. In a further embodiment of the aforementioned embodiments is a compound of Formula (IIIc) wherein $R^1$ and $R^2$ together with the carbon atoms to which they are attached, form an optionally substituted heteroaryl ring.

In a further embodiment of the aforementioned embodiments is a compound of Formula (IIIc) wherein $R^8$ is selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl). In a further embodiment of the aforementioned embodiments is a compound of Formula (IIIc) wherein $R^8$ is selected from the group consisting of hydrogen, and optionally substituted $C_1$-$C_6$alkyl. In a further embodiment of the aforementioned embodiments is a compound of Formula (IIIc) wherein $R^8$ is optionally substituted $C_1$-$C_6$alkyl. In a further embodiment of the aforementioned embodiments is a compound of Formula (IIIc) wherein $R^8$ is methyl. In a further embodiment of the aforementioned embodiments is a compound of Formula (IIIc) wherein $R^8$ is optionally substituted $C_1$-$C_6$alkyl. In a further embodiment of the aforementioned embodiments is a compound of Formula (IIIc) wherein $R^8$ is ethyl. In a further embodiment of the aforementioned embodiments is a compound of Formula (IIIc) wherein $R^8$ is optionally substituted $C_1$-$C_6$alkyl. In a further embodiment of the aforementioned embodiments is a compound of Formula (IIIc) wherein $R^8$ is hydrogen.

In another embodiment of the aforementioned embodiments is a compound of Formula (IIIc) wherein $R^{20}$ is —$R^{34}R^{35}$. In another embodiment of the aforementioned embodiments is a compound of Formula (IIIc) wherein $R^{20}$ is —$R^{34}R^{35}$, and $R^{34}$ is optionally substituted $C_1$-$C_6$alkyl. In another embodiment of the aforementioned embodiments is a compound of Formula (IIIc) wherein $R^{20}$ is —$R^{34}R^{35}$, and $R^{34}$ is optionally substituted $C_3$-$C_{10}$cycloalkyl. In another embodiment of the aforementioned embodiments is a compound of Formula (IIIc) wherein $R^{20}$ is —$R^{34}R^{35}$, and $R^{34}$ is optionally substituted aryl. In another embodiment of the aforementioned embodiments is a compound of Formula (IIIc) wherein $R^{20}$ is —$R^{34}R^{35}$, and $R^{34}$ is optionally substituted —($C_1$-$C_2$alkylene)-(aryl). In another embodiment of the aforementioned embodiments is a compound of Formula (IIIc) wherein $R^{20}$ is —$R^{34}R^{35}$, and $R^{34}$ is optionally substituted heteroaryl. In another embodiment of the aforementioned embodiments is a compound of Formula (IIIc) wherein $R^{20}$ is —$R^{34}R^{35}$, and $R^{34}$ is optionally substituted $C_2$-$C_9$heterocycloalkyl. In another embodiment of the aforementioned embodiments is a compound of Formula (IIIc) wherein $R^{20}$ is —$R^{34}R^{35}$, and $R^{34}$ is optionally substituted —($C_1$-$C_2$alkylene)-(heteroaryl). In another embodiment of the aforementioned embodiments is a compound of Formula (IIIc) wherein $R^{20}$ is —$R^{34}R^{35}$, and $R^{35}$ is —($C_1$-$C_6$alkyl)-$R^{30}$. In another embodiment of the aforementioned embodiments is a compound of Formula (IIIc) wherein $R^{20}$ is —$R^{34}R^{35}$, and $R^{35}$ is —O($C_2$-$C_6$alkyl)-$R^{30}$. In another embodiment of the aforementioned embodiments is a compound of Formula (IIIc) wherein $R^{20}$ is —$R^{34}R^{35}$, and $R^{35}$ is —N($R^{12}$)($C_2$-$C_6$alkyl)-$R^{30}$. In a further embodiment of the aforementioned embodiments is a compound of Formula (IIIc) wherein $R^{30}$ is $R^{36a}$. In a further embodiment of the aforementioned embodiments is a compound of Formula (IIIc) wherein $R^{30}$ is $R^{36b}$. In a further embodiment of the aforementioned embodiments is a compound of Formula (IIIc) wherein $R^{30}$ is $R^{36c}$.

In another embodiment of the aforementioned embodiments is a compound of Formula (IIIc) wherein $R^{20}$ is —$R^{31}$. In a further embodiment of the aforementioned embodiments is a compound of Formula (IIIc) wherein $R^{31}$ is $R^{36a}$. In a further embodiment of the aforementioned embodiments is a compound of Formula (IIIc) wherein $R^{31}$ is $R^{36c}$.

In another embodiment of the aforementioned embodiments is a compound of Formula (IIIc) wherein $R^{36a}$ is

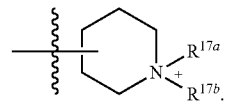

In another embodiment of the aforementioned embodiments is a compound of Formula (IIIc) wherein $R^{36a}$ is

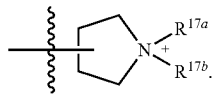

In another embodiment of the aforementioned embodiments is a compound of Formula (IIIc) wherein $R^{36a}$ is

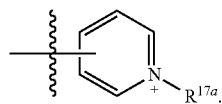

In another embodiment of the aforementioned embodiments is a compound of Formula (IIIc) wherein $R^{36b}$ is

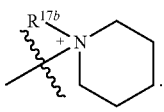

In another embodiment of the aforementioned embodiments is a compound of Formula (IIIc) wherein $R^{36b}$ is

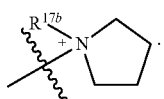

In another embodiment of the aforementioned embodiments is a compound of Formula (IIIc) wherein $R^{36b}$ is

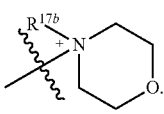

In another embodiment of the aforementioned embodiments is a compound of Formula (IIIc) wherein $R^{36b}$ is

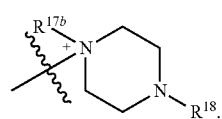

In another embodiment of the aforementioned embodiments is a compound of Formula (IIIc) wherein $R^{36b}$ is

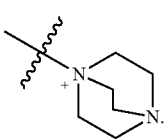

In another embodiment of the aforementioned embodiments is a compound of Formula (IIIc) wherein $R^{36b}$ is

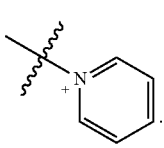

In another embodiment of the aforementioned embodiments is a compound of Formula (IIIc) wherein $R^{36b}$ is

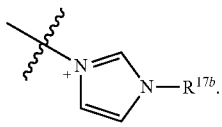

In another embodiment of the aforementioned embodiments is a compound of Formula (IIIc) wherein $R^{36c}$ is

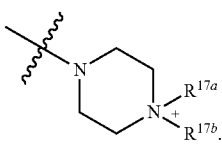

In a further embodiment of the compound of Formula (IIIc) wherein $R^{36c}$ is

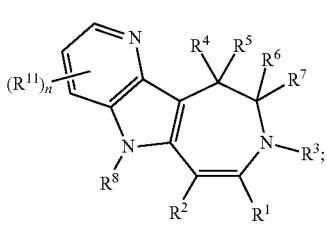

In a further embodiment of the aforementioned embodiments is a compound of Formula (IIIc) wherein $R^{17a}$ is methyl. In a further embodiment of the aforementioned embodiments is a compound of Formula (IIIc) wherein $R^{17a}$ is ethyl. In a further embodiment of the aforementioned embodiments is a compound of Formula (IIIc) wherein $R^{17b}$ is methyl optionally substituted with phenyl, —C(=O)OH or —S(=O)$_2$OH. In a further embodiment of the aforementioned embodiments is a compound of Formula (IIIc) wherein $R^{17a}$ is ethyl optionally substituted with phenyl, —C(=O)OH or —S(=O)$_2$OH.

In another embodiment of the aforementioned embodiments is a compound of Formula (IIIc) wherein n is 0. In another embodiment of the aforementioned embodiments is a compound of Formula (IIIc) wherein n is 1. In another embodiment of the aforementioned embodiments is a compound of Formula (IIIc) wherein n is 1 and $R^{11}$ is $C_1$-$C_6$alkyl. In another embodiment of the aforementioned embodiments is a compound of Formula (IIIc) wherein n is 1 and $R^{11}$ is $C_1$-$C_6$haloalkyl.

In some embodiments provided herein, the compound of Formula (III) has the structure of Formula (IIId), or a pharmaceutically acceptable salt or solvate thereof:

Formula (IIId)

wherein:

$R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R^2$ is selected from the group consisting of —CN, —C(=O)OR$^{25}$, —C(=O)N(R$^{25}$)R$^{26}$,

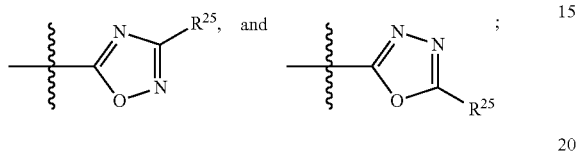

, and

;

or $R^1$ and $R^2$ together with the carbon atoms to which they are attached, form an optionally substituted $C_2$-$C_9$heterocycloalkyl ring or an optionally substituted heteroaryl ring;

$R^3$ is —C(=O)R$^{20}$ or —S(=O)$_2$R$^{20}$;

$R^4$ and $R^5$ are each independently selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl; or $R^4$ and $R^5$ together with the carbon atom to which they are attached, form an optionally substituted $C_3$-$C_6$cycloalkyl ring or an optionally substituted $C_2$-$C_7$heterocycloalkyl ring;

$R^6$ is selected from the group consisting of hydrogen, halogen, optionally substituted $C_1$-$C_6$alkyl, optionally substituted $C_2$-$C_6$alkenyl, optionally substituted $C_2$-$C_6$alkynyl, and —C(=O)N(R$^{27}$)R$^{28}$;

$R^7$ is selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl;

$R^8$ is selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl);

each $R^{11}$ is independently selected from the group consisting of halogen, —CN, amino, alkylamino, $C_1$-$C_6$alkyl, $C_1$-$C_6$haloalkyl, $C_1$-$C_6$alkoxy, $C_1$-$C_6$haloalkoxy, $C_3$-$C_8$cycloalkyl, $C_2$-$C_9$heterocycloalkyl, aryl, heteroaryl, —C(=O) OR$^{12}$, —C(=O)N(R$^{13}$)R$^{14}$;

each $R^{12}$ is independently selected from the group consisting of hydrogen and $C_1$-$C_6$alkyl;

each $R^{13}$ and $R^{14}$ are each independently selected from the group consisting of hydrogen and $C_1$-$C_6$alkyl; or $R^{13}$ and $R^{14}$ together with the nitrogen atom to which they are attached, form an optionally substituted $C_2$-$C_9$heterocycloalkyl ring;

n is 0, 1, 2, or 3;

$R^{20}$ is selected from the group consisting of —R$^{34}$R$^{35}$ or —R$^{31}$;

$R^{34}$ is selected from the group consisting of optionally substituted $C_1$-$C_6$alkyl, optionally substituted $C_3$-$C_{10}$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl);

$R^{35}$ is —($C_1$-$C_6$alkyl)-R$^{30}$, —O($C_2$-$C_6$alkyl)-R$^{30}$, or —N(R$^{12}$)($C_2$-$C_6$alkyl)-R$^{30}$;

$R^{30}$ is $R^{36a}$, $R^{36b}$, or $R^{36c}$;

$R^{31}$ is $R^{36a}$ or $R^{36c}$;

$R^{36a}$ is

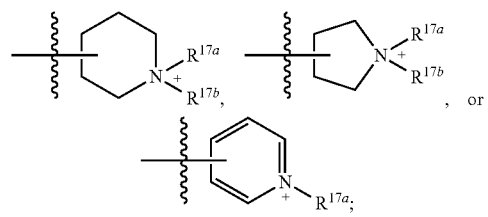

$R^{36b}$ is

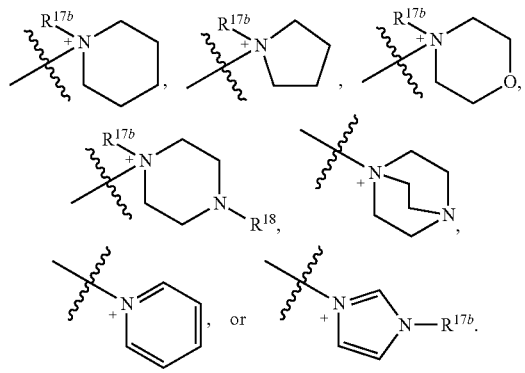

$R^{36c}$ is

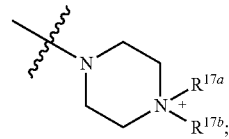

$R^{17a}$ is $C_1$-$C_6$alkyl;

$R^{17b}$ is $C_1$-$C_6$alkyl optionally substituted with phenyl, —C(=O)OH or —S(=O)$_2$OH;

$R^{18}$ is hydrogen, —OH, —($C_0$-$C_6$alkyl)-C(=O)OH, or $C_1$-$C_6$alkyl;

$R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); and $R^{27}$ and $R^{28}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{27}$ and $R^{28}$ together with the nitrogen atom to which they are attached, form an optionally substituted $C_2$-$C_9$heterocycloalkyl ring.

In one embodiment is a compound of Formula (IIId) wherein $R^4$ and $R^5$ are each independently selected from the group consisting of hydrogen, halogen, and optionally substituted $C_1$-$C_6$alkyl. In another embodiment is a compound of Formula (IIId) wherein $R^4$ and $R^5$ are each independently selected from the group consisting of hydrogen and optionally substituted $C_1$-$C_6$alkyl. In another embodiment is a compound of Formula (IIId) wherein $R^4$ and $R^5$ are each hydrogen. In another embodiment is a compound of Formula (IIId) wherein $R^4$ and $R^5$ are each independently optionally substituted $C_1$-$C_6$alkyl. In another embodiment is a compound of Formula (IIId) wherein $R^4$ and $R^5$ are each methyl. In another embodiment is a compound of Formula (IIId) wherein $R^4$ and $R^5$ form an optionally substituted $C_3$-$C_6$cycloalkyl ring or an optionally substituted $C_2$-$C_7$heterocycloalkyl ring. In some embodiments is a compound of Formula (IIId) wherein $R^4$ and $R^5$ form an optionally substituted $C_3$-$C_6$cycloalkyl ring. In some embodiments is a compound of Formula (IIId) wherein $R^4$ and $R^5$ form an optionally substituted $C_2$-$C_7$heterocycloalkyl ring.

In another embodiment is a compound of Formula (IIId) wherein $R^6$ and $R^7$ are each independently selected from the group consisting of hydrogen, halogen, and optionally substituted $C_1$-$C_6$alkyl. In another embodiment is a compound of Formula (IIId) wherein $R^6$ and $R^7$ are each independently selected from the group consisting of hydrogen and optionally substituted $C_1$-$C_6$alkyl. In another embodiment is a compound of Formula (IIId) wherein $R^6$ and $R^7$ are each independently optionally substituted $C_1$-$C_6$alkyl. In another embodiment is a compound of Formula (IIId) wherein $R^6$ and $R^7$ are each methyl. In another embodiment is a compound of Formula (IIId) wherein $R^6$ and $R^7$ are each hydrogen.

In another embodiment is a compound of Formula (IIId) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted aryl. In another embodiment is a compound of Formula (IIId) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted heteroaryl. In another embodiment is a compound of Formula (IIId) wherein $R^6$ and $R^7$ are hydrogen, $R^4$ and $R^5$ are methyl, $R^3$ is —C(O)$R^{20}$, and $R^{20}$ is optionally substituted aryl. In another embodiment is a compound of Formula (IIId) wherein $R^6$ and $R^7$ are hydrogen, $R^4$ and $R^5$ are methyl, $R^3$ is —C(O)$R^{20}$, and $R^{20}$ is optionally substituted heteroaryl.

In another embodiment is a compound of Formula (IIId) wherein $R^6$ and $R^7$ are hydrogen, $R^4$ and $R^5$ are independently optionally substituted $C_1$-$C_6$alkyl, $R^3$ is —S(O)$_2$$R^{20}$, and $R^{20}$ is optionally substituted aryl. In another embodiment is a compound of Formula (IIId) wherein $R^6$ and $R^7$ are hydrogen, $R^4$ and $R^5$ are independently optionally substituted $C_1$-$C_6$alkyl, $R^3$ is —S(O)$_2$$R^{20}$, and $R^{20}$ is optionally substituted heteroaryl. In another embodiment is a compound of Formula (IIId) wherein $R^6$ and $R^7$ are hydrogen, $R^4$ and $R^5$ are methyl, $R^3$ is —S(O)$_2$$R^{20}$, and $R^{20}$ is optionally substituted aryl. In another embodiment is a compound of Formula (IIId) wherein $R^6$ and $R^7$ are hydrogen, $R^4$ and $R^5$ are methyl, $R^3$ is —S(O)$_2$$R^{20}$, and $R^{20}$ is optionally substituted heteroaryl.

In a further embodiment of the aforementioned embodiments is a compound of Formula (IIId) wherein $R^2$ is selected from the group consisting of —CN, —C(O)O$R^{25}$, —C(O)N($R^{25}$)$R^{26}$,

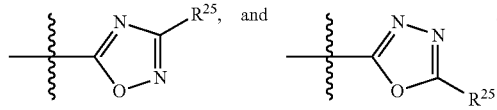

In a further embodiment of the aforementioned embodiments is a compound of Formula (IIId) wherein $R^2$ is —CN.

In a further embodiment of the aforementioned embodiments is a compound of Formula (IIId) wherein $R^2$ is —C(O)O$R^{25}$. In a further embodiment of the aforementioned embodiments is a compound of Formula (IIId) wherein $R^2$ is —C(O)O$R^{25}$, and $R^{25}$ is independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IIId) wherein $R^2$ is —C(O)O$R^{25}$, and $R^{25}$ is independently selected from the group consisting of hydrogen, and optionally substituted $C_1$-$C_6$alkyl. In a further embodiment of the aforementioned embodiments is a compound of Formula (IIId) wherein $R^2$ is —C(O)O$R^{25}$, and $R^{25}$ is hydrogen. In a further embodiment of the aforementioned embodiments is a compound of Formula (IIId) wherein $R^2$ is —C(O)O$R^{25}$, and $R^{25}$ is optionally substituted $C_1$-$C_6$alkyl. In a further embodiment of the aforementioned embodiments is a compound of Formula (IIId) wherein $R^2$ is —C(O)O$R^{25}$, and $R^{25}$ is unsubstituted $C_1$-$C_6$alkyl. In a further embodiment of the aforementioned embodiments is a compound of Formula (IIId) wherein $R^2$ is —C(O)O$R^{25}$, and $R^{25}$ is methyl. In a further embodiment of the aforementioned embodiments is a compound of Formula (IIId) wherein $R^2$ is —C(O)O$R^{25}$, and $R^{25}$ is ethyl.

In a further embodiment of the aforementioned embodiments is a compound of Formula (IIId) wherein $R^2$ is —C(O)N($R^{25}$)$R^{26}$. In a further embodiment of the aforementioned embodiments is a compound of Formula (IIId) wherein $R^2$ is —C(O)N($R^{25}$)$R^{26}$, and $R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IIId) wherein $R^2$ is —C(O)N($R^{25}$)$R^{26}$, and $R^{25}$ and $R^{26}$ are each independently selected from the group consisting of hydrogen, and optionally substituted $C_1$-$C_6$alkyl. In a further embodiment of the aforementioned embodiments is a compound of Formula (IIId) wherein $R^2$ is —C(O)N($R^{25}$)$R^{26}$, and $R^{25}$ and $R^{26}$ are hydrogen. In a further embodiment of the aforementioned embodiments is a compound of Formula (IIId) wherein $R^2$ is —C(O)N($R^{25}$)$R^{26}$, and $R^{25}$ and $R^{26}$ are each independently optionally substituted $C_1$-$C_6$alkyl. In a further embodiment of the aforementioned embodiments is a compound of Formula (IIId) wherein $R^2$ is —C(O)N($R^{25}$)$R^{26}$, $R^{25}$ is hydrogen, and $R^{26}$ is optionally substituted $C_1$-$C_6$alkyl. In a further embodiment of the aforementioned embodiments is a compound of Formula (IIId) wherein $R^2$ is —C(O)N($R^{25}$)$R^{26}$, and $R^{25}$ and $R^{26}$ are each independently unsubstituted $C_1$-$C_6$alkyl. In a further embodiment of the aforementioned embodiments is a compound of Formula (IIId) wherein $R^2$ is —C(O)N($R^{25}$)$R^{26}$, $R^{25}$ is hydrogen, and $R^{26}$ are methyl. In a further embodiment of the aforementioned embodiments is a compound of Formula (IIId) wherein $R^2$ is —C(O)N($R^{25}$)$R^{26}$, and $R^{25}$ and $R^{26}$ are methyl. In a further embodiment of the aforementioned embodiments is a compound of Formula (IIId) wherein $R^2$ is —C(O)N($R^{25}$)$R^{26}$, and $R^{25}$ and $R^{26}$ are ethyl.

In a further embodiment of the aforementioned embodiments is a compound of Formula (IIId) wherein $R^2$ is

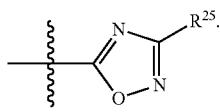

In a further embodiment of the aforementioned embodiments is a compound of Formula (IIId) wherein $R^2$ is

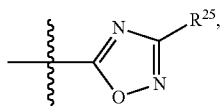

and $R^{25}$ is optionally substituted $C_1$-$C_6$alkyl. In a further embodiment of the aforementioned embodiments is a compound of Formula (IIId) wherein $R^2$ is

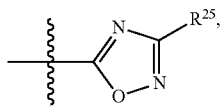

and $R^{25}$ is methyl. In a further embodiment of the aforementioned embodiments is a compound of Formula (IIId) wherein $R^2$ is

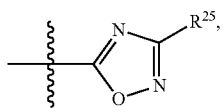

and $R^{25}$ is optionally substituted $C_1$-$C_6$alkyl. In a further embodiment of the aforementioned embodiments is a compound of Formula (IIId) wherein $R^2$ is

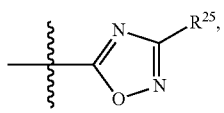

and $R^{25}$ is ethyl.

In a further embodiment of the aforementioned embodiments is a compound of Formula (IIId) wherein $R^2$ is

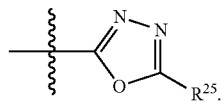

In a further embodiment of the aforementioned embodiments is a compound of Formula (IIId) wherein $R^2$ is

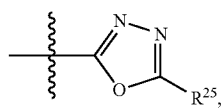

and $R^{25}$ is optionally substituted $C_1$-$C_6$alkyl. In a further embodiment of the aforementioned embodiments is a compound of Formula (IIId) wherein $R^2$ is

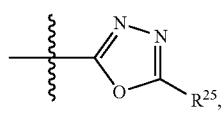

and $R^{25}$ is methyl. In a further embodiment of the aforementioned embodiments is a compound of Formula (IIId) wherein $R^2$ is

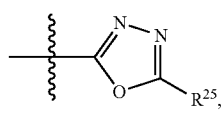

and $R^{25}$ is optionally substituted $C_1$-$C_6$alkyl. In a further embodiment of the aforementioned embodiments is a compound of Formula (IIId) wherein $R^2$ is

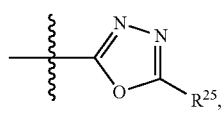

and $R^{25}$ is ethyl.

In a further embodiment of the aforementioned embodiments is a compound of Formula (IIId) wherein $R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IIId) wherein $R^1$ is hydrogen. In a further embodiment of the aforementioned embodiments is a compound of Formula (IIId) wherein $R^1$ is optionally substituted $C_1$-$C_6$alkyl. In a further embodiment of the aforementioned embodiments is a compound of Formula (IIId) wherein $R^1$ is methyl. In a further embodiment of the aforementioned embodiments is a compound of Formula (IIId) wherein $R^1$ is optionally substituted $C_2$-$C_6$alkenyl. In a further embodiment of the aforementioned embodiments is a compound of Formula (IIId) wherein $R^1$ is optionally substituted $C_2$-$C_6$alkynyl.

In a further embodiment of the aforementioned embodiments is a compound of Formula (IIId) wherein $R^1$ and $R^2$ together with the carbon atoms to which they are attached, form an optionally substituted $C_2$-$C_9$heterocycloalkyl ring or an optionally substituted heteroaryl ring. In a further embodiment of the aforementioned embodiments is a compound of Formula (IIId) wherein $R^1$ and $R^2$ together with the carbon atoms to which they are attached, form an optionally substituted $C_2$-$C_9$heterocycloalkyl ring. In a further embodiment of the aforementioned embodiments is a compound of Formula (IIId) wherein $R^1$ and $R^2$ together with the carbon atoms to which they are attached, form an optionally substituted heteroaryl ring.

In a further embodiment of the aforementioned embodiments is a compound of Formula (IIId) wherein $R^8$ is selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl). In a further embodiment of the aforementioned embodiments is a compound of Formula (IIId) wherein $R^8$ is selected from the group consisting of hydrogen, and optionally substituted $C_1$-$C_6$alkyl. In a further embodiment of the aforementioned embodiments is a compound of Formula (IIId) wherein $R^8$ is optionally substituted $C_1$-$C_6$alkyl. In a further embodiment of the aforementioned embodiments is a compound of Formula (IIId) wherein $R^8$ is methyl. In a further embodiment of the aforementioned embodiments is a compound of Formula (IIId) wherein $R^8$ is optionally substituted $C_1$-$C_6$alkyl. In a further embodiment of the aforementioned embodiments is a compound of Formula (IIId) wherein $R^8$ is ethyl. In a further embodiment of the aforementioned embodiments is a compound of Formula (IIId) wherein $R^8$ is optionally substituted $C_1$-$C_6$alkyl. In a further embodiment of the aforementioned embodiments is a compound of Formula (IIId) wherein $R^8$ is hydrogen.

In another embodiment of the aforementioned embodiments is a compound of Formula (IIId) wherein $R^{20}$ is —$R^{34}R^{35}$. In another embodiment of the aforementioned embodiments is a compound of Formula (IIId) wherein $R^{20}$ is —$R^{34}R^{35}$, and $R^{34}$ is optionally substituted $C_1$-$C_6$alkyl. In another embodiment of the aforementioned embodiments is a compound of Formula (IIId) wherein $R^{20}$ is —$R^{34}R^{35}$, and $R^{34}$ is optionally substituted $C_3$-$C_{10}$cycloalkyl. In another embodiment of the aforementioned embodiments is a compound of Formula (IIId) wherein $R^{20}$ is —$R^{34}R^{35}$, and $R^{34}$ is optionally substituted aryl. In another embodiment of the aforementioned embodiments is a compound of Formula (IIId) wherein $R^{20}$ is —$R^{34}R^{35}$, and $R^{34}$ is optionally substituted —($C_1$-$C_2$alkylene)-(aryl). In another embodiment of the aforementioned embodiments is a compound of Formula (IIId) wherein $R^{20}$ is —$R^{34}R^{35}$, and $R^{34}$ is optionally substituted heteroaryl. In another embodiment of the aforementioned embodiments is a compound of Formula (IIId) wherein $R^{20}$ is —$R^{34}R^{35}$, and $R^{34}$ is optionally substituted $C_2$-$C_9$heterocycloalkyl. In another embodiment of the aforementioned embodiments is a compound of Formula (IIId) wherein $R^{20}$ is —$R^{34}R^{35}$, and $R^{34}$ is optionally substituted —($C_1$-$C_2$alkylene)-(heteroaryl). In another embodiment of the aforementioned embodiments is a compound of Formula (IIId) wherein $R^{20}$ is —$R^{34}R^{35}$, and $R^{35}$ is —($C_1$-$C_6$alkyl)-$R^{30}$. In another embodiment of the aforementioned embodiments is a compound of Formula (IIId) wherein $R^{20}$ is —$R^{34}R^{35}$, and $R^{35}$ is —$O(C_2$-$C_6$alkyl)-$R^{30}$. In another embodiment of the aforementioned embodiments is a compound of Formula (IIId) wherein $R^{20}$ is —$R^{34}R^{35}$, and $R^{35}$ is —$N(R^{12})(C_2$-$C_6$alkyl)-$R^{30}$. In a further embodiment of the aforementioned embodiments is a compound of Formula (IIId) wherein $R^{30}$ is $R^{36a}$. In a further embodiment of the aforementioned embodiments is a compound of Formula (IIId) wherein $R^{30}$ is $R^{36b}$. In a further embodiment of the aforementioned embodiments is a compound of Formula (IIId) wherein $R^{30}$ is $R^{36c}$.

In another embodiment of the aforementioned embodiments is a compound of Formula (IIId) wherein $R^{20}$ is —$R^{31}$. In a further embodiment of the aforementioned embodiments is a compound of Formula (IIId) wherein $R^{31}$ is $R^{36a}$. In a further embodiment of the aforementioned embodiments is a compound of Formula (IIId) wherein $R^{31}$ is $R^{36c}$.

In another embodiment of the aforementioned embodiments is a compound of Formula (IIId) wherein $R^{36a}$ is

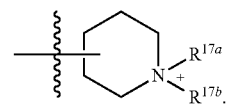

In another embodiment of the aforementioned embodiments is a compound of Formula (IIId) wherein $R^{36a}$ is

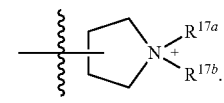

In another embodiment of the aforementioned embodiments is a compound of Formula (IIId) wherein $R^{36a}$ is

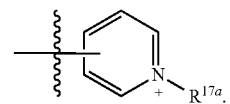

In another embodiment of the aforementioned embodiments is a compound of Formula (IIId) wherein $R^{36b}$ is

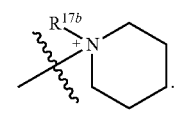

in another embodiment of the aforementioned embodiments is a compound of Formula (IIId) wherein $R^{36b}$ is

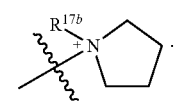

In another embodiment of the aforementioned embodiments is a compound of Formula (IIId) wherein $R^{36b}$ is

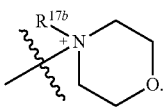

In another embodiment of the aforementioned embodiments is a compound of Formula (IIId) wherein $R^{36b}$ is

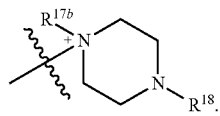

In another embodiment of the aforementioned embodiments is a compound of Formula (IIId) wherein $R^{36b}$ is

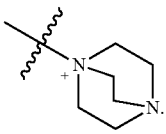

In another embodiment of the aforementioned embodiments is a compound of Formula (IIId) wherein $R^{36b}$ is

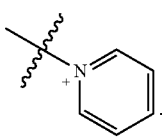

In another embodiment of the aforementioned embodiments is a compound of Formula (IIId) wherein $R^{36b}$ is

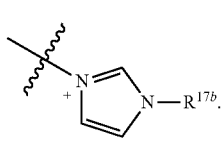

In another embodiment of the aforementioned embodiments is a compound of Formula (IIId) wherein $R^{36c}$ is

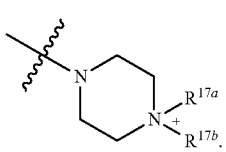

In another embodiment is a compound of Formula (IIId) wherein $R^{36c}$ is

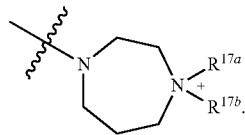

In a further embodiment of the aforementioned embodiments is a compound of Formula (IIId) wherein $R^{17a}$ is methyl. In a further embodiment of the aforementioned embodiments is a compound of Formula (IIId) wherein $R^{17a}$ is ethyl. In a further embodiment of the aforementioned embodiments is a compound of Formula (IIId) wherein $R^{17b}$ is methyl optionally substituted with phenyl, —C(=O)OH or —S(=O)$_2$OH. In a further embodiment of the aforementioned embodiments is a compound of Formula (IIId) wherein $R^{17a}$ is ethyl optionally substituted with phenyl, —C(=O)OH or —S(=O)$_2$OH.

In another embodiment of the aforementioned embodiments is a compound of Formula (IIId) wherein n is 0. In another embodiment of the aforementioned embodiments is a compound of Formula (IIId) wherein n is 1. In another embodiment of the aforementioned embodiments is a compound of Formula (IIId) wherein n is 1 and $R^{11}$ is $C_1$-$C_6$alkyl. In another embodiment of the aforementioned embodiments is a compound of Formula (IIId) wherein n is 1 and $R^{11}$ is $C_1$-$C_6$haloalkyl.

In some embodiments provided herein, the compound of Formula (III) has the structure of Formula (IIIe), or a pharmaceutically acceptable salt or solvate thereof:

Formula (IIIe)

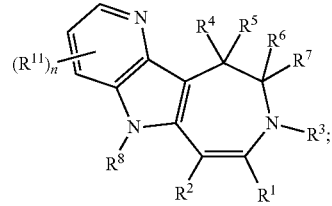

wherein:
  $R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);
  $R^2$ is selected from the group consisting of —CN, —C(=O)OR$^{25}$, —C(=O)N(R$^{25}$)R$^{26}$,

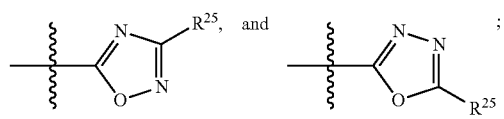

or $R^1$ and $R^2$ together with the carbon atoms to which they are attached, form an optionally substituted $C_2$-$C_9$heterocycloalkyl ring or an optionally substituted heteroaryl ring;

$R^3$ is —C(=O)$R^{20}$ or —S(=O)$_2R^{20}$;

$R^4$ and $R^5$ are each independently selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl; or $R^4$ and $R^5$ together with the carbon atom to which they are attached, form an optionally substituted $C_3$-$C_6$cycloalkyl ring or an optionally substituted $C_2$-$C_7$heterocycloalkyl ring;

$R^6$ is selected from the group consisting of hydrogen, halogen, optionally substituted $C_1$-$C_6$alkyl, optionally substituted $C_2$-$C_6$alkenyl, optionally substituted $C_2$-$C_6$alkynyl, and —C(=O)N($R^{27}$)$R^{28}$;

$R^7$ is selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl;

$R^8$ is selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl);

each $R^{11}$ is independently selected from the group consisting of halogen, —CN, amino, alkylamino, $C_1$-$C_6$alkyl, $C_1$-$C_6$haloalkyl, $C_1$-$C_6$alkoxy, $C_1$-$C_6$haloalkoxy, $C_3$-$C_8$cycloalkyl, $C_2$-$C_9$heterocycloalkyl, aryl, heteroaryl, —C(=O)O$R^{12}$, —C(=O)N($R^{13}$)$R^{14}$;

each $R^{12}$ is independently selected from the group consisting of hydrogen and $C_1$-$C_6$alkyl;

each $R^{13}$ and $R^{14}$ are each independently selected from the group consisting of hydrogen and $C_1$-$C_6$alkyl; or $R^{13}$ and $R^{14}$ together with the nitrogen atom to which they are attached, form an optionally substituted $C_2$-$C_9$heterocycloalkyl ring;

n is 0, 1, 2, or 3;

$R^{20}$ is selected from the group consisting of —$R^{34}R^{35}$ or —$R^{31}$;

$R^{34}$ is selected from the group consisting of optionally substituted $C_1$-$C_6$alkyl, optionally substituted $C_3$-$C_{10}$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl);

$R^{35}$ is —($C_1$-$C_6$alkyl)-$R^{30}$, —O($C_2$-$C_6$alkyl)-$R^{30}$, or —N($R^{12}$)($C_2$-$C_6$alkyl)-$R^{30}$;

$R^{30}$ is $R^{36a}$, $R^{36b}$, or $R^{36c}$;

$R^{31}$ is $R^{36a}$ or $R^{36c}$;

$R^{36a}$ is

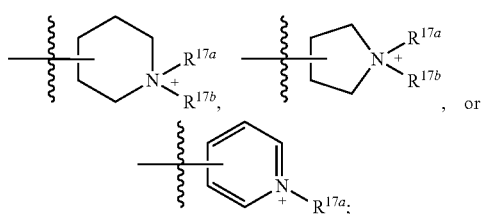

$R^{36b}$ is

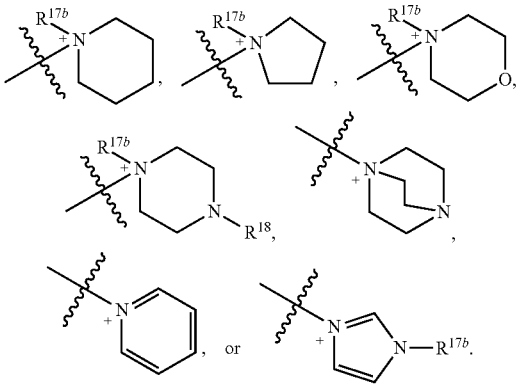

$R^{36c}$ is

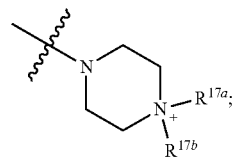

$R^{17a}$ is $C_1$-$C_6$alkyl;

$R^{17b}$ is $C_1$-$C_6$alkyl optionally substituted with phenyl, —C(=O)OH or —S(=O)$_2$OH;

$R^{18}$ is hydrogen, —OH, —($C_0$-$C_6$alkyl)-C(=O)OH, or $C_1$-$C_6$alkyl;

$R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); and $R^{27}$ and $R^{28}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{27}$ and $R^{28}$ together with the nitrogen atom to which they are attached, form an optionally substituted $C_2$-$C_9$heterocycloalkyl ring.

In one embodiment is a compound of Formula (IIIe) wherein $R^4$ and $R^5$ are each independently selected from the group consisting of hydrogen, halogen, and optionally substituted $C_1$-$C_6$alkyl. In another embodiment is a compound of Formula (IIIe) wherein $R^4$ and $R^5$ are each independently selected from the group consisting of hydrogen and optionally substituted $C_1$-$C_6$alkyl. In another embodiment is a compound of Formula (IIIe) wherein $R^4$ and $R^5$ are each hydrogen. In another embodiment is a compound of Formula (IIIe) wherein $R^4$ and $R^5$ are each independently optionally substituted $C_1$-$C_6$alkyl. In another embodiment is a compound of Formula (IIIe) wherein $R^4$ and $R^5$ are each methyl. In another embodiment is a compound of Formula (IIIe) wherein $R^4$ and $R^5$ form an optionally substituted $C_3$-$C_6$cycloalkyl ring or an optionally substituted $C_2$-$C_7$heterocycloalkyl ring. In some embodiments is a compound of Formula (IIIe) wherein $R^4$ and $R^5$ form an optionally substituted $C_3$-$C_6$cycloalkyl ring. In some embodiments is a compound of Formula (IIIe) wherein $R^4$ and $R^5$ form an optionally substituted $C_2$-$C_7$heterocycloalkyl ring.

In another embodiment is a compound of Formula (IIIe) wherein $R^6$ and $R^7$ are each independently selected from the group consisting of hydrogen, halogen, and optionally substituted $C_1$-$C_6$alkyl. In another embodiment is a compound of Formula (IIIe) wherein $R^6$ and $R^7$ are each independently selected from the group consisting of hydrogen and optionally substituted $C_1$-$C_6$alkyl. In another embodiment is a compound of Formula (IIIe) wherein $R^6$ and $R^7$ are each independently optionally substituted $C_1$-$C_6$alkyl. In another embodiment is a compound of Formula (IIIe) wherein $R^6$ and $R^7$ are each methyl. In another embodiment is a compound of Formula (IIIe) wherein $R^6$ and $R^7$ are each hydrogen.

In another embodiment is a compound of Formula (IIIe) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted aryl. In another embodiment is a compound of Formula (IIIe) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted heteroaryl. In another embodiment is a compound of Formula (IIIe) wherein $R^6$ and $R^7$ are hydrogen, $R^4$ and $R^5$ are methyl, $R^3$ is —C(O)$R^{20}$, and $R^{20}$ is optionally substituted aryl. In another embodiment is a compound of Formula (IIIe) wherein $R^6$ and $R^7$ are hydrogen, $R^4$ and $R^5$ are methyl, $R^3$ is —C(O)$R^{20}$, and $R^{20}$ is optionally substituted heteroaryl.

In another embodiment is a compound of Formula (IIIe) wherein $R^6$ and $R^7$ are hydrogen, $R^4$ and $R^5$ are independently optionally substituted $C_1$-$C_6$alkyl, $R^3$ is —S(O)$_2R^{20}$, and $R^{20}$ is optionally substituted aryl. In another embodiment is a compound of Formula (IIIe) wherein $R^6$ and $R^7$ are hydrogen, $R^4$ and $R^5$ are independently optionally substituted $C_1$-$C_6$alkyl, $R^3$ is —S(O)$_2R^{20}$, and $R^{20}$ is optionally substituted heteroaryl. In another embodiment is a compound of Formula (IIIe) wherein $R^6$ and $R^7$ are hydrogen, $R^4$ and $R^5$ are methyl, $R^3$ is —S(O)$_2R^{20}$, and $R^{20}$ is optionally substituted aryl. In another embodiment is a compound of Formula (IIIe) wherein $R^6$ and $R^7$ are hydrogen, $R^4$ and $R^5$ are methyl, $R^3$ is —S(O)$_2R^{20}$, and $R^{20}$ is optionally substituted heteroaryl.

In a further embodiment of the aforementioned embodiments is a compound of Formula (IIIe) wherein $R^2$ is selected from the group consisting of —CN, —C(O)O$R^{25}$, —C(O)N($R^{25}$)$R^{26}$,

[chemical structures showing two isoxazole-type rings with $R^{25}$ substituents], and In a further embodiment of the aforementioned embodiments is a compound of Formula (IIIe) wherein $R^2$ is —CN.

In a further embodiment of the aforementioned embodiments is a compound of Formula (IIIe) wherein $R^2$ is —C(O)O$R^{25}$. In a further embodiment of the aforementioned embodiments is a compound of Formula (IIIe) wherein $R^2$ is —C(O)O$R^{25}$, and $R^{25}$ is independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IIIe) wherein $R^2$ is —C(O)O$R^{25}$, and $R^{25}$ is independently selected from the group consisting of hydrogen, and optionally substituted $C_1$-$C_6$alkyl. In a further embodiment of the aforementioned embodiments is a compound of Formula (IIIe) wherein $R^2$ is —C(O)O$R^{25}$, and $R^{25}$ is hydrogen. In a further embodiment of the aforementioned embodiments is a compound of Formula (IIIe) wherein $R^2$ is —C(O)O$R^{25}$, and $R^{25}$ is optionally substituted $C_1$-$C_6$alkyl. In a further embodiment of the aforementioned embodiments is a compound of Formula (IIIe) wherein $R^2$ is —C(O)O$R^{25}$, and $R^{25}$ is unsubstituted $C_1$-$C_6$alkyl. In a further embodiment of the aforementioned embodiments is a compound of Formula (IIIe) wherein $R^2$ is —C(O)O$R^{25}$, and $R^{25}$ is methyl. In a further embodiment of the aforementioned embodiments is a compound of Formula (IIIe) wherein $R^2$ is —C(O)O$R^{25}$, and $R^{25}$ is ethyl.

In a further embodiment of the aforementioned embodiments is a compound of Formula (IIIe) wherein $R^2$ is —C(O)N($R^{25}$)$R^{26}$. In a further embodiment of the aforementioned embodiments is a compound of Formula (IIIe) wherein $R^2$ is —C(O)N($R^{25}$)$R^{26}$, and $R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IIIe) wherein $R^2$ is —C(O)N($R^{25}$)$R^{26}$, and $R^{25}$ and $R^{26}$ are each independently selected from the group consisting of hydrogen, and optionally substituted $C_1$-$C_6$alkyl. In a further embodiment of the aforementioned embodiments is a compound of Formula (IIIe) wherein $R^2$ is —C(O)N($R^{25}$)$R^{26}$, and $R^{25}$ and $R^{26}$ are hydrogen. In a further embodiment of the aforementioned embodiments is a compound of Formula (IIIe) wherein $R^2$ is —C(O)N($R^{25}$)$R^{26}$, and $R^{25}$ and $R^{26}$ are each independently optionally substituted $C_1$-$C_6$alkyl. In a further embodiment of the aforementioned embodiments is a compound of Formula (IIIe) wherein $R^2$ is —C(O)N($R^{25}$)$R^{26}$, $R^{25}$ is hydrogen, and $R^{26}$ is optionally substituted $C_1$-$C_6$alkyl. In a further embodiment of the aforementioned embodiments is a compound of Formula (IIIe) wherein $R^2$ is —C(O)N($R^{25}$)$R^{26}$, and $R^{25}$ and $R^{26}$ are each independently unsubstituted $C_1$-$C_6$alkyl. In a further embodiment of the aforementioned embodiments is a compound of Formula (IIIe) wherein $R^2$ is —C(O)N($R^{25}$)$R^{26}$, $R^{25}$ is hydrogen, and $R^{26}$ are methyl. In a further embodiment of the aforementioned embodiments is a compound of Formula (IIIe) wherein $R^2$ is —C(O)N($R^{25}$)$R^{26}$, and $R^{25}$ and $R^{26}$ are methyl. In a further embodiment of the aforementioned embodiments is a compound of Formula (IIIe) wherein $R^2$ is —C(O)N($R^{25}$)$R^{26}$, and $R^{25}$ and $R^{26}$ are ethyl.

In a further embodiment of the aforementioned embodiments is a compound of Formula (IIIe) wherein $R^2$ is

[chemical structure showing an isoxazole ring with $R^{25}$ substituent]

In a further embodiment of the aforementioned embodiments is a compound of Formula (IIIe) wherein $R^2$ is

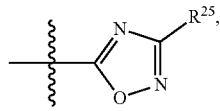

and $R^{25}$ is optionally substituted $C_1$-$C_6$alkyl. In a further embodiment of the aforementioned embodiments is a compound of Formula (IIIe) wherein $R^2$ is

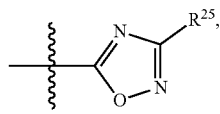

and $R^{25}$ is methyl. In a further embodiment of the aforementioned embodiments is a compound of Formula (IIIe) wherein $R^2$ is

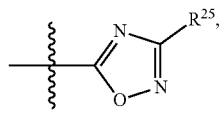

and $R^{25}$ is optionally substituted $C_1$-$C_6$alkyl. In a further embodiment of the aforementioned embodiments is a compound of Formula (IIIe) wherein $R^2$ i

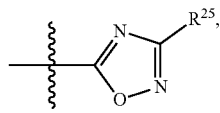

and $R^{25}$ is ethyl.

In a further embodiment of the aforementioned embodiments is a compound of Formula (IIIe) wherein $R^2$ is

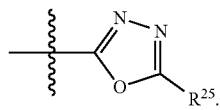

In a further embodiment of the aforementioned embodiments is a compound of Formula (IIIe) wherein $R^2$ is

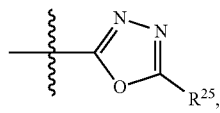

and $R^{25}$ is optionally substituted $C_1$-$C_6$alkyl. In a further embodiment of the aforementioned embodiments is a compound of Formula (IIIe) wherein $R^2$ is

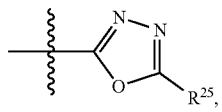

and $R^{25}$ is methyl. In a further embodiment of the aforementioned embodiments is a compound of Formula (IIIe) wherein $R^2$ is

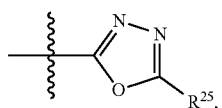

and $R^{25}$ is optionally substituted $C_1$-$C_6$alkyl. In a further embodiment of the aforementioned embodiments is a compound of Formula (IIIe) wherein $R^2$ is

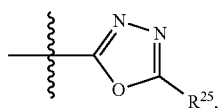

and $R^{25}$ is ethyl.

In a further embodiment of the aforementioned embodiments is a compound of Formula (IIIe) wherein $R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IIIe) wherein $R^1$ is hydrogen. In a further embodiment of the aforementioned embodiments is a compound of Formula (IIIe) wherein $R^1$ is optionally substituted $C_1$-$C_6$alkyl. In a further embodiment of the aforementioned embodiments is a compound of Formula (IIIe) wherein $R^1$ is methyl. In a further embodiment of the aforementioned embodiments is a compound of Formula (IIIe) wherein $R^1$ is optionally substituted $C_2$-$C_6$alkenyl. In a further embodiment of the aforementioned embodiments is a compound of Formula (IIIe) wherein $R^1$ is optionally substituted $C_2$-$C_6$alkynyl.

In a further embodiment of the aforementioned embodiments is a compound of Formula (IIIe) wherein $R^1$ and $R^2$ together with the carbon atoms to which they are attached, form an optionally substituted $C_2$-$C_9$heterocycloalkyl ring or an optionally substituted heteroaryl ring. In a further embodiment of the aforementioned embodiments is a compound of Formula (IIIe) wherein $R^1$ and $R^2$ together with the carbon atoms to which they are attached, form an optionally substituted $C_2$-$C_9$heterocycloalkyl ring. In a further embodiment of the aforementioned embodiments is a compound of Formula (IIIe) wherein $R^1$ and $R^2$ together with the carbon atoms to which they are attached, form an optionally substituted heteroaryl ring.

In a further embodiment of the aforementioned embodiments is a compound of Formula (IIIe) wherein $R^8$ is selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl). In a further embodiment of the aforementioned embodiments is a compound of Formula (IIIe) wherein $R^8$ is selected from the group consisting of hydrogen, and optionally substituted $C_1$-$C_6$alkyl. In a further embodiment of the aforementioned embodiments is a compound of Formula (IIIe) wherein $R^8$ is optionally substituted $C_1$-$C_6$alkyl. In a further embodiment of the aforementioned embodiments is a compound of Formula (IIIe) wherein $R^8$ is methyl. In a further embodiment of the aforementioned embodiments is a compound of Formula (IIIe) wherein $R^8$ is optionally substituted $C_1$-$C_6$alkyl. In a further embodiment of the aforementioned embodiments is a compound of Formula (IIIe) wherein $R^8$ is ethyl. In a further embodiment of the aforementioned embodiments is a compound of Formula (IIIe) wherein $R^8$ is optionally substituted $C_1$-$C_6$alkyl. In a further embodiment of the aforementioned embodiments is a compound of Formula (IIIe) wherein $R^8$ is hydrogen.

In another embodiment of the aforementioned embodiments is a compound of Formula (IIIe) wherein $R^{20}$ is —$R^{34}R^{35}$. In another embodiment of the aforementioned embodiments is a compound of Formula (IIIe) wherein $R^{20}$ is —$R^{34}R^{35}$, and $R^{34}$ is optionally substituted $C_1$-$C_6$alkyl. In another embodiment of the aforementioned embodiments is a compound of Formula (IIIe) wherein $R^{20}$ is —$R^{34}R^{35}$, and $R^{34}$ is optionally substituted $C_3$-$C_{10}$cycloalkyl. In another embodiment of the aforementioned embodiments is a compound of Formula (IIIe) wherein $R^{20}$ is —$R^{34}R^{35}$, and $R^{34}$ is optionally substituted aryl. In another embodiment of the aforementioned embodiments is a compound of Formula (IIIe) wherein $R^{20}$ is —$R^{34}R^{35}$, and $R^{34}$ is optionally substituted —($C_1$-$C_2$alkylene)-(aryl). In another embodiment of the aforementioned embodiments is a compound of Formula (IIIe) wherein $R^{20}$ is —$R^{34}R^{35}$, and $R^{34}$ is optionally substituted heteroaryl. In another embodiment of the aforementioned embodiments is a compound of Formula (IIIe) wherein $R^{20}$ is —$R^{34}R^{35}$, and $R^{34}$ is optionally substituted $C_2$-$C_9$heterocycloalkyl. In another embodiment of the aforementioned embodiments is a compound of Formula (IIIe) wherein $R^{20}$ is —$R^{34}R^{35}$, and $R^{34}$ is optionally substituted —($C_1$-$C_2$alkylene)-(heteroaryl). In another embodiment of the aforementioned embodiments is a compound of Formula (IIIe) wherein $R^{20}$ is —$R^{34}R^{35}$, and $R^{35}$ is —($C_1$-$C_6$alkyl)-$R^{30}$. In another embodiment of the aforementioned embodiments is a compound of Formula (IIIe) wherein $R^{20}$ is —$R^{34}R^{35}$, and $R^{35}$ is —$O(C_2$-$C_6$alkyl)-$R^{30}$. In another embodiment of the aforementioned embodiments is a compound of Formula (IIIe) wherein $R^{20}$ is —$R^{34}R^{35}$, and $R^{35}$ is —$N(R^{12})(C_2$-$C_6$alkyl)-$R^{30}$. In a further embodiment of the aforementioned embodiments is a compound of Formula (IIIe) wherein $R^{30}$ is $R^{36a}$. In a further embodiment of the aforementioned embodiments is a compound of Formula (IIIe) wherein $R^{30}$ is $R^{36b}$. In a further embodiment of the aforementioned embodiments is a compound of Formula (IIIe) wherein $R^{30}$ is $R^{36c}$.

In another embodiment of the aforementioned embodiments is a compound of Formula (IIIe) wherein $R^{20}$ is —$R^{31}$. In a further embodiment of the aforementioned embodiments is a compound of Formula (IIIe) wherein $R^{31}$ is $R^{36a}$. In a further embodiment of the aforementioned embodiments is a compound of Formula (IIIe) wherein $R^{31}$ is $R^{36c}$.

In another embodiment of the aforementioned embodiments is a compound of Formula (IIIe) wherein $R^{36a}$ is

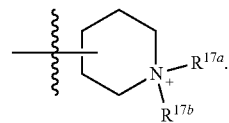

In another embodiment of the aforementioned embodiments is a compound of Formula (IIIe) wherein $R^{36a}$ is

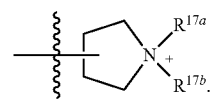

In another embodiment of the aforementioned embodiments is a compound of Formula (IIIe) wherein $R^{36a}$ is

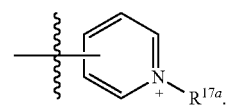

In another embodiment of the aforementioned embodiments is a compound of Formula (IIIe) wherein $R^{36b}$ is

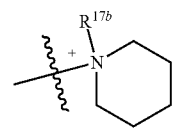

In another embodiment of the aforementioned embodiments is a compound of Formula (IIIe) wherein $R^{36b}$ is

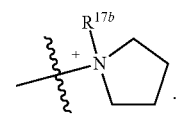

In another embodiment of the aforementioned embodiments is a compound of Formula (IIIe) wherein $R^{36b}$ is

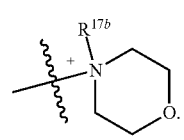

In another embodiment of the aforementioned embodiments is a compound of Formula (IIIe) wherein $R^{36b}$ is

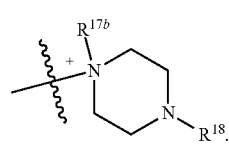

In another embodiment of the aforementioned embodiments is a compound of Formula (IIIe) wherein $R^{36b}$ is

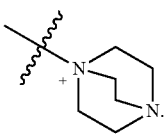

In another embodiment of the aforementioned embodiments is a compound of Formula (IIIe) wherein $R^{36b}$ is

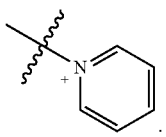

In another embodiment of the aforementioned embodiments is a compound of Formula (IIIe) wherein $R^{36b}$ is

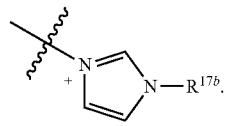

In another embodiment of the aforementioned embodiments is a compound of Formula (IIIe) wherein $R^{36c}$ is

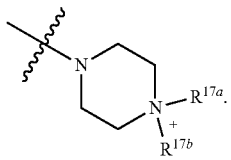

In another embodiment is a compound of Formula (IIIe) wherein $R^{36c}$ is

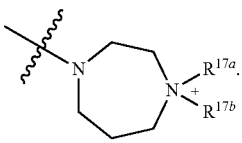

In a further embodiment of the aforementioned embodiments is a compound of Formula (IIIe) wherein $R^{17a}$ is methyl. In a further embodiment of the aforementioned embodiments is a compound of Formula (IIIe) wherein $R^{17a}$ is ethyl. In a further embodiment of the aforementioned embodiments is a compound of Formula (IIIe) wherein $R^{17b}$ is methyl optionally substituted with phenyl, —C(=O)OH or —S(=O)$_2$OH. In a further embodiment of the aforementioned embodiments is a compound of Formula (IIIe) wherein $R^{17a}$ is ethyl optionally substituted with phenyl, —C(=O)OH or —S(=O)$_2$OH.

In another embodiment of the aforementioned embodiments is a compound of Formula (IIIe) wherein n is 0. In another embodiment of the aforementioned embodiments is a compound of Formula (IIIe) wherein n is 1. In another embodiment of the aforementioned embodiments is a compound of Formula (IIIe) wherein n is 1 and $R^{11}$ is $C_1$-$C_6$alkyl. In another embodiment of the aforementioned embodiments is a compound of Formula (IIIe) wherein n is 1 and $R^{11}$ is $C_1$-$C_6$haloalkyl.

In some embodiments provided herein, the compound of Formula (III) has the structure of Formula (IIIf), or a pharmaceutically acceptable salt or solvate thereof:

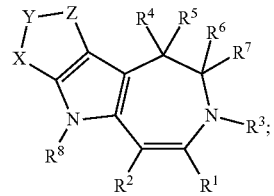

Formula (IIIf)

wherein:

—X—Y—Z— is selected from

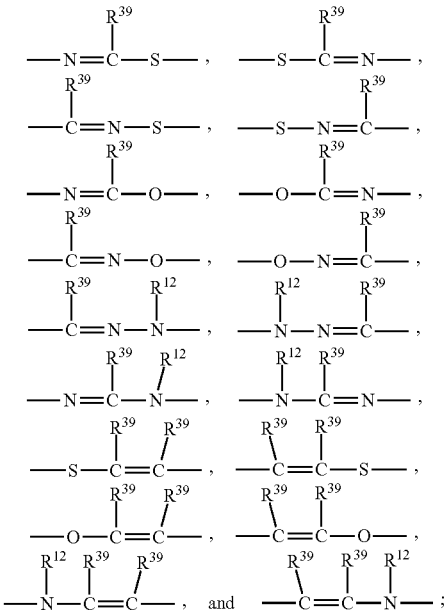

$R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$—$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R^2$ is selected from the group consisting of —CN, —C(=O)O$R^{25}$, —C(=O)N($R^{25}$)$R^{26}$,

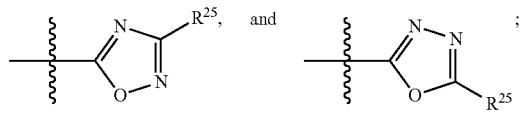

or $R^1$ and $R^2$ together with the carbon atoms to which they are attached, form an optionally substituted $C_2$-$C_9$heterocycloalkyl ring or an optionally substituted heteroaryl ring;

$R^3$ is —C(=O)$R^{20}$ or —S(=O)$_2R^{20}$;

$R^4$ and $R^5$ are each independently selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl; or $R^4$ and $R^5$ together with the carbon atom to which they are attached, form an optionally substituted $C_3$-$C_6$cycloalkyl ring or an optionally substituted $C_2$-$C_7$heterocycloalkyl ring;

$R^6$ is selected from the group consisting of hydrogen, halogen, optionally substituted $C_1$-$C_6$alkyl, optionally substituted $C_2$-$C_6$alkenyl, optionally substituted $C_2$-$C_6$alkynyl, and —C(=O)N($R^{27}$)$R^{28}$;

$R^7$ is selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl;

$R^8$ is selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl);

$R^9$ and $R^{10}$ together with the carbon atoms to which they are attached, form a phenyl ring substituted with $(R^{11})_n$; or $R^9$ and $R^{10}$ together with the carbon atoms to which they are attached, form a nitrogen containing 6-membered heteroaryl ring substituted with $(R^{11})_n$; or $R^9$ and $R^{10}$ together with the carbon atoms to which they are attached, form a 5-membered heteroaryl ring substituted with $(R^{39})_p$ and $(R^{12})_q$;

each $R^{11}$ is independently selected from the group consisting of halogen, —CN, amino, alkylamino, $C_1$-$C_6$alkyl, $C_1$-$C_6$haloalkyl, $C_1$-$C_6$alkoxy, $C_1$-$C_6$haloalkoxy, $C_3$-$C_8$cycloalkyl, $C_2$-$C_9$heterocycloalkyl, aryl, heteroaryl, —C(=O)O$R^{12}$, —C(=O)N($R^{13}$)$R^{14}$;

$R^{12}$ is selected from the group consisting of hydrogen and $C_1$-$C_6$alkyl;

each $R^{13}$ and $R^{14}$ are each independently selected from the group consisting of hydrogen and $C_1$-$C_6$alkyl; or $R^{13}$ and $R^{14}$ together with the nitrogen atom to which they are attached, form an optionally substituted $C_2$-$C_9$heterocycloalkyl ring;

$R^{39}$ is selected from the group consisting of hydrogen, halogen, —CN, amino, alkylamino, $C_1$-$C_6$alkyl, $C_1$-$C_6$haloalkyl, $C_1$-$C_6$alkoxy, $C_1$-$C_6$haloalkoxy, $C_3$-$C_8$cycloalkyl, $C_2$-$C_9$heterocycloalkyl, aryl, heteroaryl, —C(=O)O$R^{12}$, —C(=O)N($R^{13}$)$R^{14}$;

n is 0, 1, 2, or 3;
p is 0 or 1;
q is 0 or 1;

$R^{20}$ is selected from the group consisting of —$R^{34}R^{35}$ or —$R^{31}$;

$R^{34}$ is selected from the group consisting of optionally substituted $C_1$-$C_6$alkyl, optionally substituted $C_3$-$C_{10}$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl);

$R^{35}$ is —($C_1$-$C_6$alkyl)-$R^{30}$, —O($C_2$-$C_6$alkyl)-$R^{30}$, or —N($R^{12}$)($C_2$-$C_6$alkyl)-$R^{30}$;

$R^{30}$ is $R^{36a}$, $R^{36b}$, or $R^{36c}$;

$R^{31}$ is $R^{36a}$ or $R^{36c}$;

$R^{36a}$ is

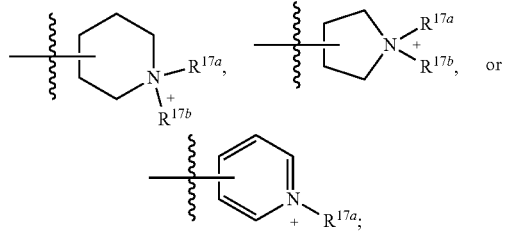

$R^{36b}$ is

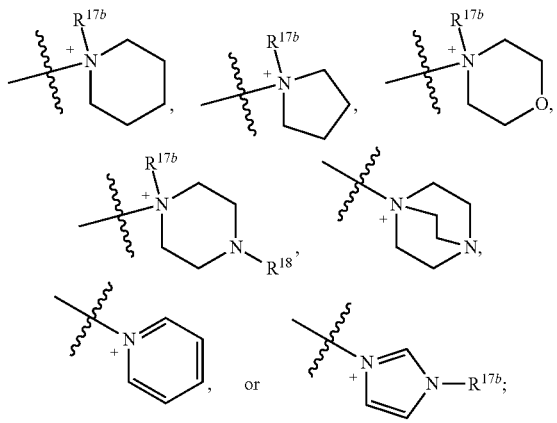

$R^{36c}$ is

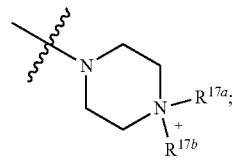

$R^{17a}$ is $C_1$-$C_6$alkyl;
$R^{17b}$ is $C_1$-$C_6$alkyl optionally substituted with phenyl, —C(=O)OH or —S(=O)$_2$OH;
$R^{18}$ is hydrogen, —OH, —($C_0$-$C_6$alkyl)-C(=O)OH, or $C_1$-$C_6$alkyl;

$R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); and $R^{27}$ and $R^{28}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted C$_2$-C$_9$heterocycloalkyl, optionally substituted heteroaryl, and optionally substituted —(C$_1$-C$_2$alkylene)-(heteroaryl); or R$^{27}$ and R$^{28}$ together with the nitrogen atom to which they are attached, form an optionally substituted C$_2$-C$_9$heterocycloalkyl ring.

In one embodiment is a compound of Formula (IIIf) wherein —X—Y—Z— is

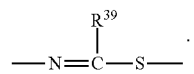

In another embodiment is a compound of Formula (IIIf) wherein —X—Y—Z— is

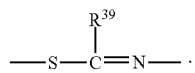

In another embodiment is a compound of Formula (IIIf) wherein —X—Y—Z— is

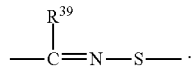

In another embodiment is a compound of Formula (IIIf) wherein —X—Y—Z— is

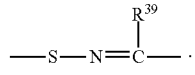

In another embodiment is a compound of Formula (IIIf) wherein —X—Y—Z— is

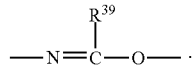

In another embodiment is a compound of Formula (IIIf) wherein —X—Y—Z— is

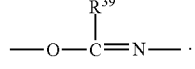

In another embodiment is a compound of Formula (IIIf) wherein —X—Y—Z— is

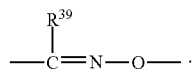

In another embodiment is a compound of Formula (IIIf) wherein —X—Y—Z— is

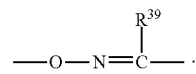

In another embodiment is a compound of Formula (IIIf) wherein —X—Y—Z— is

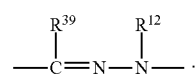

In another embodiment is a compound of Formula (IIIf) wherein —X—Y—Z— is

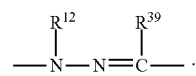

In another embodiment is a compound of Formula (IIIf) wherein —X—Y—Z— is

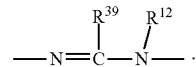

In another embodiment is a compound of Formula (IIIf) wherein —X—Y—Z— is

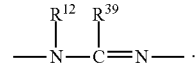

In another embodiment is a compound of Formula (IIIf) wherein —X—Y—Z— is

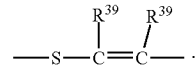

In another embodiment is a compound of Formula (IIIf) wherein —X—Y—Z— is

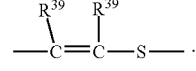

In another embodiment is a compound of Formula (IIIf) wherein —X—Y—Z— is

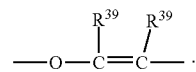

In another embodiment is a compound of Formula (IIIf) wherein —X—Y—Z— is

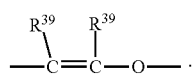

In another embodiment is a compound of Formula (IIIf) wherein —X—Y—Z— is

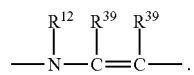

In another embodiment is a compound of Formula (IIIf) wherein —X—Y—Z— is

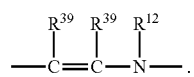

In one embodiment is a compound of Formula (IIIf) wherein $R^4$ and $R^5$ are each independently selected from the group consisting of hydrogen, halogen, and optionally substituted $C_1$-$C_6$alkyl. In another embodiment is a compound of Formula (IIIf) wherein $R^4$ and $R^5$ are each independently selected from the group consisting of hydrogen and optionally substituted $C_1$-$C_6$alkyl. In another embodiment is a compound of Formula (IIIf) wherein $R^4$ and $R^5$ are each hydrogen. In another embodiment is a compound of Formula (IIIf) wherein $R^4$ and $R^5$ are each independently optionally substituted $C_1$-$C_6$alkyl. In another embodiment is a compound of Formula (IIIf) wherein $R^4$ and $R^5$ are each methyl. In another embodiment is a compound of Formula (IIIf) wherein $R^4$ and $R^5$ form an optionally substituted $C_3$-$C_6$cycloalkyl ring or an optionally substituted $C_2$-$C_7$heterocycloalkyl ring. In some embodiments is a compound of Formula (IIIf) wherein $R^4$ and $R^5$ form an optionally substituted $C_3$-$C_6$cycloalkyl ring. In some embodiments is a compound of Formula (IIIf) wherein $R^4$ and $R^5$ form an optionally substituted $C_2$-$C_7$heterocycloalkyl ring.

In another embodiment is a compound of Formula (IIIf) wherein $R^6$ and $R^7$ are each independently selected from the group consisting of hydrogen, halogen, and optionally substituted $C_1$-$C_6$alkyl. In another embodiment is a compound of Formula (IIIf) wherein $R^6$ and $R^7$ are each independently selected from the group consisting of hydrogen and optionally substituted $C_1$-$C_6$alkyl. In another embodiment is a compound of Formula (IIIf) wherein $R^6$ and $R^7$ are each independently optionally substituted $C_1$-$C_6$alkyl. In another embodiment is a compound of Formula (IIIf) wherein $R^6$ and $R^7$ are each methyl. In another embodiment is a compound of Formula (IIIf) wherein $R^6$ and $R^7$ are each hydrogen.

In another embodiment is a compound of Formula (IIIf) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted aryl. In another embodiment is a compound of Formula (IIIf) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted heteroaryl. In another embodiment is a compound of Formula (IIIf) wherein $R^6$ and $R^7$ are hydrogen, $R^4$ and $R^5$ are methyl, $R^3$ is —C(O)$R^{20}$, and $R^{20}$ is optionally substituted aryl. In another embodiment is a compound of Formula (IIIf) wherein $R^6$ and $R^7$ are hydrogen, $R^4$ and $R^5$ are methyl, $R^3$ is —C(O)$R^{20}$, and $R^{20}$ is optionally substituted heteroaryl.

In another embodiment is a compound of Formula (IIIf) wherein $R^6$ and $R^7$ are hydrogen, $R^4$ and $R^5$ are independently optionally substituted $C_1$-$C_6$alkyl, $R^3$ is —S(O)$_2$$R^{20}$, and $R^{20}$ is optionally substituted aryl. In another embodiment is a compound of Formula (IIIf) wherein $R^6$ and $R^7$ are hydrogen, $R^4$ and $R^5$ are independently optionally substituted $C_1$-$C_6$alkyl, $R^3$ is —S(O)$_2$$R^{20}$, and $R^{20}$ is optionally substituted heteroaryl. In another embodiment is a compound of Formula (IIIf) wherein $R^6$ and $R^7$ are hydrogen, $R^4$ and $R^5$ are methyl, $R^3$ is —S(O)$_2$$R^{20}$, and $R^{20}$ is optionally substituted aryl. In another embodiment is a compound of Formula (IIIf) wherein $R^6$ and $R^7$ are hydrogen, $R^4$ and $R^5$ are methyl, $R^3$ is —S(O)$_2$$R^{20}$, and $R^{20}$ is optionally substituted heteroaryl.

In a further embodiment of the aforementioned embodiments is a compound of Formula (IIIf) wherein $R^2$ is selected from the group consisting of —CN, —C(O)O$R^{25}$, —C(O)N($R^{25}$)$R^{26}$,

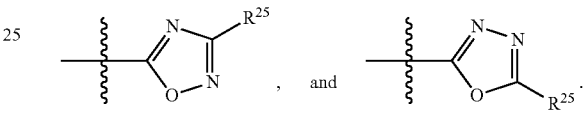

In a further embodiment of the aforementioned embodiments is a compound of Formula (IIIf) wherein $R^2$ is —CN.

In a further embodiment of the aforementioned embodiments is a compound of Formula (IIIf) wherein $R^2$ is —C(O)O$R^{25}$. In a further embodiment of the aforementioned embodiments is a compound of Formula (IIIf) wherein $R^2$ is —C(O)O$R^{25}$, and $R^{25}$ is independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IIIf) wherein $R^2$ is —C(O)O$R^{25}$, and $R^{25}$ is independently selected from the group consisting of hydrogen, and optionally substituted $C_1$-$C_6$alkyl. In a further embodiment of the aforementioned embodiments is a compound of Formula (IIIf) wherein $R^2$ is —C(O)O$R^{25}$, and $R^{25}$ is hydrogen. In a further embodiment of the aforementioned embodiments is a compound of Formula (IIIf) wherein $R^2$ is —C(O)O$R^{25}$, and $R^{25}$ is optionally substituted $C_1$-$C_6$alkyl. In a further embodiment of the aforementioned embodiments is a compound of Formula (IIIf) wherein $R^2$ is —C(O)O$R^{25}$, and $R^{25}$ is unsubstituted $C_1$-$C_6$alkyl. In a further embodiment of the aforementioned embodiments is a compound of Formula (IIIf) wherein $R^2$ is —C(O)O$R^{25}$, and $R^{25}$ is methyl. In a further embodiment of the aforementioned embodiments is a compound of Formula (IIIf) wherein $R^2$ is —C(O)O$R^{25}$, and $R^{25}$ is ethyl.

In a further embodiment of the aforementioned embodiments is a compound of Formula (IIIf) wherein $R^2$ is —C(O)N($R^{25}$)$R^{26}$. In a further embodiment of the aforementioned embodiments is a compound of Formula (IIIf) wherein $R^2$ is —C(O)N($R^{25}$)$R^{26}$, and $R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl). In a further embodiment of the aforementioned embodiments is a compound of Formula (IIIf) wherein R$^2$ is —C(O)N(R$^{25}$)R$^{26}$, and R$^{25}$ and R$^{26}$ are each independently selected from the group consisting of hydrogen, and optionally substituted C$_1$-C$_6$alkyl. In a further embodiment of the aforementioned embodiments is a compound of Formula (IIIf) wherein R$^2$ is —C(O)N(R$^{25}$)R$^{26}$, and R$^{25}$ and R$^{26}$ are hydrogen. In a further embodiment of the aforementioned embodiments is a compound of Formula (IIIf) wherein R$^2$ is —C(O)N(R$^{25}$)R$^{26}$, and R$^{25}$ and R$^{26}$ are each independently optionally substituted C$_1$-C$_6$alkyl. In a further embodiment of the aforementioned embodiments is a compound of Formula (IIIf) wherein R$^2$ is —C(O)N(R$^{25}$)R$^{26}$, R$^{25}$ is hydrogen, and R$^{26}$ is optionally substituted C$_1$-C$_6$alkyl. In a further embodiment of the aforementioned embodiments is a compound of Formula (IIIf) wherein R$^2$ is —C(O)N(R$^{25}$)R$^{26}$, and R$^{25}$ and R$^{26}$ are each independently unsubstituted C$_1$-C$_6$alkyl. In a further embodiment of the aforementioned embodiments is a compound of Formula (IIIf) wherein R$^2$ is —C(O)N(R$^{25}$)R$^{26}$, R$^{25}$ is hydrogen, and R$^{26}$ is methyl. In a further embodiment of the aforementioned embodiments is a compound of Formula (IIIf) wherein R$^2$ is —C(O)N(R$^{25}$)R$^{26}$, and R$^{25}$ and R$^{26}$ are methyl. In a further embodiment of the aforementioned embodiments is a compound of Formula (IIIf) wherein R$^2$ is —C(O)N(R$^{25}$)R$^{26}$, and R$^{25}$ and R$^{26}$ are ethyl.

In a further embodiment of the aforementioned embodiments is a compound of Formula (IIIf) wherein R$^2$ is

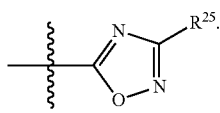

In a further embodiment of the aforementioned embodiments is a compound of Formula (IIIf) wherein R$^2$ is

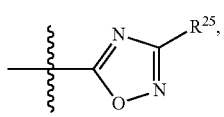

and R$^{25}$ is optionally substituted C$_1$-C$_6$alkyl. In a further embodiment of the aforementioned embodiments is a compound of Formula (IIIf) wherein R$^2$ is

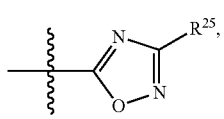

and R$^{25}$ is methyl. In a further embodiment of the aforementioned embodiments is a compound of Formula (IIIf) wherein R$^2$ is

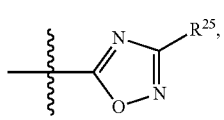

and R$^{25}$ is optionally substituted C$_1$-C$_6$alkyl. In a further embodiment of the aforementioned embodiments is a compound of Formula (IIIf) wherein R$^2$ is

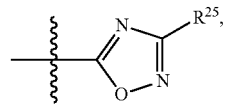

and R$^{25}$ is ethyl.

In a further embodiment of the aforementioned embodiments is a compound of Formula (IIIf) wherein R$^2$ is

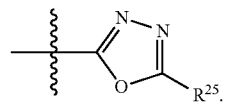

In a further embodiment of the aforementioned embodiments is a compound of Formula (IIIf) wherein R$^2$ is

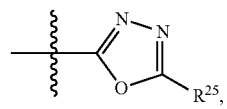

and R$^{25}$ is optionally substituted C$_1$-C$_6$alkyl. In a further embodiment of the aforementioned embodiments is a compound of Formula (IIIf) wherein R$^2$ is

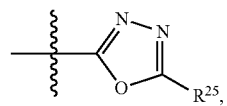

and R$^{25}$ is methyl. In a further embodiment of the aforementioned embodiments is a compound of Formula (IIIf) wherein R$^2$ is

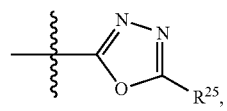

and R$^{25}$ is optionally substituted C$_1$-C$_6$alkyl. In a further embodiment of the aforementioned embodiments is a compound of Formula (IIIf) wherein R$^2$ is

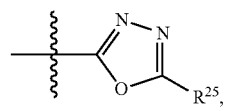

and R$^{25}$ is ethyl.

In a further embodiment of the aforementioned embodiments is a compound of Formula (IIIf) wherein R$^1$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IIIf) wherein $R^1$ is hydrogen. In a further embodiment of the aforementioned embodiments is a compound of Formula (IIIf) wherein $R^1$ is optionally substituted $C_1$-$C_6$alkyl. In a further embodiment of the aforementioned embodiments is a compound of Formula (IIIf) wherein $R^1$ is methyl. In a further embodiment of the aforementioned embodiments is a compound of Formula (IIIf) wherein $R^1$ is optionally substituted $C_2$-$C_6$alkenyl. In a further embodiment of the aforementioned embodiments is a compound of Formula (IIIf) wherein $R^1$ is optionally substituted $C_2$-$C_6$alkynyl.

In a further embodiment of the aforementioned embodiments is a compound of Formula (IIIf) wherein $R^1$ and $R^2$ together with the carbon atoms to which they are attached, form an optionally substituted $C_2$-$C_9$heterocycloalkyl ring or an optionally substituted heteroaryl ring. In a further embodiment of the aforementioned embodiments is a compound of Formula (IIIf) wherein $R^1$ and $R^2$ together with the carbon atoms to which they are attached, form an optionally substituted $C_2$-$C_9$heterocycloalkyl ring. In a further embodiment of the aforementioned embodiments is a compound of Formula (IIIf) wherein $R^1$ and $R^2$ together with the carbon atoms to which they are attached, form an optionally substituted heteroaryl ring.

In a further embodiment of the aforementioned embodiments is a compound of Formula (IIIf) wherein $R^8$ is selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl). In a further embodiment of the aforementioned embodiments is a compound of Formula (IIIf) wherein $R^8$ is selected from the group consisting of hydrogen, and optionally substituted $C_1$-$C_6$alkyl. In a further embodiment of the aforementioned embodiments is a compound of Formula (IIIf) wherein $R^8$ is optionally substituted $C_1$-$C_6$alkyl. In a further embodiment of the aforementioned embodiments is a compound of Formula (IIIf) wherein $R^8$ is methyl. In a further embodiment of the aforementioned embodiments is a compound of Formula (IIIf) wherein $R^8$ is optionally substituted $C_1$-$C_6$alkyl. In a further embodiment of the aforementioned embodiments is a compound of Formula (IIIf) wherein $R^8$ is ethyl. In a further embodiment of the aforementioned embodiments is a compound of Formula (IIIf) wherein $R^8$ is optionally substituted $C_1$-$C_6$alkyl. In a further embodiment of the aforementioned embodiments is a compound of Formula (IIIf) wherein $R^8$ is hydrogen.

In another embodiment of the aforementioned embodiments is a compound of Formula (IIIf) wherein $R^{20}$ is —$R^{34}R^{35}$. In another embodiment of the aforementioned embodiments is a compound of Formula (IIIf) wherein $R^{20}$ is —$R^{34}R^{35}$, and $R^{34}$ is optionally substituted $C_1$-$C_6$alkyl. In another embodiment of the aforementioned embodiments is a compound of Formula (IIIf) wherein $R^{20}$ is —$R^{34}R^{35}$, and $R^{34}$ is optionally substituted $C_3$-$C_{10}$cycloalkyl. In another embodiment of the aforementioned embodiments is a compound of Formula (IIIf) wherein $R^{20}$ is —$R^{34}R^{35}$, and $R^{34}$ is optionally substituted aryl. In another embodiment of the aforementioned embodiments is a compound of Formula (IIIf) wherein $R^{20}$ is —$R^{34}R^{35}$, and $R^{34}$ is optionally substituted —($C_1$-$C_2$alkylene)-(aryl). In another embodiment of the aforementioned embodiments is a compound of Formula (IIIf) wherein $R^{20}$ is —$R^{34}R^{35}$, and $R^{34}$ is optionally substituted heteroaryl. In another embodiment of the aforementioned embodiments is a compound of Formula (IIIf) wherein $R^{20}$ is —$R^{34}R^{35}$, and $R^{34}$ is optionally substituted $C_2$-$C_9$heterocycloalkyl. In another embodiment of the aforementioned embodiments is a compound of Formula (IIIf) wherein $R^{20}$ is —$R^{34}R^{35}$, and $R^{34}$ is optionally substituted —($C_1$-$C_2$alkylene)-(heteroaryl). In another embodiment of the aforementioned embodiments is a compound of Formula (IIIf) wherein $R^{20}$ is —$R^{34}R^{35}$, and $R^{35}$ is —($C_1$-$C_6$alkyl)-$R^{30}$. In another embodiment of the aforementioned embodiments is a compound of Formula (IIIf) wherein $R^{20}$ is —$R^{34}R^{35}$, and $R^{35}$ is —O($C_2$-$C_6$alkyl)-$R^{30}$. In another embodiment of the aforementioned embodiments is a compound of Formula (IIIf) wherein $R^{20}$ is —$R^{34}R^{35}$, and $R^{35}$ is —N($R^{12}$)($C_2$-$C_6$alkyl)-$R^{30}$. In a further embodiment of the aforementioned embodiments is a compound of Formula (IIIf) wherein $R^{30}$ is $R^{36a}$. In a further embodiment of the aforementioned embodiments is a compound of Formula (IIIf) wherein $R^{30}$ is $R^{36b}$. In a further embodiment of the aforementioned embodiments is a compound of Formula (IIIf) wherein $R^{30}$ is $R^{36c}$.

In another embodiment of the aforementioned embodiments is a compound of Formula (IIIf) wherein $R^{20}$ is —$R^{31}$. In a further embodiment of the aforementioned embodiments is a compound of Formula (IIIf) wherein $R^{31}$ is $R^{36a}$. In a further embodiment of the aforementioned embodiments is a compound of Formula (IIIf) wherein $R^{31}$ is $R^{36c}$.

In another embodiment of the aforementioned embodiments is a compound of Formula (IIIf) wherein $R^{36a}$ is

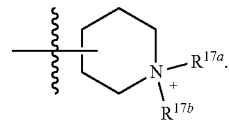

In another embodiment of the aforementioned embodiments is a compound of Formula (IIIf) wherein $R^{36a}$ is

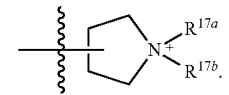

In another embodiment of the aforementioned embodiments is a compound of Formula (IIIf) wherein $R^{36a}$ is

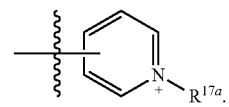

In another embodiment of the aforementioned embodiments is a compound of Formula (IIIf) wherein $R^{36b}$ is

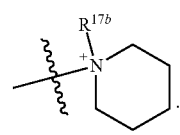

In another embodiment of the aforementioned embodiments is a compound of Formula (IIIf) wherein $R^{36b}$ is

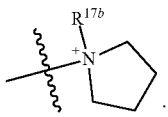

In another embodiment of the aforementioned embodiments is a compound of Formula (IIIf) wherein $R^{36b}$ is

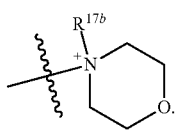

In another embodiment of the aforementioned embodiments is a compound of Formula (IIIf) wherein $R^{36b}$ is

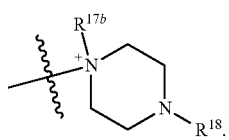

In another embodiment of the aforementioned embodiments is a compound of Formula (IIIf) wherein $R^{36b}$ is

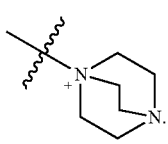

In another embodiment of the aforementioned embodiments is a compound of Formula (IIIf) wherein $R^{36b}$ is

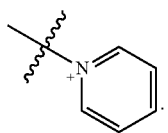

In another embodiment of the aforementioned embodiments is a compound of Formula (IIIf) wherein $R^{36b}$ is

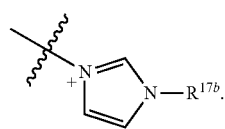

in another embodiment of the aforementioned embodiments is a compound of Formula (IIIf) wherein $R^{36c}$ is

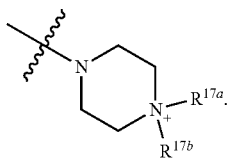

In another embodiment is a compound of Formula (IIIf) wherein $R^{36c}$ is

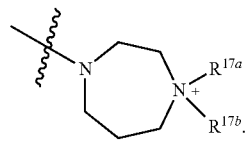

In a further embodiment of the aforementioned embodiments is a compound of Formula (IIIf) wherein $R^{17a}$ is methyl. In a further embodiment of the aforementioned embodiments is a compound of Formula (IIIf) wherein $R^{17a}$ is ethyl. In a further embodiment of the aforementioned embodiments is a compound of Formula (IIIf) wherein $R^{17b}$ is methyl optionally substituted with phenyl, —C(=O)OH or —S(=O)$_2$OH. In a further embodiment of the aforementioned embodiments is a compound of Formula (IIIf) wherein $R^{17a}$ is ethyl optionally substituted with phenyl, —C(=O)OH or —S(=O)$_2$OH.

In yet another aspect, provided herein is a compound having the structure of Formula (IV), or a pharmaceutically acceptable salt or solvate thereof:

Formula (IV)

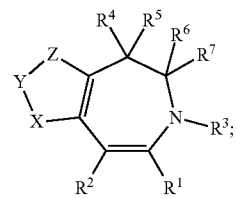

wherein:
—X—Y—Z— is selected from

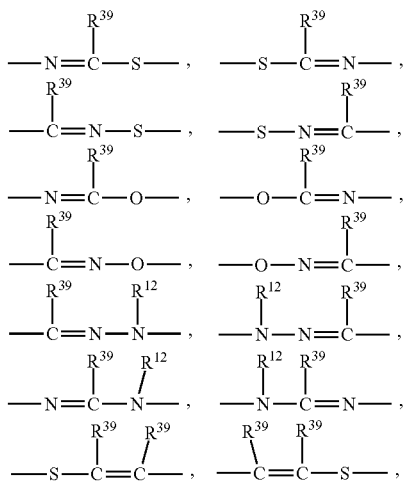

-continued

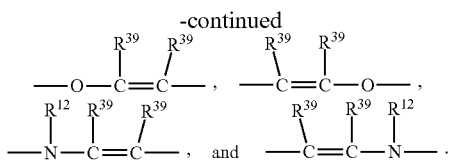

R¹ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

R² is selected from the group consisting of —CN, —C(=O)OR²⁵, —C(=O)N(R²⁵)R²⁶,

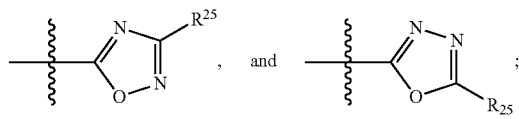

or R¹ and R² together with the carbon atoms to which they are attached, form an optionally substituted $C_2$-$C_9$heterocycloalkyl ring or an optionally substituted heteroaryl ring;

R³ is —C(=O)R²⁰ or —S(=O)₂R²⁰;

R⁴ and R⁵ are each independently selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl; or R⁴ and R⁵ together with the carbon atom to which they are attached, form an optionally substituted $C_3$-$C_6$cycloalkyl ring or an optionally substituted $C_2$-$C_7$heterocycloalkyl ring;

R⁶ is selected from the group consisting of hydrogen, halogen, optionally substituted $C_1$-$C_6$alkyl, optionally substituted $C_2$-$C_6$alkenyl, optionally substituted $C_2$-$C_6$alkynyl, and —C(=O)N(R²⁷)R²⁸;

R⁷ is selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl;

each R¹² is independently selected from the group consisting of hydrogen and $C_1$-$C_6$alkyl;

each R¹³ and R¹⁴ are each independently selected from the group consisting of hydrogen and $C_1$-$C_6$alkyl; or R¹³ and R¹⁴ together with the nitrogen atom to which they are attached, form an optionally substituted $C_2$-$C_9$heterocycloalkyl ring;

each R³⁹ is independently selected from the group consisting of hydrogen, halogen, —CN, amino, alkylamino, $C_1$-$C_6$alkyl, $C_1$-$C_6$haloalkyl, $C_1$-$C_6$alkoxy, $C_1$-$C_6$haloalkoxy, $C_3$-$C_8$cycloalkyl, $C_2$-$C_9$heterocycloalkyl, aryl, heteroaryl, —C(=O) OR¹², and —C(=O)N(R¹³)R¹⁴;

R²⁰ is selected from the group consisting of —R³⁴R³⁵ or —R³¹;

R³⁴ is selected from the group consisting of optionally substituted $C_1$-$C_6$alkyl, optionally substituted $C_3$-$C_{10}$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl);

R³⁵ is —($C_1$-$C_6$alkyl)-R³⁰, —O($C_2$-$C_6$alkyl)-R³⁰, or —N(R¹²)($C_2$-$C_6$alkyl)-R³⁰;

R³⁰ is R³⁶ᵃ, R³⁶ᵇ, or R³⁶ᶜ;

R³¹ is R³⁶ᵃ or R³⁶ᶜ;

R³⁶ᵃ is

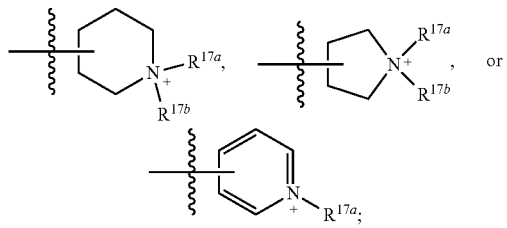

R³⁶ᵇ is

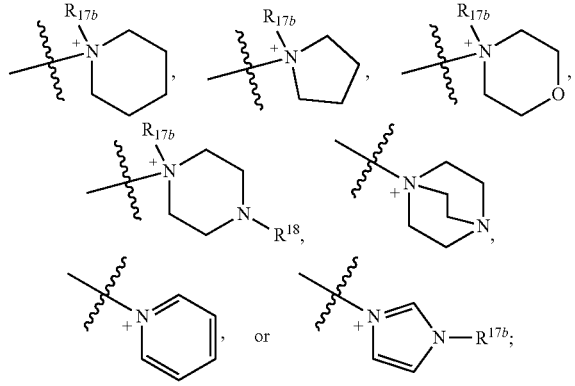

R³⁶ᶜ is

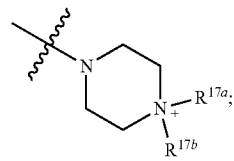

R¹⁷ᵃ is $C_1$-$C_6$alkyl;

R¹⁷ᵇ is $C_1$-$C_6$alkyl optionally substituted with phenyl, —C(=O)OH or —S(=O)₂OH;

R¹⁸ is hydrogen, —OH, —($C_0$-$C_6$alkyl)-C(=O)OH, or $C_1$-$C_6$alkyl;

R²⁵ and R²⁶ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); and R²⁷ and R²⁸ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{27}$ and $R^{28}$ together with the nitrogen atom to which they are attached, form an optionally substituted $C_2$-$C_9$heterocycloalkyl ring.

In one embodiment is a compound of Formula (IV) wherein —X—Y—Z— is

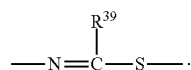

In another embodiment is a compound of Formula (IV) wherein —X—Y—Z— is

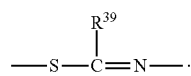

In another embodiment is a compound of Formula (IV) wherein —X—Y—Z— is

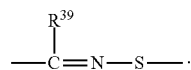

In another embodiment is a compound of Formula (IV) wherein —X—Y—Z— is

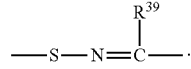

In another embodiment is a compound of Formula (IV) wherein —X—Y—Z— is

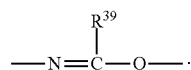

In another embodiment is a compound of Formula (IV) wherein —X—Y—Z— is

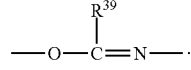

In another embodiment is a compound of Formula (IV) wherein —X—Y—Z— is

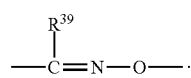

In another embodiment is a compound of Formula (IV) wherein —X—Y—Z— is

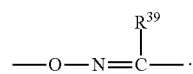

In another embodiment is a compound of Formula (IV) wherein —X—Y—Z— is

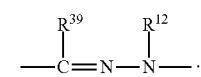

In another embodiment is a compound of Formula (IV) wherein —X—Y—Z— is

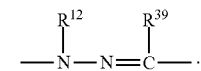

In another embodiment is a compound of Formula (IV) wherein —X—Y—Z— is

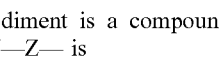

In another embodiment is a compound of Formula (IV) wherein —X—Y—Z— is

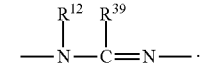

In another embodiment is a compound of Formula (IV) wherein —X—Y—Z— is

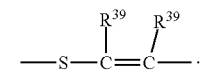

In another embodiment is a compound of Formula (IV) wherein —X—Y—Z— is

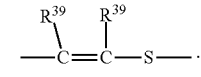

In another embodiment is a compound of Formula (IV) wherein —X—Y—Z— is

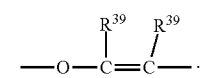

In another embodiment is a compound of Formula (IV) wherein —X—Y—Z— is

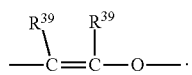

In another embodiment is a compound of Formula (IV) wherein —X—Y—Z— is

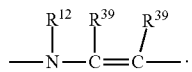

In another embodiment is a compound of Formula (IV) wherein —X—Y—Z— is

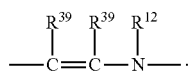

In another embodiment is a compound of Formula (IV) wherein $R^4$ and $R^5$ are each independently selected from the group consisting of hydrogen, halogen, and optionally substituted $C_1$-$C_6$alkyl. In another embodiment is a compound of Formula (IV) wherein $R^4$ and $R^5$ are each independently selected from the group consisting of hydrogen and optionally substituted $C_1$-$C_6$alkyl. In another embodiment is a compound of Formula (IV) wherein $R^4$ and $R^5$ are each hydrogen. In another embodiment is a compound of Formula (IV) wherein $R^4$ and $R^5$ are each independently optionally substituted $C_1$-$C_6$alkyl. In another embodiment is a compound of Formula (IV) wherein $R^4$ and $R^5$ are each methyl. In another embodiment is a compound of Formula (IV) wherein $R^4$ and $R^5$ form an optionally substituted $C_3$-$C_6$cycloalkyl ring or an optionally substituted $C_2$-$C_7$heterocycloalkyl ring. In some embodiments is a compound of Formula (IV) wherein $R^4$ and $R^5$ form an optionally substituted $C_3$-$C_6$cycloalkyl ring. In some embodiments is a compound of Formula (IV) wherein $R^4$ and $R^5$ form an optionally substituted $C_2$-$C_7$heterocycloalkyl ring.

In another embodiment is a compound of Formula (IV) wherein $R^6$ and $R^7$ are each independently selected from the group consisting of hydrogen, halogen, and optionally substituted $C_1$-$C_6$alkyl. In another embodiment is a compound of Formula (IV) wherein $R^6$ and $R^7$ are each independently selected from the group consisting of hydrogen and optionally substituted $C_1$-$C_6$alkyl. In another embodiment is a compound of Formula (IV) wherein $R^6$ and $R^7$ are each independently optionally substituted $C_1$-$C_6$alkyl. In another embodiment is a compound of Formula (IV) wherein $R^6$ and $R^7$ are each methyl. In another embodiment is a compound of Formula (IV) wherein $R^6$ and $R^7$ are each hydrogen.

In another embodiment is a compound of Formula (IV) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted aryl. In another embodiment is a compound of Formula (IV) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted heteroaryl. In another embodiment is a compound of Formula (IV) wherein $R^6$ and $R^7$ are hydrogen, $R^4$ and $R^5$ are methyl, $R^3$ is —C(O)$R^{20}$, and $R^{20}$ is optionally substituted aryl. In another embodiment is a compound of Formula (IV) wherein $R^6$ and $R^7$ are hydrogen, $R^4$ and $R^5$ are methyl, $R^3$ is —C(O)$R^{20}$, and $R^{20}$ is optionally substituted heteroaryl.

In another embodiment is a compound of Formula (IV) wherein $R^6$ and $R^7$ are hydrogen, $R^4$ and $R^5$ are independently optionally substituted $C_1$-$C_6$alkyl, $R^3$ is —S(O)$_2R^{20}$, and $R^{20}$ is optionally substituted aryl. In another embodiment is a compound of Formula (IV) wherein $R^6$ and $R^7$ are hydrogen, $R^4$ and $R^5$ are independently optionally substituted $C_1$-$C_6$alkyl, $R^3$ is —S(O)$_2R^{20}$, and $R^{20}$ is optionally substituted heteroaryl. In another embodiment is a compound of Formula (IV) wherein $R^6$ and $R^7$ are hydrogen, $R^4$ and $R^5$ are methyl, $R^3$ is —S(O)$_2R^{20}$, and $R^{20}$ is optionally substituted aryl. In another embodiment is a compound of Formula (IV) wherein $R^6$ and $R^7$ are hydrogen, $R^4$ and $R^5$ are methyl, $R^3$ is —S(O)$_2R^{20}$, and $R^{20}$ is optionally substituted heteroaryl.

In a further embodiment of the aforementioned embodiments is a compound of Formula (IV) wherein $R^2$ is selected from the group consisting of —CN, —C(O)O$R^{25}$, —C(O)N($R^{25}$)$R^{26}$,

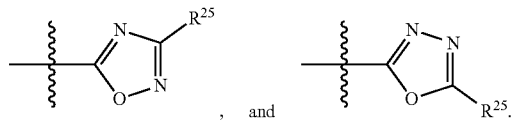

In a further embodiment of the aforementioned embodiments is a compound of Formula (IV) wherein $R^2$ is —CN.

In a further embodiment of the aforementioned embodiments is a compound of Formula (IV) wherein $R^2$ is —C(O)O$R^{25}$. In a further embodiment of the aforementioned embodiments is a compound of Formula (IV) wherein $R^2$ is —C(O)O$R^{25}$, and $R^{25}$ is independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IV) wherein $R^2$ is —C(O)O$R^{25}$, and $R^{25}$ is independently selected from the group consisting of hydrogen, and optionally substituted $C_1$-$C_6$alkyl. In a further embodiment of the aforementioned embodiments is a compound of Formula (IV) wherein $R^2$ is —C(O)O$R^{25}$, and $R^{25}$ is hydrogen. In a further embodiment of the aforementioned embodiments is a compound of Formula (IV) wherein $R^2$ is —C(O)O$R^{25}$, and $R^{25}$ is optionally substituted $C_1$-$C_6$alkyl. In a further embodiment of the aforementioned embodiments is a compound of Formula (IV) wherein $R^2$ is —C(O)O$R^{25}$, and $R^{25}$ is unsubstituted $C_1$-$C_6$alkyl. In a further embodiment of the aforementioned embodiments is a compound of Formula (IV) wherein $R^2$ is —C(O)O$R^{25}$, and $R^{25}$ is methyl. In a further embodiment of the aforementioned embodiments is a compound of Formula (IV) wherein $R^2$ is —C(O)O$R^{25}$, and $R^{25}$ is ethyl.

In a further embodiment of the aforementioned embodiments is a compound of Formula (IV) wherein $R^2$ is —C(O)N($R^{25}$)$R^{26}$. In a further embodiment of the aforementioned embodiments is a compound of Formula (IV) wherein $R^2$ is —C(O)N($R^{25}$)$R^{26}$, and $R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl). In a further embodiment of the aforementioned embodiments is a compound of Formula (IV) wherein R$^2$ is —C(O)N(R$^{25}$)R$^{26}$, and R$^{25}$ and R$^{26}$ are each independently selected from the group consisting of hydrogen, and optionally substituted C$_1$-C$_6$alkyl. In a further embodiment of the aforementioned embodiments is a compound of Formula (IV) wherein R$^2$ is —C(O)N(R$^{25}$)R$^{26}$, and R$^{25}$ and R$^{26}$ are hydrogen. In a further embodiment of the aforementioned embodiments is a compound of Formula (IV) wherein R$^2$ is —C(O)N(R$^{25}$)R$^{26}$, and R$^{25}$ and R$^{26}$ are each independently optionally substituted C$_1$-C$_6$alkyl. In a further embodiment of the aforementioned embodiments is a compound of Formula (IV) wherein R$^2$ is —C(O)N(R$^{25}$)R$^{26}$, R$^{25}$ is hydrogen, and R$^{26}$ is optionally substituted C$_1$-C$_6$alkyl. In a further embodiment of the aforementioned embodiments is a compound of Formula (IV) wherein R$^2$ is —C(O)N(R$^{25}$)R$^{26}$, and R$^{25}$ and R$^{26}$ are each independently unsubstituted C$_1$-C$_6$alkyl. In a further embodiment of the aforementioned embodiments is a compound of Formula (IV) wherein R$^2$ is —C(O)N(R$^{25}$)R$^{26}$, R$^{25}$ is hydrogen, and R$^{26}$ are methyl. In a further embodiment of the aforementioned embodiments is a compound of Formula (IV) wherein R$^2$ is —C(O)N(R$^{25}$)R$^{26}$, and R$^{25}$ and R$^{26}$ are methyl. In a further embodiment of the aforementioned embodiments is a compound of Formula (IV) wherein R$^2$ is —C(O)N(R$^{25}$)R$^{26}$, and R$^{25}$ and R$^{26}$ are ethyl.

In a further embodiment of the aforementioned embodiments is a compound of Formula (IV) wherein R$^2$ is

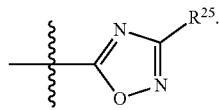

In a further embodiment of the aforementioned embodiments is a compound of Formula (IV) wherein R$^2$ is

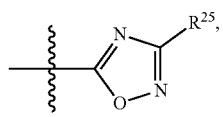

and R$^{25}$ is optionally substituted C$_1$-C$_6$alkyl. In a further embodiment of the aforementioned embodiments is a compound of Formula (IV) wherein R$^2$ is

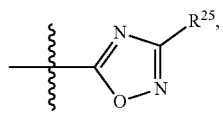

and R$^{25}$ is methyl. In a further embodiment of the aforementioned embodiments is a compound of Formula (IV) wherein R$^2$ is

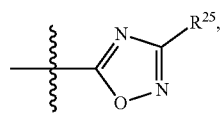

and R$^{25}$ is optionally substituted C$_1$-C$_6$alkyl. In a further embodiment of the aforementioned embodiments is a compound of Formula (IV) wherein R$^2$ is

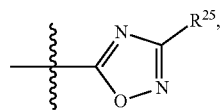

and R$^{25}$ is ethyl.

In a further embodiment of the aforementioned embodiments is a compound of Formula (IV) wherein R$^2$ is

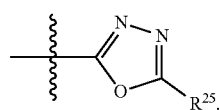

In a further embodiment of the aforementioned embodiments is a compound of Formula (IV) wherein R$^2$ is

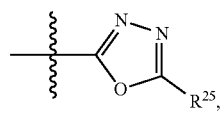

and R$^{25}$ is optionally substituted C$_1$-C$_6$alkyl. In a further embodiment of the aforementioned embodiments is a compound of Formula (IV) wherein R$^2$ is

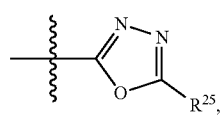

and R$^{25}$ is methyl. In a further embodiment of the aforementioned embodiments is a compound of Formula (IV) wherein R$^2$ is

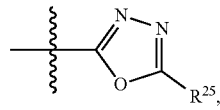

and R$^{25}$ is optionally substituted C$_1$-C$_6$alkyl. In a further embodiment of the aforementioned embodiments is a compound of Formula (IV) is

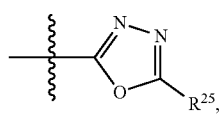

and $R^{25}$ is ethyl.

In a further embodiment of the aforementioned embodiments is a compound of Formula (IV) wherein $R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IV) wherein $R^1$ is hydrogen. In a further embodiment of the aforementioned embodiments is a compound of Formula (IV) wherein $R^1$ is optionally substituted $C_1$-$C_6$alkyl. In a further embodiment of the aforementioned embodiments is a compound of Formula (IV) wherein $R^1$ is methyl. In a further embodiment of the aforementioned embodiments is a compound of Formula (IV) wherein $R^1$ is optionally substituted $C_2$-$C_6$alkenyl. In a further embodiment of the aforementioned embodiments is a compound of Formula (IV) wherein $R^1$ is optionally substituted $C_2$-$C_6$alkynyl.

In a further embodiment of the aforementioned embodiments is a compound of Formula (IV) wherein $R^1$ and $R^2$ together with the carbon atoms to which they are attached, form an optionally substituted $C_2$-$C_9$heterocycloalkyl ring or an optionally substituted heteroaryl ring. In a further embodiment of the aforementioned embodiments is a compound of Formula (IV) wherein $R^1$ and $R^2$ together with the carbon atoms to which they are attached, form an optionally substituted $C_2$-$C_9$heterocycloalkyl ring. In a further embodiment of the aforementioned embodiments is a compound of Formula (IV) wherein $R^1$ and $R^2$ together with the carbon atoms to which they are attached, form an optionally substituted heteroaryl ring.

In another embodiment of the aforementioned embodiments is a compound of Formula (IV) wherein $R^{20}$ is —$R^{34}R^{35}$. In another embodiment of the aforementioned embodiments is a compound of Formula (IV) wherein $R^{20}$ is —$R^{34}R^{35}$, and $R^{34}$ is optionally substituted $C_1$-$C_6$alkyl. In another embodiment of the aforementioned embodiments is a compound of Formula (IV) wherein $R^{20}$ is —$R^{34}R^{35}$, and $R^{34}$ is optionally substituted $C_3$-$C_{10}$cycloalkyl. In another embodiment of the aforementioned embodiments is a compound of Formula (IV) wherein $R^{20}$ is —$R^{34}R^{35}$, and $R^{34}$ is optionally substituted aryl. In another embodiment of the aforementioned embodiments is a compound of Formula (IV) wherein $R^{20}$ is —$R^{34}R^{35}$, and $R^{34}$ is optionally substituted —($C_1$-$C_2$alkylene)-(aryl). In another embodiment of the aforementioned embodiments is a compound of Formula (IV) wherein $R^{20}$ is —$R^{34}R^{35}$, and $R^{34}$ is optionally substituted heteroaryl. In another embodiment of the aforementioned embodiments is a compound of Formula (IV) wherein $R^{20}$ is —$R^{34}R^{35}$, and $R^{34}$ is optionally substituted $C_2$-$C_9$heterocycloalkyl. In another embodiment of the aforementioned embodiments is a compound of Formula (IV) wherein $R^{20}$ is —$R^{34}R^{35}$, and $R^{34}$ is optionally substituted —($C_1$-$C_2$alkylene)-(heteroaryl). In another embodiment of the aforementioned embodiments is a compound of Formula (IV) wherein $R^{20}$ is —$R^{34}R^{35}$, and $R^{35}$ is —($C_1$-$C_6$alkyl)-$R^{30}$. In another embodiment of the aforementioned embodiments is a compound of Formula (IV) wherein $R^{20}$ is —$R^{34}R^{35}$, and $R^{35}$ is —O($C_2$-$C_6$alkyl)-$R^{30}$. In another embodiment of the aforementioned embodiments is a compound of Formula (IV) wherein $R^{20}$ is —$R^{34}R^{35}$, and $R^{35}$ is —N($R^{12}$)($C_2$-$C_6$alkyl)-$R^{30}$. In a further embodiment of the aforementioned embodiments is a compound of Formula (IV) wherein $R^{30}$ is $R^{36a}$. In a further embodiment of the aforementioned embodiments is a compound of Formula (IV) wherein $R^{30}$ is $R^{36b}$. In a further embodiment of the aforementioned embodiments is a compound of Formula (IV) wherein $R^{30}$ is $R^{36c}$.

In another embodiment of the aforementioned embodiments is a compound of Formula (IV) wherein $R^{20}$ is —$R^{31}$. In a further embodiment of the aforementioned embodiments is a compound of Formula (IV) wherein $R^{31}$ is $R^{36a}$. In a further embodiment of the aforementioned embodiments is a compound of Formula (IV) wherein $R^{31}$ is $R^{36c}$.

In another embodiment of the aforementioned embodiments is a compound of Formula (IV) wherein $R^{36a}$ is

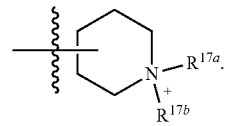

In another embodiment of the aforementioned embodiments is a compound of Formula (IV) wherein $R^{36a}$ is

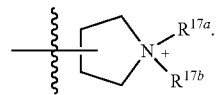

In another embodiment of the aforementioned embodiments is a compound of Formula (IV) wherein $R^{36a}$ is

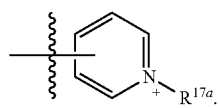

In another embodiment of the aforementioned embodiments is a compound of Formula (IV) wherein $R^{36b}$ is

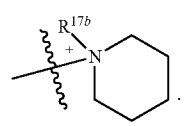

In another embodiment of the aforementioned embodiments is a compound of Formula (IV) wherein $R^{36b}$ is

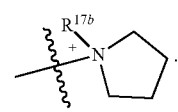

In another embodiment of the aforementioned embodiments is a compound of Formula (IV) wherein $R^{36b}$ is

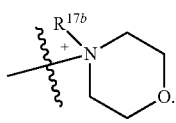

In another embodiment of the aforementioned embodiments is a compound of Formula (IV) wherein $R^{36b}$ is

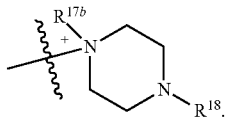

In another embodiment of the aforementioned embodiments is a compound of Formula (IV) wherein $R^{36b}$ is

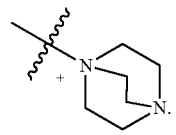

In another embodiment of the aforementioned embodiments is a compound of Formula (IV) wherein $R^{36b}$ is

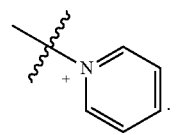

In another embodiment of the aforementioned embodiments is a compound of Formula (IV) wherein $R^{36b}$ is

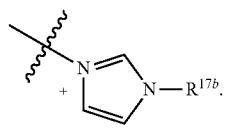

In another embodiment of the aforementioned embodiments is a compound of Formula (IV) wherein $R^{36c}$ is

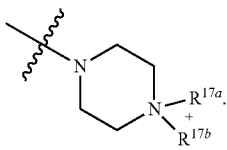

In another embodiment is a compound of Formula (IV) wherein $R^{36c}$ is

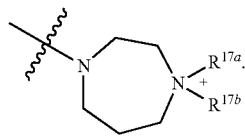

In a further embodiment of the aforementioned embodiments is a compound of Formula (IV) wherein $R^{17a}$ is methyl. In a further embodiment of the aforementioned embodiments is a compound of Formula (IV) wherein $R^{17a}$ is ethyl. In a further embodiment of the aforementioned embodiments is a compound of Formula (IV) wherein $R^{17b}$ is methyl optionally substituted with phenyl, —C(=O)OH or —S(=O)$_2$OH. In a further embodiment of the aforementioned embodiments is a compound of Formula (IV) wherein $R^{17a}$ is ethyl optionally substituted with phenyl, —C(=O)OH or —S(=O)$_2$OH.

In some embodiments provided herein, the compound of Formula (IV) has the structure of Formula (IVa), or a pharmaceutically acceptable salt or solvate thereof:

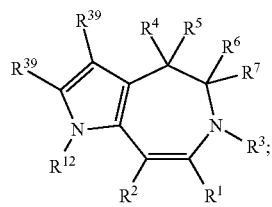

Formula (IVa)

wherein:
$R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R^2$ is selected from the group consisting of —CN, —C(=O)OR$^{25}$, —C(=O)N(R$^{25}$)R$^{26}$,

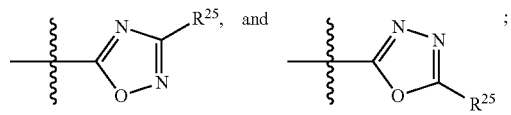

or $R^1$ and $R^2$ together with the carbon atoms to which they are attached, form an optionally substituted $C_2$-$C_9$heterocycloalkyl ring or an optionally substituted heteroaryl ring;

$R^3$ is —C(=O)R$^{20}$ or —S(=O)$_2$R$^{20}$;

$R^4$ and $R^5$ are each independently selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl; or $R^4$ and $R^5$ together with the carbon atom to which they are attached, form an optionally substituted $C_3$-$C_6$cycloalkyl ring or an optionally substituted $C_2$-$C_7$heterocycloalkyl ring;

$R^6$ is selected from the group consisting of hydrogen, halogen, optionally substituted $C_1$-$C_6$alkyl, optionally substituted $C_2$-$C_6$alkenyl, optionally substituted $C_2$-$C_6$alkynyl, and —C(=O)N($R^{27}$)$R^{28}$;

$R^7$ is selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl;

each $R^{12}$ is independently selected from the group consisting of hydrogen and $C_1$-$C_6$alkyl;

each $R^{13}$ and $R^{14}$ are each independently selected from the group consisting of hydrogen and $C_1$-$C_6$alkyl; or $R^{13}$ and $R^{14}$ together with the nitrogen atom to which they are attached, form an optionally substituted $C_2$-$C_9$heterocycloalkyl ring;

each $R^{39}$ is independently selected from the group consisting of hydrogen, halogen, —CN, amino, alkylamino, $C_1$-$C_6$alkyl, $C_1$-$C_6$haloalkyl, $C_1$-$C_6$alkoxy, $C_1$-$C_6$haloalkoxy, $C_3$-$C_8$cycloalkyl, $C_2$-$C_9$heterocycloalkyl, aryl, heteroaryl, —C(=O)O$R^{12}$, and —C(=O)N($R^{13}$)$R^{14}$;

$R^{20}$ is selected from the group consisting of —$R^{34}R^{35}$ or —$R^{31}$;

$R^{34}$ is selected from the group consisting of optionally substituted $C_1$-$C_6$alkyl, optionally substituted $C_3$-$C_{10}$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl);

$R^{35}$ is —($C_1$-$C_6$alkyl)-$R^{30}$, —O($C_2$-$C_6$alkyl)-$R^{30}$, or —N($R^{12}$)($C_2$-$C_6$alkyl)-$R^{30}$;

$R^{30}$ is $R^{36a}$, $R^{36b}$, or $R^{36c}$;

$R^{31}$ is $R^{36a}$ or $R^{36c}$;

$R^{36a}$ is

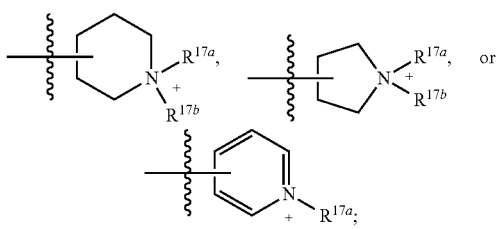

$R^{36b}$ is

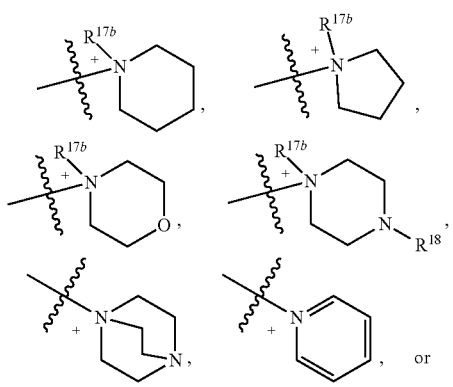

-continued

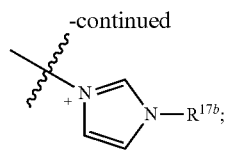

$R^{36c}$ is

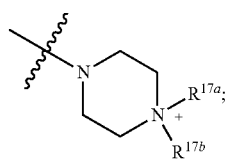

$R^{17a}$ is $C_1$-$C_6$alkyl;

$R^{17b}$ is $C_1$-$C_6$alkyl optionally substituted with phenyl, —C(=O)OH or —S(=O)$_2$OH;

$R^{18}$ is hydrogen, —OH, —($C_0$-$C_6$alkyl)-C(=O)OH, or $C_1$-$C_6$alkyl;

$R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); and $R^{27}$ and $R^{28}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{27}$ and $R^{28}$ together with the nitrogen atom to which they are attached, form an optionally substituted $C_2$-$C_9$heterocycloalkyl ring.

In one embodiment is a compound of Formula (IVa) wherein $R^4$ and $R^5$ are each independently selected from the group consisting of hydrogen, halogen, and optionally substituted $C_1$-$C_6$alkyl. In another embodiment is a compound of Formula (IVa) wherein $R^4$ and $R^5$ are each independently selected from the group consisting of hydrogen and optionally substituted $C_1$-$C_6$alkyl. In another embodiment is a compound of Formula (IVa) wherein $R^4$ and $R^5$ are each hydrogen. In another embodiment is a compound of Formula (IVa) wherein $R^4$ and $R^5$ are each independently optionally substituted $C_1$-$C_6$alkyl. In another embodiment is a compound of Formula (IVa) wherein $R^4$ and $R^5$ are each methyl. In another embodiment is a compound of Formula (IVa) wherein $R^4$ and $R^5$ form an optionally substituted $C_3$-$C_6$cycloalkyl ring or an optionally substituted $C_2$-$C_7$heterocycloalkyl ring. In some embodiments is a compound of Formula (IVa) wherein $R^4$ and $R^5$ form an optionally substituted $C_3$-$C_6$cycloalkyl ring. In some embodiments is a compound of Formula (IVa) wherein $R^4$ and $R^5$ form an optionally substituted $C_2$-$C_7$heterocycloalkyl ring.

In another embodiment is a compound of Formula (IVa) wherein $R^6$ and $R^7$ are each independently selected from the group consisting of hydrogen, halogen, and optionally substituted $C_1$-$C_6$alkyl. In another embodiment is a compound of Formula (IVa) wherein $R^6$ and $R^7$ are each independently selected from the group consisting of hydrogen and optionally substituted $C_1$-$C_6$alkyl. In another embodiment is a compound of Formula (IVa) wherein $R^6$ and $R^7$ are each independently optionally substituted $C_1$-$C_6$alkyl. In another embodiment is a compound of Formula (IVa) wherein $R^6$ and $R^7$ are each methyl. In another embodiment is a compound of Formula (IVa) wherein $R^6$ and $R^7$ are each hydrogen.

In another embodiment is a compound of Formula (IVa) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted aryl. In another embodiment is a compound of Formula (IVa) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted heteroaryl. In another embodiment is a compound of Formula (IVa) wherein $R^6$ and $R^7$ are hydrogen, $R^4$ and $R^5$ are methyl, $R^3$ is —C(O)$R^{20}$, and $R^{20}$ is optionally substituted aryl. In another embodiment is a compound of Formula (IVa) wherein $R^6$ and $R^7$ are hydrogen, $R^4$ and $R^5$ are methyl, $R^3$ is —C(O)$R^{20}$, and $R^{20}$ is optionally substituted heteroaryl.

In another embodiment is a compound of Formula (IVa) wherein $R^6$ and $R^7$ are hydrogen, $R^4$ and $R^5$ are independently optionally substituted $C_1$-$C_6$alkyl, $R^3$ is —S(O)$_2R^{20}$, and $R^{20}$ is optionally substituted aryl. In another embodiment is a compound of Formula (IVa) wherein $R^6$ and $R^7$ are hydrogen, $R^4$ and $R^5$ are independently optionally substituted $C_1$-$C_6$alkyl, $R^3$ is —S(O)$_2R^{20}$, and $R^{20}$ is optionally substituted heteroaryl. In another embodiment is a compound of Formula (IVa) wherein $R^6$ and $R^7$ are hydrogen, $R^4$ and $R^5$ are methyl, $R^3$ is —S(O)$_2R^{20}$, and $R^{20}$ is optionally substituted aryl. In another embodiment is a compound of Formula (IVa) wherein $R^6$ and $R^7$ are hydrogen, $R^4$ and $R^5$ are methyl, $R^3$ is —S(O)$_2R^{20}$, and $R^{20}$ is optionally substituted heteroaryl.

In a further embodiment of the aforementioned embodiments is a compound of Formula (IVa) wherein $R^2$ is selected from the group consisting of —CN, —C(O)O$R^{25}$, —C(O)N($R^{25}$)$R^{26}$,

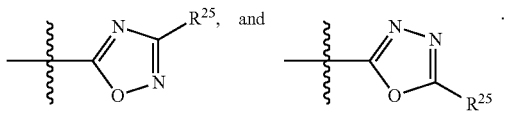

In a further embodiment of the aforementioned embodiments is a compound of Formula (IVa) wherein $R^2$ is —CN.

In a further embodiment of the aforementioned embodiments is a compound of Formula (IVa) wherein $R^2$ is —C(O)O$R^{25}$. In a further embodiment of the aforementioned embodiments is a compound of Formula (IVa) wherein $R^2$ is —C(O)O$R^{25}$, and $R^{25}$ is independently selected from the group consisting of hydrogen, optionally substituted $C_1$-$C_6$alkyl, optionally substituted $C_3$-$C_8$cycloalkyl, optionally substituted aryl, optionally substituted —(C$_1$-C$_2$alkylene)-(aryl), optionally substituted $C_2$-$C_9$heterocycloalkyl, optionally substituted heteroaryl, and optionally substituted —(C$_1$-C$_2$alkylene)-(heteroaryl). In a further embodiment of the aforementioned embodiments is a compound of Formula (IVa) wherein $R^2$ is —C(O)O$R^{25}$, and $R^{25}$ is independently selected from the group consisting of hydrogen, and optionally substituted $C_1$-$C_6$alkyl. In a further embodiment of the aforementioned embodiments is a compound of Formula (IVa) wherein $R^2$ is —C(O)O$R^{25}$, and $R^{25}$ is hydrogen. In a further embodiment of the aforementioned embodiments is a compound of Formula (IVa) wherein $R^2$ is —C(O)O$R^{25}$, and $R^{25}$ is optionally substituted $C_1$-$C_6$alkyl. In a further embodiment of the aforementioned embodiments is a compound of Formula (IVa) wherein $R^2$ is —C(O)O$R^{25}$, and $R^{25}$ is unsubstituted $C_1$-$C_6$alkyl. In a further embodiment of the aforementioned embodiments is a compound of Formula (IVa) wherein $R^2$ is —C(O)O$R^{25}$, and $R^{25}$ is methyl. In a further embodiment of the aforementioned embodiments is a compound of Formula (IVa) wherein $R^2$ is —C(O)O$R^{25}$, and $R^{25}$ is ethyl.

In a further embodiment of the aforementioned embodiments is a compound of Formula (IVa) wherein $R^2$ is —C(O)N($R^{25}$)$R^{26}$. In a further embodiment of the aforementioned embodiments is a compound of Formula (IVa) wherein $R^2$ is —C(O)N($R^{25}$)$R^{26}$, and $R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —(C$_1$-C$_2$alkylene)-(aryl), optionally substituted $C_2$-$C_9$heterocycloalkyl, optionally substituted heteroaryl, and optionally substituted —(C$_1$-C$_2$alkylene)-(heteroaryl). In a further embodiment of the aforementioned embodiments is a compound of Formula (IVa) wherein $R^2$ is —C(O)N($R^{25}$)$R^{26}$, and $R^{25}$ and $R^{26}$ are each independently selected from the group consisting of hydrogen, and optionally substituted $C_1$-$C_6$alkyl. In a further embodiment of the aforementioned embodiments is a compound of Formula (IVa) wherein $R^2$ is —C(O)N($R^{25}$)$R^{26}$, and $R^{25}$ and $R^{26}$ are hydrogen. In a further embodiment of the aforementioned embodiments is a compound of Formula (IVa) wherein $R^2$ is —C(O)N($R^{25}$)$R^{26}$, and $R^{25}$ and $R^{26}$ are each independently optionally substituted $C_1$-$C_6$alkyl. In a further embodiment of the aforementioned embodiments is a compound of Formula (IVa) wherein $R^2$ is —C(O)N($R^{25}$)$R^{26}$, $R^{25}$ is hydrogen, and $R^{26}$ is optionally substituted $C_1$-$C_6$alkyl. In a further embodiment of the aforementioned embodiments is a compound of Formula (IVa) wherein $R^2$ is —C(O)N($R^{25}$)$R^{26}$, and $R^{25}$ and $R^{26}$ are each independently unsubstituted $C_1$-$C_6$alkyl. In a further embodiment of the aforementioned embodiments is a compound of Formula (IVa) wherein $R^2$ is —C(O)N($R^{25}$)$R^{26}$, $R^{25}$ is hydrogen, and $R^{26}$ are methyl. In a further embodiment of the aforementioned embodiments is a compound of Formula (IVa) wherein $R^2$ is —C(O)N($R^{25}$)$R^{26}$, and $R^{25}$ and $R^{26}$ are methyl. In a further embodiment of the aforementioned embodiments is a compound of Formula (IVa) wherein $R^2$ is —C(O)N($R^{25}$)$R^{26}$, and $R^{25}$ and $R^{26}$ are ethyl.

In a further embodiment of the aforementioned embodiments is a compound of Formula (IVa) wherein $R^2$ is

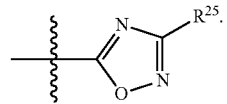

In a further embodiment of the aforementioned embodiments is a compound of Formula (IVa) wherein $R^2$ is

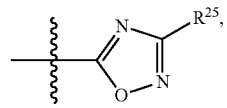

and $R^{25}$ is optionally substituted $C_1$-$C_6$alkyl. In a further embodiment of the aforementioned embodiments is a compound of Formula (IVa) wherein $R^2$ is

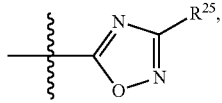

and $R^{25}$ is methyl. In a further embodiment of the aforementioned embodiments is a compound of Formula (IVa) wherein $R^2$ is

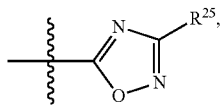

and $R^{25}$ is optionally substituted $C_1$-$C_6$alkyl. In a further embodiment of the aforementioned embodiments is a compound of Formula (IVa) wherein $R^2$ is

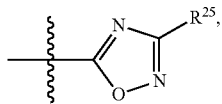

and $R^{25}$ is ethyl.

In a further embodiment of the aforementioned embodiments is a compound of Formula (IVa) wherein $R^2$ is

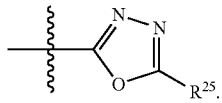

In a further embodiment of the aforementioned embodiments is a compound of Formula (IVa) wherein $R^2$ is

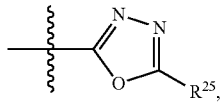

and $R^{25}$ is optionally substituted $C_1$-$C_6$alkyl. In a further embodiment of the aforementioned embodiments is a compound of Formula (IVa) wherein $R^2$ is

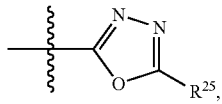

and $R^{25}$ is methyl. In a further embodiment of the aforementioned embodiments is a compound of Formula (IVa) wherein $R^2$ is

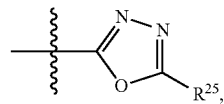

and $R^{25}$ is optionally substituted $C_1$-$C_6$alkyl. In a further embodiment of the aforementioned embodiments is a compound of Formula (IVa) wherein $R^2$ is

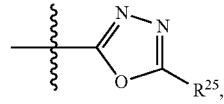

and $R^{25}$ is ethyl.

In a further embodiment of the aforementioned embodiments is a compound of Formula (IVa) wherein $R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IVa) wherein $R^1$ is hydrogen. In a further embodiment of the aforementioned embodiments is a compound of Formula (IVa) wherein $R^1$ is optionally substituted $C_1$-$C_6$alkyl. In a further embodiment of the aforementioned embodiments is a compound of Formula (IVa) wherein $R^1$ is methyl. In a further embodiment of the aforementioned embodiments is a compound of Formula (IVa) wherein $R^1$ is optionally substituted $C_2$-$C_6$alkenyl. In a further embodiment of the aforementioned embodiments is a compound of Formula (IVa) wherein $R^1$ is optionally substituted $C_2$-$C_6$alkynyl.

In a further embodiment of the aforementioned embodiments is a compound of Formula (IVa) wherein $R^1$ and $R^2$ together with the carbon atoms to which they are attached, form an optionally substituted $C_2$-$C_9$heterocycloalkyl ring or an optionally substituted heteroaryl ring. In a further embodiment of the aforementioned embodiments is a compound of Formula (IVa) wherein $R^1$ and $R^2$ together with the carbon atoms to which they are attached, form an optionally substituted $C_2$-$C_9$heterocycloalkyl ring. In a further embodiment of the aforementioned embodiments is a compound of Formula (IVa) wherein $R^1$ and $R^2$ together with the carbon atoms to which they are attached, form an optionally substituted heteroaryl ring.

In another embodiment of the aforementioned embodiments is a compound of Formula (IVa) wherein $R^{20}$ is —$R^{34}R^{35}$. In another embodiment of the aforementioned embodiments is a compound of Formula (IVa) wherein $R^{20}$ is —$R^{34}R^{35}$, and $R^{34}$ is optionally substituted $C_1$-$C_6$alkyl. In another embodiment of the aforementioned embodiments is a compound of Formula (IVa) wherein $R^{20}$ is —$R^{34}R^{35}$, and $R^{34}$ is optionally substituted $C_3$-$C_{10}$cycloalkyl. In another embodiment of the aforementioned embodiments is a compound of Formula (IVa) wherein $R^{20}$ is —$R^{34}R^{35}$, and $R^{34}$ is optionally substituted aryl. In another embodiment of the aforementioned embodiments is a compound of Formula (IVa) wherein $R^{20}$ is —$R^{34}R^{35}$, and $R^{34}$ is optionally substituted —($C_1$-$C_2$alkylene)-(aryl). In another embodiment of the aforementioned embodiments is a compound of Formula (IVa) wherein $R^{20}$ is —$R^{34}R^{35}$, and $R^{34}$ is optionally substituted heteroaryl. In another embodiment of the aforementioned embodiments is a compound of Formula (IVa) wherein $R^{20}$ is —$R^{34}R^{35}$, and $R^{34}$ is optionally substituted $C_2$-$C_9$heterocycloalkyl. In another embodiment of the aforementioned embodiments is a compound of Formula (IVa) wherein $R^{20}$ is —$R^{34}R^{35}$, and $R^{34}$ is optionally substituted —($C_1$-$C_2$alkylene)-(heteroaryl). In another embodiment of the aforementioned embodiments is a compound of Formula (IVa) wherein $R^{20}$ is —$R^{34}R^{35}$, and $R^{35}$ is —($C_1$-$C_6$alkyl)-$R^{30}$. In another embodiment of the aforementioned embodiments is a compound of Formula (IVa) wherein $R^{20}$ is —$R^{34}R^{35}$, and $R^{35}$ is —O($C_2$-$C_6$alkyl)-$R^{30}$. In another embodiment of the aforementioned embodiments is a compound of Formula (IVa) wherein $R^{20}$ is —$R^{34}R^{35}$, and $R^{35}$ is —N($R^{12}$)($C_2$-$C_6$alkyl)-$R^{30}$. In a further embodiment of the aforementioned embodiments is a compound of Formula (IVa) wherein $R^{30}$ is $R^{36a}$. In a further embodiment of the aforementioned embodiments is a compound of Formula (IVa) wherein $R^{30}$ is $R^{36b}$. In a further embodiment of the aforementioned embodiments is a compound of Formula (IVa) wherein $R^{30}$ is $R^{36c}$.

In another embodiment of the aforementioned embodiments is a compound of Formula (IVa) wherein $R^{20}$ is —$R^{31}$. In a further embodiment of the aforementioned embodiments is a compound of Formula (IVa) wherein $R^{31}$ is $R^{36a}$ In a further embodiment of the aforementioned embodiments is a compound of Formula (IVa) wherein $R^{31}$ is $R^{36c}$.

In another embodiment of the aforementioned embodiments is a compound of Formula (IVa) wherein $R^{36a}$ is

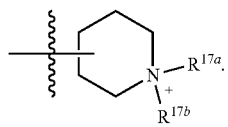

In another embodiment of the aforementioned embodiments is a compound of Formula (IVa) wherein $R^{36a}$ is

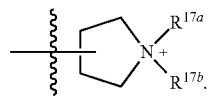

In another embodiment of the aforementioned embodiments is a compound of Formula (IVa) wherein $R^{36a}$ is

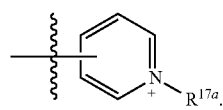

In another embodiment of the aforementioned embodiments is a compound of Formula (IVa) wherein $R^{36b}$ is

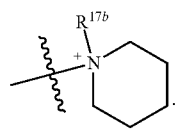

In another embodiment of the aforementioned embodiments is a compound of Formula (IVa) wherein $R^{36b}$ is

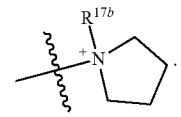

In another embodiment of the aforementioned embodiments is a compound of Formula (IVa) wherein $R^{36b}$ is

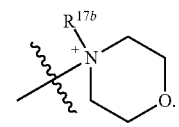

In another embodiment of the aforementioned embodiments is a compound of Formula (IVa) wherein $R^{36b}$ is

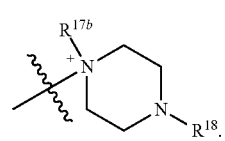

In another embodiment of the aforementioned embodiments is a compound of Formula (IVa) wherein $R^{36b}$ is

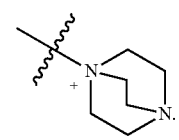

In another embodiment of the aforementioned embodiments is a compound of Formula (IVa) wherein $R^{36b}$ is

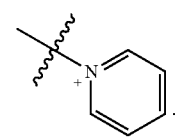

In another embodiment of the aforementioned embodiments is a compound of Formula (IVa) wherein $R^{36b}$ is

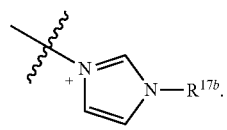

In another embodiment of the aforementioned embodiments is a compound of Formula (IVa) wherein $R^{36c}$ is

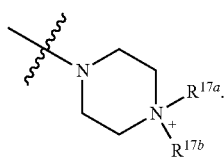

In another embodiment is a compound of Formula (IVa) wherein $R^{36c}$ is

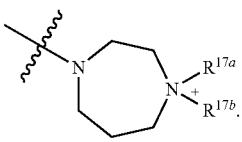

In a further embodiment of the aforementioned embodiments is a compound of Formula (IVa) wherein $R^{17a}$ is methyl. In a further embodiment of the aforementioned embodiments is a compound of Formula (IVa) wherein $R^{17a}$ is ethyl. In a further embodiment of the aforementioned embodiments is a compound of Formula (IVa) wherein $R^{17b}$ is methyl optionally substituted with phenyl, —C(=O)OH or —S(=O)$_2$OH. In a further embodiment of the aforementioned embodiments is a compound of Formula (IVa) wherein $R^{17a}$ is ethyl optionally substituted with phenyl, —C(=O)OH or —S(=O)$_2$OH.

In some embodiments provided herein, the compound of Formula (IV) has the structure of Formula (IVb), or a pharmaceutically acceptable salt or solvate thereof:

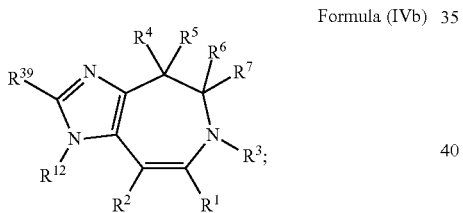

Formula (IVb)

wherein:
$R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);
$R^2$ is selected from the group consisting of —CN, —C(=O)OR$^{25}$, —C(=O)N(R$^{25}$)R$^{26}$,

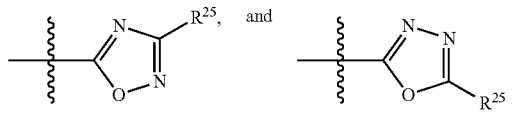

or $R^1$ and $R^2$ together with the carbon atoms to which they are attached, form an optionally substituted $C_2$-$C_9$heterocycloalkyl ring or an optionally substituted heteroaryl ring;

$R^3$ is —C(=O)R$^{20}$ or —S(=O)$_2$R$^{20}$;
$R^4$ and $R^5$ are each independently selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl; or $R^4$ and $R^5$ together with the carbon atom to which they are attached, form an optionally substituted $C_3$-$C_6$cycloalkyl ring or an optionally substituted $C_2$-$C_7$heterocycloalkyl ring;
$R^6$ is selected from the group consisting of hydrogen, halogen, optionally substituted $C_1$-$C_6$alkyl, optionally substituted $C_2$-$C_6$alkenyl, optionally substituted $C_2$-$C_6$alkynyl, and —C(=O)N(R$^{27}$)R$^{28}$;
$R^7$ is selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl;
each $R^{12}$ is independently selected from the group consisting of hydrogen and $C_1$-$C_6$alkyl;
$R^{13}$ and $R^{14}$ are independently selected from the group consisting of hydrogen and $C_1$-$C_6$alkyl; or $R^{13}$ and $R^{14}$ together with the nitrogen atom to which they are attached, form an optionally substituted $C_2$-$C_9$heterocycloalkyl ring;
$R^{39}$ is selected from the group consisting of hydrogen, halogen, —CN, amino, alkylamino, $C_1$-$C_6$alkyl, $C_1$-$C_6$haloalkyl, $C_1$-$C_6$alkoxy, $C_1$-$C_6$haloalkoxy, $C_3$-$C_8$cycloalkyl, $C_2$-$C_9$heterocycloalkyl, aryl, heteroaryl, —C(=O)OR$^{12}$, and —C(=O)N(R$^{13}$)R$^{14}$;
$R^{20}$ is selected from the group consisting of —R$^{34}$R$^{35}$ or —R$^{31}$;
$R^{34}$ is selected from the group consisting of optionally substituted $C_1$-$C_6$alkyl, optionally substituted $C_3$-$C_{10}$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl);
$R^{35}$ is —($C_1$-$C_6$alkyl)-R$^{30}$, —O($C_2$-$C_6$alkyl)-R$^{30}$, or —N(R$^{12}$)($C_2$-$C_6$alkyl)-R$^{30}$;
$R^{30}$ is R$^{36a}$, R$^{36b}$, or R$^{36c}$;
$R^{31}$ is R$^{36a}$ or R$^{36c}$;
$R^{36a}$ is

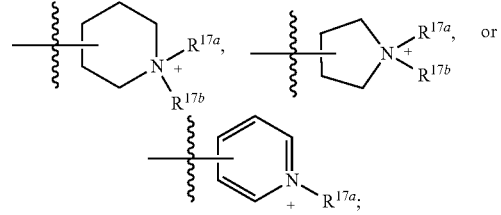

$R^{36b}$ is

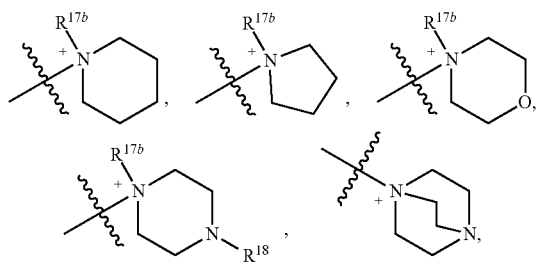

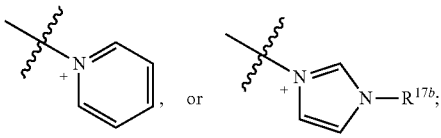

$R^{36c}$ is

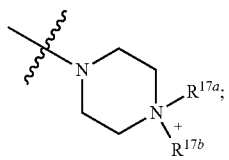

$R^{17a}$ is $C_1$-$C_6$alkyl;

$R^{17b}$ is $C_1$-$C_6$alkyl optionally substituted with phenyl, —C(=O)OH or —S(=O)$_2$OH;

$R^{18}$ is hydrogen, —OH, —($C_0$-$C_6$alkyl)-C(=O)OH, or $C_1$-$C_6$alkyl;

$R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); and $R^{27}$ and $R^{28}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{27}$ and $R^{28}$ together with the nitrogen atom to which they are attached, form an optionally substituted $C_2$-$C_9$heterocycloalkyl ring.

In one embodiment is a compound of Formula (IVb) wherein $R^4$ and $R^5$ are each independently selected from the group consisting of hydrogen, halogen, and optionally substituted $C_1$-$C_6$alkyl. In another embodiment is a compound of Formula (IVb) wherein $R^4$ and $R^5$ are each independently selected from the group consisting of hydrogen and optionally substituted $C_1$-$C_6$alkyl. In another embodiment is a compound of Formula (IVb) wherein $R^4$ and $R^5$ are each hydrogen. In another embodiment is a compound of Formula (IVb) wherein $R^4$ and $R^5$ are each independently optionally substituted $C_1$-$C_6$alkyl. In another embodiment is a compound of Formula (IVb) wherein $R^4$ and $R^5$ are each methyl. In another embodiment is a compound of Formula (IVb) wherein $R^4$ and $R^5$ form an optionally substituted $C_3$-$C_6$cycloalkyl ring or an optionally substituted $C_2$-$C_7$heterocycloalkyl ring. In some embodiments is a compound of Formula (IVb) wherein $R^4$ and $R^5$ form an optionally substituted $C_3$-$C_6$cycloalkyl ring. In some embodiments is a compound of Formula (IVb) wherein $R^4$ and $R^5$ form an optionally substituted $C_2$-$C_7$heterocycloalkyl ring.

In another embodiment is a compound of Formula (IVb) wherein $R^6$ and $R^7$ are each independently selected from the group consisting of hydrogen, halogen, and optionally substituted $C_1$-$C_6$alkyl. In another embodiment is a compound of Formula (IVb) wherein $R^6$ and $R^7$ are each independently selected from the group consisting of hydrogen and optionally substituted $C_1$-$C_6$alkyl. In another embodiment is a compound of Formula (IVb) wherein $R^6$ and $R^7$ are each independently optionally substituted $C_1$-$C_6$alkyl. In another embodiment is a compound of Formula (IVb) wherein $R^6$ and $R^7$ are each methyl. In another embodiment is a compound of Formula (IVb) wherein $R^6$ and $R^7$ are each hydrogen.

In another embodiment is a compound of Formula (IVb) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted aryl. In another embodiment is a compound of Formula (IVb) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted heteroaryl. In another embodiment is a compound of Formula (IVb) wherein $R^6$ and $R^7$ are hydrogen, $R^4$ and $R^5$ are methyl, $R^3$ is —C(O)$R^{20}$, and $R^{20}$ is optionally substituted aryl. In another embodiment is a compound of Formula (IVb) wherein $R^6$ and $R^7$ are hydrogen, $R^4$ and $R^5$ are methyl, $R^3$ is —C(O)$R^{20}$, and $R^{20}$ is optionally substituted heteroaryl.

In another embodiment is a compound of Formula (IVb) wherein $R^6$ and $R^7$ are hydrogen, $R^4$ and $R^5$ are independently optionally substituted $C_1$-$C_6$alkyl, $R^3$ is —S(O)$_2R^{20}$, and $R^{20}$ is optionally substituted aryl. In another embodiment is a compound of Formula (IVb) wherein $R^6$ and $R^7$ are hydrogen, $R^4$ and $R^5$ are independently optionally substituted $C_1$-$C_6$alkyl, $R^3$ is —S(O)$_2R^{20}$, and $R^{20}$ is optionally substituted heteroaryl. In another embodiment is a compound of Formula (IVb) wherein $R^6$ and $R^7$ are hydrogen, $R^4$ and $R^5$ are methyl, $R^3$ is —S(O)$_2R^{20}$, and $R^{20}$ is optionally substituted aryl. In another embodiment is a compound of Formula (IVb) wherein $R^6$ and $R^7$ are hydrogen, $R^4$ and $R^5$ are methyl, $R^3$ is —S(O)$_2R^{20}$, and $R^{20}$ is optionally substituted heteroaryl.

In a further embodiment of the aforementioned embodiments is a compound of Formula (IVb) wherein $R^2$ is selected from the group consisting of —CN, —C(O)O$R^{25}$, —C(O)N($R^{25}$)$R^{26}$,

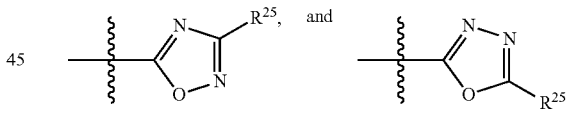

In a further embodiment of the aforementioned embodiments is a compound of Formula (IVb) wherein $R^2$ is —CN.

In a further embodiment of the aforementioned embodiments is a compound of Formula (IVb) wherein $R^2$ is —C(O)O$R^{25}$. In a further embodiment of the aforementioned embodiments is a compound of Formula (IVb) wherein $R^2$ is —C(O)O$R^{25}$, and $R^{25}$ is independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IVb) wherein $R^2$ is —C(O)O$R^{25}$, and $R^{25}$ is independently selected from the group consisting of hydrogen, and optionally substituted $C_1$-$C_6$alkyl. In a further embodiment of the aforementioned embodiments is a compound of Formula (IVb) wherein $R^2$ is —C(O)OR$^{25}$, and R$^{25}$ is hydrogen. In a further embodiment of the aforementioned embodiments is a compound of Formula (IVb) wherein R$^2$ is —C(O)OR$^{25}$, and R$^{25}$ is optionally substituted C$_1$-C$_6$alkyl. In a further embodiment of the aforementioned embodiments is a compound of Formula (IVb) wherein R$^2$ is —C(O)OR$^{25}$, and R$^{25}$ is unsubstituted C$_1$-C$_6$alkyl. In a further embodiment of the aforementioned embodiments is a compound of Formula (IVb) wherein R$^2$ is —C(O)OR$^{25}$, and R$^{25}$ is methyl. In a further embodiment of the aforementioned embodiments is a compound of Formula (IVb) wherein R$^2$ is —C(O)OR$^{25}$, and R$^{25}$ is ethyl.

In a further embodiment of the aforementioned embodiments is a compound of Formula (IVb) wherein R$^2$ is —C(O)N(R$^{25}$)R$^{26}$. In a further embodiment of the aforementioned embodiments is a compound of Formula (IVb) wherein R$^2$ is —C(O)N(R$^{25}$)R$^{26}$, and R$^{25}$ and R$^{26}$ are each independently selected from the group consisting of hydrogen, optionally substituted C$_1$-C$_6$alkyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl). In a further embodiment of the aforementioned embodiments is a compound of Formula (IVb) wherein R$^2$ is —C(O)N(R$^{25}$)R$^{26}$, and R$^{25}$ and R$^{26}$ are each independently selected from the group consisting of hydrogen, and optionally substituted C$_1$-C$_6$alkyl. In a further embodiment of the aforementioned embodiments is a compound of Formula (IVb) wherein R$^2$ is —C(O)N(R$^{25}$)R$^{26}$, and R$^{25}$ and R$^{26}$ are hydrogen. In a further embodiment of the aforementioned embodiments is a compound of Formula (IVb) wherein R$^2$ is —C(O)N(R$^{25}$)R$^{26}$, and R$^{25}$ and R$^{26}$ are each independently optionally substituted C$_1$-C$_6$alkyl. In a further embodiment of the aforementioned embodiments is a compound of Formula (IVb) wherein R$^2$ is —C(O)N(R$^{25}$)R$^{26}$, R$^{25}$ is hydrogen, and R$^{26}$ is optionally substituted C$_1$-C$_6$alkyl. In a further embodiment of the aforementioned embodiments is a compound of Formula (IVb) wherein R$^2$ is —C(O)N(R$^{25}$)R$^{26}$, and R$^{25}$ and R$^{26}$ are each independently unsubstituted C$_1$-C$_6$alkyl. In a further embodiment of the aforementioned embodiments is a compound of Formula (IVb) wherein R$^2$ is —C(O)N(R$^{25}$)R$^{26}$, R$^{25}$ is hydrogen, and R$^{26}$ are methyl. In a further embodiment of the aforementioned embodiments is a compound of Formula (IVb) wherein R$^2$ is —C(O)N(R$^{25}$)R$^{26}$, and R$^{25}$ and R$^{26}$ are methyl. In a further embodiment of the aforementioned embodiments is a compound of Formula (IVb) wherein R$^2$ is —C(O)N(R$^{25}$)R$^{26}$, and R$^{25}$ and R$^{26}$ are ethyl.

In a further embodiment of the aforementioned embodiments is a compound of Formula (IVb) wherein R$^2$ is

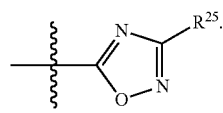

In a further embodiment of the aforementioned embodiments is a compound of Formula (IVb) wherein R$^2$ is

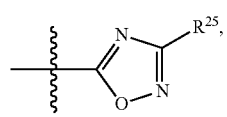

and R$^{25}$ is optionally substituted C$_1$-C$_6$alkyl. In a further embodiment of the aforementioned embodiments is a compound of Formula (IVb) wherein R$^2$ is

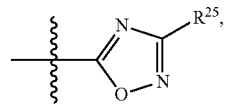

and R$^{25}$ is methyl. In a further embodiment of the aforementioned embodiments is a compound of Formula (IVb) wherein R$^2$ is

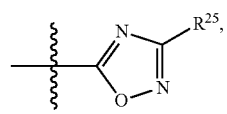

and R$^{25}$ is optionally substituted C$_1$-C$_6$alkyl. In a further embodiment of the aforementioned embodiments is a compound of Formula (IVb) wherein R$^2$ is

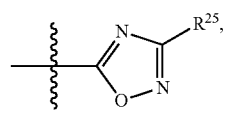

and R$^{25}$ is ethyl.

In a further embodiment of the aforementioned embodiments is a compound of Formula (IVb) wherein R$^2$ is

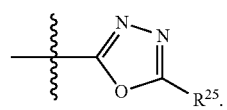

In a further embodiment of the aforementioned embodiments is a compound of Formula (IVb) wherein R$^2$ is

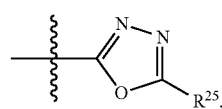

and R$^{25}$ is optionally substituted C$_1$-C$_6$alkyl. In a further embodiment of the aforementioned embodiments is a compound of Formula (IVb) wherein R$^2$ is

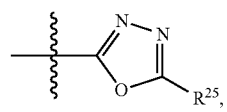

and R$^{25}$ is methyl. In a further embodiment of the aforementioned embodiments is a compound of Formula (IVb) wherein R$^2$ is

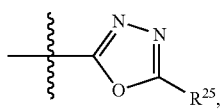

and $R^{25}$ is optionally substituted $C_1$-$C_6$alkyl. In a further embodiment of the aforementioned embodiments is a compound of Formula (IVb) wherein $R^2$ is

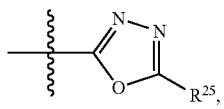

and $R^{25}$ is ethyl.

In a further embodiment of the aforementioned embodiments is a compound of Formula (IVb) wherein $R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IVb) wherein $R^1$ is hydrogen. In a further embodiment of the aforementioned embodiments is a compound of Formula (IVb) wherein $R^1$ is optionally substituted $C_1$-$C_6$alkyl. In a further embodiment of the aforementioned embodiments is a compound of Formula (IVb) wherein $R^1$ is methyl. In a further embodiment of the aforementioned embodiments is a compound of Formula (IVb) wherein $R^1$ is optionally substituted $C_2$-$C_6$alkenyl. In a further embodiment of the aforementioned embodiments is a compound of Formula (IVb) wherein $R^1$ is optionally substituted $C_2$-$C_6$alkynyl.

In a further embodiment of the aforementioned embodiments is a compound of Formula (IVb) wherein $R^1$ and $R^2$ together with the carbon atoms to which they are attached, form an optionally substituted $C_2$-$C_9$heterocycloalkyl ring or an optionally substituted heteroaryl ring. In a further embodiment of the aforementioned embodiments is a compound of Formula (IVb) wherein $R^1$ and $R^2$ together with the carbon atoms to which they are attached, form an optionally substituted $C_2$-$C_9$heterocycloalkyl ring. In a further embodiment of the aforementioned embodiments is a compound of Formula (IVb) wherein $R^1$ and $R^2$ together with the carbon atoms to which they are attached, form an optionally substituted heteroaryl ring.

In another embodiment of the aforementioned embodiments is a compound of Formula (IVb) wherein $R^{20}$ is —$R^{34}R^{35}$. In another embodiment of the aforementioned embodiments is a compound of Formula (IVb) wherein $R^{20}$ is —$R^{34}R^{35}$, and $R^{34}$ is optionally substituted $C_1$-$C_6$alkyl. In another embodiment of the aforementioned embodiments is a compound of Formula (IVb) wherein $R^{20}$ is —$R^{34}R^{35}$, and $R^{34}$ is optionally substituted $C_3$-$C_{10}$cycloalkyl. In another embodiment of the aforementioned embodiments is a compound of Formula (IVb) wherein $R^{20}$ is —$R^{34}R^{35}$, and $R^{34}$ is optionally substituted aryl. In another embodiment of the aforementioned embodiments is a compound of Formula (IVb) wherein $R^{20}$ is —$R^{34}R^{35}$, and $R^{34}$ is optionally substituted —($C_1$-$C_2$alkylene)-(aryl). In another embodiment of the aforementioned embodiments is a compound of Formula (IVb) wherein $R^{20}$ is —$R^{34}R^{35}$, and $R^{34}$ is optionally substituted heteroaryl. In another embodiment of the aforementioned embodiments is a compound of Formula (IVb) wherein $R^{20}$ is —$R^{34}R^{35}$, and $R^{34}$ is optionally substituted $C_2$-$C_9$heterocycloalkyl. In another embodiment of the aforementioned embodiments is a compound of Formula (IVb) wherein $R^{20}$ is —$R^{34}R^{35}$, and $R^{34}$ is optionally substituted —($C_1$-$C_2$alkylene)-(heteroaryl). In another embodiment of the aforementioned embodiments is a compound of Formula (IVb) wherein $R^{20}$ is —$R^{34}R^{35}$, and $R^{35}$ is —($C_1$-$C_6$alkyl)-$R^{30}$. In another embodiment of the aforementioned embodiments is a compound of Formula (IVb) wherein $R^{20}$ is —$R^{34}R^{35}$, and $R^{35}$ is —O($C_2$-$C_6$alkyl)-$R^{30}$. In another embodiment of the aforementioned embodiments is a compound of Formula (IVb) wherein $R^{20}$ is —$R^{34}R^{35}$, and $R^{35}$ is —N($R^{12}$)($C_2$-$C_6$alkyl)-$R^{30}$. In a further embodiment of the aforementioned embodiments is a compound of Formula (IVb) wherein $R^{30}$ is $R^{36a}$. In a further embodiment of the aforementioned embodiments is a compound of Formula (IVb) wherein $R^{30}$ is $R^{36b}$. In a further embodiment of the aforementioned embodiments is a compound of Formula (IVb) wherein $R^{30}$ is $R^{36c}$.

In another embodiment of the aforementioned embodiments is a compound of Formula (IVb) wherein $R^{20}$ is —$R^{31}$. In a further embodiment of the aforementioned embodiments is a compound of Formula (IVb) wherein $R^{31}$ is $R^{36a}$. In a further embodiment of the aforementioned embodiments is a compound of Formula (IVb) wherein $R^{31}$ is $R^{36c}$.

In another embodiment of the aforementioned embodiments is a compound of Formula (IVb) wherein $R^{36a}$ is

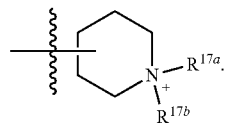

In another embodiment of the aforementioned embodiments is a compound of Formula (IVb) wherein $R^{36a}$ is

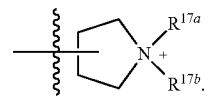

In another embodiment of the aforementioned embodiments is a compound of Formula (IVb) wherein $R^{36a}$ is

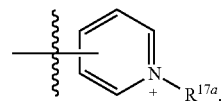

In another embodiment of the aforementioned embodiments is a compound of Formula (IVb) wherein $R^{36b}$ is

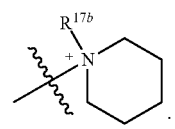

In another embodiment of the aforementioned embodiments is a compound of Formula (IVb) wherein $R^{36b}$ is

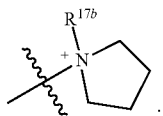

In another embodiment of the aforementioned embodiments is a compound of Formula (IVb) wherein $R^{36b}$ is

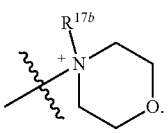

In another embodiment of the aforementioned embodiments is a compound of Formula (IVb) wherein $R^{36b}$ is

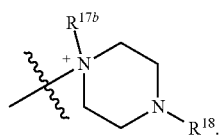

In another embodiment of the aforementioned embodiments is a compound of Formula (IVb) wherein $R^{36b}$ is

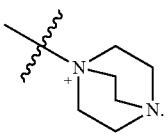

In another embodiment of the aforementioned embodiments is a compound of Formula (IVb) wherein $R^{36b}$ is

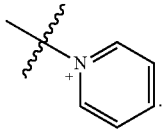

In another embodiment of the aforementioned embodiments is a compound of Formula (IVb) wherein $R^{36b}$ is

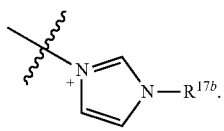

In another embodiment of the aforementioned embodiments is a compound of Formula (IVb) wherein $R^{36c}$ is

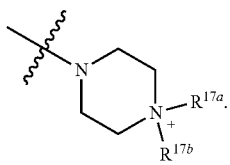

In another embodiment is a compound of Formula (IVb) wherein $R^{36c}$ is

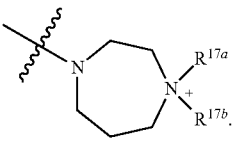

In a further embodiment of the aforementioned embodiments is a compound of Formula (IVb) wherein $R^{17a}$ is methyl. In a further embodiment of the aforementioned embodiments is a compound of Formula (IVb) wherein $R^{17a}$ is ethyl. In a further embodiment of the aforementioned embodiments is a compound of Formula (IVb) wherein $R^{17b}$ is methyl optionally substituted with phenyl, —C(=O)OH or —S(=O)$_2$OH. In a further embodiment of the aforementioned embodiments is a compound of Formula (IVb) wherein $R^{17a}$ is ethyl optionally substituted with phenyl, —C(=O)OH or —S(=O)$_2$OH.

In some embodiments provided herein, the compound of Formula (IV) has the structure of Formula (IVc), or a pharmaceutically acceptable salt or solvate thereof:

Formula (IVc)

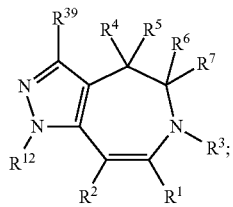

wherein:
$R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R^2$ is selected from the group consisting of —CN, —C(=O)OR$^{25}$, —C(=O)N(R$^{25}$)R$^{26}$,

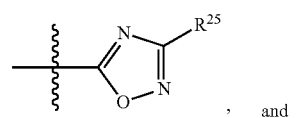 , and 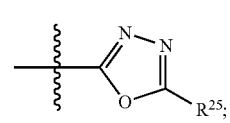 ;

or $R^1$ and $R^2$ together with the carbon atoms to which they are attached, form an optionally substituted $C_2$-$C_9$heterocycloalkyl ring or an optionally substituted heteroaryl ring;

$R^3$ is —C(=O)$R^{20}$ or —S(=O)$_2R^{20}$;

$R^4$ and $R^5$ are each independently selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl; or $R^4$ and $R^5$ together with the carbon atom to which they are attached, form an optionally substituted $C_3$-$C_6$cycloalkyl ring or an optionally substituted $C_2$-$C_7$heterocycloalkyl ring;

$R^6$ is selected from the group consisting of hydrogen, halogen, optionally substituted $C_1$-$C_6$alkyl, optionally substituted $C_2$-$C_6$alkenyl, optionally substituted $C_2$-$C_6$alkynyl, and —C(=O)N($R^{27}$)$R^{28}$;

$R^7$ is selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl;

each $R^{12}$ is independently selected from the group consisting of hydrogen and $C_1$-$C_6$alkyl;

$R^{13}$ and $R^{14}$ are independently selected from the group consisting of hydrogen and $C_1$-$C_6$alkyl; or $R^{13}$ and $R^{14}$ together with the nitrogen atom to which they are attached, form an optionally substituted $C_2$-$C_9$heterocycloalkyl ring;

$R^{39}$ is selected from the group consisting of hydrogen, halogen, —CN, amino, alkylamino, $C_1$-$C_6$alkyl, $C_1$-$C_6$haloalkyl, $C_1$-$C_6$alkoxy, $C_1$-$C_6$haloalkoxy, $C_3$-$C_8$cycloalkyl, $C_2$-$C_9$heterocycloalkyl, aryl, heteroaryl, —C(=O)O$R^{12}$, and —C(=O)N($R^{13}$)$R^{14}$;

$R^{20}$ is selected from the group consisting of —$R^{34}R^{35}$ or —$R^{31}$;

$R^{34}$ is selected from the group consisting of optionally substituted $C_1$-$C_6$alkyl, optionally substituted $C_3$-$C_{10}$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl);

$R^{35}$ is —($C_1$-$C_6$alkyl)-$R^{30}$, —O($C_2$-$C_6$alkyl)-$R^{30}$, or —N($R^{12}$)($C_2$-$C_6$alkyl)-$R^{30}$;

$R^{30}$ is $R^{36a}$, $R^{36b}$, or $R^{36c}$;

$R^{31}$ is $R^{36a}$ or $R^{36c}$;

$R^{36a}$ is

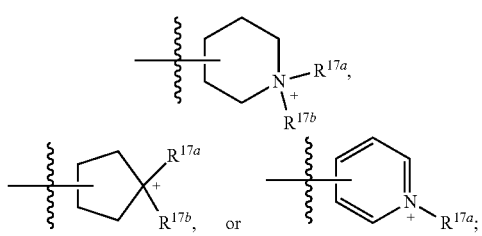

$R^{36b}$ is

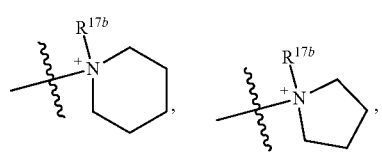

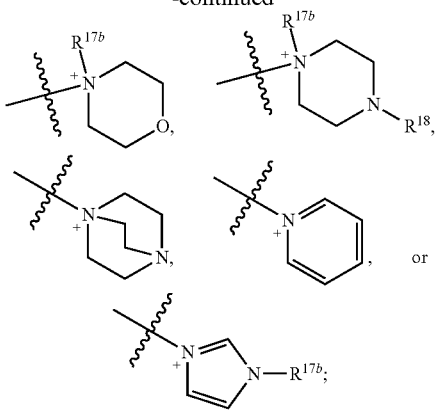

$R^{36c}$ is

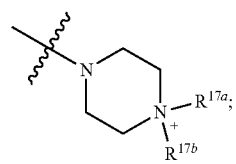

$R^{17a}$ is $C_1$-$C_6$alkyl;

$R^{17b}$ is $C_1$-$C_6$alkyl optionally substituted with phenyl, —C(=O)OH or —S(=O)$_2$OH;

$R^{18}$ is hydrogen, —OH, —($C_0$-$C_6$alkyl)-C(=O)OH, or $C_1$-$C_6$alkyl;

$R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); and $R^{27}$ and $R^{28}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{27}$ and $R^{28}$ together with the nitrogen atom to which they are attached, form an optionally substituted $C_2$-$C_9$heterocycloalkyl ring.

In one embodiment is a compound of Formula (IVc) wherein $R^4$ and $R^5$ are each independently selected from the group consisting of hydrogen, halogen, and optionally substituted $C_1$-$C_6$alkyl. In another embodiment is a compound of Formula (IVc) wherein $R^4$ and $R^5$ are each independently selected from the group consisting of hydrogen and optionally substituted $C_1$-$C_6$alkyl. In another embodiment is a compound of Formula (IVc) wherein $R^4$ and $R^5$ are each hydrogen. In another embodiment is a compound of Formula (IVc) wherein $R^4$ and $R^5$ are each independently optionally substituted $C_1$-$C_6$alkyl. In another embodiment is a compound of Formula (IVc) wherein $R^4$ and $R^5$ are each methyl. In another embodiment is a compound of Formula (IVc) wherein $R^4$ and $R^5$ form an optionally substituted $C_3$-$C_6$cycloalkyl ring or an optionally substituted $C_2$-$C_7$heterocycloalkyl ring. In some embodiments is a compound of Formula (IVc) wherein $R^4$ and $R^5$ form an optionally substituted $C_3$-$C_6$cycloalkyl ring. In some embodiments is a compound of Formula (IVc) wherein $R^4$ and $R^5$ form an optionally substituted $C_2$-$C_7$heterocycloalkyl ring.

In another embodiment is a compound of Formula (IVc) wherein $R^6$ and $R^7$ are each independently selected from the group consisting of hydrogen, halogen, and optionally substituted $C_1$-$C_6$alkyl. In another embodiment is a compound of Formula (IVc) wherein $R^6$ and $R^7$ are each independently selected from the group consisting of hydrogen and optionally substituted $C_1$-$C_6$alkyl. In another embodiment is a compound of Formula (IVc) wherein $R^6$ and $R^7$ are each independently optionally substituted $C_1$-$C_6$alkyl. In another embodiment is a compound of Formula (IVc) wherein $R^6$ and $R^7$ are each methyl. In another embodiment is a compound of Formula (IVc) wherein $R^6$ and $R^7$ are each hydrogen.

In another embodiment is a compound of Formula (IVc) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted aryl. In another embodiment is a compound of Formula (IVc) wherein $R^6$ and $R^7$ are hydrogen, $R^4$ and $R^5$ are independently optionally substituted $C_1$-$C_6$alkyl, $R^3$ is —C(O)$R^{20}$, and $R^{20}$ is optionally substituted heteroaryl. In another embodiment is a compound of Formula (IVc) wherein $R^6$ and $R^7$ are hydrogen, $R^4$ and $R^5$ are methyl, $R^3$ is —C(O)$R^{20}$, and $R^{20}$ is optionally substituted aryl. In another embodiment is a compound of Formula (IVc) wherein $R^6$ and $R^7$ are hydrogen, $R^4$ and $R^5$ are methyl, $R^3$ is —C(O)$R^{20}$, and $R^{20}$ is optionally substituted heteroaryl.

In another embodiment is a compound of Formula (IVc) wherein $R^6$ and $R^7$ are hydrogen, $R^4$ and $R^5$ are independently optionally substituted $C_1$-$C_6$alkyl, $R^3$ is —S(O)$_2R^{20}$, and $R^{20}$ is optionally substituted aryl. In another embodiment is a compound of Formula (IVc) wherein $R^6$ and $R^7$ are hydrogen, $R^4$ and $R^5$ are independently optionally substituted $C_1$-$C_6$alkyl, $R^3$ is —S(O)$_2R^{20}$, and $R^{20}$ is optionally substituted heteroaryl. In another embodiment is a compound of Formula (IVc) wherein $R^6$ and $R^7$ are hydrogen, $R^4$ and $R^5$ are methyl, $R^3$ is —S(O)$_2R^{20}$, and $R^{20}$ is optionally substituted aryl. In another embodiment is a compound of Formula (IVc) wherein $R^6$ and $R^7$ are hydrogen, $R^4$ and $R^5$ are methyl, $R^3$ is —S(O)$_2R^{20}$, and $R^{20}$ is optionally substituted heteroaryl.

In a further embodiment of the aforementioned embodiments is a compound of Formula (IVc) wherein $R^2$ is selected from the group consisting of —CN, —C(O)O$R^{25}$, —C(O)N($R^{25}$)$R^{26}$,

[structures of two isoxazole/oxadiazole rings bearing $R^{25}$, and]

In a further embodiment of the aforementioned embodiments is a compound of Formula (IVc) wherein $R^2$ is —CN.

In a further embodiment of the aforementioned embodiments is a compound of Formula (IVc) wherein $R^2$ is —C(O)O$R^{25}$. In a further embodiment of the aforementioned embodiments is a compound of Formula (IVc) wherein $R^2$ is —C(O)O$R^{25}$, and $R^{25}$ is independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IVc) wherein $R^2$ is —C(O)O$R^{25}$, and $R^{25}$ is independently selected from the group consisting of hydrogen, and optionally substituted $C_1$-$C_6$alkyl. In a further embodiment of the aforementioned embodiments is a compound of Formula (IVc) wherein $R^2$ is —C(O)O$R^{25}$, and $R^{25}$ is hydrogen. In a further embodiment of the aforementioned embodiments is a compound of Formula (IVc) wherein $R^2$ is —C(O)O$R^{25}$, and $R^{25}$ is optionally substituted $C_1$-$C_6$alkyl. In a further embodiment of the aforementioned embodiments is a compound of Formula (IVc) wherein $R^2$ is —C(O)O$R^{25}$, and $R^{25}$ is unsubstituted $C_1$-$C_6$alkyl. In a further embodiment of the aforementioned embodiments is a compound of Formula (IVc) wherein $R^2$ is —C(O)O$R^{25}$, and $R^{25}$ is methyl. In a further embodiment of the aforementioned embodiments is a compound of Formula (IVc) wherein $R^2$ is —C(O)O$R^{25}$, and $R^{25}$ is ethyl.

In a further embodiment of the aforementioned embodiments is a compound of Formula (IVc) wherein $R^2$ is —C(O)N($R^{25}$)$R^{26}$. In a further embodiment of the aforementioned embodiments is a compound of Formula (IVc) wherein $R^2$ is —C(O)N($R^{25}$)$R^{26}$, and $R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IVc) wherein $R^2$ is —C(O)N($R^{25}$)$R^{26}$, and $R^{25}$ and $R^{26}$ are each independently selected from the group consisting of hydrogen, and optionally substituted $C_1$-$C_6$alkyl. In a further embodiment of the aforementioned embodiments is a compound of Formula (IVc) wherein $R^2$ is —C(O)N($R^{25}$)$R^{26}$, and $R^{25}$ and $R^{26}$ are hydrogen. In a further embodiment of the aforementioned embodiments is a compound of Formula (IVc) wherein $R^2$ is —C(O)N($R^{25}$)$R^{26}$, and $R^{25}$ and $R^{26}$ are each independently optionally substituted $C_1$-$C_6$alkyl. In a further embodiment of the aforementioned embodiments is a compound of Formula (IVc) wherein $R^2$ is —C(O)N($R^{25}$)$R^{26}$, $R^{25}$ is hydrogen, and $R^{26}$ is optionally substituted $C_1$-$C_6$alkyl. In a further embodiment of the aforementioned embodiments is a compound of Formula (IVc) wherein $R^2$ is —C(O)N($R^{25}$)$R^{26}$, and $R^{25}$ and $R^{26}$ are each independently unsubstituted $C_1$-$C_6$alkyl. In a further embodiment of the aforementioned embodiments is a compound of Formula (IVc) wherein $R^2$ is —C(O)N($R^{25}$)$R^{26}$, $R^{25}$ is hydrogen, and $R^{26}$ are methyl. In a further embodiment of the aforementioned embodiments is a compound of Formula (IVc) wherein $R^2$ is —C(O)N($R^{25}$)$R^{26}$, and $R^{25}$ and $R^{26}$ are methyl. In a further embodiment of the aforementioned embodiments is a compound of Formula (IVc) wherein $R^2$ is —C(O)N($R^{25}$)$R^{26}$, and $R^{25}$ and $R^{26}$ are ethyl.

In a further embodiment of the aforementioned embodiments is a compound of Formula (IVc) wherein $R^2$ is

[structure of isoxazole ring bearing $R^{25}$.]

In a further embodiment of the aforementioned embodiments is a compound of Formula (IVc) wherein $R^2$ is

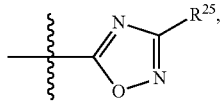

and $R^{25}$ is optionally substituted $C_1$-$C_6$alkyl. In a further embodiment of the aforementioned embodiments is a compound of Formula (IVc) wherein $R^2$ is

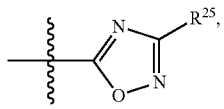

and $R^{25}$ is methyl. In a further embodiment of the aforementioned embodiments is a compound of Formula (IVc) wherein $R^2$ is

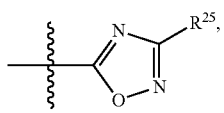

and $R^{25}$ is optionally substituted $C_1$-$C_6$alkyl. In a further embodiment of the aforementioned embodiments is a compound of Formula (IVc) wherein $R^2$ is

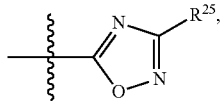

and $R^{25}$ is ethyl.

In a further embodiment of the aforementioned embodiments is a compound of Formula (IVc) wherein $R^2$ is

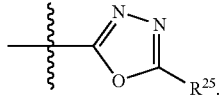

In a further embodiment of the aforementioned embodiments is a compound of Formula (IVc) wherein $R^2$ is

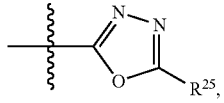

and $R^{25}$ is optionally substituted $C_1$-$C_6$alkyl. In a further embodiment of the aforementioned embodiments is a compound of Formula (IVc) wherein $R^2$ is

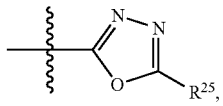

and $R^{25}$ is methyl. In a further embodiment of the aforementioned embodiments is a compound of Formula (IVc) wherein $R^2$ is

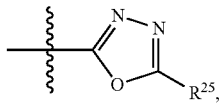

and $R^{25}$ is optionally substituted $C_1$-$C_6$alkyl. In a further embodiment of the aforementioned embodiments is a compound of Formula (IVc) wherein $R^2$ is

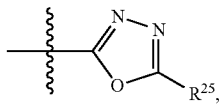

and $R^{25}$ is ethyl.

In a further embodiment of the aforementioned embodiments is a compound of Formula (IVc) wherein $R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl). In a further embodiment of the aforementioned embodiments is a compound of Formula (IVc) wherein $R^1$ is hydrogen. In a further embodiment of the aforementioned embodiments is a compound of Formula (IVc) wherein $R^1$ is optionally substituted $C_1$-$C_6$alkyl. In a further embodiment of the aforementioned embodiments is a compound of Formula (IVc) wherein $R^1$ is methyl. In a further embodiment of the aforementioned embodiments is a compound of Formula (IVc) wherein $R^1$ is optionally substituted $C_2$-$C_6$alkenyl. In a further embodiment of the aforementioned embodiments is a compound of Formula (IVc) wherein $R^1$ is optionally substituted $C_2$-$C_6$alkynyl.

In a further embodiment of the aforementioned embodiments is a compound of Formula (IVc) wherein $R^1$ and $R^2$ together with the carbon atoms to which they are attached, form an optionally substituted $C_2$-$C_9$heterocycloalkyl ring or an optionally substituted heteroaryl ring. In a further embodiment of the aforementioned embodiments is a compound of Formula (IVc) wherein $R^1$ and $R^2$ together with the carbon atoms to which they are attached, form an optionally substituted $C_2$-$C_9$heterocycloalkyl ring. In a further embodiment of the aforementioned embodiments is a compound of Formula (IVc) wherein $R^1$ and $R^2$ together with the carbon atoms to which they are attached, form an optionally substituted heteroaryl ring.

In another embodiment of the aforementioned embodiments is a compound of Formula (IVc) wherein $R^{20}$ is —$R^{34}R^{35}$. In another embodiment of the aforementioned embodiments is a compound of Formula (IVc) wherein $R^{20}$ is —$R^{34}R^{35}$, and $R^{34}$ is optionally substituted $C_1$-$C_6$alkyl. In another embodiment of the aforementioned embodiments is a compound of Formula (IVc) wherein $R^{20}$ is —$R^{34}R^{35}$, and $R^{34}$ is optionally substituted $C_3$-$C_{10}$cycloalkyl. In another embodiment of the aforementioned embodiments is a compound of Formula (IVc) wherein $R^{20}$ is —$R^{34}R^{35}$, and $R^{34}$ is optionally substituted aryl. In another embodiment of the aforementioned embodiments is a compound of Formula (IVc) wherein $R^{20}$ is —$R^{34}R^{35}$, and $R^{34}$ is optionally substituted —($C_1$-$C_2$alkylene)-(aryl). In another embodiment of the aforementioned embodiments is a compound of Formula (IVc) wherein $R^{20}$ is —$R^{34}R^{35}$, and $R^{34}$ is optionally substituted heteroaryl. In another embodiment of the aforementioned embodiments is a compound of Formula (IVc) wherein $R^{20}$ is —$R^{34}R^{35}$, and $R^{34}$ is optionally substituted $C_2$-$C_9$heterocycloalkyl. In another embodiment of the aforementioned embodiments is a compound of Formula (IVc) wherein $R^{20}$ is —$R^{34}R^{35}$, and $R^{34}$ is optionally substituted —($C_1$-$C_2$alkylene)-(heteroaryl). In another embodiment of the aforementioned embodiments is a compound of Formula (IVc) wherein $R^{20}$ is —$R^{34}R^{35}$, and $R^{35}$ is —($C_1$-$C_6$alkyl)-$R^{30}$. In another embodiment of the aforementioned embodiments is a compound of Formula (IVc) wherein $R^{20}$ is —$R^{34}R^{35}$, and $R^{35}$ is —$O(C_2$-$C_6$alkyl)-$R^{30}$. In another embodiment of the aforementioned embodiments is a compound of Formula (IVc) wherein $R^{20}$ is —$R^{34}R^{35}$, and $R^{35}$ is —$N(R^{12})(C_2$-$C_6$alkyl)-$R^{30}$. In a further embodiment of the aforementioned embodiments is a compound of Formula (IVc) wherein $R^{30}$ is $R^{36a}$. In a further embodiment of the aforementioned embodiments is a compound of Formula (IVc) wherein $R^{30}$ is $R^{36b}$. In a further embodiment of the aforementioned embodiments is a compound of Formula (IVc) wherein $R^{30}$ is $R^{36c}$.

In another embodiment of the aforementioned embodiments is a compound of Formula (IVc) wherein $R^{20}$ is —$R^{31}$. In a further embodiment of the aforementioned embodiments is a compound of Formula (IVc) wherein $R^{31}$ is $R^{36a}$ In a further embodiment of the aforementioned embodiments is a compound of Formula (IVc) wherein $R^{31}$ is $R^{36c}$.

In another embodiment of the aforementioned embodiments is a compound of Formula (IVc) wherein $R^{36a}$ is

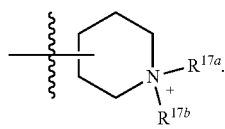

In another embodiment of the aforementioned embodiments is a compound of Formula (IVc) wherein $R^{36a}$ is

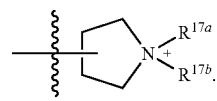

In another embodiment of the aforementioned embodiments is a compound of Formula (IVc) wherein $R^{36a}$ is

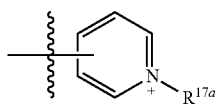

In another embodiment of the aforementioned embodiments is a compound of Formula (IVc) wherein $R^{36b}$ is

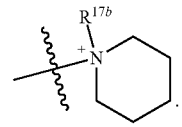

In another embodiment of the aforementioned embodiments is a compound of Formula (IVc) wherein $R^{36b}$ is

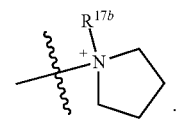

In another embodiment of the aforementioned embodiments is a compound of Formula (IVc) wherein $R^{36b}$ is

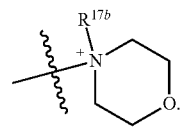

In another embodiment of the aforementioned embodiments is a compound of Formula (IVc) wherein $R^{36b}$ is

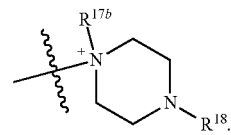

In another embodiment of the aforementioned embodiments is a compound of Formula (IVc) wherein $R^{36b}$ is

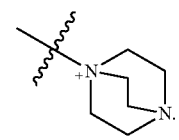

In another embodiment of the aforementioned embodiments is a compound of Formula (IVc) wherein $R^{36b}$ is

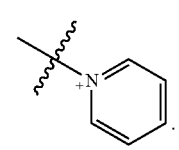

In another embodiment of the aforementioned embodiments is a compound of Formula (IVc) wherein $R^{36b}$ is

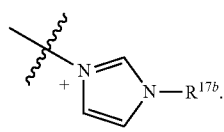

In another embodiment of the aforementioned embodiments is a compound of Formula (IVc) wherein $R^{36c}$ is

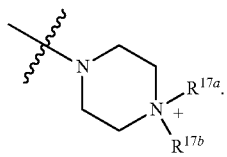

In another embodiment is a compound of Formula (IVc) wherein $R^{36c}$ is

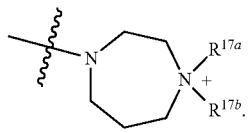

In a further embodiment of the aforementioned embodiments is a compound of Formula (IVc) wherein $R^{17a}$ is methyl. In a further embodiment of the aforementioned embodiments is a compound of Formula (IVc) wherein $R^{17a}$ is ethyl. In a further embodiment of the aforementioned embodiments is a compound of Formula (IVc) wherein $R^{17b}$ is methyl optionally substituted with phenyl, —C(=O)OH or —S(=O)$_2$OH. In a further embodiment of the aforementioned embodiments is a compound of Formula (IVc) wherein $R^{17a}$ is ethyl optionally substituted with phenyl, —C(=O)OH or —S(=O)$_2$OH.

Any combination of the groups described above for the various variables is contemplated herein. Throughout the specification, groups and substituents thereof can be chosen by one skilled in the field to provide stable moieties and compounds.

In some embodiments is a compound selected from:

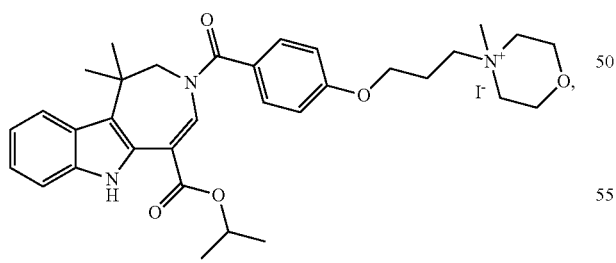

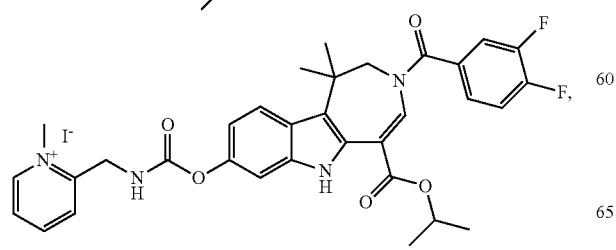

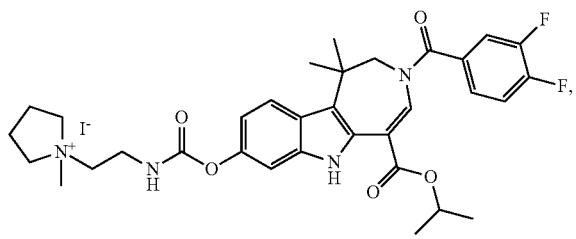

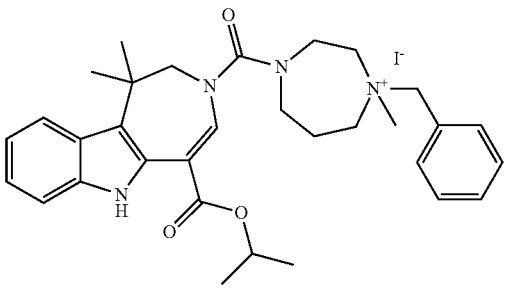

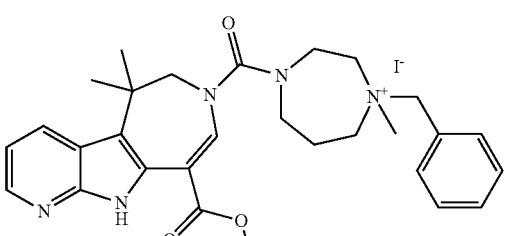

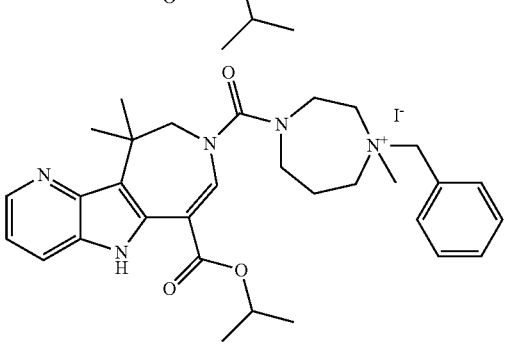

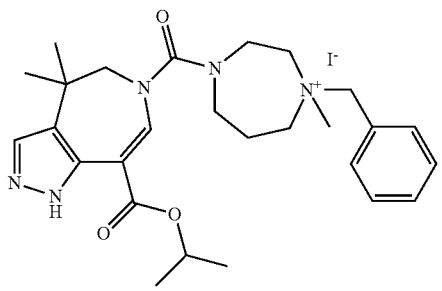

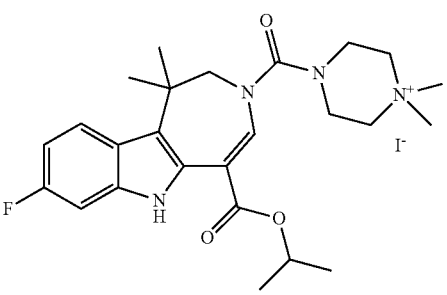

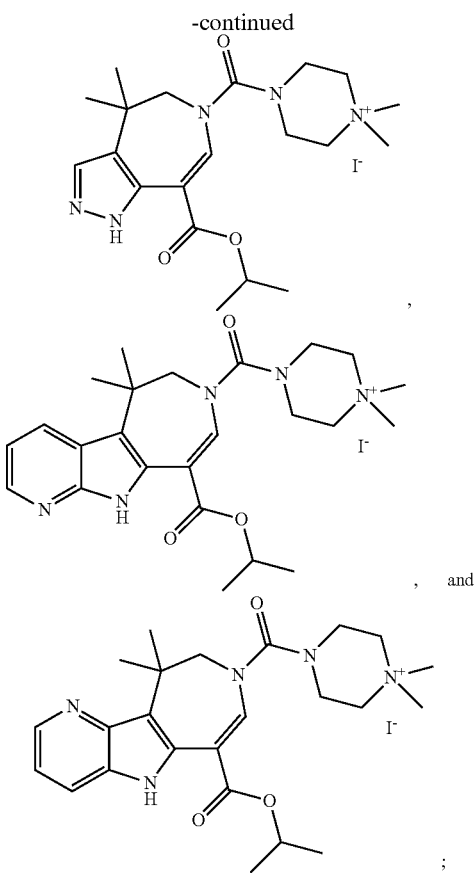

or a pharmaceutically acceptable salt, or pharmaceutically acceptable solvate thereof.

In some embodiments, the therapeutic agent(s) (e.g. compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc)) is present in the pharmaceutical composition as a pharmaceutically acceptable salt. In some embodiments, any compound described above is suitable for any method or composition described herein.

In certain embodiments, the compounds presented herein possess one or more stereocenters and each center independently exists in either the R or S configuration. The compounds presented herein include all diastereomeric, enantiomeric, and epimeric forms as well as the appropriate mixtures thereof. Stereoisomers are obtained, if desired, by methods such as, stereoselective synthesis and/or the separation of stereoisomers by chiral chromatographic columns. In some embodiments, a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) is used as a single enantiomer. In some embodiments, a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) is used as a racemic mixture.

The methods and formulations described herein include the use of N-oxides (if appropriate), crystalline forms (also known as polymorphs), or pharmaceutically acceptable salts of compounds having the structures presented herein, as well as active metabolites of these compounds having the same type of activity.

In some situations, compounds may exist as tautomers. All tautomers are included within the scope of the compounds presented herein.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like.

Prodrug forms of the herein described compounds, wherein the prodrug is metabolized in vivo to produce a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), as set forth herein are included within the scope of the claims. In some cases, some of the herein-described compounds may be a prodrug for another derivative or active compound.

In specific embodiments, the compounds described herein exist in solvated forms with pharmaceutically acceptable solvents such as water, ethanol, and the like. In other embodiments, the compounds described herein exist in unsolvated form.

In some embodiments, the compounds of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) described herein include solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol.

In some embodiments, sites on the compounds of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) disclosed herein are susceptible to various metabolic reactions. Therefore incorporation of appropriate substituents at the places of metabolic reactions will reduce, minimize or eliminate the metabolic pathways. In specific embodiments, the appropriate substituent to decrease or eliminate the susceptibility of the aromatic ring to metabolic reactions is, by way of example only, a halogen, deuterium or an alkyl group.

In some embodiments, the compounds of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) disclosed herein are isotopically-labeled, which are identical to those recited in the various formulae and structures presented herein, but for the fact that one or more atoms are replaced by an atom having an atomic mass or mass number different from the atomic mass or mass number usually found in nature. In some embodiments, one or more hydrogen atoms are replaced with deuterium. In some embodiments, metabolic sites on the compounds described herein are deuterated. In some embodiments, substitution with deuterium affords certain therapeutic advantages resulting from greater metabolic stability, such as, for example, increased in vivo half-life or reduced dosage requirements.

In some embodiments, compounds described herein, such as compounds of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), are in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, melting points, density, hardness, crystal shape, optical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning Calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UV-VIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Throughout the specification, groups and substituents thereof can be chosen to provide stable moieties and compounds.

Additional FXR Modulators

Disclosed herein are additional FXR modulators which have been structurally modified to incorporate a quaternary amine functional group. The quaternary amine FXR modulators described herein retain FXR activity, but are not absorbed into the systemic circulation. Thus, the quaternary amines described herein provide an optimal delivery for an orally administered FXR modulator. The quaternary amines are potent FXR modulators which induce the expression and/or protein levels of FXR in the intestine. However, the quaternary amines will have little or no systemic exposure, thereby minimizing potential deleterious side effects of systemic exposure.

Scheme A (FIG. 1) depicts a general procedure for the identification of quaternary amine FXR modulators. Following the identification of systemically administered FXR modulator compound containing a basic nitrogen atom (FXR Modulator A), the corresponding quaternary amine (FXR Modulator B) is then synthesized and tested in various FXR assays to establish that the FXR Modulator B is not systemically available, but retains FXR activity.

Figure 2:
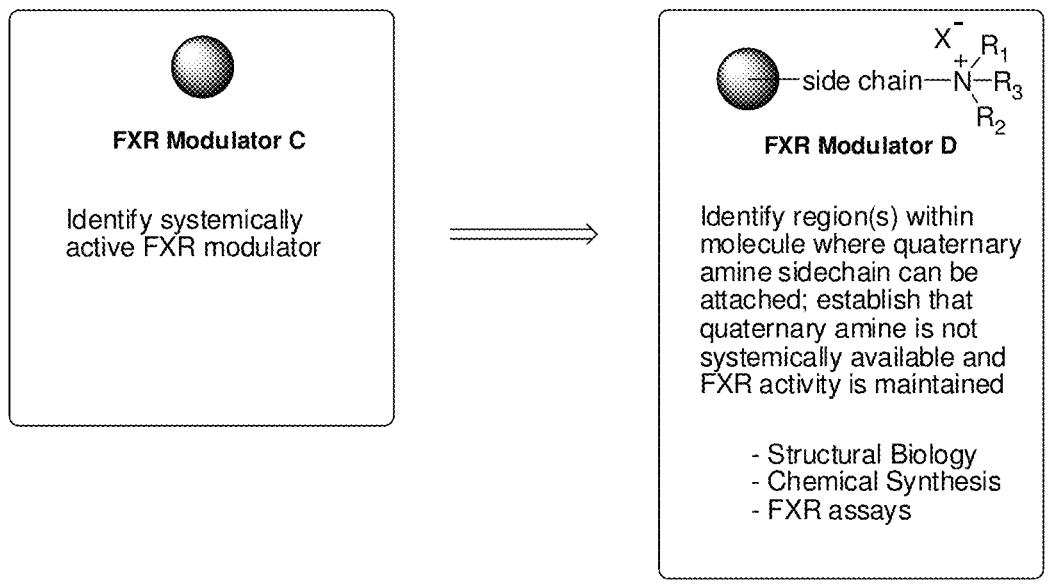
FIG. 2 illustrates Scheme B which depicts another general procedure for the identification of quaternary amine FXR modulators.

Scheme B (FIG. 2) depicts another general procedure for the identification of quaternary amine FXR modulators. Following the identification of systemically active FXR modulator compound (FXR Modulator C), a region within the FXR modulator molecule is identified whereby a side chain containing a quaternary amine is attached to the molecule. The corresponding quaternary amine (FXR Modulator D) is then synthesized and tested in various FXR assays to establish that the FXR Modulator D is not systemically available, but retains FXR activity.

The procedures outlined in Scheme A (FIG. 1) and Scheme B (FIG. 2) are illustrated by, but not limited to, the following examples:

FXR modulators described in WO 2003/099821 are structurally modified to incorporate a quaternary amine in the compound. In some embodiments, FXR modulators described in WO 2006/109633 are structurally modified to attach to the compound a quaternary amine side chain. The quaternary amine is FXR active, but not systemically available (Scheme C). The compounds, and methods for their synthesis, disclosed in WO 2003/099821 are incorporated herein by reference.

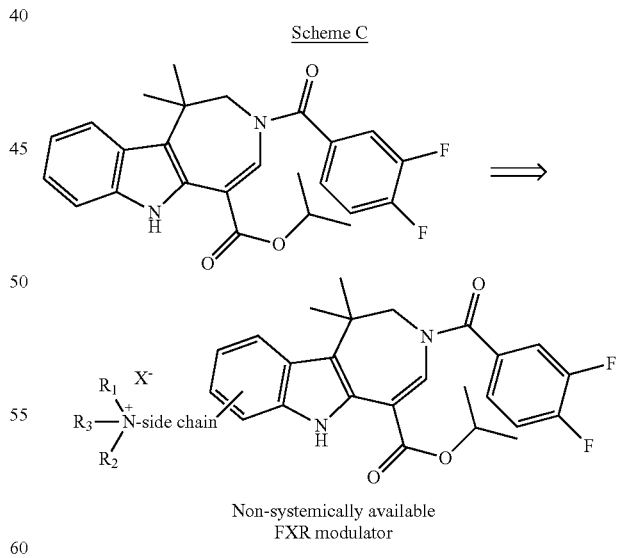

FXR modulators described in WO 2005/009387 are structurally modified to incorporate a quaternary amine in the compound. In some embodiments, FXR modulators described in WO 2005/009387 are structurally modified to attach to the compound a quaternary amine side chain. The quaternary amine is FXR active, but not systemically available (Scheme D). The compounds, and methods for their synthesis, disclosed in WO 2005/009387 are incorporated herein by reference.

Scheme D

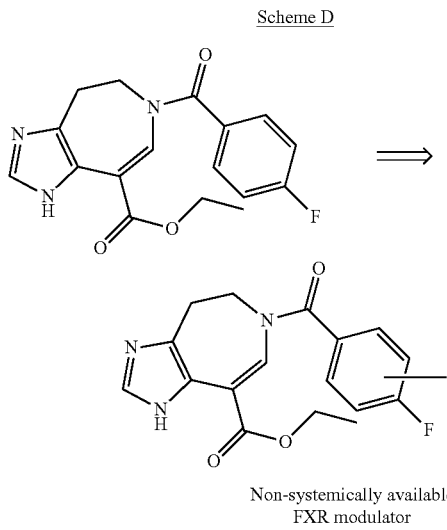

Non-systemically available FXR modulator

FXR modulators described in WO 2005/056554 are structurally modified to incorporate a quaternary amine in the compound. In some embodiments, FXR modulators described in WO 2005/056554 are structurally modified to form a quaternary amine from a basic nitrogen in the compound. The quaternary amine is FXR active, but not systemically available (Scheme E). The compounds, and methods for their synthesis, disclosed in WO 2005/056554 are incorporated herein by reference.

Scheme E

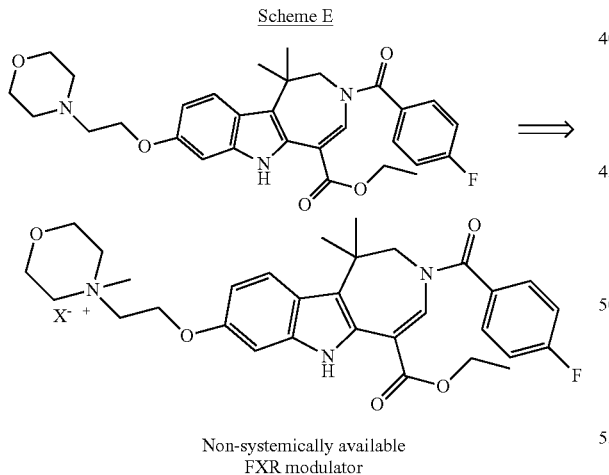

Non-systemically available FXR modulator

FXR modulators described in WO 2006/020680 are structurally modified to incorporate a quaternary amine in the compound. In some embodiments, FXR modulators described in WO 2006/020680 are structurally modified to attach to the compound a quaternary amine side chain. The quaternary amine is FXR active, but not systemically available (Scheme F). The compounds, and methods for their synthesis, disclosed in WO 2006/020680 are incorporated herein by reference.

Scheme F

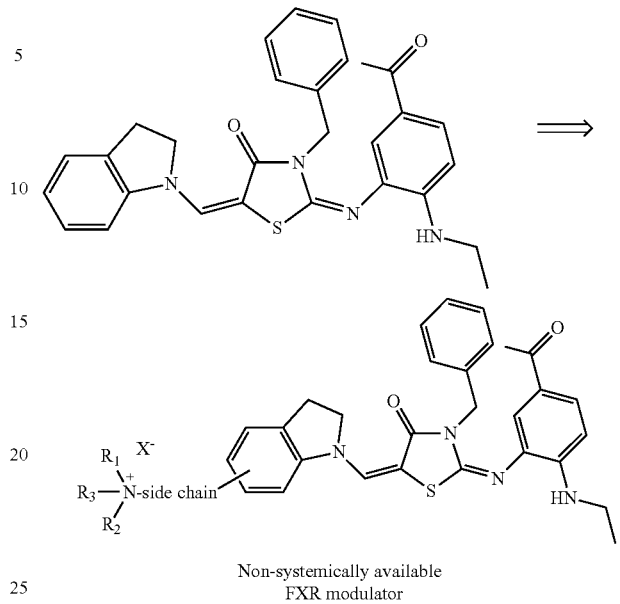

Non-systemically available FXR modulator

FXR modulators described in WO 2007/070796 are structurally modified to incorporate a quaternary amine in the compound. In some embodiments, FXR modulators described in WO 2007/070796 are structurally modified to form a quaternary amine from a basic nitrogen in the compound. The quaternary amine is FXR active, but not systemically available (Scheme G). The compounds, and methods for their synthesis, disclosed in WO 2007/070796 are incorporated herein by reference.

Scheme G

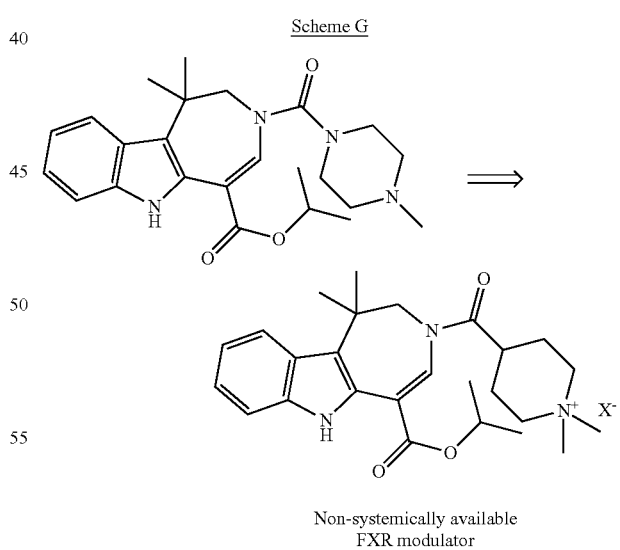

Non-systemically available FXR modulator

FXR modulators described in WO 2008/073825 are structurally modified to incorporate a quaternary amine in the compound. In some embodiments, FXR modulators described in WO 2008/073825 are structurally modified to attach to the compound a quaternary amine side chain. The quaternary amine is FXR active, but not systemically available (Scheme H). The compounds, and methods for their synthesis, disclosed in WO 2008/073825 are incorporated herein by reference.

Scheme H

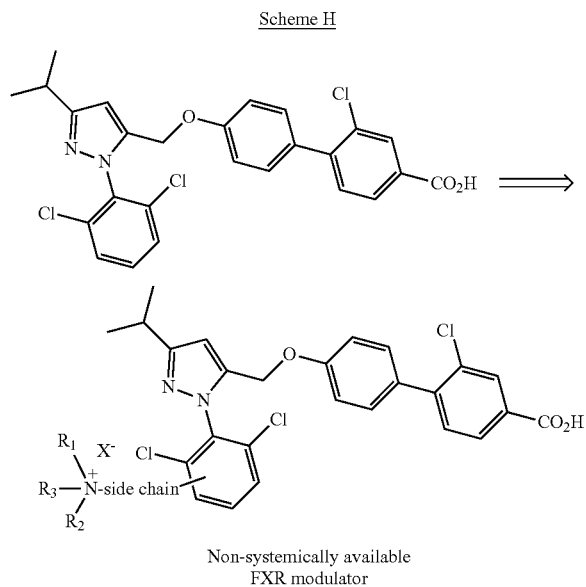

Non-systemically available
FXR modulator

FXR modulators described in US 2009/0131409 are structurally modified to incorporate a quaternary amine in the compound. In some embodiments, FXR modulators described in US 2009/0131409 are structurally modified to attach to the compound a quaternary amine side chain. The quaternary amine is FXR active, but not systemically available (Scheme I). The compounds, and methods for their synthesis, disclosed in US 2009/0131409 are incorporated herein by reference.

Scheme I

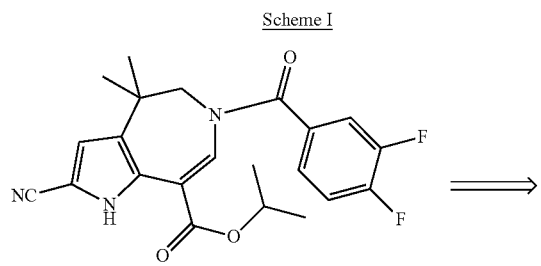

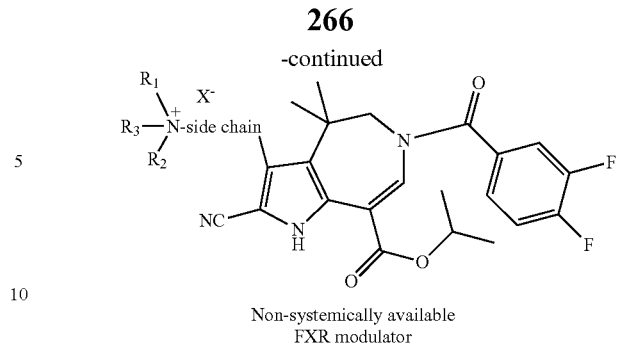

Non-systemically available
FXR modulator

FXR modulators described in US 2009/0137554 are structurally modified to incorporate a quaternary amine in the compound. In some embodiments, FXR modulators described in US 2009/0137554 are structurally modified to attach to the compound a quaternary amine side chain. The quaternary amine is FXR active, but not systemically available (Scheme J). The compounds, and methods for their synthesis, disclosed in US 2009/0137554 are incorporated herein by reference.

Scheme J

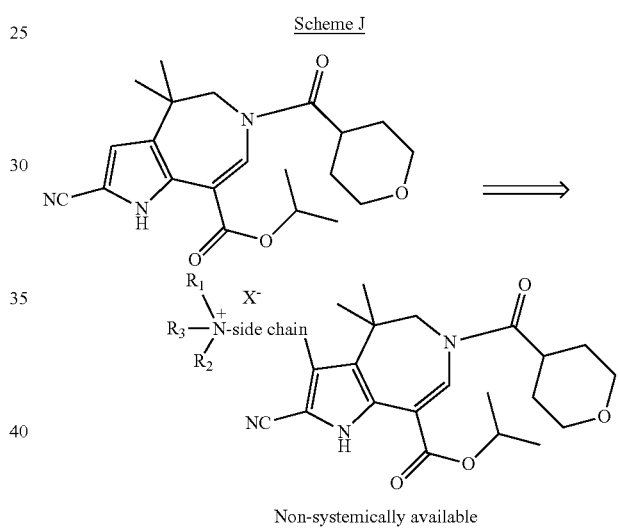

Non-systemically available
FXR modulator

FXR modulators described in WO 2010/036362 are structurally modified to incorporate a quaternary amine in the compound. In some embodiments, FXR modulators described in WO 2010/036362 are structurally modified to form a quaternary amine from a basic nitrogen in the compound. The quaternary amine is FXR active, but not systemically available (Scheme K). The compounds, and methods for their synthesis, disclosed in WO 2010/036362 are incorporated herein by reference.

Scheme K

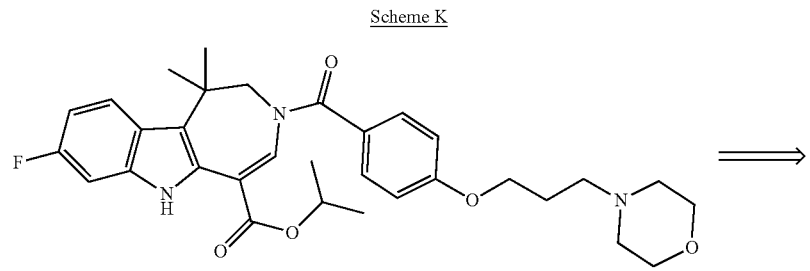

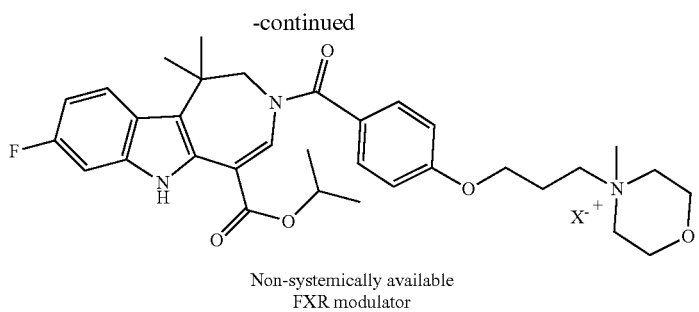

Non-systemically available
FXR modulator

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics. In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4$^{th}$ Ed., Vols. A and B (Plenum 2000, 2001), and Green and Wuts, Protective Groups in Organic Synthesis 3$^{rd}$ Ed., (Wiley 1999) (all of which are incorporated by reference for such disclosure). General methods for the preparation of compound as disclosed herein may be derived from reactions and the reactions may be modified by the use of appropriate reagents and conditions, for the introduction of the various moieties found in the formulae as provided herein.

Use of Protecting Groups

In the reactions described, it may be necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. It is preferred that each protective group be removable by a different means. Protective groups that are cleaved under totally disparate reaction conditions fulfill the requirement of differential removal.

Protective groups can be removed by acid, base, reducing conditions (such as, for example, hydrogenolysis), and/or oxidative conditions. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, which include conversion to alkyl esters, or they may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a Pd$^0$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

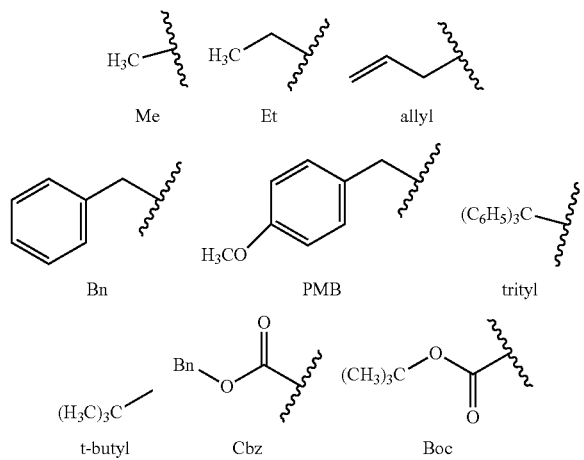

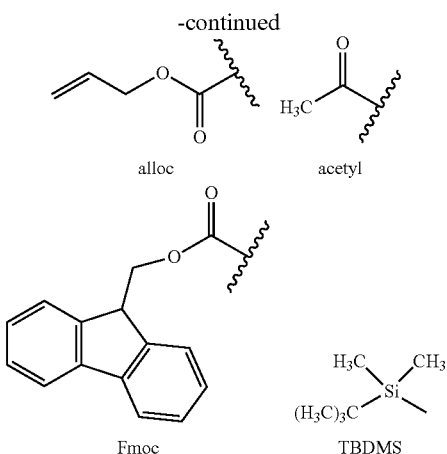

alloc    acetyl    Fmoc    TBDMS

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

Certain Terminology

Unless defined otherwise, all technical and scientific terms used herein have the same meaning as is commonly understood to which the claimed subject matter belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "Advanced Organic Chemistry $4^{th}$ Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substituents).

An "alkyl" group refers to an aliphatic hydrocarbon group. The alkyl groups may or may not include units of unsaturation. The alkyl moiety may be a "saturated alkyl" group, which means that it does not contain any units of unsaturation (i.e. a carbon-carbon double bond or a carbon-carbon triple bond). The alkyl group may also be an "unsaturated alkyl" moiety, which means that it contains at least one unit of unsaturation. The alkyl moiety, whether saturated or unsaturated, may be branched, straight chain, or cyclic.

The "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). The alkyl group of the compounds described herein may be designated as "$C_1$-$C_6$ alkyl" or similar designations. By way of example only, "$C_1$-$C_6$ alkyl" indicates that there are one to six carbon atoms in the alkyl chain, i.e., the alkyl chain is selected from the group consisting of methyl, ethyl, n-propyl, isopropyl, n-butyl, iso-butyl, sec-butyl, t-butyl, n-pentyl, iso-pentyl, neo-pentyl, hexyl, propen-3-yl (allyl), cyclopropylmethyl, cyclobutylmethyl, cyclopentylmethyl, cyclohexylmethyl. Alkyl groups can be substituted or unsubstituted. Depending on the structure, an alkyl group can be a monoradical or a diradical (i.e., an alkylene group).

An "alkoxy" refers to a "—O-alkyl" group, where alkyl is as defined herein.

The term "alkenyl" refers to a type of alkyl group in which two atoms of the alkyl group form a double bond that is not part of an aromatic group. Non-limiting examples of an alkenyl group include —CH=$CH_2$, —C($CH_3$)=$CH_2$, —CH=CHCH$_3$, —CH=C($CH_3$)$_2$ and —C($CH_3$)=CHCH$_3$. The alkenyl moiety may be branched, straight chain, or cyclic (in which case, it would also be known as a "cycloalkenyl" group). Alkenyl groups may have 2 to 6 carbons. Alkenyl groups can be substituted or unsubstituted. Depending on the structure, an alkenyl group can be a monoradical or a diradical (i.e., an alkenylene group).

The term "alkynyl" refers to a type of alkyl group in which the two atoms of the alkyl group form a triple bond. Non-limiting examples of an alkynyl group include —C≡CH, —C≡CCH$_3$, —C≡CCH$_2$CH$_3$ and —C≡CCH$_2$CH$_2$CH$_3$. The "R" portion of the alkynyl moiety may be branched, straight chain, or cyclic. An alkynyl group can have 2 to 6 carbons. Alkynyl groups can be substituted or unsubstituted. Depending on the structure, an alkynyl group can be a monoradical or a diradical (i.e., an alkynylene group).

"Amino" refers to a —NH$_2$ group.

The term "alkylamine" or "alkylamino" refers to the —N(alkyl)$_x$H$_y$ group, where alkyl is as defined herein and x and y are selected from the group x=1, y=1 and x=2, y=0. When x=2, the alkyl groups, taken together with the nitrogen to which they are attached, can optionally form a cyclic ring system. "Dialkylamino" refers to a —N(alkyl)$_2$ group, where alkyl is as defined herein.

The term "aromatic" refers to a planar ring having a delocalized π-electron system containing 4n+2 π electrons, where n is an integer. Aromatic rings can be formed from five, six, seven, eight, nine, or more than nine atoms. Aromatics can be optionally substituted. The term "aromatic" includes both aryl groups (e.g., phenyl, naphthalenyl) and heteroaryl groups (e.g., pyridinyl, quinolinyl).

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, and naphthalenyl. Depending on the structure, an aryl group can be a monoradical or a diradical (i.e., an arylene group).

"Carboxy" refers to —CO$_2$H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

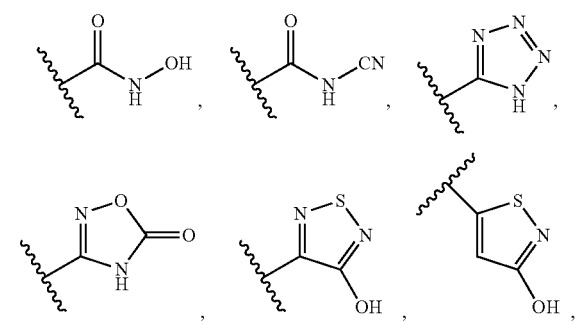

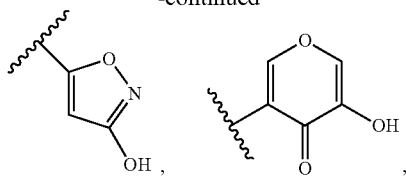

and the like.

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. Illustrative examples of cycloalkyl groups include, but are not limited to, the following moieties:

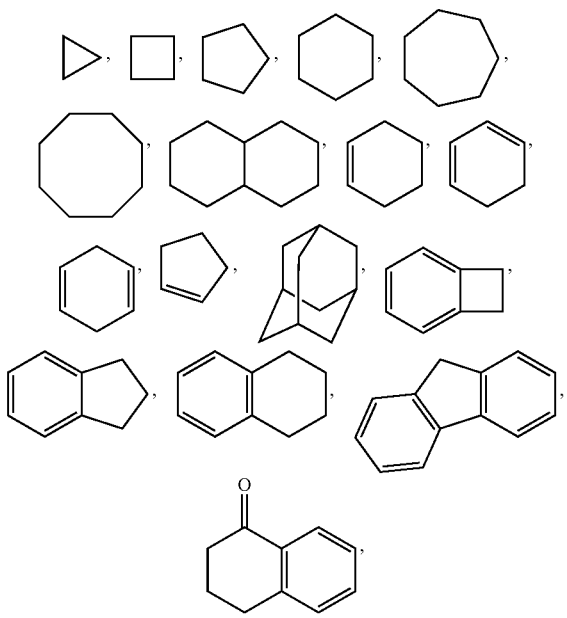

and the like.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. Polycyclic heteroaryl groups may be fused or non-fused. Illustrative examples of heteroaryl groups include the following moieties:

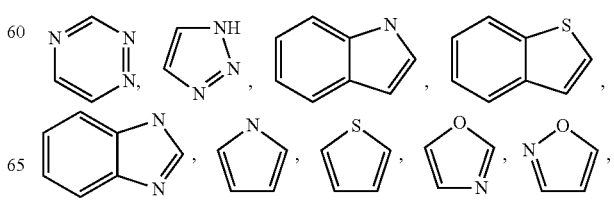

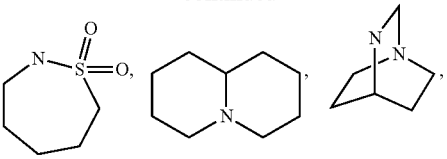

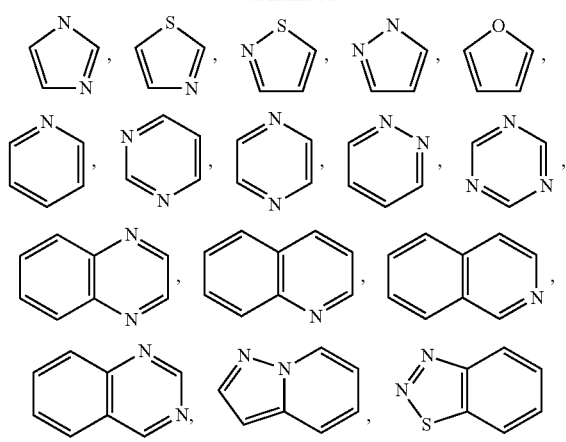

and the like.

A "heterocycloalkyl" group or "heteroalicyclic" group refers to a cycloalkyl group, wherein at least one skeletal ring atom is a heteroatom selected from nitrogen, oxygen and sulfur. The radicals may be fused with an aryl or heteroaryl. Illustrative examples of heterocycloalkyl groups, also referred to as non-aromatic heterocycles, include:

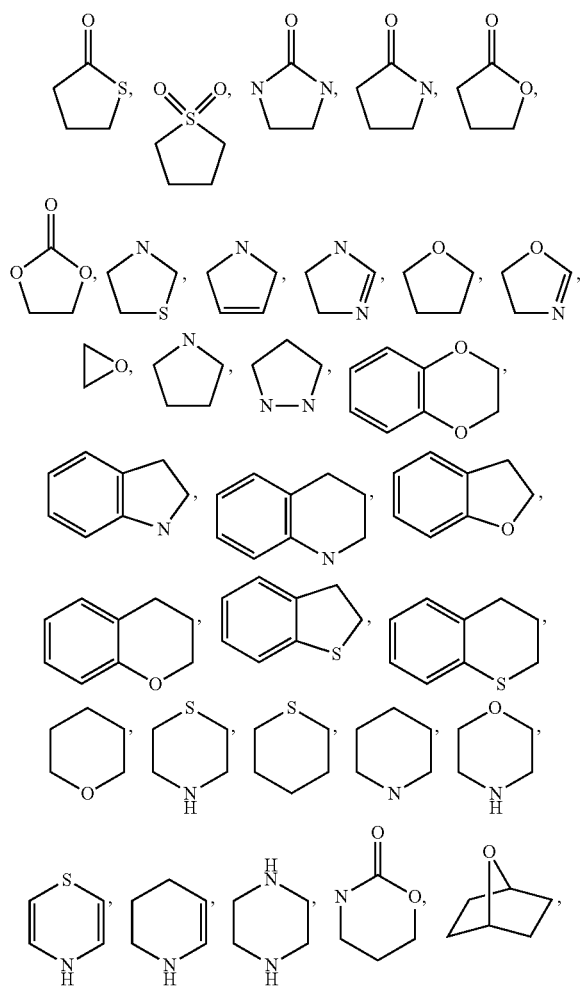

and the like. The term heteroalicyclic also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring).

The term "halo" or, alternatively, "halogen" means fluoro, chloro, bromo and iodo.

The term "haloalkyl" refers to an alkyl group that is substituted with one or more halogens. The halogens may be the same or they may be different. Non-limiting examples of haloalkyls include —CH$_2$C$_1$, —CF$_3$, —CHF$_2$, —CH$_2$CF$_3$, —CF$_2$CF$_3$, —CF(CH$_3$)$_3$, and the like.

The terms "fluoroalkyl" and "fluoroalkoxy" include alkyl and alkoxy groups, respectively, that are substituted with one or more fluorine atoms. Non-limiting examples of fluoroalkyls include —CF$_3$, —CHF$_2$, —CH$_2$F, —CH$_2$CF$_3$, —CF$_2$CF$_3$, —CF$_2$CF$_2$CF$_3$, —CF(CH$_3$)$_3$, and the like. Non-limiting examples of fluoroalkoxy groups, include —OCF$_3$, —OCHF$_2$, —OCH$_2$F, —OCH$_2$CF$_3$, —OCF$_2$CF$_3$, —OCF$_2$CF$_2$CF$_3$, —OCF(CH$_3$)$_2$, and the like.

The term "heteroalkyl" refers to an alkyl radical where one or more skeletal chain atoms is selected from an atom other than carbon, e.g., oxygen, nitrogen, sulfur, phosphorus, silicon, or combinations thereof. The heteroatom(s) may be placed at any interior position of the heteroalkyl group. Examples include, but are not limited to, —CH$_2$—O—CH$_3$, —CH$_2$—CH$_2$—O—CH$_3$, —CH$_2$—NH—CH$_3$, —CH$_2$—CH$_2$—NH—CH$_3$, —CH$_2$—N(CH$_3$)—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH$_2$—NH—OCH$_3$, —CH$_2$—O—Si(CH$_3$)$_3$, —CH$_2$—CH=N—OCH$_3$, and —CH=CH—N(CH$_3$)—CH$_3$. In addition, up to two heteroatoms may be consecutive, such as, by way of example, —CH$_2$—NH—OCH$_3$ and —CH$_2$—O—Si(CH$_3$)$_3$. Excluding the number of heteroatoms, a "heteroalkyl" may have from 1 to 6 carbon atoms.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

As used herein, the substituent "R" appearing by itself and without a number designation refers to a substituent selected from among from alkyl, haloalkyl, heteroalkyl, alkenyl, cycloalkyl, aryl, heteroaryl (bonded through a ring carbon), and heterocycloalkyl.

The term "optionally substituted" or "substituted" means that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halo, acyl, acyloxy, —$CO_2H$, —$CO_2$-alkyl, nitro, haloalkyl, fluoroalkyl, and amino, including mono- and di-substituted amino groups (e.g. —$NH_2$, —NHR, —$N(R)_2$), and the protected derivatives thereof. In some embodiments, optional substituents are independently selected from halogen, —CN, —$NH_2$, —NH ($CH_3$), —$N(CH_3)_2$, —OH, —$CO_2H$, —$CO_2$alkyl, —C(=O)$NH_2$, —C(=O)NH(alkyl), —C(=O)N(alkyl)$_2$, —S(=O)$_2NH_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some embodiments, optional substituents are independently selected from halogen, —CN, —$NH_2$, —OH, —NH($CH_3$), —N($CH_3$)$_2$, —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (=O).

The methods and formulations described herein include the use of crystalline forms (also known as polymorphs), or pharmaceutically acceptable salts of compounds having the structure of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), as well as active metabolites of these compounds having the same type of activity.

As used herein, the term "about" or "approximately" means within 20%, preferably within 10%, and more preferably within 5% of a given value or range.

The term a "therapeutically effective amount" as used herein refers to the amount of an FXR modulator that, when administered to a mammal in need, is effective to at least partially ameliorate or to at least partially prevent diseases, disorders or conditions described herein.

As used herein, the term "expression" includes the process by which polynucleotides are transcribed into mRNA and translated into peptides, polypeptides, or proteins.

The term "activator" is used in this specification to denote any molecular species that results in activation of the indicated receptor, regardless of whether the species itself binds to the receptor or a metabolite of the species binds to the receptor when the species is administered topically. Thus, the activator can be a ligand of the receptor or it can be an activator that is metabolized to the ligand of the receptor, i.e., a metabolite that is formed in tissue and is the actual ligand.

The term "antagonist" as used herein, refers to a small-molecule agent that binds to a nuclear hormone receptor and subsequently decreases the agonist induced transcriptional activity of the nuclear hormone receptor.

The term "agonist" as used herein, refers to a small-molecule agent that binds to a nuclear hormone receptor and subsequently increases nuclear hormone receptor transcriptional activity in the absence of a known agonist.

The term "inverse agonist" as used herein, refers to a small-molecule agent that binds to a nuclear hormone receptor and subsequently decreases the basal level of nuclear hormone receptor transcriptional activity that is present in the absence of a known agonist.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "FXR modulator" includes FXR agonists, antagonists and tissue selective FXR modulators, as well as other agents that induce the expression and/or protein levels of FXR in cells.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human. Those skilled in the art recognize that a therapy which reduces the severity of a pathology in one species of mammal is predictive of the effect of the therapy on another species of mammal.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In some embodiments, the quaternary amine FXR modulator compounds of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) are orally administered to a subject in need thereof. In some embodiments, the quaternary amine FXR modulator compounds of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) orally administered to a subject in need thereof are not absorbed into the systemic circulation. Thus, the quaternary amine FXR modulator compounds of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) described herein provide an optimal delivery for an orally administered FXR modulator. The quaternary amines are potent FXR modulators which induce the expression and/or protein levels of FXR in the intestine. However, the quaternary amines will have little or no systemic exposure, thereby minimizing potential deleterious side effects of systemic exposure.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Compositions and Methods of Administration of FXR Modulators

Administration of FXR modulators as described herein can be in any pharmacological form including a therapeutically effective amount of an FXR modulator alone or in combination with a pharmaceutically acceptable carrier.

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Additional details about suitable excipients for pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999), herein incorporated by reference for such disclosure.

A pharmaceutical composition, as used herein, refers to a mixture of a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) described herein, with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) can be used singly or in combination with one or more therapeutic agents as components of mixtures (as in combination therapy).

The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. In some embodiments, the pharmaceutical compositions described herein, which include a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) described herein, are orally administered. Moreover, the pharmaceutical compositions described herein, which include a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) described herein, can be formulated into any suitable dosage form, including but not limited to, aqueous oral dispersions, liquids, gels, syrups, elixirs, slurries, suspensions, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

Dose administration can be repeated depending upon the pharmacokinetic parameters of the dosage formulation and the route of administration used.

It is especially advantageous to formulate compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the FXR modulator and the particular therapeutic effect to be achieved and (b) the limitations inherent in the art of compounding such an active compound for the treatment of sensitivity in individuals. The specific dose can be readily calculated by one of ordinary skill in the art, e.g., according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the FXR modulator activities disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

Toxicity and therapeutic efficacy of such FXR modulators can be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. FXR modulators that exhibit large therapeutic indices are preferred. While FXR modulators that exhibit toxic side effects may be used, care should be taken to design a delivery system that targets such modulators to the site of affected tissue in order to minimize potential damage to uninfected cells and, thereby, reduce side effects.

The data obtained from the cell culture assays and animal studies can be used in formulating a range of dosage for use in humans. The dosage of such FXR modulators lies preferably within a range of circulating concentrations that include the $ED_{50}$ with little or no toxicity. The dosage may vary within this range depending upon the dosage form employed and the route of administration utilized. For any FXR modulator used in a method described herein, the therapeutically effective dose can be estimated initially from cell culture assays. A dose may be formulated in animal models to achieve a circulating plasma concentration range that includes the $IC_{50}$ (i.e., the concentration of FXR modulator that achieves a half-maximal inhibition of symptoms) as determined in cell culture. Such information can be used to more accurately determine useful doses in humans. Levels in plasma may be measured, for example, by high performance liquid chromatography.

Methods of Dosing and Treatment Regimens

The compounds described herein can be used in the preparation of medicaments for the modulation of FXR, or for the treatment of diseases or conditions that would benefit, at least in part, from modulation of FXR. In addition, a method for treating any of the diseases or conditions described herein in a subject in need of such treatment, involves administration of pharmaceutical compositions containing at least one compound described herein, or a pharmaceutically acceptable salt, or pharmaceutically acceptable solvate or hydrate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be determined in a manner recognized in the field according to the particular circumstances surrounding the case, including, e.g., the specific agent being administered, the route of administration, the condition being treated, and the subject or host being treated. In general, however, doses employed for adult human treatment will typically be in the range of about 0.01 mg per day to about 5000 mg per day, in some embodiments, about 1 mg per day to about 1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The daily dosages appropriate for the compounds described herein described herein are from about 0.001 mg/kg to about 30 mg/kg. In one embodiment, the daily dosages are from about 0.01 mg/kg to about 10 mg/kg. An indicated daily dosage in the larger mammal, including, but not limited to, humans, is in the range from about 0.1 mg to about 1000 mg, conveniently administered in a single dose or in divided doses, including, but not limited to, up to four times a day or in extended release form. Suitable unit dosage forms for oral administration include from about 1 to about 500 mg active ingredient. In one embodiment, the unit dosage is about 1 mg, about 5 mg, about, 10 mg, about 20 mg, about 50 mg, about 100 mg, about 200 mg, about 250 mg, about 400 mg, or about 500 mg. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

EXAMPLES

The following examples are offered for purposes of illustration, and are not intended to limit the scope of the claims provided herein. All literature citations in these examples and throughout this specification are incorporated herein by references for all legal purposes to be served thereby. The starting materials and reagents used for the synthesis of the compounds described herein may be synthesized or can be obtained from commercial sources, such as, but not limited to, Sigma-Aldrich, Acros Organics, Fluka, and Fischer Scientific Example 1: Synthesis of Compound 13

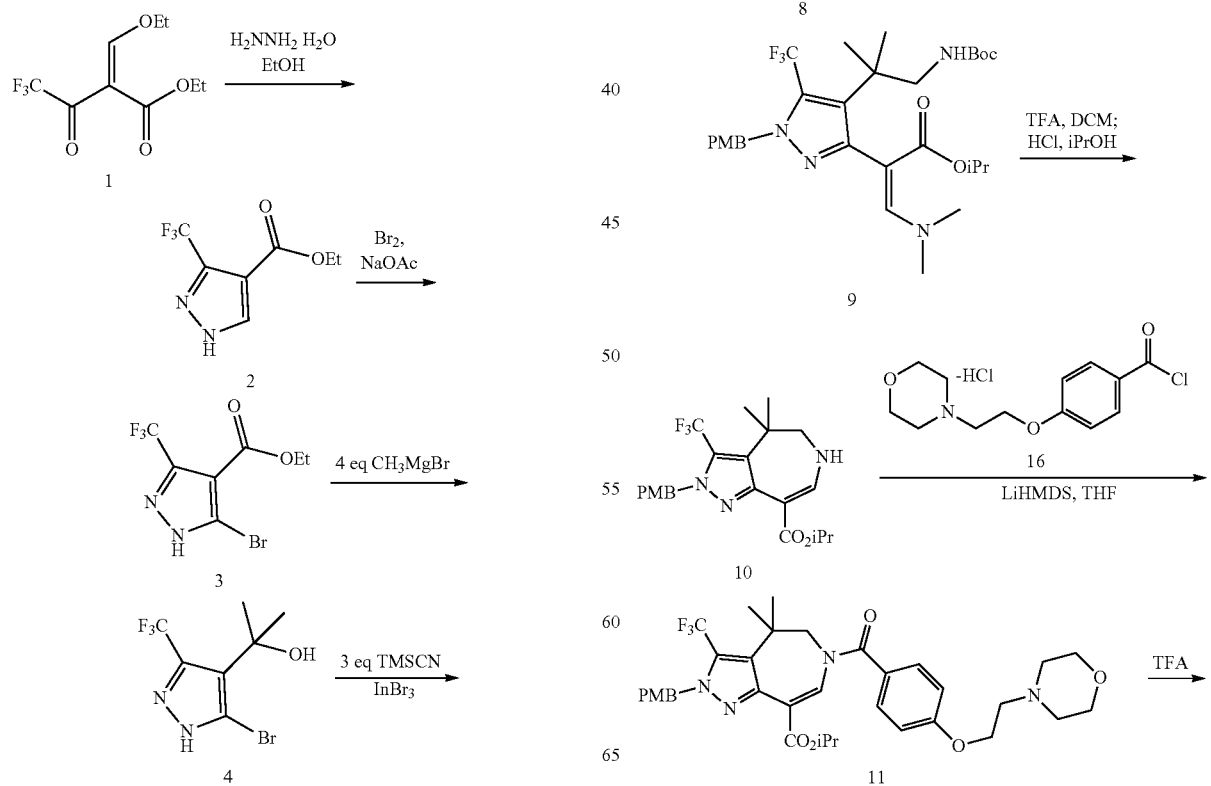

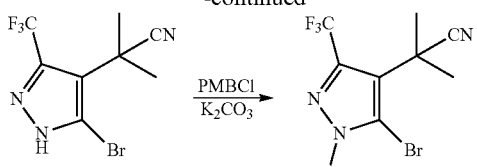

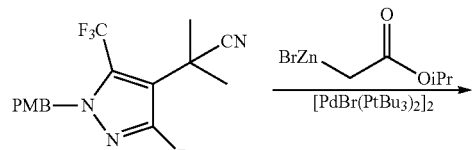

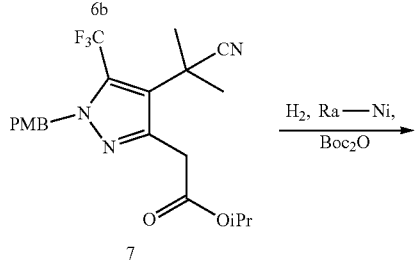

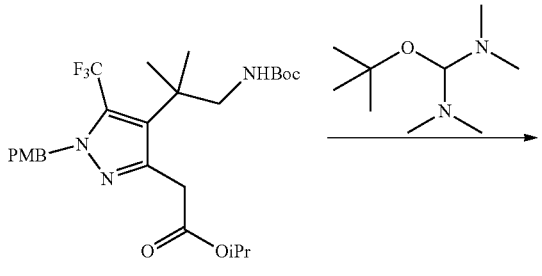

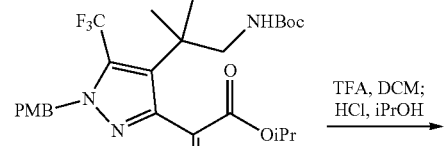

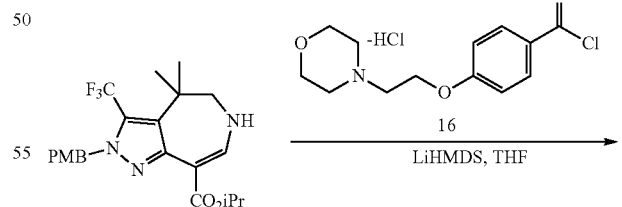

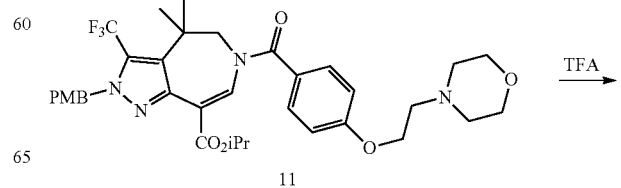

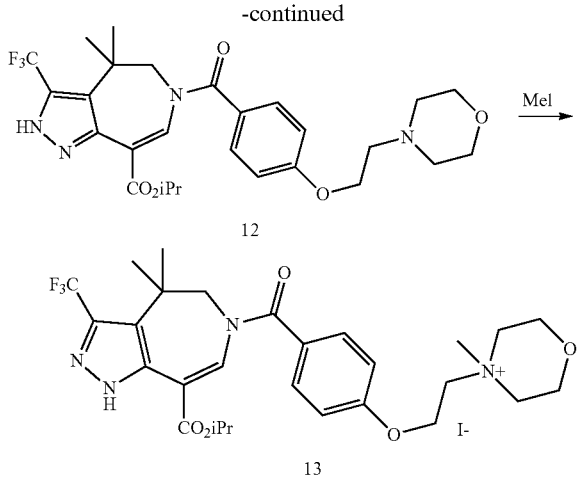

To a solution of ethyl-(4,4,4,-trifluoro)-3-oxobutyrate (20 g, 0.11 mol) in acetic anhydride (33.3 g, 0.33 mol) was added triethyl orthoformate (24.1 g, 0.165 mol). The reaction mixture was heated at 120° C. for 2.5 h. The low-boiling components were removed and the residue was distilled under reduced pressure to give ethyl 2-ethoxymethyllene-4,4,4-trifluoro-3-oxobutytate (1) (23.5 g, 91%) as an oil, which was used without further purification.

To a stirred solution of 1 (23.5 g, 98 mmol) in EtOH (150 mL), was added hydrazine (3.8 g, 117 mmol) dropwise at 0° C. The reaction mixture was allowed to warm to room temperature and stirred for 15 h. The mixture was concentrated and the residue was dissolved in EtOAc (200 mL). The solution was washed with water, 0.5N HCl, saturated NaHCO$_3$, and brine. The organic phase was dried over Na$_2$SO$_4$ and concentrated to dryness to afford crude compound 2 (18 g, 88%) as a yellow solid, which was used without further purification. $^1$H NMR (400 MHz, CD$_3$OD): δ 8.31 (1H, d, J=0.8 Hz), 4.29 (2H, q, J=7.2 Hz), 1.34 (3H, J=7.2 Hz).

Compound 2 (5 g) was dissolved in acetic acid (40 mL), added sodium acetate (5.9 g). To the suspended solution was added a solution of Br$_2$ (3.7 mL) in acetic acid (5 mL) dropwise. The resulting mixture was stirred at room temperature for 15 minutes, and then heated at 100° C. in a sealed-tube for 3 hr. The solvent and excess Br$_2$ were removed in vacuo, the residue was suspended in ice-water (100 mL), then added saturated NaHCO$_3$ dropwise to adjust pH ~6. The white precipitate was collected by filtration, washed with water (2×20 mL). The solid was dried under vacuum to provide 3 (6.35 g, 92%) which was used without further purification.

Compound 3 (5 g) was dissolved in dry THF (30 mL) and cooled with ice-water bath. MeMgCl (26 mL, 3M in THF) was added dropwise under N$_2$. The resulting mixture was stirred at 0° C. for 30 minutes and then at room temperature for 5 h. The reaction mixture was cooled to 0° C., quenched with saturated NH$_4$Cl solution. The organic phase was washed water and brine, dried over Na$_2$SO$_4$, filtered and concentrated to afford a yellow oil. The residue was triturated with CH$_2$Cl$_2$ and hexanes to give the product as a solid 4 (4.7 g, 98%) which was used for the next reaction without further purification.

To a suspension of Indium (III) bromide (6.5 g, 18.3 mmol) in dichloromethane (500 mL) was added trimethylsilyl cyanide (69 mL, 549.4 mmol). To this mixture was added dropwise at room temperature compound 4 (50.0 g, 183.1 mmol) in dichloromethane (1500 mL). The resulting mixture was stirred at room temperature overnight. Saturated NaHCO$_3$ was added and the mixture was filtered through a celite pad. The residue was partitioned between saturated aqueous NaHCO$_3$ and dichloromethane and the aqueous layer was extracted one more time with ethyl acetate. Combine organic layers were dried over MgSO$_4$, filtered and concentrated. The crude product was purified by column chromatography (SiO$_2$, DCM to DCM/MeOH=30/1) to afford compound 5 as a brown oil (50 g*2 batch; 107.1 g).

To a solution of compound 5 (3 g, 10.6 mmol) in CH$_3$CN, was added K$_2$CO$_3$ (4.08 g, 31.9 mmol) and PMBCl (1.7 mL, 12.7 mmol). The mixture was heated at reflux for 2 h. The reaction was cooled to room temperature and the inorganic solid was removed by filtration. The mother liquid was concentrated in vacuo to afford a mixture of 6a and 6b (3.6 g, 3:1 of 6b:6a as determined by $^1$H NMR) as a yellow oil. The mixture was dissolved in CH$_2$Cl$_2$ (1 mL), and then TFA (2.3 mL) was added. The reaction mixture was stirred at room temperature for 1 h. The solvent was removed in vacuo and the residue was dissolved in CH$_3$CN (6 mL). To this solution was added K$_2$CO$_3$ (0.34 g) and PMBCl (0.43 mL). The resulting mixture was heated at 90° C. for 1.5 h. The reaction was cooled to room temperature and the inorganic solid was removed by filtration. The mother liquid was concentrated in vacuo to afford a mixture of 6a and 6b (3.6 g, 10:1 of 6b:6a as measured by $^1$H NMR) as a yellow oil. The mixture was dissolved in CH$_2$Cl$_2$ (1 mL), and then TFA (2.3 mL) was added. The mixture was stirred at room temperature for 1 h. The solvent was removed in vacuo and the residue was dissolved in CH$_3$CN (6 mL). To this solution was added K$_2$CO$_3$ (0.11 g) and PMBCl (0.14 mL). The resulting mixture was heated at 90° C. for 1.5 h. The reaction was cooled to room temperature and the inorganic solid was removed by filtration. The mother liquid was concentrated in vacuo and the crude product was purified by column chromatography to afford yellow oil of highly enriched 6b regioisomer (3.2 g, 75%, 50:1 of 6b:6a as measured by $^1$H NMR).

To a suspension of zinc dust (4.1 g, 31.0 mmol) in dry ether (40 mL) was added dropwise HCl (2M solution in ether; 2 mL). The suspension was heated to reflux, and isopropyl bromoacetate (4 mL, 31.0 mmol) was added dropwise. The solution was heated at reflux 4 h then cooled to room temperature. To a solution of 6b (1.3 g, 3.2 mmol) in anhydrous THF (40 mL) was added (Pd(I)BrP(tBu)$_3$)$_2$ (0.37 g, 0.48 mmol) under Ar. A solution of (2-isopropoxy-2-oxoethyl) zinc bromide (6.6 mL of the prepared solution, 5.12 mmol) was added dropwise. The resulting mixture was stirred in an oil bath, temperature starting from RT to 80° C. within 10 minutes, and then the reaction was heated at 80° C. for 0.5 h. The reaction mixture was cooled to room temperature and quenched with saturated aqueous NH$_4$Cl (100 mL). After extraction of the product with ethyl acetate, the crude product was purified by column chromatography (SiO$_2$, Hex/EA=9/1→Hex/EA=6/1) to afford 7 (1.1 g, 81%) as an ivory oil.

To a solution of compound 7 (7.8 g, 18.42 mmol) in THF (80 mL) and iPrOH (160 mL) was added Boc anhydride (8.04 g, 36.84 mmol) and Ra—Ni slurry in water (40 mL). The resulting mixture was hydrogenated at H$_2$ 40 psi for 4 h. The catalyst was carefully removed by filtration. The filtrate was concentrated in vacuo. The crude product was purified by column chromatography (SiO$_2$, HX/EA=5/1) to afford sticky oil 8 (6.9 g, 71%).

Compound 8 (6.9 g, 13.08 mmol) in Bredereck's reagent (5 mL) was flushed with nitrogen, and then heated at 115° C. in a sealed tube for 3 h. The mixture was diluted with CH$_2$Cl$_2$ (500 mL). The organic phase was washed with water and brine, dried over MgSO$_4$, filtered and concentrated. The crude mixture was purified by column chromatography (SiO$_2$, Hx/EA=2/1) to afford sticky oil 9 (6.8 g, 89%).

To a solution of compound 9 (6.8 g, 11.67 mmol) in dry CH$_2$Cl$_2$ (50 mL) was added TFA (30 mL). The solution was stirred at room temperature for 15 minutes. The solvent was removed in vacuo. The residue was diluted with CH$_2$Cl$_2$ (500 mL), washed with saturated aqueous NaHCO$_3$ and brine, dried over MgSO$_4$, filtered and concentrated to afford the free amine intermediate. To a solution of the intermediate in iPrOH (100 mL) was added concentrated HCl in water (3.4 mL). The resulting mixture was heated at 100° C. in a sealed tube for 18 h. The solvent was removed in vacuo. The residue was dissolved in CH$_2$Cl$_2$ (500 mL), washed with saturated aqueous NaHCO$_3$ and brine, dried over MgSO$_4$, filtered and concentrated. The crude product was purified by column chromatography (SiO$_2$, Hx/EA=2/1) to afford solid 10 (3.7 g, 72%).

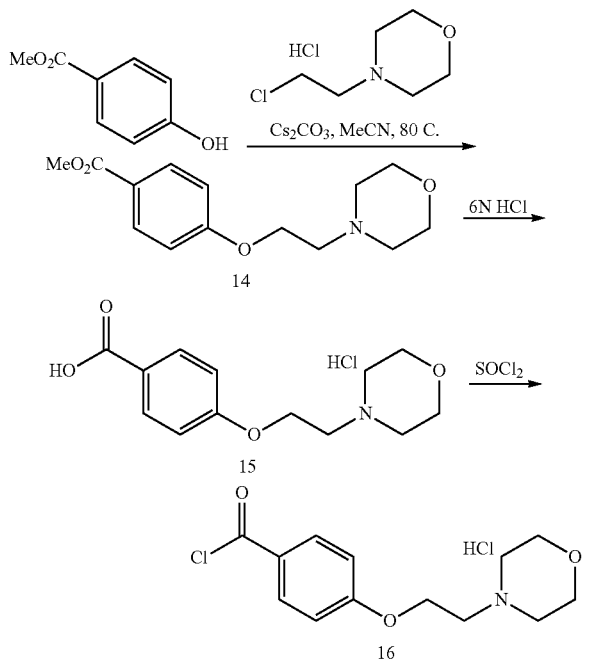

To a solution of methyl 4-hydroxybenzoate (68.1 g) in acetonitrile (1.3 L) was added N-(2-chloroethyl)morpholine HCl salt (99.9 g) and Cs$_2$CO$_3$ (291.7 g). The resulting mixture was stirred and heated at reflux overnight. The reaction mixture was cooled to room temperature and the inorganic solid was removed by filtration. The solvent was evaporated. The oily residue was dissolved in EtOAc/hexane mixture (3:1, 500 mL) and washed with water (500 mL). The aqueous layer was re-extracted with EtOAc/hexane (3:1, 2×100 mL). The combined organic extracts were evaporated in vacuo to give a crude product 14 (126.1 g) as a pale-yellow oil which was used without purification.

Crude ester 14 (126.1 g) was suspended in 6N HCl (880 mL) and the reaction mixture was heated at reflux overnight. The reaction mixture was concentrated in vacuo to remove most of the water and then the mixture was cooled at 0° C. The resulting precipitate was filtered and washed with cold 2N HCl (2×100 mL) to give a white solid which was dried in high vacuum to give compound 15 HCl salt (112.9 g, 82%).

Compound 15 HCl salt (112.8 g) was suspended in SOCl$_2$ (450 mL) and heated at 90° C. for 12 h. The excess SOCl$_2$ was removed in vacuo to ~2 vol (225 mL) and the product was precipitated with heptane (560 mL) to provide a white solid. The solid was filtered, washed with heptane and dried on high vacuo to afford acid chloride 16 HCl salt (116 g, 98%).

To a solution of 10 (800 mg, 1.83 mmol) in dry THF (100 mL) was added acid chloride 16 (1.12 g). LiHMDS (1M in Hex, 9.15 mL) was then added dropwise at 0° C. The resulting mixture was stirred for 30 min. The reaction was quenched with saturated NH$_4$Cl and extracted with ethyl acetate. The organic layer was dried over MgSO$_4$ and concentrated under reduced pressure. The crude product was purified by column chromatography (SiO$_2$, only EA) to give compound 11 (1.0 g, 81%) as an ivory foam.

A solution of 11 (2 g, 3.46 mmol) in TFA (20 mL) was heated at 90° C. in a sealed tube for 10 minutes. The TFA was removed in vacuo and the crude product was diluted in EtOAc and washed with NaHCO$_3$. The organic layer was concentrated and purified by column chromatography (SiO$_2$, DCM/Hx/EA=10/20/0.5) to afford 12 (1.3 g, 82%) as a white solid.

To a solution of 12 (18 mg) in CH$_2$Cl$_2$ (4 mL) was added CH$_3$I (9.3 mg) at 0° C. The resulting mixture was stirred at 45° C. for 5 h in a sealed-tube. The white precipitate was collected by filtration and washed with CH$_2$Cl$_2$ (2×2 mL). The solid was then dried in high vacuum to afford compound 13 (18.5 mg, 82%) as a white solid. MS (LCMS) m/z 565.4 [M+H]$^+$.

Example 2: Synthesis of 4-(5-(ethoxycarbonyl)-1,1-dimethyl-1,2,3,6-tetrahydroazepino[4,5-b]indole-3-carbonyl)-1,1-dimethylpiperazin-1-ium iodide (20)

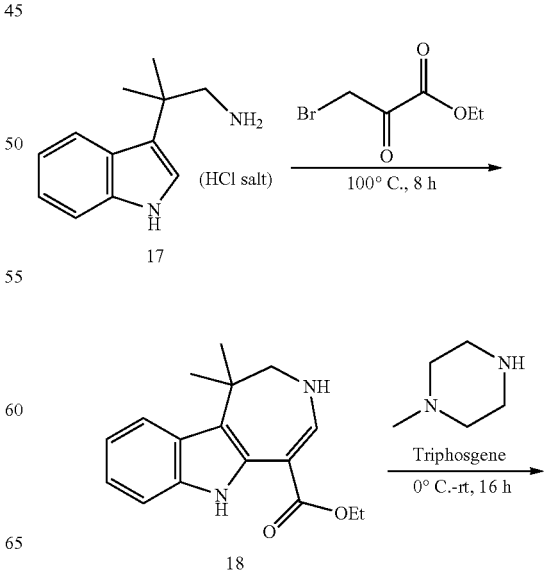

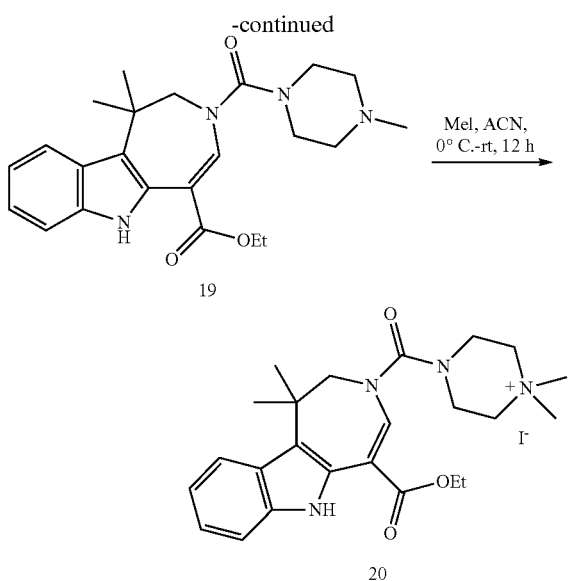

7.53-7.51 (m, 2H), 7.05-6.96 (m, 2H), 4.35-4.30 (t, J=14.0 & 7.4 Hz, 2H), 3.74 (s, 2H), 3.65 (m, 4H), 3.41 (m, 4H), 3.16 (s, 6H), 4.15-4.14 (m, 6H), 1.36-1.33 (t, J=14.0 & 7.2 Hz, 3H). MS (LCMS) m/z 425.2 [M+H]+.

Example 3: Synthesis of Compound 25

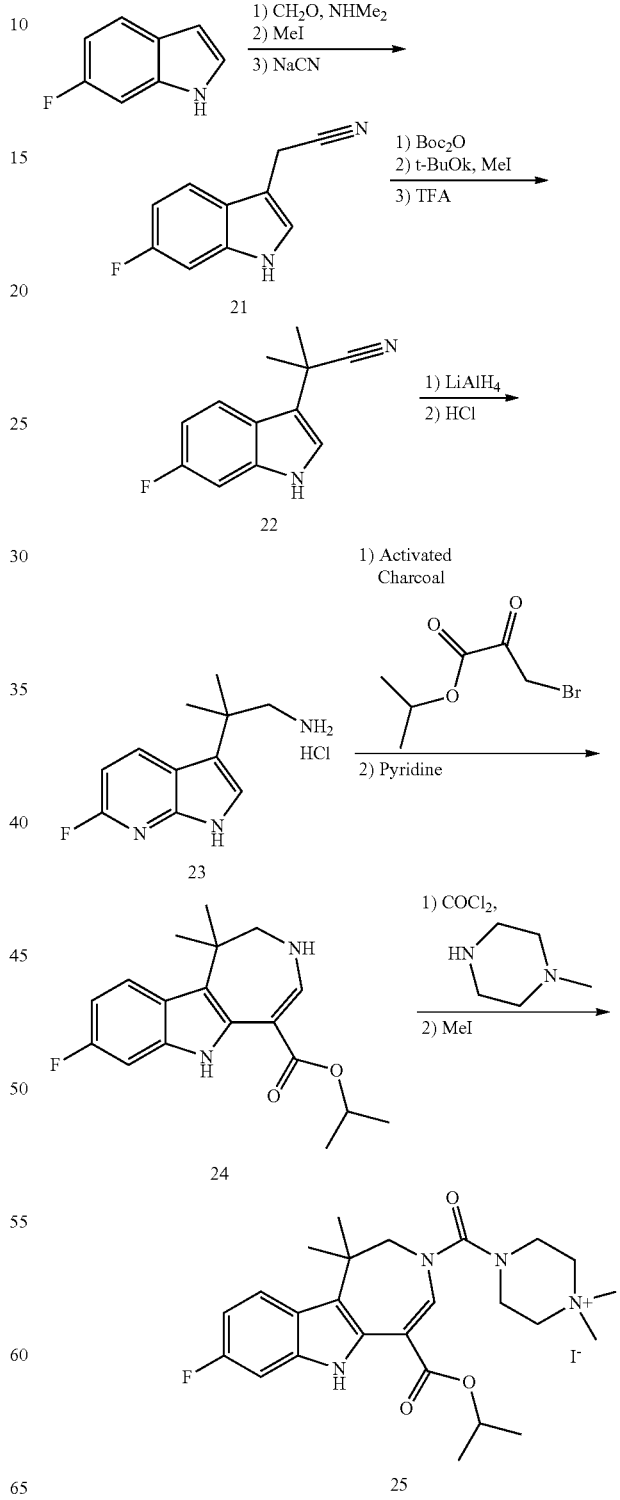

HCl in dioxane (4.0 N, 3.0 mL, 12 mmol) was added dropwise to a solution of 2-(1H-indol-3-yl)propylamine (17) (1.9 g, 11 mmol) in ethanol (50 mL), followed by decolorizing charcoal (200 mg). The mixture stirred for 10 min. Ethyl bromopyruvate (1.8 mL, 14 mmol) was then added to and the stirred mixture was heated at reflux for 6 h. The reaction mixture was cooled and concentrated to a minimum volume, diluted with pyridine (20 mL) and heated at 100° C. for 8 h. The mixture was cooled, diluted with Et$_2$O and filtered through Celite®. The filtrate was washed with water (2×40 mL), 0.1N HCl (2×40 mL), and brine. The organic layer was dried (Na$_2$SO$_4$), concentrated in vacuo and purified by flash column chromatography (0-15% EtOAc/Hex) to afford ethyl 1,1-dimethyl-1,2,3,6-tetrahydroazepino[4,5-b]indole-5-carboxylate (18) (1.2 g, 40%) as a pale yellow solid. 1H NMR (400 MHz, CDCl$_3$) δ 10.93 (s, 1H), 7.87 (d, J=7.9 Hz, 1H), 7.78 (d, J=7.9 Hz, 1H), 7.32 (d, J=8.2 Hz, 1H), 7.10-6.96 (m, 2H), 5.29 (s, 1H), 4.26 (q, J=7.1 Hz, 2H), 3.24 (s, 2H), 1.54 (s, 6H), 1.34 (t, J=7.1 Hz, 3H); MS (ESI) m/z=285 [M+H]+.

Diisopropylethylamine (0.12 mL, 66.9 mmol) was added dropwise to a stirred solution of compound 18 (0.1 g, 3.52 mmol) in dichloromethane (10 mL) at 0° C. Triphosgene (0.18 g, 6.19 mmol) was added and the reaction mixture was stirred at the same temperature for 90 min. 1-methylpiperazine (0.2 mL, 1.76 mmol) was added and the reaction mixture was stirred at room temperature for 16 h. The reaction mixture was concentrated under reduced pressure and purified by flash column chromatography (70% EtOAc/Hex) to afford compound 19 (0.07 g, 49%) as a yellow solid. $^1$H NMR (400 MHz, DMSO-d$_6$) δ 10.79 (s, 1H), 7.77-7.67 (m, 2H), 7.51 (d, J=8.1 Hz, 1H), 7.08-6.99 (m, 1H), 6.99-6.90 (m, 1H), 4.30 (q, J=7.1 Hz, 2H), 3.33-3.25 (m, 2H), 2.52-2.47 (m, 4H), 2.35-2.30 (m, 4H), 2.19 (s, 3H), 1.43 (s, 6H), 1.33 (t, J=7.0 Hz, 3H). LC-MS m/z=411.2 [M+H]+.

A solution of 19 (18 mg, 4.38×10-5 mol) in acetonitrile (3.5 mL) was cooled in an ice-water bath. To this solution was added iodomethane (4 μL, 6.5×10$^{-5}$ mol) in acetonitrile (0.5 mL) dropwise. The reaction mixture was stirred overnight at ambient temperature. The reaction mixture was concentrated and triturated in diethyl ether to afford compound 20 (9 mg, 37%) as a yellow solid. $^1$H NMR (400 MHz, DMSO-d$_6$) δ 10.79 (s, 1H), 7.73-7.71 (m, 2H), Compound 25 is prepared from 6-fluoro-1H-indole as outlined in the scheme and Examples 1 and 2.

Example 4: Synthesis of Compound 31

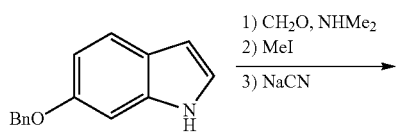

1) CH₂O, NHMe₂
2) MeI
3) NaCN

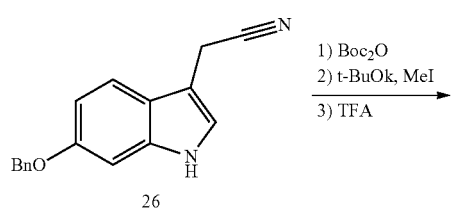

26

1) Boc₂O
2) t-BuOk, MeI
3) TFA

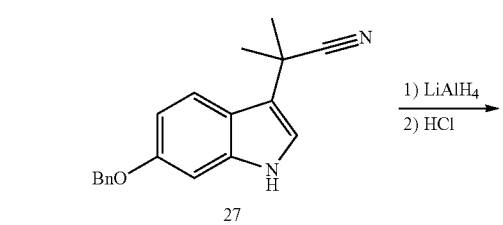

27

1) LiAlH₄
2) HCl

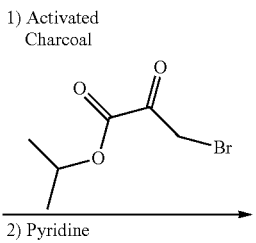

28

1) Activated Charcoal

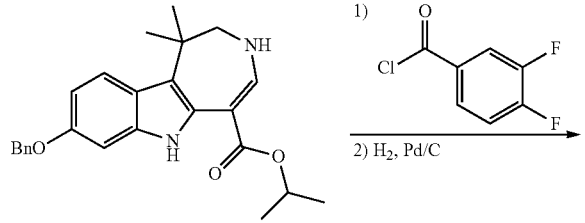

2) Pyridine

29

1)

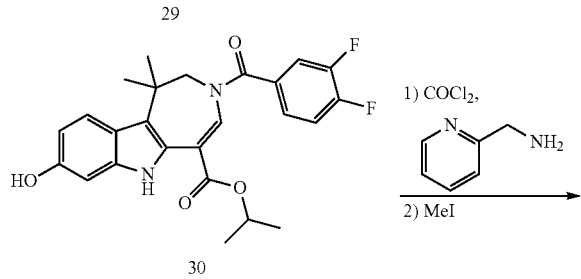

2) H₂, Pd/C

30

1) COCl₂,

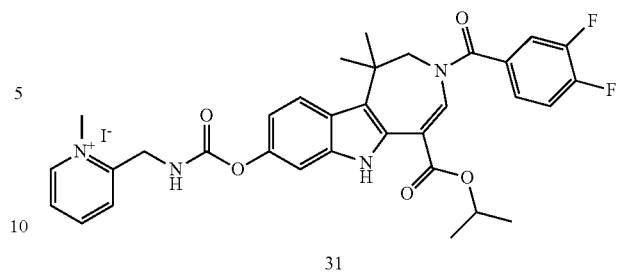

31

Compound 31 is prepared from 6-(benzyloxy)-1H-indole as outlined in the scheme and Examples 1 and 2.

Example 5: Synthesis of (E)-4-(8-(isopropoxycarbonyl)-4,4-dimethyl-1,4,5,6-tetrahydropyrazolo[3,4-d]azepine-6-carbonyl)-1,1-dimethylpiperazin-1-ium iodide (37)

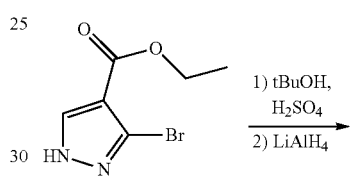

1) tBuOH, H₂SO₄
2) LiAlH₄

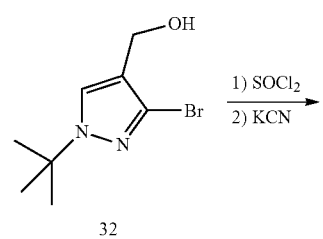

32

1) SOCl₂
2) KCN

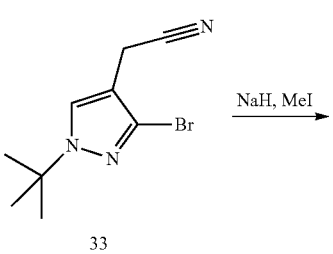

33

NaH, MeI

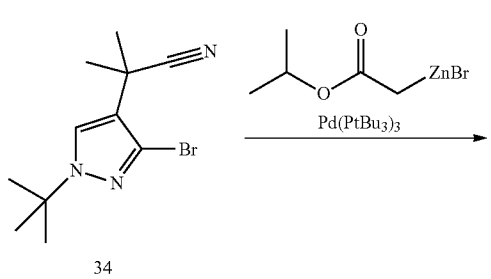

34

2) MeI

Pd(PtBu₃)₃

-continued

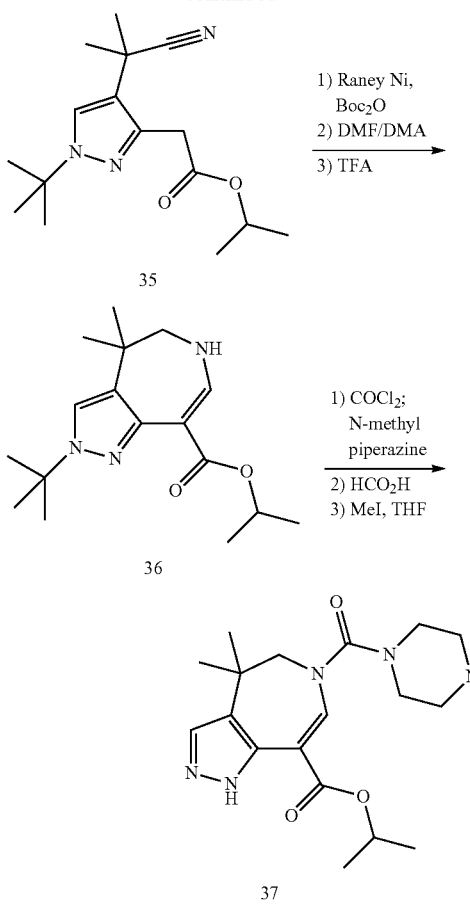

Compound 37 is prepared from ethyl 3-bromo-1H-pyrazole-4-carboxylate as outlined in the scheme and Examples 1 and 2.

Example 6: Synthesis of Compound 42

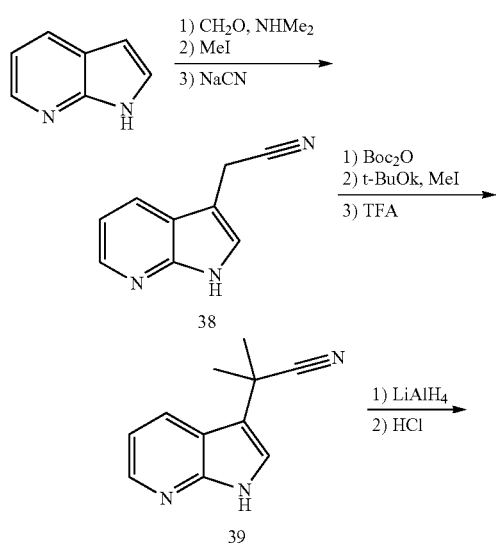

-continued

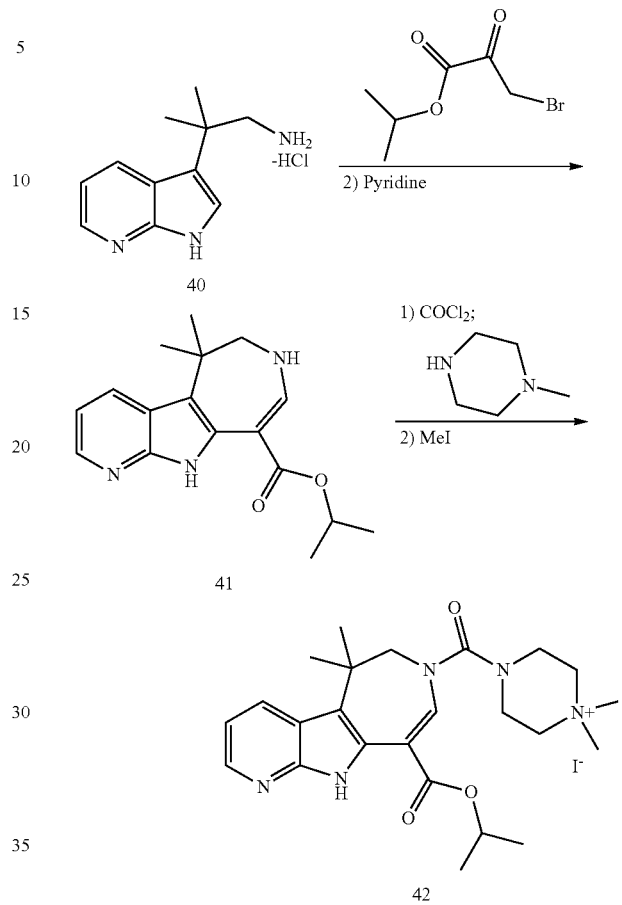

Compound 42 is prepared from 1H-pyrrolo[2,3-b]pyridine as outlined in the scheme and Examples 1 and 2.

Example 7: FXR Agonist Tranactivation Assay

CV-1 cells were transiently cotransfected with pCMV6-NR1H4 (FXR), pCMV6-RXRA and reporter plasmid pEcREX7-TK-Luc. Five hours after transfection, cells were trypsinized and dispensed into 96-well plates at a concentration of 10,000 cells per well.

Compound Dilution and Addition: Starting from 3.33 mM of compound in DMSO solution a 10-point 3-fold serial dilution was made by diluting 5 μl of compound into 10 μl of DMSO. The serially diluted compound was then diluted 1:33 into DMEM. This medium was then diluted ten-fold into the culture medium with the cells (10 μl/well). All concentration points are assayed in duplicate. Plates were incubated at 37° C. for 20 hours.

Luciferase activity Readout: After the incubation 20 μl of culture medium were removed from each well and mixed with 50 μl of assay solution (Pierce™ Gaussia Luciferase Flash Assay Kit). The luminescence was measured immediately after addition of the Luc substrate with an Envision microplate reader.

Data Reduction and Analysis: The raw data was uploaded to CDD and dose-response curves were generated using the Levenberg-Marquardt algorithm integrated into CDD. As a positive control 10 uM XL-335 and as a negative control DMSO is included on each plate and used to normalize the data with the CDD built-in normalization function. At 10 µM, compound 20 showed 86% activation compared to the positive control and compound 13 was inactive.

Example 8: Gene Expression Assay $C_{57}BL/6$ mice (3 per group) were dosed p.o. with 10 mg/kg of compound 20. Livers were collected at 4 hours post dosing and transferred into RNALater solution immediately. Tissues were stored at 4° C. until RNA isolation. RNA was isolated, quantified and amplified; qPCR was performed using SuperScript® III Platinum® SYBR®Green One-Step qRT-PCR Kit (Cat no. 11736-051). Primers used are as listed: Mouse Cyp7A1: For: (SEQ. ID NO: 1) GCTTGTAGAGAGCCACACCAA Rev: (SEQ. ID NO: 2) AGTGGTGGCAAAATTCCCA; Mouse SHP: For: (SEQ. ID NO: 3) GTACCTGAAGGGCACGATCC Rev: (SEQ. ID NO: 4) AGCCTCCTGTTGCAGGTGT; Mouse GAPDH: For: (SEQ. ID NO: 5) TGGATTTGGACGCATTGGTC Rev: (SEQ. ID NO: 6) TTTGCACTGGTACGTGTTGAT. The data is shown in Table 1.

TABLE 1

| Target Gene | Avg. % mRNA induction | ±S.E.M. |
|---|---|---|
| SHP | 266 | 60 |
| CYP7a | 57 | 22 |

Example 9: Phase 1 Study to Evaluate Safety of a Compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) in Subjects with Non-Alcoholic Steatohepatitis (NASH) and Advanced Fibrosis The primary objective of this study is to characterize the safety, tolerability and dose-limiting toxicities (DLTs) for a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) when administered orally to subjects with biopsy-proven NASH with advanced liver fibrosis.

The safety and tolerability of multiple doses of a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc);

The effects of 2 dose levels (25 mg and 50 mg) of a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) on insulin resistance and glucose homeostasis; and Effects of a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) on hepatocellular function as measured by assessment of liver enzymes and biochemical markers of hepatic and metabolic function and inflammation.

Patients: Eligible subjects will be men and women 18 years to 75 years of age.

Criteria:

Inclusion Criteria:

Institutional Review Board (IRB approved written Informed Consent and privacy language as per national regulation (eg, Health Insurance Portability and Accountability Act [HIPAA] Authorization for US sites) must be obtained from the subject or legally authorized representative prior to any study related procedures, including screening evaluations and tests Subject is ≥18 years of age and <76 years old at the time of consent Subject has had a percutaneous liver biopsy within 12 months from Screening that shows a definitive diagnosis of NASH with advanced (Brunt stage 3) hepatic fibrosis Exclusion Criteria:

Subject is a pregnant or lactating female

Subject with current, significant alcohol consumption or a history of significant alcohol consumption for a period of more than 3 consecutive months any time within 1 year prior to screening. Significant alcohol consumption is defined as more than 20 gram per day in females and more than 30 grams per day in males, on average (a standard drink in the US is considered to be 14 grams of alcohol).

Subject is unable to reliably quantify alcohol consumption based upon local study physician judgment.

Subject uses drugs historically associated with nonalcoholic fatty liver disease (NAFLD) (amiodarone, methotrexate, systemic glucocorticoids, tetracyclines, tamoxifen, estrogens at doses greater than those used for hormone replacement, anabolic steroids, valproic acid, and other known hepatotoxins) for more than 2 weeks in the year prior to Screening.

Subject requires use of drugs with a narrow therapeutic window metabolized by CYP3A4 such as fast acting opioids (alfentanil and fentanyl), immunosuppressive drugs (cyclosporine, sirolimus, and tacrolimus), some cardiovascular agents (ergotamine, quinidine and dihydroergotamine), and select psychotropic agents (pimozide).

Subject has prior or has planned (during the study period) bariatric surgery (eg, gastroplasty, Roux-en-Y gastric bypass).

Subject has concurrent infection including diagnoses of fever of unknown origin and evidence of possible central line sepsis (subjects must be afebrile at the start of therapy).

Subject with a platelet count below 100,000/mm3 at Screening.

Subject with clinical evidence of hepatic decompensation as defined by the presence of any of the following abnormalities at Screening:

Serum albumin less than 3.5 grams/deciliter (g/dL).

An INR greater than 1.1.

Direct bilirubin greater than 1.3 milligrams per deciliter (mg/dL).

Subject has a history of bleeding esophageal varices, ascites or hepatic encephalopathy Subject has a history of hepatitis C. Patients found on screening to have hepatitis C antibody, even if PCR negative for HCV RNA, are excluded from this study.

Subject has evidence of other forms of chronic liver disease:

Hepatitis B as defined by presence of hepatitis B surface antigen.

Evidence of ongoing autoimmune liver disease as defined by compatible liver histology.

Primary biliary cirrhosis as defined by the presence of at least 2 of these criteria (i) Biochemical evidence of cholestasis based mainly on alkaline phosphatase elevation (ii) Presence of anti-mitochondrial antibody (iii) Histologic evidence of nonsuppurative destructive cholangitis and destruction of interlobular bile ducts.
Primary sclerosing cholangitis.
Wilson's disease as defined by ceruloplasmin below the limits of normal and compatible liver histology.
Alpha-1-antitrypsin deficiency as defined by diagnostic features in liver histology (confirmed by alpha-1 antitrypsin level less than normal; exclusion at the discretion of the study physician).
History of hemochromatosis or iron overload as defined by presence of 3+ or 4+ stainable iron on liver biopsy.
Drug-induced liver disease as defined on the basis of typical exposure and history.
Known bile duct obstruction.
Suspected or proven liver cancer.
Any other type of liver disease other than NASH.
Subject with serum ALT greater than 300 units per liter (U/L) at Screening.
Subject with serum creatinine of 1.5 mg/dL or greater at Screening.
Subject using of any prescription or over-the-counter medication or herbal remedy that are believed to improve or treat NASH or liver disease or obesity during the period beginning 30 days prior to randomization. Subjects who are using Vitamin E or omega-3 fatty acids may continue their use.
Subject had major surgery within 8 weeks prior to Day 0, significant traumatic injury, or anticipation of need for major surgical procedure during the course of the study.
Subject with a history of biliary diversion.
Subject with known positivity for Human Immunodeficiency Virus infection.
Subject with an active, serious medical disease with likely life expectancy of less than 5 years.
Subject with active substance abuse, including inhaled or injection drugs, in the year prior to Screening.
Subject who has clinically significant and uncontrolled cardiovascular disease (eg, uncontrolled hypertension, myocardial infarction, unstable angina), New York Heart Association Grade II or greater congestive heart failure, serious cardiac arrhythmia requiring medication, or Grade II or greater peripheral vascular disease within 12 months prior to Day 0.
Subject has participated in an investigational new drug (IND) trial in the 30 days before randomization.
Subject has a clinically significant medical or psychiatric condition considered a high risk for participation in an investigational study.
Subject has any other condition which, in the opinion of the Investigator, would impede compliance or hinder completion of the study.
Subject has been previously exposed to GR MD 02.
Subject with known allergies to the study drug or any of its excipients.
Subject with malignant disease (other than basal and squamous cell carcinoma of the skin and in situ carcinoma of the cervix) with at least 5 years of follow-up showing no recurrence.
Subject has an abnormal chest x-ray indicative of acute or chronic lung disease on screening examination.

Study Design:
Allocation: Randomized
Endpoint Classification: Safety/Efficacy Study
Intervention Model: Parallel Assignment
Masking: Double Blind (Subject, Investigator)
Primary Purpose: Treatment
Primary Outcome Measures:
The primary objective of this study is to characterize the safety, which includes the tolerability and dose-limiting toxicity (DLT), for a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) when administered intravenously to subjects with biopsy-proven NASH with advanced liver fibrosis. Specifically, this measure will be assessed by number of subjects experiencing treatment emergent adverse events indicative of DLT.

Secondary Outcome Measures:
A secondary objective is to characterize the first-dose PK profile of compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc). The PK profile is assessed by the AUC (area under the plasma concentration versus time curve) and Cmax (peak plasma concentration) of a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc).

A secondary objective for the study is to characterize the PK profile and serum level accumulation of a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) following administration of daily oral doses beginning 3 days after the first dose.

A secondary objective is to evaluate change in serum alanine aminotransferase (ALT), aspartate aminotransferase (AST), ratio of AST:ALT, alkaline phosphatase, and gamma glutamyl transpeptidase (GGTP); change in AST/platelet ratio index. [Time Frame: Baseline; Week 7 (End of Study)] [Designated as safety issue: No]

A secondary objective for this study is to evaluate change in serum alanine aminotransferase (ALT), aspartate aminotransferase (AST), ratio of AST:ALT, alkaline phosphatase, and gamma glutamyl transpeptidase (GGTP) levels; and change in AST/platelet ratio index.

A secondary objective for this study is to evaluate changes in exploratory pharmacodynamic biomarkers in serum [Time Frame: Baseline; Week 7 (End of Study)] [Designated as safety issue: No]

A secondary objective for this study is to evaluate levels of exploratory pharmacodynamic biomarkers in serum including galectin-3, inflammatory, cell-death, and fibrosis markers Hepatocellular function as measured by assessment of liver enzymes and biochemical markers of hepatic and metabolic function.

| Arms | Assigned Interventions |
|---|---|
| Active Comparator: Cohort 1 Patient receives dose of compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) or placebo | Drug: Compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) Drug: Placebo |
| Active Comparator: Cohort 2 Patient receives dose of compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) or Placebo | Drug: Compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) Drug: Placebo |
| Active Comparator: Cohort 3 Patient receives dose of compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) or placebo | Drug: Compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) Drug: Placebo |

This study is a dose ranging study to assess in sequential fashion, the safety, tolerability, and dose limiting toxicities (DLTs) of a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc), in subjects with biopsy-proven NASH with advanced fibrosis. This is a dose escalation design comprised of 3 sequential cohorts to evaluate the safety of a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) when administered orally once a day for 7 weeks. Each cohort will consist of 8 subjects, 6 randomized to receive a compound of Formula (I), (Ia), (Ib), (Ic), (Id), (Ie), (If), (II), (IIa), (IIb), (IIc), (III), (IIIa), (IIIb), (IIIc), (IIId), (IIIe), (IIIf), (IV), (IVa), (IVb), or (IVc) and 2 randomized to receive placebo. Based on data safety monitoring board (DSMB) and FDA review, 2 additional cohorts may be implemented, consisting of 8 subjects.

The examples and embodiments described herein are for illustrative purposes only and in some embodiments, various modifications or changes are to be included within the purview of disclosure and scope of the appended claims.

What is claimed is:

1. A compound having the structure of Formula (IV), or a pharmaceutically acceptable salt thereof:

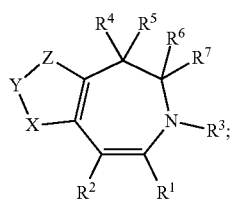

Formula (IV)

wherein:

—X—Y—Z— is selected from

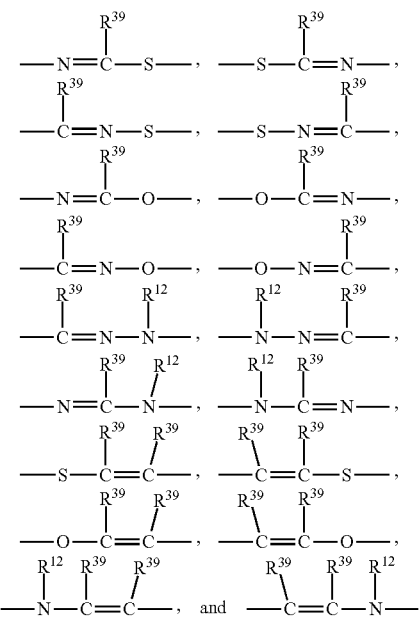

$R^1$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R^2$ is selected from the group consisting of —CN, —C(=O)O$R^{25}$, —C(=O)N($R^{25}$)$R^{26}$,

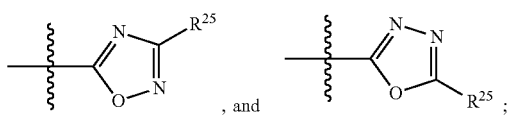

, and or $R^1$ and $R^2$ together with the carbon atoms to which they are attached, form an optionally substituted $C_2$-$C_9$heterocycloalkyl ring or an optionally substituted heteroaryl ring;

$R^3$ is —C(=O)$R^{20}$ or —S(=O)$_2R_{20}$;

$R^4$ and $R^5$ are each independently selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl; or $R^4$ and $R^5$ together with the carbon atom to which they are attached, form an optionally substituted $C_3$-$C_6$cycloalkyl ring or an optionally substituted $C_2$-$C_7$heterocycloalkyl ring;

$R^6$ is selected from the group consisting of hydrogen, halogen, optionally substituted $C_1$-$C_6$alkyl, optionally substituted $C_2$-$C_6$alkenyl, optionally substituted $C_2$-$C_6$alkynyl, and —C(=O)N($R^{27}$)$R^{28}$;

$R^7$ is selected from the group consisting of hydrogen, halogen, optionally substituted $C_1$-$C_6$alkyl, optionally substituted $C_1$-$C_6$alkoxy, optionally substituted $C_2$-$C_6$alkenyl, and optionally substituted $C_2$-$C_6$alkynyl;

each $R^{12}$ is independently selected from the group consisting of hydrogen and $C_1$-$C_6$alkyl;

each $R^{13}$ and $R^{14}$ are each independently selected from the group consisting of hydrogen and $C_1$-$C_6$alkyl; or $R^{13}$ and $R^{14}$ together with the nitrogen atom to which they are attached, form an optionally substituted $C_2$-$C_9$heterocycloalkyl ring;

each $R^{39}$ is independently selected from the group consisting of hydrogen, halogen, —CN, amino, alkylamino, $C_1$-$C_6$alkyl, $C_1$-$C_6$haloalkyl, $C_1$-$C_6$alkoxy, $C_1$-$C_6$haloalkoxy, $C_3$-$C_8$cycloalkyl, $C_2$-$C_9$heterocycloalkyl, aryl, heteroaryl, —C(=O)OR$^{12}$, and —C(=O)N(R$^{13}$)R$^{14}$;

$R^{20}$ is selected from the group consisting of —R$^{34}$R$^{35}$ or —R$^{31}$;

$R^{34}$ is selected from the group consisting of optionally substituted $C_1$-$C_6$alkyl, optionally substituted $C_3$-$C_{10}$cycloalkyl, optionally substituted aryl, optionally substituted —($C_1$-$C_2$alkylene)-(aryl), optionally substituted heteroaryl, optionally substituted $C_2$-$C_9$heterocycloalkyl, and optionally substituted —($C_1$-$C_2$alkylene)-(heteroaryl);

$R^{35}$ is —($C_1$-$C_6$alkyl)-R$^{30}$, —O($C_2$-$C_6$alkyl)-R$^{30}$, or —N(R$^{12}$)($C_2$-$C_6$alkyl)-R$^{30}$;

$R^{30}$ is $R^{36a}$, $R^{36b}$, or $R^{36c}$;

$R^{31}$ is $R^{36a}$ or $R^{36c}$;

$R^{36a}$ is

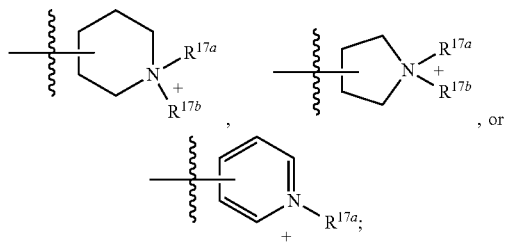

$R^{36b}$ is

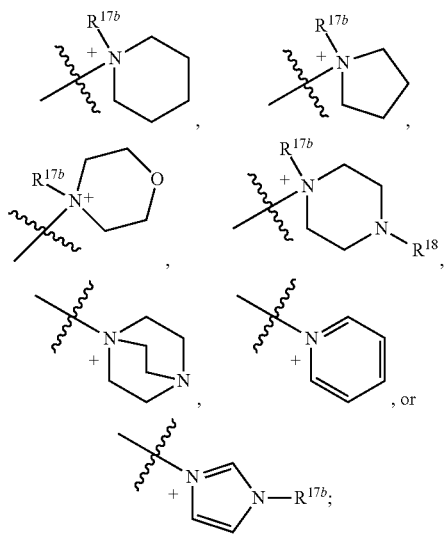

$R^{36c}$ is

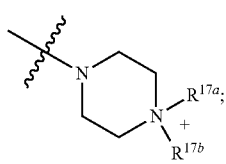

$R^{17a}$ is $C_1$-$C_6$alkyl;

$R^{17b}$ is $C_1$-$C_6$alkyl optionally substituted with phenyl, —C(=O)OH or —S(=O)$_2$OH;

$R^{18}$ is hydrogen, —OH, —($C_0$-$C_6$alkyl)-C(=O)OH, or $C_1$-$C_6$alkyl;

$R^{25}$ and $R^{26}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); and $R^{27}$ and $R^{28}$ are each independently selected from the group consisting of hydrogen, optionally substituted $C_1$-$C_6$alkyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or $R^{27}$ and $R^{28}$ together with the nitrogen atom to which they are attached, form an optionally substituted $C_2$-$C_9$heterocycloalkyl ring.

2. The compound of claim 1 having the structure of Formula (IVc), or a pharmaceutically acceptable salt thereof:

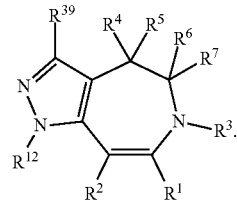

Formula (IVc)

3. The compound of claim 2, or a pharmaceutically acceptable salt thereof, wherein $R^3$ is —C(=O)R$^{20}$.

4. The compound of claim 3, or a pharmaceutically acceptable salt thereof, wherein $R^{20}$ is —R$^{34}$R$^{35}$.

5. The compound of claim 4, or a pharmaceutically acceptable salt thereof, wherein $R^{34}$ is selected from the group consisting of optionally substituted $C_1$-$C_6$alkyl, optionally substituted $C_3$-$C_{10}$cycloalkyl, and optionally substituted aryl.

6. The compound of claim 5, or a pharmaceutically acceptable salt thereof, wherein $R^{34}$ is optionally substituted aryl and $R^{35}$ is —O($C_2$-$C_6$alkyl)—R$^{30}$.

7. The compound of claim 6, or a pharmaceutically acceptable salt thereof, wherein $R^{30}$ is $R^{36b}$ or $R^{36c}$.

8. The compound of claim 7, or a pharmaceutically acceptable salt thereof, wherein $R^{36b}$ is

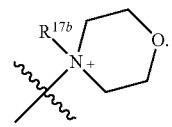

9. The compound of claim 2, or a pharmaceutically acceptable salt thereof, wherein $R^{39}$ is selected from the group consisting of hydrogen, $C_1$-$C_6$alkyl, and $C_1$-$C_6$haloalkyl.

10. The compound of claim 2, or a pharmaceutically acceptable salt thereof, wherein $R^1$, $R^6$, $R^7$, and $R^{12}$ are each hydrogen.

11. The compound of claim 2, or a pharmaceutically acceptable salt thereof, wherein $R^4$ and $R^5$ are methyl.

12. The compound of claim 2, or a pharmaceutically acceptable salt thereof, wherein $R^2$ is —C(O)$OR^{25}$.

13. The compound of claim 12, or a pharmaceutically acceptable salt thereof, wherein $R^{25}$ is optionally substituted $C_1$-$C_6$alkyl.

14. The compound of claim 12, or a pharmaceutically acceptable salt thereof, wherein $R^{25}$ is isopropyl.

15. A pharmaceutical composition comprising a pharmaceutically acceptable diluent, excipient or binder, and a compound of claim 2; or a pharmaceutically acceptable salt thereof.

16. A compound having the structure:

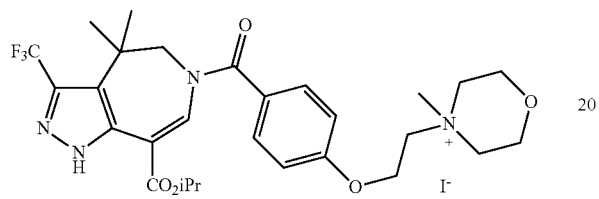

or a pharmaceutically acceptable salt thereof.

* * * * *

SEQUENCE LISTING

```
<160> NUMBER OF SEQ ID NOS: 6

<210> SEQ ID NO 1
<211> LENGTH: 21
<212> TYPE: DNA
<213> ORGANISM: Mouse

<400> SEQUENCE: 1
gcttgtagag agccacacca a                                          21

<210> SEQ ID NO 2
<211> LENGTH: 19
<212> TYPE: DNA
<213> ORGANISM: Mouse

<400> SEQUENCE: 2
agtggtggca aaattccca                                             19

<210> SEQ ID NO 3
<211> LENGTH: 20
<212> TYPE: DNA
<213> ORGANISM: Mouse

<400> SEQUENCE: 3
gtacctgaag ggcacgatcc                                            20

<210> SEQ ID NO 4
<211> LENGTH: 19
<212> TYPE: DNA
<213> ORGANISM: Mouse

<400> SEQUENCE: 4
```

```
agcctcctgt tgcaggtgt                                    19

<210> SEQ ID NO 5
<211> LENGTH: 20
<212> TYPE: DNA
<213> ORGANISM: Mouse

<400> SEQUENCE: 5
tggatttgga cgcattggtc                                   20

<210> SEQ ID NO 6
<211> LENGTH: 21
<212> TYPE: DNA
<213> ORGANISM: Mouse

<400> SEQUENCE: 6
tttgcactgg tacgtgttga t                                 21
```